US010463676B2

(12) United States Patent
Shao et al.

(10) Patent No.: US 10,463,676 B2
(45) Date of Patent: Nov. 5, 2019

(54) MODIFIED-RELEASE DOSAGE FORMS OF 5-HT$_{2C}$ AGONISTS USEFUL FOR WEIGHT MANAGEMENT

(71) Applicant: Arena Pharmaceuticals, Inc., San Diego, CA (US)

(72) Inventors: Zezhi Jesse Shao, San Diego, CA (US); Anthony C. Blackburn, San Diego, CA (US); Andrew J. Grottick, Chula Vista, CA (US); Michael E. Morgan, San Diego, CA (US); Jaimie Karyn Rueter, San Diego, CA (US); Anna Shifrina, Alameda, CA (US); Scott Stirn, Rancho Santa Fe, CA (US); Libo Yang, San Diego, CA (US); Woo Hyun Yoon, San Diego, CA (US)

(73) Assignee: Arena Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 16/241,337

(22) Filed: Jan. 7, 2019

(65) Prior Publication Data

US 2019/0275055 A1 Sep. 12, 2019

Related U.S. Application Data

(63) Continuation of application No. 15/429,221, filed on Feb. 10, 2017, now Pat. No. 10,226,471, which is a continuation of application No. 13/820,107, filed as application No. PCT/US2011/049914 on Aug. 31, 2011, now abandoned.

(60) Provisional application No. 61/403,143, filed on Sep. 10, 2010, provisional application No. 61/402,578, filed on Sep. 1, 2010.

(51) Int. Cl.
| | |
|---|---|
| *A61K 31/55* | (2006.01) |
| *A61K 9/00* | (2006.01) |
| *C07D 223/16* | (2006.01) |
| *A61P 1/14* | (2006.01) |
| *A61K 9/28* | (2006.01) |
| *A61K 9/20* | (2006.01) |
| *A23P 20/12* | (2016.01) |
| *A61K 31/155* | (2006.01) |
| *A61K 31/135* | (2006.01) |
| *A61K 45/06* | (2006.01) |

(52) U.S. Cl.
CPC .............. *A61K 31/55* (2013.01); *A23P 20/12* (2016.08); *A61K 9/0053* (2013.01); *A61K 9/2013* (2013.01); *A61K 9/2018* (2013.01); *A61K 9/2054* (2013.01); *A61K 9/2846* (2013.01); *A61K 9/2866* (2013.01); *A61K 31/135* (2013.01); *A61K 31/155* (2013.01); *A61K 45/06* (2013.01); *A61P 1/14* (2018.01); *C07D 223/16* (2013.01)

(58) Field of Classification Search
CPC .................. A61K 31/55; A61P 1/14
See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,098,911 A | 3/1992 | Ibrahim |
| 5,178,786 A | 1/1993 | Jahnke et al. |
| 5,247,080 A | 9/1993 | Berger et al. |
| 5,275,915 A | 1/1994 | Kojima et al. |
| 5,362,728 A | 11/1994 | Asberom et al. |
| 5,387,685 A | 2/1995 | Powell et al. |
| 5,397,793 A | 3/1995 | Shaber et al. |
| 5,412,119 A | 5/1995 | Brussee et al. |
| 5,422,355 A | 6/1995 | White et al. |
| 5,472,712 A | 12/1995 | Oshlack et al. |
| 5,677,297 A | 10/1997 | Waldeck et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |

(Continued)

FOREIGN PATENT DOCUMENTS

| | | |
|---|---|---|
| AU | 515 236 | 3/1981 |
| CA | 1090797 | 12/1980 |

(Continued)

OTHER PUBLICATIONS

U.S. Appl. No. 60/372,058, filed Apr. 12, 2002, Smith et al.

(Continued)

*Primary Examiner* — Gina C Justice
(74) *Attorney, Agent, or Firm* — Fish & Richardson P.C.

(57) ABSTRACT

The present invention relates to methods for weight management that utilize modified-release dosage forms comprising (R)-8-chloro-1-methyl-2,3,4,5-tetrahydro-1H-3-benzazepine salts and crystalline forms thereof. The present invention further relates to (R)-8-chloro-1-methyl-2,3,4,5-tetrahydro-1H-3-benzazepine salts, crystalline forms thereof and modified-release dosage forms comprising them.

15 Claims, 58 Drawing Sheets

(56) References Cited

U.S. PATENT DOCUMENTS

| | | |
|---|---|---|
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,466 B2 | 1/2007 | McClure et al. |
| 7,173,037 B2 | 2/2007 | Alonso-Alija et al. |
| 7,211,591 B2 | 5/2007 | Tajima et al. |
| 7,229,991 B2 | 6/2007 | Merla et al. |
| 7,230,024 B2 | 6/2007 | Carpino et al. |
| 7,232,823 B2 | 6/2007 | Carpino et al. |
| 7,241,805 B2 | 7/2007 | Oberegger |
| 7,514,422 B2 | 4/2009 | Smith et al. |
| 7,704,993 B2 | 4/2010 | Smith et al. |
| 7,977,329 B2 | 7/2011 | Smith et al. |
| 8,153,621 B2 | 4/2012 | Behan et al. |
| 8,168,614 B2 | 5/2012 | Baker |
| 8,168,624 B2 | 5/2012 | Agarwal et al. |
| 8,168,782 B2 | 5/2012 | Weigl et al. |
| 8,207,158 B2 | 6/2012 | Smith et al. |
| 8,273,734 B1 | 9/2012 | Smith et al. |
| 8,299,241 B2 | 10/2012 | Gharbaoui et al. |
| 8,367,657 B2 | 2/2013 | Wolgast |
| 8,501,935 B2 | 8/2013 | Weigl et al. |
| 8,546,379 B2 | 10/2013 | Smith et al. |
| 8,575,149 B2 | 11/2013 | Smith et al. |
| 8,697,686 B2 | 4/2014 | Agarwal |
| 8,802,845 B2 | 8/2014 | Weigl et al. |
| 8,846,906 B2 | 9/2014 | Smith et al. |
| 8,946,207 B2 | 2/2015 | Wolgast et al. |
| 8,980,881 B2 | 3/2015 | Agarwal |
| 8,993,750 B2 | 3/2015 | Smith et al. |
| 8,999,970 B2 | 4/2015 | Anderson |
| 9,045,431 B2 | 6/2015 | Blackburn |
| 9,102,627 B2 | 8/2015 | Wolgast et al. |
| 9,169,213 B2 | 10/2015 | Sanchez |
| 9,248,133 B2 | 2/2016 | Blackburn et al. |
| 9,365,521 B2 | 6/2016 | Blackburn et al. |
| 9,770,455 B2 | 9/2017 | Anderson et al. |
| 2003/0105106 A1 | 6/2003 | Chiang et al. |
| 2003/0225057 A1 | 12/2003 | Smith et al. |
| 2004/0097483 A1 | 5/2004 | Zeng et al. |
| 2004/0101575 A1 | 5/2004 | Hinz |
| 2005/0020573 A1 | 1/2005 | Smith et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2008/0255093 A1 | 10/2008 | Tam et al. |
| 2009/0143576 A1 | 6/2009 | Weigl et al. |
| 2010/0004223 A1 | 1/2010 | Agarwal et al. |
| 2010/0113603 A1 | 5/2010 | Aronne |
| 2010/0173894 A1 | 7/2010 | Smith et al. |
| 2010/0285125 A1 | 11/2010 | Devarajan et al. |
| 2010/0305316 A1 | 12/2010 | Gharbaoui et al. |
| 2011/0015438 A1 | 1/2011 | Carlos et al. |
| 2012/0135982 A1 | 5/2012 | Smith et al. |
| 2012/0142967 A1 | 6/2012 | De Mattei et al. |
| 2012/0252786 A1 | 10/2012 | Behan et al. |
| 2012/0252787 A1 | 10/2012 | Anderson et al. |
| 2012/0252788 A1 | 10/2012 | Smith et al. |
| 2012/0264743 A1 | 10/2012 | Agarwal et al. |
| 2013/0315994 A1 | 11/2013 | Shao et al. |
| 2014/0148442 A1 | 5/2014 | Blackburn et al. |
| 2015/0038701 A1 | 2/2015 | Weigl et al. |
| 2015/0196567 A1 | 7/2015 | Anderson et al. |
| 2015/0297610 A1 | 10/2015 | Sanchez et al. |
| 2016/0009654 A1 | 1/2016 | Agarwal et al. |
| 2016/0024014 A1 | 1/2016 | Smith et al. |
| 2016/0151381 A1 | 6/2016 | Blackburn et al. |
| 2016/0185729 A1 | 6/2016 | Wolgast et al. |
| 2016/0250223 A1 | 9/2016 | Smith et al. |
| 2017/0096398 A1 | 4/2017 | Blackburn et al. |
| 2017/0239263 A1 | 8/2017 | Sanchez et al. |
| 2017/0246179 A1 | 8/2017 | Shao et al. |

FOREIGN PATENT DOCUMENTS

| | | |
|---|---|---|
| CA | 2197789 | 2/1996 |
| CA | 2325741 | 10/1999 |
| CN | 102126988 | 7/2011 |
| DE | 1944121 | 3/1970 |
| DE | 1914456 | 6/1971 |
| DE | 3315106 | 11/1983 |
| DE | 3418270 | 11/1985 |
| EP | 0 002 765 | 7/1979 |
| EP | 0 027 695 | 10/1980 |
| EP | 0 007 070 | 1/1983 |
| EP | 0161350 | 11/1985 |
| EP | 0174118 | 3/1986 |
| EP | 0 080 779 | 7/1986 |
| EP | 0096838 | 4/1987 |
| EP | 0285287 | 10/1988 |
| EP | 0331130 | 9/1989 |
| EP | 0285919 | 10/1994 |
| EP | 0987235 | 3/2000 |
| EP | 1074549 | 2/2001 |
| EP | 1411881 | 4/2004 |
| EP | 1838677 | 9/2009 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 62-267250 | 11/1987 |
| JP | 5-339263 | 12/1993 |
| JP | 6-298746 | 10/1994 |
| JP | 8-134048 | 5/1996 |
| JP | 9-30960 | 2/1997 |
| JP | 9-87258 | 3/1997 |
| JP | 2001-76413 | 3/2001 |
| JP | 2005-528330 | 9/2005 |
| JP | 2010-500393 | 1/2010 |
| JP | 2010/510241 | 4/2010 |
| KR | 10-2009-0007651 | 1/2009 |
| WO | WO 88/07526 | 10/1988 |
| WO | WO 88/07858 | 10/1988 |
| WO | WO 91/19698 | 12/1991 |
| WO | WO 93/00094 | 1/1993 |
| WO | WO 93/03015 | 2/1993 |
| WO | WO 93/16997 | 9/1993 |
| WO | WO 95/13274 | 5/1995 |
| WO | WO 96/04271 | 2/1996 |
| WO | WO 96/05194 | 2/1996 |
| WO | WO 96/33993 | 10/1996 |
| WO | WO 97/24364 | 7/1997 |
| WO | WO 98/06701 | 2/1998 |
| WO | WO 98/40385 | 9/1998 |
| WO | WO 99/24411 | 5/1999 |
| WO | WO 2002/40471 | 5/2002 |
| WO | WO 2002/48124 | 6/2002 |
| WO | WO 2002/074746 | 9/2002 |
| WO | WO 2003/000663 | 1/2003 |
| WO | WO 2003/027068 | 4/2003 |
| WO | WO 2003/057161 | 7/2003 |
| WO | WO 2003/062205 | 7/2003 |
| WO | WO 2003/062392 | 7/2003 |
| WO | WO 2003/086303 | 10/2003 |
| WO | WO 2003/086306 | 10/2003 |
| WO | WO 2003/086306 | 2/2004 |
| WO | WO 2004/037788 | 5/2004 |
| WO | WO 2005/003096 | 1/2005 |
| WO | WO 2005/016902 | 2/2005 |
| WO | WO 2005/019179 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO 2006/006933 | 1/2006 |

(56) References Cited

FOREIGN PATENT DOCUMENTS

| WO | WO 2006/013209 | 2/2006 |
|---|---|---|
| WO | WO 2006/043710 | 4/2006 |
| WO | WO 2006/069363 | 6/2006 |
| WO | WO 2006/071740 | 7/2006 |
| WO | WO 2007/120517 | 10/2007 |
| WO | WO 2007/120517 | 6/2008 |
| WO | WO 2008/070111 | 6/2008 |
| WO | WO 2008/070111 | 8/2008 |
| WO | WO 2008/153632 | 12/2008 |
| WO | WO 2008/156707 | 12/2008 |
| WO | WO 2009/080691 | 7/2009 |
| WO | WO 2009/097416 | 8/2009 |
| WO | WO 2009/111004 | 9/2009 |
| WO | WO 2010/038690 | 4/2010 |
| WO | WO 2010/148207 | 12/2010 |
| WO | WO 2012/030938 | 3/2012 |
| WO | WO 2012/030951 | 3/2012 |
| WO | WO 2012/030953 | 3/2012 |
| WO | WO 2012/030957 | 3/2012 |

OTHER PUBLICATIONS

U.S. Appl. No. 60/405,495, filed Aug. 23, 2002, Smith et al.
U.S. Appl. No. 60/434,607, filed Dec. 18, 2002, Smith et al.
U.S. Appl. No. 60/479,280, filed Jun. 17, 2003, Smith et al.
U.S. Appl. No. 60/512,967, filed Oct. 21, 2003, Burbaum et al.
U.S. Appl. No. 60/638,221, filed Dec. 21, 2004, Agarwal et al.
U.S. Appl. No. 60/789,191, filed Apr. 3, 2006, Lu et al.
U.S. Appl. No. 60/873,036, filed Dec. 5, 2006, Gharbaoui et al.
U.S. Appl. No. 61/068,102, filed Mar. 4, 2008, Carlos et al.
U.S. Appl. No. 61/268,930, filed Jun. 18, 2009, Demattei et al.
"Arena Pharmaceuticals Reports Successful Phase 1a Safety and Clinical Pharmacology Trial Results of Novel Anti-Obesity Compound," Press Release, Jul. 14, 2004, 2 pages.
"Arena Pharmaceuticals Announces Results of its Phase 1b Safety Study for its Novel Anti-Obesity Compound," Press Release, Nov. 30, 2004, 2 pages.
"Arena Pharmaceuticals Initiates Clinical Trial of Novel Anti-Obesity Drug," Press Release, Feb. 24, 2004, 1 page.
"Arena Pharmaceuticals Initiates Phase 1b Clinical Trial of Novel Anti-Obesity Drug," Press Release, Jul. 26, 2004, 1 page.
"Arena Pharmaceuticals Initiates Phase 2 Efficacy Study for its Novel Anti-Obesity Compound," Press Release, Dec. 22, 2004, 2 pages.
"Remington's Pharmaceutical Sciences" 17th ed., Mack Publishing Company, Easton Pa.: xv-xvi, 1409-1423 (1985).
"Silver Lining to the Cloud Over Anorexogen-Related Cardiac Valvulpathy?" Editorial, Annals of Internal Medicine, 134(4): 335-337 (2001).
"Technology of Controlled Release," Jun. 27, 2003, Popular edition, First print, issued by Kentaro Shima, CMC Publishing Co., Ltd., p. 11 to p. 14, middle paragraph (English Translation).
'ClinicalTrials.gov' [Online]. "BLOOM: Behavioral Modification and Lorcaserin for Overweight and Obesity Management," Oct. 2006, [retrieved on Aug. 29, 2016]. Retrieved from Internet: URL<https://clinicaltrials.gov/ct2/show/study/NCT00395135>, 3 pages.
'ClinicalTrials.gov' [Online]. "Pharmacokinet Properties of Lorcaserin in Subjects With Renal Impairment," Jan. 2009, [retrieved on Aug. 29, 2016]. Retrieved from Internet: URL<https://clinicaltrials.gov/ct2/show/study/NCT00828438>, 3 pages.
Abdelghany and Pauli, "Lorcaserin: A novel, selective 5-HT2C-receptor agonist for the treatment of obesity,", Formulary Journal (Jun. 1, 2010).
Arena Pharmaceuticals Initiates Lorcaserin Phase 3 Obesity Clinical Trial, Press Release, 2006, available at http://invest.arenapharm.com/releasedetail.cfm?ReleaseiD=320295.
Bagnol et al., "Obesity and Hypothalamic Signaling: Role of GPCRs," Presentation, Arena Pharmaceuticals, Inc., Jul. 30, 2010, 30 pages.
Bai et al., "The Use of Lorcaserin in the Management of Obesity: A Critical Appraisal," Drug Design, Development & Therapy, 2011, 1-7.
Baindur et al., "(±)-3-Allyl-7-halo-8-hydroxy-1-phenyl-2,3,4,5-tetrahydro-1H-3-benzazepines as Selective High Affinity D1 Dopamine Receptor Antagonists: Synthesis and Structure—Activity Relationship," J. Med. Chem., 35:67-72 (1992).
Barnes, "Pharmacological Strategies for Relapse Prevention in Schizophrenia," Psychiatry 3(10): 37-40 (2004).
Barnett, "Review on Dopamine Receptors," Drugs of the Future, 1986, 11(1): 49-56.
Bays, "Lorcaserin and Adiposopathy: 5-HT 2c Agonism as a Treatment for 'Sick Fat' and Metabolic Disease," Expert Rev. Cardiovasc. Ther., Nov. 2009, 7: 1429-1445.
Berge et al., "Pharmaceutical Salts," Journal of Pharmaceutical Sciences, 66(1): 1-19 (1977).
Bickerdike, "5-HT2C Receptor Agonists as Potential Drugs for the Treatment of Obesity," Current Topics in Medicinal Chemistry, 3: 885-897 (2003).
Biel, "Bronchodilators, N-substituted Derivatives of 1-(3',4'-Dihdroxyphenyl)-2-aminoethanol(Arterenol)," J. Am. Chem. Soc. 76: 3149-3153 (1954).
Binetti et al., "Behavior Disorders in Alzheimer Disease: A Transcultural Perspective," Arch Neurol., 55: 539-544 (1998).
Bos et al., "Novel Agonists of 5HT2C receptors. Synthesis & biological evaluation of Substituted 2-{Indol-1-yl}-1-methylethylamines and 2-(Indeno[1,2-b]pyrrol-1-yl)-1-methylethylamines," Improved Therapeutics for Obsessive Compulsive Disorder, J. Med. Chem., 40(17): 2762-2769 (1997).
Bosch et al., "Studies on the Synthesis of Pentacyclic Strychnos Indole Alkaloids. Photocyclization of N-Chloroacetyl-1,2,3,4,5,6-hexahydro-1,5-methanoazocino [4,3-b] Indole Derivatives," Tetrahedron, 41(12): 2557-66 (1985).
Bremner, "Seven Membered Rings," Institute for Biomolecular Science, Dept. of Chemistry, University of Wollongong; "Progress in Heterocyclic Chemistry 13," Pergamon Press, Ch. 7: 340-77 (2001).
Brittain, Polymorphism in Pharmaceutical Solids, "Generation of Polymorphs, Hydrates, Solvates, and Amorphous Solids," 1999, Chapter 5, 183-219.
Brooks et al., "Obstructive Sleep Apnea in Obese Noninsulin-Dependent Diabetic Patients: Effect of Continuous Positive Airway Pressure Treatment on Insulin Responsiveness," Journal of Clinical Endocrinology and Metabolism, 1994, 79: 1681-1685.
Byrn et al., "Pharmaceutical Solids: A strategic approach to regulatory consideration," Pharmaceutical Research, 12(7): 945-954 (1995).
Caira, "Crystalline polymorphism of organic compounds," Topics in Current Chemistry, 198(2): 163-208 (1998).
Callahan et al., Fluoxetine Increases the Anorectic and Long-Term Dopamine-Depleting Effects of Phentermine, Synapse, 38(4): 471-6 (2000).
Carey and Sunderg, "Advanced Organic Chemistry, Part B: Reactions and Synthesis, second edition," 1983, Plenum Press, New York, pp. 96-98.
CAS Registry No. 006640-24-01 (2007).
CAS Registry No. 149454-12-6 (1993).
CAS Registry No. 27487-50-9 (1984).
CAS Registry No. 27487-51-0 (1984).
CAS Registry No. 400878-20-8 (2002).
CAS Registry No. 46906-45-0 (1984).
CAS Registry No. 620948-34-7 and 620948-93-8 (2007).
Casy et al., "Some Arylalkylamino Analogs of Acyclic Analgetics," J. Med. Chem., 11(3): 599-601 (1968).
Chahal et al., Iddb Meeting Report 2000, May 17-18.
Chang et al., "Dopamine Receptor Binding Properties of Some 2,3,4,5-tetrahydro-1H-3-benzazepine-7-ols with Non-Aromatic Substituents in the 5-Position," Bioorganic & Medicinal Chemistry Letters, 2(5): 399-402 (1992).
Chemical abstract (online) Accession No. 1980: 407990.

(56) References Cited

OTHER PUBLICATIONS

Chen et al., "Metabolism and Disposition of Lorcaserin, a Novel Selective Serotonin 5-HT2C Receptor Agonist, in Rats, Mice, Monkeys and Humans, Drug Metabolism Rev.," 40: p. 131 (2008) ("Chen").

Cheng, "Fen/Phen and Valvular Heart Disease: The Final Link Has Now Been Established," Circulation 2000; 102; e180.

Chumpradit et al., "(±-7-Chloro-8-hydroxyl-1-(4'-[125I]iodophenyl)-3-methyl-2,3,4,5-tetraydro-1H-3-benzazepine: A Potential CNS D-1 Dopamine Receptor Imaging Agent," J. Med. Chem., 32: 1431-35 (1989).

Clark et al., "1,9-Alkano-bridged 2,3,4,5-tetrahydro-1H-3-benzazepines with Affinity for the α2-Adrenoceptor and the 5-HT1A Receptor," J. Med. Chem., 33: 633-41 (1990).

Clinical Trial NCT00768612. "Study Evaluating Safety and Tolerability of Vabicaserin in Patients with Sudden Worsening of Schizophrenia Study," (2008).

Cole et al., "Establishing a standard definition for child overweight and obesity worldwide: international survey," BMJ, May 2000, 1-6.

Connolly et al., "Selections from Current Literature: Pharmacological Treatment of Obesity," Family Practice, 15(1): 88-93 (1998).

Deady et al., "Synthesis of Some Tetrahydro-2- and 3-benzazepines, and of Hexahydro-3-benzazocine," JCS Perkin I, 782-3 (1973).

Demarinis et al., "Development of an Affinity Ligand for Purification of α2-Adrenoceptors from Human Platelet Membranes," J. Med. Chem., 27: 918-921 (1984).

Detailed Factual and Legal Basis for Paragraph IV Certification Regarding U.S. Pat. No. 6,953,787; U.S. Pat. No. 7,514,422; U.S. Pat. No. 7,977,329; U.S. Pat. No. 8,168,624; U.S. Pat. No. 8,207,158; U.S. Pat. No. 8,273,734; U.S. Pat. No. 8,367,657; U.S. Pat. No. 8,546,379; U.S. Pat. No. 8,575,149; U.S. Pat. No. 8,697,686; U.S. Pat. No. 8,946,207; U.S. Pat. No. 8,980,881; U.S. Pat. No. 8,999,970; and U.S. Pat. No. 9,169,213, Included in Generic Pharmaceutical Company's Notice Letter dated Feb. 21, 2017, 103 pages [redacted].

Detailed Factual and Legal Basis for Paragraph IV Certification Regarding U.S. Pat. No. 8,168,624; U.S. Pat. No. 8,697,686; U.S. Pat. No. 8,980,881; U.S. Pat. No. 8,999,970; and U.S. Pat. No. 9,169,213, Included in Generic Pharmaceutical Company's Notice Letter dated Sep. 1, 2016, 90 pages [redacted].

Detailed Factual and Legal Basis for Paragraph IV Certification Regarding U.S. Pat. No. 8,168,624; U.S. Pat. No. 8,697,686; U.S. Pat. No. 9,980,881; U.S. Pat. No. 8,999,970; and U.S. Pat. No. 9,169,213, Included in Generic Pharmaceutical Company's Notice Letter dated Sep. 7, 2016, 87 pages [redacted].

Detailed Factual and Legal Basis for Paragraph IV Certification Regarding U.S. Pat. No. 8,168,624; U.S. Pat. No. 8,999,970; and U.S. Pat. No. 9,169,213, Included in Generic Pharmaceutical Company's Notice Letter dated Aug. 24, 2016, 65 pages [redacted].

Detailed Factual and Legal Basis for Paragraph IV Certification regarding U.S. Pat. No. 6,953,787; U.S. Pat. No. 7,514,422; U.S. Pat. No. 7,977,329; U.S. Pat. No. 8,207,158; U.S. Pat. No. 8,273,734; U.S. Pat. No. 8,367,657; U.S. Pat. No. 8,946,207; U.S. Pat. No. 8,546,379; U.S. Pat. No. 8,575,149; U.S. Pat. No. 8,168,624; U.S. Pat. No. 8,697,686; U.S. Pat. No. 8,980,881; U.S. Pat. No. 8,999,970; and U.S. Pat. No. 9,169,213, Included in Generic Pharmaceutical Company's Notice Letter dated Aug. 19, 2016, 233 pages [redacted].

Deurenberg et al., "Body mass index and percent body fat: a meta-analysis among different ethnic groups," International Journal of Obesity, 1998, 22: 1164-1171.

Dhonnchadha et al., "Anxiolytic-Like Effects of 5-HT2 Ligands on Three Mouse Models of Anxiety," Behav. Brain Res. 140: 203-214 (2003).

Dhurandhar et al., "Initial weight loss as a predictor of response to obesity drugs," International Journal of Obesity, 1999, 23: 1333-1336.

Di Chiara et al., "Nucleus Accumbens Shell and Core Dopamine: Differential Role in Behavior and Addiction," Behavioural Brain Research, 137: 75-114 (2003).

Di Chiara et al., "Reward System and Addiction: What Dopamine Does and Doesn't Do," Current Opinion in Pharmacology, 7: 69-76 (2007).

Di Giovanni et al., "Serotonin/Dopamine Interaction—Focus on 5-HT2C Receptor, A New Target of Pyschotropic Drugs," Indian Journal of Experimental Biology, 40:1344-1352 (2002).

Di Matteo et al., "Role of 5-HT2C Receptors in the Control of Central Dopamine Function," Trends in Pharmacological Sciences, 22(5): 229-232 (2001).

Diagnostic and Statistical Manual of Mental Disorders, 4th Edition, Text Revision, Washington, DC, American Psychiatric Association, 2000.

Dixit et al., "Agents acting on Central Nervous System: Part XXIII-2-Substituted 1,2,3,4,6,7,12,12a-Octahydropyrazino[2,1-b][3] benzazepines & 3-Substituted 1,2,3,4, 4a, 5,6, 11-Octahydropyrazino[I,2-b][2] benzazepines," CDRI Communication No. 1969, 893-97 (1974).

Draper et al., "Novel Stereoselective Syntheses of the Fused Benzazepine Dopamine D1 Antagonist (6aS, 13bR)-11-chloro-6, 6a,7,8,9, 13b-hexahydro-7-methyl-5H-benzo[d]naphth[2, 1-b]azepin-12-ol (Sch 39166): 1. Aziridinium Salt Based Syntheses," Organic Process Research & Development, 2(3): 175-85 (1998).

Faull et al., "Prescribing in renal disease," Australian Prescriber, Feb. 2007, 30(1): 17-20.

FDA "Guidance for Industry: Pharmacokinetics in Patients with Impaired Renal Function-Study Design, Data Analysis, and Impact on Dosing and Labeling," May 1998, 19 pages.

FDA "Guidance for Industry," May 1992, 4 pages.

FDA, "Guidance for Industry: Pharmacokinetics in Patients with Impaired Renal Function-Study Design, Data Analysis, and Impact on Dosing and Labeling," Draft Guidance, Mar. 2010, 21 pages.

Fidler et al., "A One-Year Randomized Trial of Lorcaserin for Weight Loss in Obese and Overweight Adults: The BLOSSOM Trial", Journal of Clinical Endocrinology & Metabolism, vol. 96, No. 10, Oct. 1, 2011, 3067-3077.

Flannery-Schroeder, "Reducing Anxiety to Prevent Depression," Am. J. Prey. Med. 31 (6S1): S136-S142 (2006).

Frankel et al., "Brain Serotonin Transporterdistribution in Subjects with Impulsive Aggressivity: A Positron Emission Study With [11C]McN 5652," Am. J. Psychiatry, 162: 915-923 (2005).

Fuchs et al., "Total Syntheses of (+/−)-Lennoxamine and (+/−)-Aphanorphine by Intramolecular Electrophilic Aromatic Substitution Reactions of 2-Amidoacroleins," Organic Letters, 3(24): 3923-3925 (2001).

Gallant et al., "U-22, 394A: A Controlled Evaluation in Chronic Schizophrenic Patients," Current Therapy Research, 9(11): 579-81 (1967).

Gardent et al., "Sur Quelques Proprites De L'amino-2-Bromo-4 1H Benzazepine-3 Et De Ses Derives," Bulletin de la Societe Chimique de France, 2:600-5 (1968).

Garrison, "Definine Obesity: An Adventure in Cardiovascular Disease Epidemiology," J. Nutritional Biochem., 9(9): 493-500 (1998).

Gault et al., "Predicting Glomerular Function from Adjusted Serum Creatinine," Nephron, 1992, 62: 249-256.

Gerace et al., "Predictors of Weight Increases over 7 years in Fire Fighters and Paramedics," Preventive Medicine 25: 593-600 (1996).

Gobert et al., "Serotonin$_{2C}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).

Gombar et al., "Pharmacokinetics of a Series of 6-Chloro-2, 3, 4, 5-Tetrahydro-3-Subtitued-1H-3-Benzazepines in Rats," Drug Metab. Disposition, 16: 367-372 (1988).

Gould, "Salt selection for basic drugs," International Journal of Pharmaceutics, 1986, 33: 201-217.

Griesser, "Polymorphism in the Pharmaceutical Industry," ed. Rolf Hilfier, Wilkey-VCH Verlag GmbH & Co.: pp. 211-233 (2006).

Guillory, "Polymorphism in Pharmaceutical Solids," ed. Harry G. Brittain, Marcel Dekker, Inc., vol. 95: pp. 202-209 (1999).

Halford et al., "o-Phenylenediacetimide and Other Compounds Related to 3,1H-benzazepine," J. Org. Chem., 17: 1646-52 (1952).

Halford et al., "Serotonergic Drugs: Effects on Appetite Expression and Use for the Treatment of Obesity," Drugs 67(1): 27-55 (2007).

(56) References Cited

OTHER PUBLICATIONS

Halford, "Obesity Drugs in Clinical Development," Current Opinion in Investigational Drugs, 7(4): 312-318 (2006).
Hasan et al., "Syntheses of N-Chloroacyl-β-phenylethylamine Derivatives," Indian J. Chem., 9: 1022-4 (1971).
Hashima et al., "Syntheses and Biological Activities of the Marine Bryozoan Alkaloids Convolutamines A, C and F and Lutamides A and C," Bioorg & Med. Chem., 8: 1757 (2000).
Haynes et al., "Occurrence of Pharmaceutically Acceptable Anions and Cations in the Cambridge Structural Database," J. Pharm. Sci. 94(10): 2111-2120 (2005).
Heisler et al., "Activation of Central Melanocortin Pathways by Fenfluramine," Science, 297: 609-611 (2002).
Hester et al., "Azepinoindoles. I. Hexahydroazepino[4,5-b]indoles," J. Med. Chem., 11(1): 101-106 (1968).
Heys et al., "A New Entry into C7-Oxygenated Tetrahydro-1H-3-benzazepines: Efficient Labeling with Carbon-14 in the Benzo Ring," J. Org. Chem., 54(19): 4702-6 (1989).
Higgins et al., "Serotonin and Drug Reward: Focus on 5-HT2C Receptors," European Journal of Pharmacology, 480: 151-162 (2003).
Hill and Peters, "Environmental Contributions to the Obesity Epidemic," Science, May 29, 1998, 280: 1371-1374.
Hitzig, "Combined Serotonin and Dopamine Indirect Agonists Correct Alcohol Craving and Alcohol-Associated Neuroses," Journal of Substance Abuse Treatment, 11(5): 489-90 (1994).
Ichii, "Friedel-Crafts Aralkylation. II. The AICI3 CH2NO2-Catalyzed Phenethylation of Benzene and Toluene With 2-Arylethyl Chlorides in a Nitromethane Solution," Bulletin of the Chemical Society of Japan, 45(9): 2810-2813 (1972).
Im et al., "Positive Allosteric Modulator of the Human 5-HT2C Receptor," Molecular Pharmacology, 64: 78-84 (2003).
Isaac, "The 5-HT2C Receptor as a Potential Therapeutic Target for the Design of Antiobesity and Antiepileptic Drugs," Drugs of the Future, 26(4): 383-393 (2001).
Jandacek, "APD-356 (Arena)," Current Opinion in Investigational Drugs, 6(10): 1051-1056 (2005).
Jenck et al., "Antiaversive Effects of 5HT2C Receptor Agonists and Fluoxetine in a Model of Panic-Like Anxiety in Rats," European Neuropsychopharmacology, 8: 161 (1998).
Jensen et al., "Potential Role of New Therapies in Modifying Cardiovascular Risk in Overweight Patients with Metabolic Risk Factors," Obesity 14 (Suppl. 3): 143S-149S (2006).
Kaiser et al., "6-(Phenylthio)-substitued 2, 3, 4, 5-tetrahydro-1H-3-benzazepines, A Novel Class of Dopamine Receptor Antagonists and Neuroleptics," J. Med. Chem., 23(9): 975-6 (1980).
Karasu et al., Practice Guidelines for the Treatment of Patients with Major Depressive Disorder (2000).
Klein, "Outcome Success in Obesity," Obesity Res., 9(suppl. 4): 354S-358S (2001).
Klohr et al., "An Intramolecular Photocyclization to Form the Azepine[3,4,5-cd]Indole System," Synthetic Communications 18(7): 671-4 (1988).
Koplan et al., "Preventing Childhood Obesity: Health in the Balance, Executive Summary," The National Academies Press, Washington, D.C., 436 pages (excerpt includes pp. 1-19, v-xix) (2005).
Krull et al., "Synthesis and Structure/NMDA Receptor Affinity Relationships of 1-Substituted Tetrahydro-3-Benzazepines," Bioorganic & Medicinal Chem. 12(6): 1439-1451 (2004).
Kuenburg et al., "Development of a Pilot Scale Process for the Anti-Alzheimer Drug (--)-Galanthamine Using Large-Scale Phenolic Oxidative Coupling and Crystallisation-Induced Chiral Conversion," Organic Process Research & Development, 3(6): 425-31 (1999).
Lacivita et al., "Selective Agents for Serotonin2C (5-HTC2C) Receptor," Current Topics in Medicinal Chemistry, 6: 1927-1970 (2006).
Ladd et al., "Synthesis of a Dopaminergic Binding of 2-Aryldopamine Analogues: Phenethylamines, 3-Benzazepines, and 9-(Aminomethyl) Fluorenes," J. Med. Chem., 29(10): 1904-12 (1986).
Lam et al., Canadian Consensus Guidelines for the Treatment of Seasonal Affective Disorder, Clinical & Academic Publishing, Vancouver, BC, Canada (1999).
Lanteri et al., "Drugs of abuse specifically sensitive noradrenergic and serotonergic neurons via a non-dopaminergic mechanism," Neuropsychopharmacology 33(7): 1724-1734 (2008).
Lennon et al., "Azabenzocycloheptenones. Part XVIII. Amines and Amino-ketones of the Tetrahydro-3-benzazepin-1-one Series," J.C.S. Perkin I, 7: 622-6 (1975).
Lin et al., "Benzindene Prostaglandins. Synthesis of Optically Pure 15-Deoxy-U-68,215 and its Enantiomer via a Modified Intramolecular Wadsworth-Emmons-Wittig Reaction," J. Org. Chem., 52(25): 5594-601 (1987).
Loke et al., "Appetite Suppressants and Valvular Heart Disease—A Systematic Review," BMC Clinical Pharmacology, 2(6): 1-10 (2002).
Macdonald et al., "Design and Synthesis of trans-3-(2-(4-((3-(3-(5-methyl-1,2,4-oxadizaolyl))-phenyl)carboxamido)cyclohexyl)ethyl)-7-methylsulfonyl-2,3,4,5-tetrahydro-1H-3-benzazepines (SB-414796): A Potent and Selective Dopamine D3 Receptor Antagonist," J. Med. Chem., 46(23): 4952-64 (2003).
March, "Advanced Organic Chemistry, Reactions, Mechanisms and Structure; Third Edition," 1985, John Wiley & Sons (Wiley-Interscience Publication), New-York, pp. 382-384.
Martin et al., "5HT2C Receptor Agonists Pharmacological Characteristics and Therapeutic Potential," J. Pharmacol. Exp. Therap., 286(2): 913-924 (1998).
Millan et al., "5HT2C Receptors Mediate Penile Erections in Rats: Actions of Novel and Selective Agonists and Antagonists," Eur. J. Pharmacol., 325: 9-12 (1997).
Millan et al., "Serotonin {5-HT}2C receptors tonically inhibit dopamine (DA) and noradrenaline (NA), but not 5-HT, release in the frontal cortex in vivo," Neuropharmalogy, 37(7): 953-955 (1988).
Moline et al., "Postpartum Depression: A Guide for Patients and Families," Expert Consensus Guidelines Series—Treatment of Depression in Woman, 112-113 (2001).
Moreisette et al., "High-throughput cyrstallization: polymophs, salts, co-crystals and solcates of pharmaceutical solids," Advanced Drug Delivery Reviews, 56(3): 275-300 (2004).
Morris et al., "Theoretical approaches to physical transformations of active pharmaceutical ingredients during manufacturing processes," Advanced Drug Delivery Reviews, 2001, 48: 91-114.
Muller et al., "Intracellular 5-HT2C-Receptor Dephosphorylation: A New Target for Treating Drug Addiction," Trends in Pharmacological Sciences, 27(9): 455-58 (2006).
Nagase et al., "An Anhydrous Polymorphic Form of Trehalose," Carbohydrate Research 337(2): 167-173 (2002).
Nagle et al., "Efficient Synthesis of β-amino Bromides," Tetrahedron Letters, 41: 3011-4 (2000).
Nair et al., "Preparation of 2,3,4,5-Tetrahydro-3,1H-benzazepine-2-one," Indian J. Chem., 5: 169-70 (1967).
National Institute on Drug Abuse, Proc. 41st Ann. Scientific Mtg. 356-401 (1979).
National Institutes of Health et al., "Clinical guidelines on the identification, evaluation, and treatment of overweight and obesity in adults: the evidence report," Obesity Research 6 (Suppl. 2): p. SIS (1998).
Navarro-Vazquez et al., "A Study of Aryl Radical Cyclization in Enaminone Esters," J. Org. Chem., 67: 3213-20 (2002).
Neumeyer et al., "Development of a High Affinity and Stereoselective Photoaffinity Label for the D-1 Dopamine Receptor: Synthesis and Resolution of 7[125I]Iodo-8-hydroxy-3-methyl-1-(4'-azidophenyl)-2,3,4,5-tetrahydro-1H-3-benzazepine," J. Med. Chem., 33(2): 521-6 (1990).
Niendam et al., "Neurocognitive Performance and Functional Disability in the Psychosis Prodrome," Schizophrenia Research, 84: 100-111 (2006).
Ohnmacht et al., "Naphtho[2,1-b][1,5]-and [1,2-f][1,4]oxazocines as Selective NK1 Antagonists," Bioorganic & Medicinal Chem., 12(10): 2653-2666 (2004).
Okuno et al., "Photocyclization of N-chloroacetyl-2,5-dimethoxyphenethylamine. Synthesis of Pyrroloindoles," Chem. Pharm. Bull., 23(11): 2584-90 (1975).

(56) References Cited

OTHER PUBLICATIONS

O'Neil et al., "Early Weight Loss with Naltrexone SR/Bupropion SR Combination Therapy for Obesity Predicts Long-term Weight Loss," Obesity, Nov. 2009, 17(2): S109-S110.
Orito et al., "Benzolactams-1: Alkylation of 1,2,4,5-Tetrahydro-3-Methyl-3H-3-Benzazepin-2-One With Sodium Hydride and Alkyl Halide," Tetradedron 36: 1017-1021 (1980).
Orito et al., "Synthetic Studies of Heterocyclic Compounds I. Alkylation and Acylation of 1,2,4,5-Tetrahydro-3-Methyl-3H-3-Benzazepin-2-one," CASREACT, 93: 7990 (1979).
Orito et al., "Total Synthesis of Pseudo Type of Protopine Alkaloids," Heterocycles, 14(1): 11-14 (1980).
Paulekuhn et al., "Trends in Active Pharmaceutical Ingredient Salt Selection Based on Analysis of the Orange Book Database," J. Med. Chem., 50(26): 6665-6672 (2007).
Pauvert et al., "Silver Nitrate-Promoted Ring Enlargement of 1-tribromomethyl-1,2-dihydro- and 1-tribromethyl-1,2,3,4-tetrahydro-isoquinoline Derivatives: Application to the Synthesis of the Antianginal Zatebradine," Tetrahedron Letters, 44: 4203-6 (2003).
Pawan et al., "Preliminary Study on the Effects of Fenfluramine Derivative, 'S992' in Man," British Journal of Pharmacolgoy, 41(2): 416P-417P (1971).
Pecherer et al., "A Novel Synthesis of Aromatic Methoxy and Mehtylenedioxy Substitued 2,3,4,5-tetrahedro-1H-3-benzazepines," J. Het. Chem., 9: 609-16 (1972).
Pecherer et al., "The Synthesis of Some 7- and 7,8-Substituted 2,3,4,5-tetrahydro-1H-3-benzazepines," J. Het. Chem., 8(5): 779-783 (1971).
Perrone et al., "Serum Creatinine as an Index of Renal Function: New Insights into Old Concepts," Clinical Chemistry, 1992, 38(10): 1933-1953.
Perry et al., "Prospective Study of Risk Factors for Development on Non-Insulin Dependent Diabetes in Middle Aged British Men," BMJ, 310: 560-564 (1995).
Pfeiffer et al., "Dopaminergic Activity of Substituted 6-Chloro-1-phenyl-2,3,4,5-tetrahydro-1H-3-benzazepines," J. Med. Chem., 25(4): 352-8 (1982).
Piesla et al., "Atypical Antipsychotic-Like Effects of 5-HT2C Agonists," Schizophrenia Research 49: 95 (2001).
Pi-Sunyer et al., ""Clinical guidelines on the identification, evaluation, and treatment of overweight and obesity in adults: the evidence report,"" NIH, Sep. 1998, 6 (Suppl. 2): p. SIS.
Porras et al., "5-HT2A and 5-HT2C/2B Receptor Subtypes Modulate Dopamine Release Induced in Vivo by Amphetamine and Morphine in Both the Rat Nucleus Accumbens and Striatum," Neuropsychopharmacology, 26: 311-324 (2002).
Remington's Pharmaceutical Sciences, 20th ed., Lippincott Williams & Wilkins, Philadelphia, PA, 2000, 710-712.
Rigalleau et al., "Estimation of Glomerular Filtration Rate in Diabetic Subjects," Diabetes Care, Apr. 2005, 28(4): 838-843.
Rosenzweig-Lipson et al., "Vabicaserin: Effects of a Novel 5HT2C Agonist on Medial Prefrontal Cortex Neurotransmission, Cognition and Sensorimotor Gating," 29th ECNP Congress, Vienna, Austria (2007).
Roth et al., "Anorectic Efficacy of the Fenfluramine/Phentermine Combination in Rats: Additivity or Synergy?" Eur. J. Pharmacol., 373 (2-3): 127-34 (1999).
Rothman et al., "Evidence of Possible Involvement of 5-HT2B Receptors in the Cardiac Valvulopathy Associated with Fenfluramine and Other Serotonergic Medications," Circulation, 2836-41 (2000).
Rothman, "Treatment of Alcohol and Cocaine Addiction by the Combination of Pemoline and Fenfluramine: A Preliminary Case Series," Journal of Substance Abuse Treatment, 12(6): 449-53 (1995).
Rowland et al., "Anorectic Effect of Dehydroepiandrosterone Combined with Dexfenfluramine or Thionisoxetine," Eur. J. Pharmacol., 419(1): 61-4 (2001).
Rowland et al., "Comparison of Either Norepinephrine-uptake Inhibitors or Phentermine Combined with Serotonergic Agents on Food Intake Rats," Psychopharmacology (Berl), 149(1): 77-83 (2000).
Rowland et al., "Effects of the Cannabinoid Receptor Antagonist SR 141716, Alone and in Combination with Dexfenfluramine or Naloxone, on Food Intake in Rats," Psychopharmacology (Berl), 159(1): 111-6 (2001).
Rowland et al., Acute Anorectic Effect of Single and Combined Drugs in Mice Using a Non-deprivation Protocol, Psychopharmacology (Berl), 157(2): 193-6 (2001).
Schaffner et al., "Preventing Severe Mental Illnesses—New Prospects and Ethical Challenges," Schizophrenia Research, 51: 3-15 (2001).
Schlademan et al., "Synthesis of Oxo- and 1-Hydroxy-azobenzocycloalkanes," J. Chem. Soc. Perkin Trans., 2: 213-215 (1972).
Serajuddin et al., "Salt formation to improve drug solubility," Advanced Drug Delivery Reviews, 59(7): 603-616 (2007).
Silverstone, "Appetite Suppressants: a Review," Drugs, 43: 6, (1992). Abstract.
Smith et al., "Multicenter, Placebo-Controlled Trial of Lorcaserin for Weight Management.", New England Journal of Medicine, Jul. 2010, 3(36): 245-246.
Smith et al., "Lorcaserin (ADP356), A Selective 5-HT2C Agonist, Reduces Body Weight in Obese Men and Women," Obesity, 2008, 494-503.
Smith et al., "Discovery and SAR of New Benzazepines as Potent and Selective 5HT2c Receptor Agonists for the Treatment of Obesity," Bioorganic & Medicinal Chemisty Letters, 15(5): 1467-1470 (2005).
Smith et al., "Discovery and Structure—Activity Relationship of (1R)-8-Chloro-2,3,4,5-tetrahydro-1-methyl-1H-3-bezazepine (Lorcaserin), a Selective Serotonin 5-HT2c Receptor Agonist for the Treatment of Obesity," J. Med. Chem. 51: 305-313 (2008).
Smith, "5-HT2C Receptor Agonists for the Treatment of Obesity," Presentation, Arena Pharmaceuticals, Inc., Jul. 28, 2010, 30 pages.
Smith, "Discovery of Lorcaserin (APD356): A Selective 5HT2C Agonist for the Treatment of Obesity," Presentation, Arena Pharmaceuticals, Inc., (2006).
Sussman et al., "Effects of Nefazodone on Body Weight: A Pooled Analysis of Selective Serotonin Reuptake Inhibitor- and Imipramine-Controlled Trails," J. Clin. Psychiatry, 62: 256-60 (2001).
Tecott et al., "Eating Disorder and Epilepsy in Mice Lacking 5-HT2C Serotonin Receptors," Nature, 374: 542-546 (1996).
Tietze et al., "Efficient Synthesis of 2, 3, 4, 5-Tetrahydro-1H-3-Benzazepines by Intramolecular Heck Reaction," Synthesis, 876-880 (1993).
Tohda et al., "Molecular Pathopharmacology of 5-HT2C Receptors and the RNA Editing in the Brain," J. Pharma. Science, 100: 427-432 (2006).
Tsuang et al., "Towards the Prevention of Schizophrenia," Biol. Psychiatry, 48: 349-356 (2000).
Van Oekelen et al., "5-HT2A and 5-HT2C Receptors and Their Atypical Regulation Properties," Life Sciences, 72: 2429-2449 (2003).
Vanderlaan et al., "Synthesis and Oxidative Coupling of (±)-3-Sxoreticuline," J. Org. Chem., 50(6): 743-7 (1985).
Veyrat-Follet et al., "The pharmacokinetics of idraparinux, a long-acting indirect factor Xa inhibitor: population pharmacokinetic analysis from Phase III clinical trials," Journal of Thrombosis and Haemostasis, 2009, 7: 559-565.
Vink et al., "Risk Factors for Anxiety and Depression in the Elderly: A Review," J. Affect. Disord., 106: 29-44 (2008).
Wang et al. "Lorcaserin hydrochloride." Drugs of the Future vol. 32:9 (Jan. 1, 2007) p. 766.
Webb, "APD356, A Potential New Treatment for Obesity," Presentation, Arena Pharmaceuticals, Inc., Aug. 11, 2005, 43 pages.
Weinstock et al., "Separation of Potent Central and Renal Dopamine Agonist Activity in Substituted 6-Chloro-2,3,4,5-tetrahydro-7,8-dihydroxy-1-phenyl-1H-3-benzazepines," J. Med. Chem., 23(9): 973-5 (1980).

(56) References Cited

OTHER PUBLICATIONS

Wellman et al., "Synergistic Interactions Between Fenfluramine and Phentermine," Int. J. Obes., 23(7): 723-32 (1999).
Wilk, "Exchange Type Reactions Between Oxiranes or Thiiranes and 2-Hydroxyalkyl or 2-Thioalkyl Amines and Sulfides," Pol. J. Chem., 62: 895 (1988).
Williams, Chemistry Demystified, pp. 123, 126 (2003).
Winkler, "Obesity and Hemostasis," Archives of Gynecology & Obst. 261(1): 25-29 (1997).
Wise, "Addiction Becomes a Brain Disease," Neuron, 26: 27-33 (2000).
Wisner et al., "Postpartum Depression," N. Engl. J. Med., 347(3): 194-199 (2002).
Woods et al., "Annual Report: Evaluation of New Compounds for Opoid Activity," National Institute on Drug Abuse, Proceedings of the 41st Annual Scientific Meeting pp. 356-401 (1979).
Wu et al., "Amino Diol Based Asymmetric Syntheses of a Fused Benzazepine as a Selective D1 Dopamine Receptor," Organic Process Research & Development, 1(5): 359-64 (1997).
Yasuda et al., "A Novel and Stereoselective Synthesis of (±)-Cephalotaxine and its Analogue," Tetrahedron Letters, 27(18): 2023-6 (1986).
Yonemitsu et al., "Photocyclization of Pharmacodynamic Amines. IV. Novel Heterocycles from N-chloroacetyl-3,4-dimethoxyphenethylamine," J. Am. Chem. Soc., 92(19): 5686-90 (1970).
Yonemitsu et al., "Photocyclization of Pharmodynamic Amines. II. X-Ray Analysis of a Noncentrosymmetric Tetracyclic Indole," J. Am. Chem. Soc., 90(23): 6522-3 (1968).
Yonemitsu et al., "Photocyclizations of Tyrosines, Tyramines, Catecholamines, and Normescaline," J. Am. Chem. Soc., 90(3): 776-84 (1968).
Yonemitsu et al., "Photolysis of N-Chloracetyl-O-methyl-L-tyrosine to an Azaazulene," J. Am. Chem. Soc., 89(4): 1039-40 (1967).
Yoshinaga et al., "Prevention of Mildly Overweight children from Development of More Overweight Condition," Prevention Medicine, 38: 172-174 (2004).
Zhang et al., (Convolutamines A-E, Novel β-Phenylehtylamine Alkaloids from Marine Bryozoan Amathia convolute, Chem. Lett., 12: 2271-2274 (1994).
Canadian Office Action in Canadian Application No. 2,808,912, dated Jun. 30, 2017, 3 pages.
Canadian Office Action in Canadian Application No. 2,808,912, dated Apr. 4, 2018, 5 pages.
Indian Office Action in Indian Application No. 2550/DELNP/2013, dated Dec. 28, 2017, 7 pages (English Translation).
International Search Report and Written Opinion in International Application No. PCT/US2011/049914, dated Aug. 8, 2012, 17 pages.
International Preliminary Report on Patentability in International Application No. PCT/US2011/049914, dated Mar. 4, 2013, 12 pages.
Japanese Office Action in Japanese Application No. 2013-527255, dated May 19, 2017, 73 pages (English Translation).
Korean Office Action in Korean Application No. 10-2013-7008319, dated Aug. 29, 2017, 10 pages (English Translation).
Extended European Search Report in European Appln. No. 18200702.1, dated Apr. 17, 2019, 11 pages.

Figure 3.3

Day 26 Efficacy of Compound 1 after PO dosed at 24 mg/kg/day or Osmotic Pump Infusion at 15.1 mg/kg/day (Infusion Rate, 0.63 mg/kg/hr) in Fed Male SD Rats.

Figure 52. Mean $C_{max}$ of Compound 1 after PO dosed at 24 mg/kg/day or Osmotic Pump Infusion at 15.1 mg/kg/day (Infusion Rate, 0.63 mg/kg/hr) in Fed Male SD Rats.

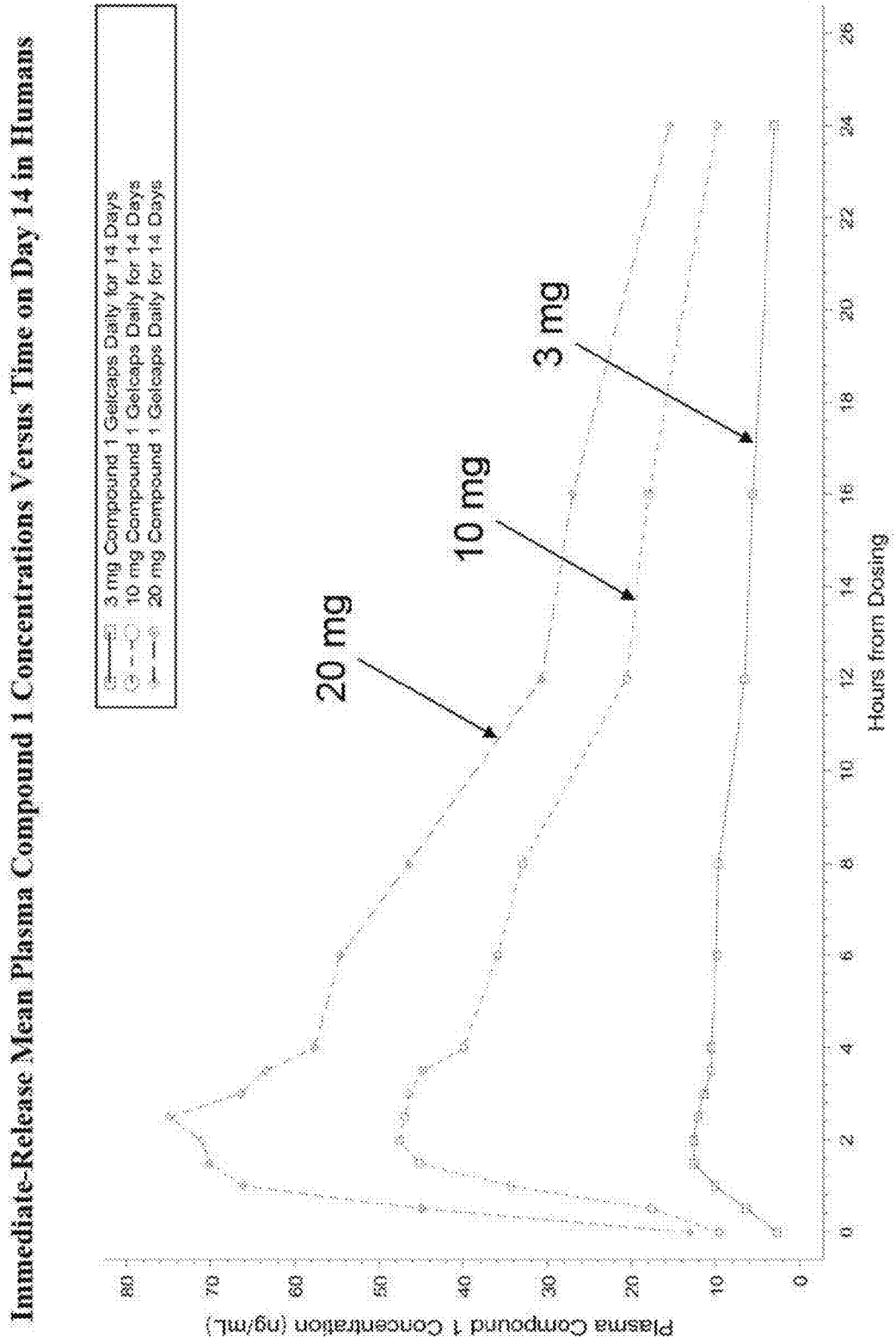

MODIFIED-RELEASE DOSAGE FORMS OF 5-HT$_{2C}$ AGONISTS USEFUL FOR WEIGHT MANAGEMENT

This application is a 35 USC 371 National Stage Entry of PCT/US2011/049914 filed Aug. 31, 2011, and claims the benefit of U.S. Provisional Application No. 61/403,143, filed Sep. 10, 2010, and 61/402,578, filed Sep. 1, 2010, each of which is incorporated by reference in its entirety for all purposes.

FIELD OF THE INVENTION

The present invention relates to methods for weight management that utilize modified-release dosage forms comprising (R)-8-chloro-1-methyl-2,3,4,5-tetrahydro-1H-3-benzazepine salts and crystalline forms thereof. The present invention further relates to (R)-8-chloro-1-methyl-2,3,4,5-tetrahydro-1H-3-benzazepine salts, crystalline forms thereof and modified-release dosage forms comprising them.

BACKGROUND OF THE INVENTION

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared (m2). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$ (see table below).

| Classification Of Weight By Body Mass Index (BMI) | |
| --- | --- |
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, *Semin. Vasc. Med.*, 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: Orlistat (Xenica™), a drug that prevents absorption of fat by the inhibition of pancreatic lipase, and Sibutramine (Reducti™), a 5-HT/noradrenaline re-uptake inhibitor. However, side effects associated with these products may limit their long-term utility. Treatment with Xenica™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure.

It is believed that the 5-HT$_{2C}$ receptor may play a role in obsessive compulsive disorder, some forms of depression, and epilepsy. Accordingly, agonists can have anti-panic properties, and properties useful for the treatment of sexual dysfunction.

In sum, the 5-HT$_{2C}$ receptor is a receptor target for the treatment of obesity and psychiatric disorders, and it can be seen that there is a need for selective 5-HT$_{2C}$ agonists which safely decrease food intake and body weight.

The salts and formulations of the present invention comprise the selective 5-HT$_{2C}$-receptor agonist (R)-8-chloro-1-methyl-2,3,4,5-tetrahydro-1H-3-benzazepine (Compound 1), and are useful for, inter alia, weight management, including weight loss and the maintenance of weight loss. Compound 1 is disclosed in PCT patent publication WO2003/086303, which is incorporated herein by reference in its entirety.

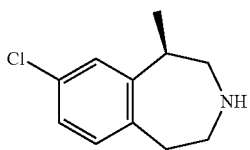

1

Various synthetic routes to (R)-8-chloro-1-methyl-2,3,4,5-tetrahydro-1H-3-benzazepine, its related salts, enantiomers, crystalline forms, and intermediates, have been reported in PCT publications, WO 2005/019179, WO 2006/069363, WO 2007/120517, WO 2008/070111, WO 2009/111004, and in U.S. provisional application 61/396,752 each of which is incorporated herein by reference in its entirety.

Combinations of (R)-8-Chloro-1-methyl-2,3,4,5-tetrahydro-1H-3-benzazepine with other agents, including without limitation, phentermine, and uses of such combinations in therapy are described in WO 2006/071740, which is incorporated herein by reference in its entirety.

The following United States provisional applications are related to (R)-8-chloro-1-methyl-2,3,4,5-tetrahydro-1H-3-benzazepine: 61/402,578; 61/403,143; 61/402,580; 61/402,628; 61/403,149; 61/402,589; 61/402,611; 61/402,565; 61/403,185; each of which is incorporated herein by reference in its entirety.

The following applications are related to (R)-8-chloro-1-methyl-2,3,4,5-tetrahydro-1H-3-benzazepine and have the same filing date as the subject application: PCT application PCT/US2011/049935 which claims priority to U.S. provisional application 61/402,580; PCT application PCT/US2011/049936 which claims priority to U.S. provisional applications 61/402,628 and 61/403,149; PCT application PCT/US2011/049953 which claims priority to United States 20 provisional application 61/402,589; PCT application PCT/US2011/049960 which claims priority to U.S. provisional application 61/402,611; and PCT application PCT/US2011/049955 which claims priority to U.S. provisional applications 61/402,565 and 61/403,185; each of which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In December 2009, Arena Pharmaceuticals submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

An immediate-release film-coated 10-mg tablet was developed for the phase 3 clinical trials and commercial launch of lorcaserin, but there remains a need for modified-release formulations to provide a delay in, and/or continuous drug-release over an extended period of time. Modified-release dosage forms elevate trough plasma levels and are suitable for use in once-a-day (q.d.) dosing regimens. Furthermore, modified-release dosage forms reduce the drug plasma concentration peak:trough ratio and can thereby decrease the incidence and severity of the adverse effects of intermittent dosing.

The choice of modified-release technology depends upon the plasma concentration profile desired and the active pharmaceutical ingredient (API) solubility. The drug molecule must have appropriate pharmacokinetics and sufficient solubility, permeability, and stability throughout the GI tract for a successful modified-release formulation. The salts and formulations described herein help meet these and other needs.

SUMMARY OF THE INVENTION

One aspect of the present invention pertains to modified-release dosage forms comprising a therapeutically effective amount of (R)-8-chloro-1-methyl-2,3,4,5-tetrahydro-1H-3-benzazepine or a pharmaceutically acceptable salt, solvate, or hydrate thereof.

One aspect of the present invention pertains to methods for weight management, comprising administering to an individual in need thereof, the modified-release dosage form of the present invention.

One aspect of the present invention pertains to a salt selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; and (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-acetamidobenzoate salt-cocrystal; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; and (R)-8-chloro-1-methyl-2,3,4,5-tetrahydro-1H-3-benzazepine hemipamoate salt; and pharmaceutically acceptable solvates and hydrates thereof.

One aspect of the present invention pertains to a pharmaceutical composition comprising a salt of the present invention, and a pharmaceutically acceptable carrier.

One aspect of the present invention pertains to processes for preparing a pharmaceutical composition comprising admixing a salt of the present invention, and a pharmaceutically acceptable carrier.

One aspect of the present invention pertains to methods for weight management, comprising administering to an individual in need thereof, a therapeutically effective amount of a salt or a pharmaceutical composition of the present invention.

One aspect of the present invention pertains to uses of salts or pharmaceutical compositions of the present invention, in the manufacture of a medicament for weight management in an individual.

One aspect of the present invention pertains to salts, and pharmaceutical compositions of the present invention, for use in a method of treatment of the human or animal body by therapy.

One aspect of the present invention pertains to modified-release dosage forms, salts, and pharmaceutical compositions of the present invention, for use in a method of weight management.

One aspect of the present invention pertains to modified-release dosage forms, salts, and pharmaceutical compositions of the present invention, for use in a method of weight management; wherein the weight management comprises one or more of: weight loss, and maintenance of weight loss.

One aspect of the present invention pertains to modified-release dosage forms, salts, and pharmaceutical compositions of the present invention, for use in a method of weight management; wherein the weight management comprises one or more of: weight loss, maintenance of weight loss, decreased food consumption, increasing meal-related satiety, reducing pre-meal hunger, and reducing intra-meal food intake.

One aspect of the present invention pertains to modified-release dosage forms, salts, and pharmaceutical compositions of the present invention, for use as an adjunct to diet and exercise for weight management.

One aspect of the present invention pertains to modified-release dosage forms, salts, and pharmaceutical compositions of the present invention, for use in a method of weight management; wherein the individual in need of weight management is selected from: an obese patient with an initial body mass index ≥30 kg/m$^2$; an overweight patient with an initial body mass index ≥27 kg/m$^2$ in the presence of at least one weight related comorbid condition; and an overweight patient with an initial body mass index ≥27 kg/m$^2$ in the presence of at least one weight related comorbid condition; wherein the weight related co-morbid condition is selected from: hypertension, dyslipidemia, cardiovascular disease, glucose intolerance, and sleep apnea.

One aspect of the present invention pertains to modified-release dosage forms, salts, and pharmaceutical compositions of the present invention, for use in a method of weight management in combination with a second anti-obesity agent.

One aspect of the present invention pertains to modified-release dosage forms, salts, and pharmaceutical compositions of the present invention, for use in a method of weight management in combination with a second anti-obesity agent selected from: chlorphentermine, clortermine, phenpentermine, and phentermine, and pharmaceutically acceptable salts, solvates, and hydrates thereof.

One aspect of the present invention pertains to modified-release dosage forms, salts, and pharmaceutical compositions of the present invention, for use in a method of weight management in combination with an anti-diabetes agent.

One aspect of the present invention pertains to modified-release dosage forms, salts, and pharmaceutical compositions of the present invention, for use in a method of weight management in combination with metformin.

One aspect of the present invention pertains to methods of manufacturing a pharmaceutical composition comprising: admixing a compound selected from: a salt of the present invention and pharmaceutically acceptable solvates and hydrates thereof, with a pharmaceutically acceptable excipient.

One aspect of the present invention pertains to methods of manufacturing a modified-release dosage form comprising: providing a compound selected from: (R)-8-chloro-1-methyl-2,3,4,5-tetrahydro-1H-3-benzazepine, and pharmaceutically acceptable salts, solvates, and hydrates thereof; and formulating the compound into a modified-release dosage form.

One aspect of the present invention pertains to methods for weight management, comprising administering to an individual in need thereof, a modified-release dosage form comprising a therapeutically effective dose of (R)-8-chloro-1-methyl-2,3,4,5-tetrahydro-1H-3-benzazepine or a pharmaceutically acceptable salt, solvate or hydrate thereof.

One aspect of the present invention pertains to modified-release dosage forms comprising a therapeutically effective dose of (R)-8-chloro-1-methyl-2,3,4,5-tetrahydro-1H-3-benzazepine or a pharmaceutically acceptable salt, solvate or hydrate thereof.

One aspect of the present invention pertains modified-release dosage forms comprising a therapeutically effective dose of a salt selected from: (R)-8-chloro-1-methyl-2,3,4,5-tetrahydro-1H-3-benzazepine and pharmaceutically acceptable salts, solvates, and hydrates thereof, for use in a method of weight management in an individual.

One aspect of the present invention pertains to certain salts of (R)-8-chloro-1-methyl-2,3,4,5-tetrahydro-1H-3-benzazepine (Compound 1) and pharmaceutically acceptable solvates and hydrates thereof.

One aspect of the present invention pertains to certain salts of (R)-8-chloro-1-methyl-2,3,4,5-tetrahydro-1H-3-benzazepine (Compound 1).

One aspect of the present invention pertains to crystalline forms of (R)-8-chloro-1-methyl-2,3,4,5-tetrahydro-1H-3-benzazepine hydroiodide salt.

One aspect of the present invention pertains to crystalline forms of (R)-8-chloro-1-methyl-2,3,4,5-tetrahydro-1H-3-benzazepine maleate salt.

One aspect of the present invention pertains to crystalline forms of (R)-8-chloro-1-methyl-2,3,4,5-tetrahydro-1H-3-benzazepine fumarate salt.

One aspect of the present invention pertains to crystalline forms of (R)-8-chloro-1-methyl-2,3,4,5-tetrahydro-1H-3-benzazepine hemifumarate salt.

One aspect of the present invention pertains to crystalline forms of (R)-8-chloro-1-methyl-2,3,4,5-tetrahydro-1H-3-benzazepine orotate salt.

One aspect of the present invention pertains to crystalline forms of (R)-8-chloro-1-methyl-2,3,4,5-tetrahydro-1H-3-benzazepine orotate salt hydrate.

One aspect of the present invention pertains to crystalline forms of (R)-8-chloro-1-methyl-2,3,4,5-tetrahydro-1H-3-benzazepine di-4-acetamidobenzoate salt-cocrystal methyl ethyl ketone solvate.

One aspect of the present invention pertains to crystalline forms of (R)-8-chloro-1-methyl-2,3,4,5-tetrahydro-1H-3-benzazepine trans-cinnamate salt.

One aspect of the present invention pertains to crystalline forms of (R)-8-chloro-1-methyl-2,3,4,5-tetrahydro-1H-3-benzazepine heminapadisilate salt.

One aspect of the present invention pertains to crystalline forms of (R)-8-chloro-1-methyl-2,3,4,5-tetrahydro-1H-3-benzazepine heminapadisilate salt solvate 1.

One aspect of the present invention pertains to crystalline forms of (R)-8-chloro-1-methyl-2,3,4,5-tetrahydro-1H-3-benzazepine heminapadisilate salt solvate 2.

One aspect of the present invention pertains to crystalline forms of (R)-8-chloro-1-methyl-2,3,4,5-tetrahydro-1H-3-benzazepine (±)-mandelate salt hydrate.

One aspect of the present invention pertains to crystalline forms of (R)-8-chloro-1-methyl-2,3,4,5-tetrahydro-1H-3-benzazepine hemipamoate salt hydrate.

One aspect of the present invention pertains to pharmaceutical compositions comprising a salt of the present invention.

One aspect of the present invention pertains to processes for preparing pharmaceutical compositions comprising admixing a salt of the present invention, and a pharmaceutically acceptable carrier.

One aspect of the present invention pertains to bulk pharmaceutical compositions suitable for the manufacture of dosage forms for weight management, comprising a salt of the present invention, and a pharmaceutically acceptable carrier.

One aspect of the present invention pertains to processes for preparing a bulk pharmaceutical composition suitable for the manufacture of dosage forms for weight management, comprising admixing a salt of the present invention, and a pharmaceutically acceptable carrier.

One aspect of the present invention pertains to methods for weight management, comprising administering to an individual in need thereof, a therapeutically effective amount of a salt, or a pharmaceutical composition of the present invention.

One aspect of the present invention pertains to the use of a salt of the present invention in the manufacture of a medicament for weight management in an individual.

One aspect of the present invention pertains to salts and pharmaceutical compositions of the present invention, for use in a method of treatment of the human or animal body by therapy.

BRIEF DESCRIPTION OF THE DRAWINGS

FIG. 58: Immediate-Release Mean Plasma Compound 1 Concentrations Versus Time on Day 14 in Humans.

DETAILED DESCRIPTION

Figure 1:
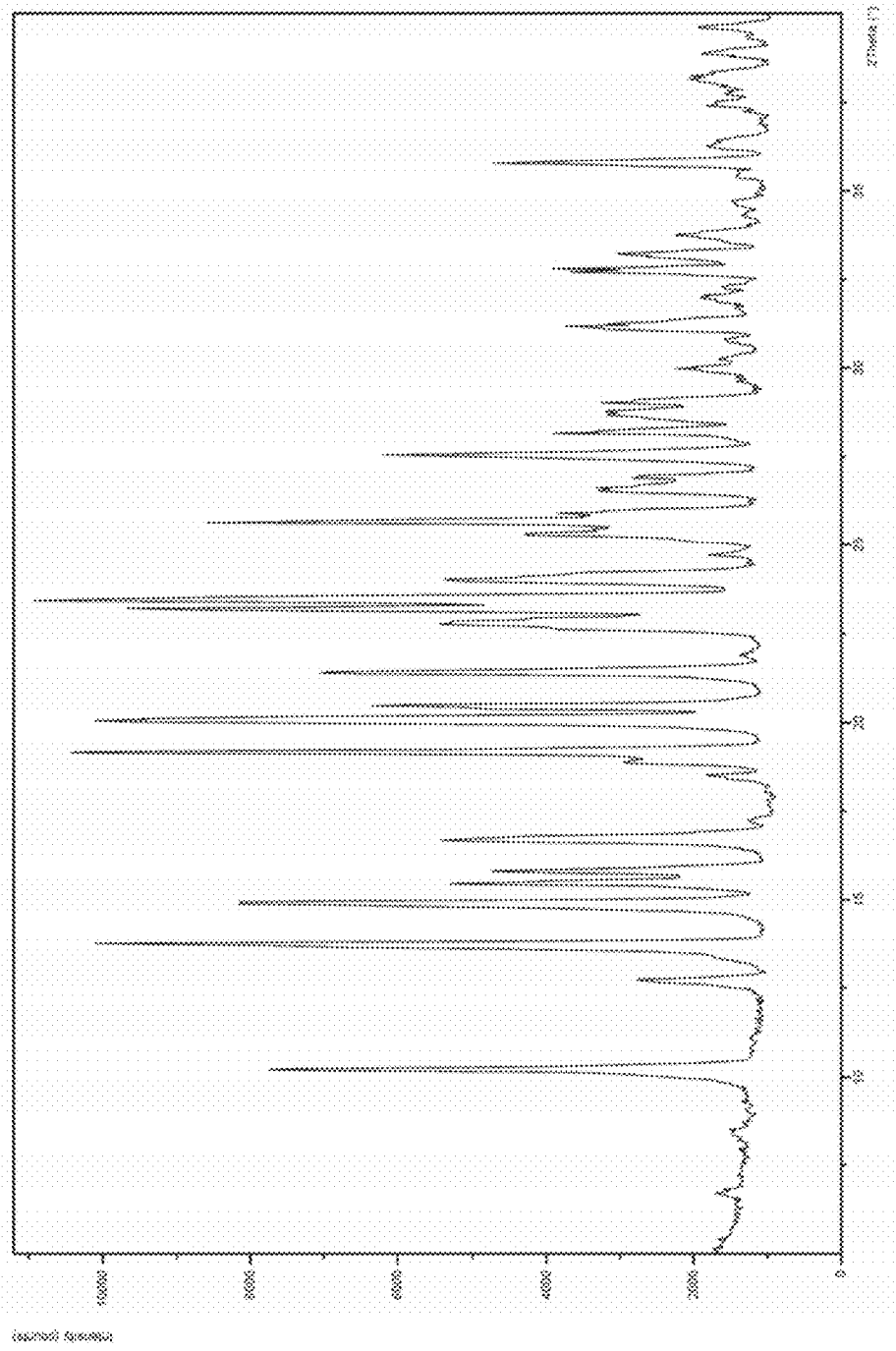
FIG. 1: PXRD of Compound 1 Hydrochloride Salt, Hemihydrate Form III.

It should be appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Definitions

For clarity and consistency, the following definitions will be used throughout this patent document.

The term "agonist" refers to a moiety that interacts with and activates a receptor, such as the $5\text{-}HT_{2C}$ serotonin receptor, and initiates a physiological or pharmacological response characteristic of that receptor.

The term "AUC" refers to the area under a plasma concentration versus time curve.

The term "$AUC_{0\text{-}t}$" refers to the area under a plasma concentration versus time curve from the time of dosing to time t.

The term "$AUC_{0\text{-}inf}$" refers to the area under a plasma concentration versus time curve from the time of dosing extrapolated to infinity.

The term "$AUC_{tau}$" refers to the area under a plasma concentration versus time curve for a given dosing interval (tau).

The term "$AUC_{last}$" refers to the area under the plasma concentration versus time curve from the time of dosing to the last sampling time. In some embodiments $AUC_{last}$ refers to the area under the plasma concentration versus time curve from the time of dosing to the last sampling time of a particular compound during the interval between any two consecutive doses of a medicament comprising the compound or a salt, solvate, or hydrate thereof, up to the last sampling time. In some embodiments, the compound is Compound 1. In some embodiments, the medicament is a modified-release dosage form.

The term "$C_{max}$" refers to the maximum (peak) plasma concentration of a particular compound during the interval between any two consecutive doses of a medicament comprising the compound or a salt, solvate, or hydrate thereof. In some embodiments, the compound is Compound 1. In some embodiments, the medicament is a modified-release dosage form.

The term "$C_{min}$" refers to the minimum (trough) plasma concentration of a particular compound during the interval between any two consecutive doses of a medicament comprising the compound or a salt, solvate, or hydrate thereof. In some embodiments, the compound is Compound 1. In some embodiments, the medicament is a modified-release dosage form.

The term "functional coating" refers to a film coating on a tablet that provides a mechanism to restrict water ingress into the tablet and subsequent diffusion of the API.

The term "individual" refers to both humans and non-human mammals. Non-human mammals include but are not limited to rodents such as mice and rats, etc. rabbits, dogs, cats, swine, cattle, sheep, horses, and non-human primates such as monkeys and apes, etc.

The term "immediate-release dosage form" refers to a formulation which rapidly disintegrates upon oral administration to a human or other animal releasing an active pharmaceutical ingredient (API) from the formulation. Examples of immediate release dosage forms comprising Compound 1 include, but are not limited to, the immediate-release formulation of Example 5 herein. In some embodiments the T80% of the immediate-release dosage form is less than 3 hours. In some embodiments the T80% of the immediate-release dosage form is less than 1 hour. In some embodiments the T80% of the immediate-release dosage form is less than 30 minutes. In some embodiments the T80% of the immediate-release dosage form is less than 10 minutes.

An "immediate-release method for weight management" comprises administering to an individual in need thereof an immediate-release dosage form.

The term "modified-release dosage form" refers to any formulation that, upon oral administration to a human or other animal, releases an API at a slower rate over an extended period of time when compared to an immediate-release dosage-form of the API. For example, a modified-release tablet comprising Compound 1 administered orally to a human or other animal releases Compound 1 more slowly and over a longer period of time than does an immediate-release tablet comprising Compound 1 administered orally to a human or other animal; and a modified-release suspension comprising Compound 1 administered orally to a human or other animal releases Compound 1 more slowly and over a longer period of time than an immediate-release suspension comprising Compound 1 administered orally to a human or other animal.

The term "total plasma exposure" refers to the total area under a drug plasma concentration versus time curve over a specified time period The term "pharmaceutical composition" refers to a composition comprising at least one active ingredient; including but not limited to Compound 1 and pharmaceutically acceptable salts, solvates, and hydrates thereof, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "rate-controlling membrane" refers to an inert membrane barrier through which a drug diffuses at a controlled rate.

The term "rate-controlling polymer" refers to an excipient which upon administration as a component of a modified-release tablet, becomes hydrated and forms a gel layer on the periphery of the tablet which modulates further water penetration and subsequent drug diffusion and release.

The term "T80%" refers to the time needed to achieve 80% cumulative release of an API from a particular formulation comprising the API.

The term "$t_{max}$" refers to the time to maximum concentration of a particular compound during the interval between any two consecutive doses of a medicament comprising the compound or a salt, solvate, or hydrate thereof. In some embodiments, the compound is Compound 1. In some embodiments, the medicament is a modified-release dosage form.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

The term "treatment" as used herein refers to one or more of the following:

(1) prevention of a disease, for example, prevention of a disease, condition or disorder in an individual that may be predisposed to the disease, condition or disorder but does not yet experience or display the pathology or symptomatology of the disease;

(2) inhibition of a disease, for example, inhibition of a disease, condition or disorder in an individual that is experiencing or displaying the pathology or symptomatology of the disease, condition or disorder (i.e., arresting further development of the pathology and/or symptomatology); and (3) amelioration of a disease, for example, amelioration of a disease, condition or disorder in an individual that is experiencing or displaying the pathology or symptomatology of the disease, condition or disorder (i.e., reversing the pathology and/or symptomatology).

Whether an individual is in need of treatment is a judgment made by a caregiver (e.g. nurse practitioner, physician, physician assistant, nurse, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by Compound 1 and pharmaceutically acceptable salts, solvates, and hydrates thereof. Accordingly, Compound 1 and pharmaceutically acceptable salts, solvates, and hydrates thereof can be used in a protective or preventive manner; or Compound 1 and pharmaceutically acceptable salts, solvates, and hydrates thereof can be used to alleviate, inhibit or ameliorate a disease, condition or disorder.

The term "weight management" as used herein refers to controlling body weight and in the context of the present invention is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight.

The term "maintenance of weight loss" or "weight maintenance" as used herein refers to preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss.

In Vivo Pharmacokinetics and Efficacy

The pharmacokinetic behavior and efficacy of modified-release dosage forms, including but not limited to extended-release dosage forms, can be simulated by dosing via minipump infusion (e.g. to rats into either intraperitoneal or subcutaneous space) Immediate release tablets can be simulated by dosing via oral gavage. Dose comparisons can be made based upon exposure or absolute dose. Studies can be run chronically or sub-chronically with an ultimate endpoint of body weight change.

Where increased efficacy is observed with continuous steady-state exposure relative to intermittent exposure and absolute dose or AUC are matched, this indicates that extended release formulations in humans are viable methods with which to improve efficacy without increasing absolute dose.

Furthermore, a reduced peak-to-trough variation in drug plasma concentration with continuous steady-state exposure relative to intermittent exposure indicates that extended release formulations in humans will decrease the incidence and severity of any adverse effects associated with intermittent treatment, by lowering the $C_{max}$ and maintaining the AUC (see Tompson et al., *Epilepsia* 2008; 49:410-417).

For drug therapy to be successful, there is an optimal drug concentration range that must be achieved. This is the therapeutic window. The consequences of being above the therapeutic concentration increases the probability of untoward side effects. If the drug plasma concentration is below the therapeutic range, clinical efficacy is limited. After oral administration of drug, the plasma concentrations rise to a maximum concentration ($C_{max}$, peak). Over time, the plasma concentration declines to a minimum (trough) concentration ($C_{min}$, trough). Therapeutically, it is desirable to reduce the drug peak-to-trough concentration differences to decrease adverse effects, while maintaining the therapeutic effects. This is accomplished by lowering the $C_{max}$, while keeping the plasma exposure (AUC) stable (Rowland and Tozer, *Clinical Pharmacokinetics: Concepts and Applications* 3d ed., Williams and Wilkins. 1995; Privitera, *Epilepsy Currents*, Vol. 8, No. 5, 2008 pp. 113-117). Modified-release dosage forms comprising Compound 1 will decrease the incidence and severity of adverse effects associated with intermittent treatment by reducing the drug peak-to-trough concentration differences, while maintaining the AUC.

Therapeutically, it is desirable to reduce $C_{max}$ and/or the rate at which drug concentration increases in order to decrease adverse effects, while maintaining therapeutic effects. For drugs that exhibit a brain to plasma exposure ratio of greater than 1, a reduction in $C_{max}$ or a reduction in the rate of drug concentration increase in plasma, results in a greater corresponding reduction in the brain. This greater reduction is important for decreasing adverse effects linked to brain drug-concentration, for example, headache. A clinical trial was performed that measured plasma and lumbar cerebrospinal fluid (CSF) concentrations of Compound 1 in healthy obese volunteers who took 10 mg of Compound 1 hydrochloride salt twice-daily for 6.5 days. Upon administration of the first dose on day 1, the human brain-to-plasma exposure ratio for Compound 1 was less than 1. Steady state was achieved in each subject after dosing for approximately 4 to 6 days. At steady state, the human brain-to-plasma exposure ratio for Compound 1 was 1.7. Modified-release dosage forms comprising Compound 1 will decrease the incidence and severity of adverse effects associated with intermittent treatment, by lowering the $C_{max}$ and/or the rate at which drug concentration increases in the plasma and in the brain, while maintaining the AUC.

Therapeutically, it is desirable to increase $t_{max}$ to decrease adverse effects, while maintaining therapeutic effects. A clinical trial was performed to evaluate the safety and pharmacokinetic profile of a single oral dose of Compound 1 (10 mg) administered to healthy male and female subjects aged 18 to 60 years (inclusive) under fed and fasted conditions. Administration of Compound 1 after a high-fat breakfast resulted in a statistically significant delay to the time of maximum plasma concentrations compared to administration in the fasted state. $C_{max}$ was reduced by approximately 10% in the fed compared to fasted state, but a lack of food effect was not proven. There was no food effect on overall exposure to Compound 1. Compound 1 was generally well tolerated when dosed in the fasted state and after a high-fat breakfast. There were a higher number of adverse events when dosed in the fasted state, (18 compared to 6) including two moderate intensity (nausea and headache) and one severe (vomiting) intensity events occurring in a single subject. Modified-release dosage forms comprising Compound 1 will decrease the incidence and severity of adverse effects associated with intermittent treatment, by increasing the while maintaining the AUC.

It has been demonstrated that chronic twice-daily oral administration of Compound 1 hydrochloride salt to rats maintained on a high fat diet produced dose-dependent reductions in food intake and body weight gain that were maintained during a 4-week study (Thomsen et al., *J. Pharinacol. Exp. Ther.,* 2008 325:577-587, hereby incorporated by reference in its entirety).

A number of experiments were performed in male Sprague-Dawley rats in order to determine whether continuous steady-state exposure of Compound 1 differentially affects body weight gain compared to intermittent exposure. Rats were administered Compound 1 either by once-daily oral gavage or by constant infusion to simulate the effect of administering a modified-release formulation of Compound 1. The objective was to determine if reducing the drug plasma concentration peak-to-trough ratio via continuous infusion, while maintaining AUC, increases body weight reduction compared to intermittent exposure. Prior to initiating the chronic experiment, preliminary pharmacokinetic experiments were conducted to determine Compound 1 plasma exposure at steady-state after once-daily oral administration for six days and after constant infusion for four days. The $AUC_{tau\ Day\ 6}$ following oral dosing and systemic clearance derived from constant infusion were used to calculate the subcutaneous osmotic minipump dose needed to achieve an $AUC_{tau}$ similar to $AUC_{tau\ Day\ 6}$ following oral dosing.

One aspect of the present invention pertains to methods for weight management, comprising administering to an individual in need thereof, a modified-release dosage form comprising a therapeutically effective dose of (R)-8-chloro-1-methyl-2,3,4,5-tetrahydro-1H-3-benzazepine or a pharmaceutically acceptable salt, solvate, or hydrate thereof.

One aspect of the present invention pertains to methods for weight management, comprising administering to an individual in need thereof, the modified-release dosage form of the present invention.

In some embodiments, the method comprises a plurality of administrations of the modified-release dosage form, with a frequency wherein the average interval between any two sequential the administrations is: at least about 24 hours; or about 24 hours.

In some embodiments, the method comprises a plurality of administrations of the modified-release dosage form, and the modified-release dosage form is administered once-a-day.

In some embodiments, the plurality of administrations is: at least about 30; at least about 180; at least about 365; or at least about 730.

In some embodiments, the method is more efficacious than an immediate-release method for weight management;

wherein the immediate-release method for weight management comprises administering to an individual in need thereof, at the frequency, the plurality of administrations of an immediate-release dosage form comprising the therapeutically effective amount of (R)-8-chloro-1-methyl-2,3,4,5-tetrahydro-1H-3-benzazepine or a pharmaceutically acceptable salt, solvate, or hydrate thereof.

In some embodiments, the method is more efficacious than an immediate-release method for weight management; wherein the immediate-release method for weight management comprises administering to an individual in need thereof, an immediate-release dosage form comprising (R)-8-chloro-1-methyl-2,3,4,5-tetrahydro-1H-3-benzazepine or a pharmaceutically acceptable salt, solvate, or hydrate thereof; and wherein the total plasma exposure of the individual to (R)-8-chloro-1-methyl-2,3,4,5-tetrahydro-1H-3-benzazepine over the course of the immediate-release method is equal to or greater than the total plasma exposure of the individual to (R)-8-chloro-1-methyl-2,3,4,5-tetrahydro-1H-3-benzazepine over the course of the method.

In some embodiments, the plasma concentration of the (R)-8-chloro-1-methyl-2,3,4,5-tetrahydro-1H-3-benzazepine in the individual has a $C_{max}$ of: less than about 60 ng/mL; less than about 40 ng/mL; less than about 20 ng/mL; or less than about 10 ng/mL.

In some embodiments, the $C_{max}$ divided by the therapeutically effective amount is equal to: less than about $1\times10^{-5}$ mL$^{-1}$; less than about $5\times10^{-6}$ mL$^{-1}$; less than about $1\times10^{-6}$ mL$^{-1}$; or less than about $5\times10^{-7}$ mL$^{-1}$.

In some embodiments, the $C_{max}$ occurs: more than 30 minutes after the administering; more than 1 hour after the administering; or more than 2 hours after the administering.

In some embodiments, the $C_{max}$ occurs: more than 3 hours after the administering; more than 6 hours after the administering; or more than 12 hours after the administering.

In some embodiments, the average peak to trough ratio of the plasma concentration of the (R)-8-chloro-1-methyl-2,3,4,5-tetrahydro-1H-3-benzazepine in the individual is: less than about 3:1; less than about 2:1; less than about 1.5:1; or less than about 1.1:1.

In some embodiments, the modified-release dosage form comprises a salt selected from: (R)-8-chloro-1-methyl-2,3,4,5-tetrahydro-1H-3-benzazepine hydrochloride and pharmaceutically acceptable solvates and hydrates thereof.

In some embodiments, the salt is (R)-8-chloro-1-methyl-2,3,4,5-tetrahydro-1H-3-benzazepine hydrochloride salt hemihydrate.

In some embodiments, the salt is (R)-8-chloro-1-methyl-2,3,4,5-tetrahydro-1H-3-benzazepine hydrochloride salt hemihydrate, Form III.

In some embodiments, the modified-release dosage form further comprises (hydroxypropyl)methyl cellulose.

In some embodiments, the modified-release dosage form further comprises one or more ingredients selected from: microcrystalline cellulose, mannitol, and magnesium stearate.

In some embodiments, the modified-release dosage form further comprises a film coating.

In some embodiments, the film coating comprises a water-soluble film coating.

In some embodiments, the film coating comprises ethyl cellulose.

In some embodiments, the film coating further comprises (hydroxypropyl)methyl cellulose.

In some embodiments, the ratio of the ethyl cellulose to the (hydroxypropyl)methyl cellulose is: about 75:25; about 80:20; or about 85:15.

In some embodiments, the modified-release dosage form comprises a core tablet and a film coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the film coating comprises a water-soluble film coating.

In some embodiments, the modified-release dosage form comprises a core tablet and a film coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the film coating comprises a water-soluble film coating.

In some embodiments, the modified-release dosage form comprises a core tablet and a film coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the film coating comprises: ethyl cellulose; and (hydroxypropyl)methyl cellulose.

In some embodiments, the modified-release dosage form comprises a core tablet and a film coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the film coating comprises: about 85% ethyl cellulose; and about 15% (hydroxypropyl)methyl cellulose; or about 75% ethyl cellulose; and about 25% (hydroxypropyl)methyl cellulose.

In some embodiments, the modified-release dosage form has a T80% of: at least 3 h; at least 6 h; at least 9 h; or at least 12 h.

In some embodiments, the modified-release dosage form comprises a salt selected from: a pharmaceutically acceptable salt of (R)-8-chloro-1-methyl-2,3,4,5-tetrahydro-1H-3-benzazepine and pharmaceutically acceptable solvates and hydrates thereof, and wherein the salt has an aqueous solubility of: less than about 200 mg/mL at about room temperature; less than about 100 mg/mL at about room temperature; less than about 50 mg/mL at about room temperature; less than about 25 mg/mL at about room temperature; less than about 10 mg/mL at about room temperature; or less than about 5 mg/mL at about room temperature.

In some embodiments, the modified-release dosage form comprises a salt selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; and (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-acetamidobenzoate salt-cocrystal; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; and (R)-8-chloro-1-methyl-2,3,4,5- tetrahydro-1H-3-benzazepine hemipamoate salt; and pharmaceutically acceptable solvates and hydrates thereof.

In some embodiments, the method comprises a plurality of administrations of the modified-release dosage form, with a frequency wherein the average interval between any two sequential administrations is at least about 24 hours.

In some embodiments, the method comprises a plurality of administrations of the modified-release dosage form, with a frequency wherein the average interval between any two sequential administrations is about 24 hours.

In some embodiments, the plasma concentration of the (R)-8-chloro-1-methyl-2,3,4,5-tetrahydro-1H-3-benzazepine in the individual has a $C_{max}$ of less than about 60 ng/mL.

In some embodiments, the plasma concentration of the (R)-8-chloro-1-methyl-2,3,4,5-tetrahydro-1H-3-benzazepine in the individual has a $C_{max}$ of less than about 40 ng/mL.

In some embodiments, the plasma concentration of the (R)-8-chloro-1-methyl-2,3,4,5-tetrahydro-1H-3-benzazepine in the individual has a $C_{max}$ of less than about 20 ng/mL.

In some embodiments, the plasma concentration of the (R)-8-chloro-1-methyl-2,3,4,5-tetrahydro-1H-3-benzazepine in the individual has a $C_{max}$ of less than about 10 ng/mL.

In some embodiments, the plasma concentration of the (R)-8-chloro-1-methyl-2,3,4,5-tetrahydro-1H-3-benzazepine in the individual has a $C_{max}$ of about 60 ng/mL to about 5 ng/mL.

In some embodiments, the plasma concentration of the (R)-8-chloro-1-methyl-2,3,4,5-tetrahydro-1H-3-benzazepine in the individual has a $C_{max}$ of about 60 ng/mL to about 10 ng/mL.

In some embodiments, the plasma concentration of the (R)-8-chloro-1-methyl-2,3,4,5-tetrahydro-1H-3-benzazepine in the individual has a $C_{max}$ of about 60 ng/mL to about 20 ng/mL.

In some embodiments, the plasma concentration of the (R)-8-chloro-1-methyl-2,3,4,5-tetrahydro-1H-3-benzazepine in the individual has a $C_{max}$ of about 60 ng/mL to about 40 ng/mL.

In some embodiments, the plasma concentration of the (R)-8-chloro-1-methyl-2,3,4,5-tetrahydro-1H-3-benzazepine in the individual has a $C_{max}$ of about 40 ng/mL to about 5 ng/mL.

In some embodiments, the plasma concentration of the (R)-8-chloro-1-methyl-2,3,4,5-tetrahydro-1H-3-benzazepine in the individual has a $C_{max}$ of about 40 ng/mL to about 10 ng/mL.

In some embodiments, the plasma concentration of the (R)-8-chloro-1-methyl-2,3,4,5-tetrahydro-1H-3-benzazepine in the individual has a $C_{max}$ of about 40 ng/mL to about 20 ng/mL.

In some embodiments, the plasma concentration of the (R)-8-chloro-1-methyl-2,3,4,5-tetrahydro-1H-3-benzazepine in the individual has a $C_{max}$ of about 20 ng/mL to about 5 ng/mL.

In some embodiments, the plasma concentration of the (R)-8-chloro-1-methyl-2,3,4,5-tetrahydro-1H-3-benzazepine in the individual has a $C_{max}$ of about 20 ng/mL to about 10 ng/mL.

In some embodiments, the plasma concentration of the (R)-8-chloro-1-methyl-2,3,4,5-tetrahydro-1H-3-benzazepine in the individual has a $C_{max}$ of about 10 ng/mL to about 5 ng/mL.

In any of the methods of the present invention, the $C_{max}$ is an average over a plurality of treated individuals.

In some embodiments, the $C_{max}$ divided by the therapeutically effective amount is equal to less than about $1 \times 10^{-5}$ $mL^{-1}$.

In some embodiments, the $C_{max}$ divided by the therapeutically effective amount is equal to less than about $5 \times 10^{-6}$ $mL^{-1}$.

In some embodiments, the $C_{max}$ divided by the therapeutically effective amount is equal to less than about $1 \times 10^{-6}$ $mL^{-1}$.

In some embodiments, the $C_{max}$ divided by the therapeutically effective amount is equal to less than about $5 \times 10^{-7}$ $mL^{-1}$.

In some embodiments, the $C_{max}$ divided by the therapeutically effective amount is equal to between about $1 \times 10^{-5}$ $mL^{-1}$ and about $1 \times 10^{-7}$ $mL^{-1}$.

In some embodiments, the $C_{max}$ divided by the therapeutically effective amount is equal to between about $1 \times 10^{-5}$ $mL^{-1}$ and about $5 \times 10^{-7}$ $mL^{-1}$.

In some embodiments, the $C_{max}$ divided by the therapeutically effective amount is equal to between about $1 \times 10^{-5}$ $mL^{-1}$ and about $1 \times 10^{-6}$ $mL^{-1}$.

In some embodiments, the $C_{max}$ divided by the therapeutically effective amount is equal to between about $1 \times 10^{-5}$ $mL^{-1}$ and about $5 \times 10^{-6}$ $mL^{-1}$.

In some embodiments, the $C_{max}$ divided by the therapeutically effective amount is equal to between about $5 \times 10^{-6}$ $mL^{-1}$ and about $1 \times 10^{-7}$ $mL^{-1}$.

In some embodiments, the $C_{max}$ divided by the therapeutically effective amount is equal to between about $5 \times 10^{-6}$ $mL^{-1}$ and about $5 \times 10^{-7}$ $mL^{-1}$.

In some embodiments, the $C_{max}$ divided by the therapeutically effective amount is equal to between about $5 \times 10^{-6}$ $mL^{-1}$ and about $1 \times 10^{-6}$ $mL^{-1}$.

In some embodiments, the $C_{max}$ divided by the therapeutically effective amount is equal to between about $1 \times 10^{-6}$ $mL^{-1}$ and about $1 \times 10^{-7}$ $mL^{-1}$.

In some embodiments, the $C_{max}$ divided by the therapeutically effective amount is equal to between about $1 \times 10^{-6}$ $mL^{-1}$ and about $5 \times 10^{-7}$ $mL^{-1}$.

In some embodiments, the $C_{max}$ divided by the therapeutically effective amount is equal to between about $5 \times 10^{-7}$ $mL^{-1}$ and about $1 \times 10^{-7}$ $mL^{-1}$.

In some embodiments, the plasma concentration of the (R)-8-chloro-1-methyl-2,3,4,5-tetrahydro-1H-3-benzazepine in the individual has a $AUC_{last}$ of at least about $1 \times 10^{-3}$ h·µg/mL.

In some embodiments, the plasma concentration of the (R)-8-chloro-1-methyl-2,3,4,5-tetrahydro-1H-3-benzazepine in the individual has a $AUC_{last}$ of at least about $1 \times 10^{-2}$ h·µg/mL.

In some embodiments, the plasma concentration of the (R)-8-chloro-1-methyl-2,3,4,5-tetrahydro-1H-3-benzazepine in the individual has a $AUC_{last}$ of at least about 0.1 h·µg/mL.

In some embodiments, the plasma concentration of the (R)-8-chloro-1-methyl-2,3,4,5-tetrahydro-1H-3-benzazepine in the individual has a $AUC_{last}$ of at least about 1 h·µg/mL.

In some embodiments, the plasma concentration of the (R)-8-chloro-1-methyl-2,3,4,5-tetrahydro-1H-3-benzazepine in the individual has a $AUC_{last}$ of at least about 10 h·µg/mL.

In some embodiments, the plasma concentration of the (R)-8-chloro-1-methyl-2,3,4,5-tetrahydro-1H-3-benzazepine in the individual has a $AUC_{last}$ of at least about 100 h·μg/mL.

In any of the methods of the present invention, the $AUC_{last}$ is an average over a plurality of treated individuals.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about 200 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about 100 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about 10 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about 1 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about 0.1 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-3}$ h·μg/mL and about $1 \times 10^{-2}$ h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-2}$ h·μg/mL and about 200 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-2}$ h·μg/mL and about 100 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-2}$ h·μg/mL and about 10 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-2}$ h·μg/mL and about 1 h·μg/mL.

In some embodiments, the plasma concentration of the (R)-8-chloro-1-methyl-2,3,4,5-tetrahydro-1H-3-benzazepine in the individual has a $AUC_{last}$ of between about $1 \times 10^{-2}$ h·μg/mL and about 0.1 h·μg/mL.

In some embodiments, the plasma concentration of the (R)-8-chloro-1-methyl-2,3,4,5-tetrahydro-1H-3-benzazepine in the individual has a $AUC_{last}$ of between about 0.1 h·μg/mL and about 200 h·μg/mL.

In some embodiments, the plasma concentration of the (R)-8-chloro-1-methyl-2,3,4,5-tetrahydro-1H-3-benzazepine in the individual has a $AUC_{last}$ of between about 0.1 h·μg/mL and about 100 h·μg/mL.

In some embodiments, the plasma concentration of the (R)-8-chloro-1-methyl-2,3,4,5-tetrahydro-1H-3-benzazepine in the individual has a $AUC_{last}$ of between about 0.1 h·μg/mL and about 10 h·μg/mL.

In some embodiments, the plasma concentration of the (R)-8-chloro-1-methyl-2,3,4,5-tetrahydro-1H-3-benzazepine in the individual has a $AUC_{last}$ of between about 0.1 h·μg/mL and about 1 h·μg/mL.

In some embodiments, the plasma concentration of the (R)-8-chloro-1-methyl-2,3,4,5-tetrahydro-1H-3-benzazepine in the individual has a $AUC_{last}$ of between about 1 h·μg/mL and about 200 h·μg/mL.

In some embodiments, the plasma concentration of the (R)-8-chloro-1-methyl-2,3,4,5-tetrahydro-1H-3-benzazepine in the individual has a $AUC_{last}$ of between about 1 h·μg/mL and about 100 h·μg/mL.

In some embodiments, the plasma concentration of the (R)-8-chloro-1-methyl-2,3,4,5-tetrahydro-1H-3-benzazepine in the individual has a $AUC_{last}$ of between about 1 h·μg/mL and about 10 h·μg/mL.

In some embodiments, the plasma concentration of the (R)-8-chloro-1-methyl-2,3,4,5-tetrahydro-1H-3-benzazepine in the individual has a $AUC_{last}$ of between about 10 h·μg/mL and about 200 h·μg/mL.

In some embodiments, the plasma concentration of the (R)-8-chloro-1-methyl-2,3,4,5-tetrahydro-1H-3-benzazepine in the individual has a $AUC_{last}$ of between about 10 h·μg/mL and about 100 h·μg/mL.

In some embodiments, the plasma concentration of the (R)-8-chloro-1-methyl-2,3,4,5-tetrahydro-1H-3-benzazepine in the individual has a $AUC_{last}$ of between about 100 h·μg/mL and about 200 h·μg/mL.

In some embodiments, the $AUC_{last}$ divided by the therapeutically effective amount is equal to at least about $1 \times 10^{-6}$ h/mL.

In some embodiments, the $AUC_{last}$ divided by the therapeutically effective amount is equal to at least about $1 \times 10^{-5}$ h/mL.

In some embodiments, the $AUC_{last}$ divided by the therapeutically effective amount is equal to at least about $1 \times 10^{-4}$ h/mL.

In some embodiments, the $AUC_{last}$ divided by the therapeutically effective amount is equal to at least about $1 \times 10^{-3}$ h/mL.

In some embodiments, the $AUC_{last}$ divided by the therapeutically effective amount is equal to at least about $1 \times 10^{-2}$ h/mL.

In some embodiments, the $AUC_{last}$ divided by the therapeutically effective amount is equal to between about $1 \times 10^{-6}$ h/mL and about 0.1 h/mL.

In some embodiments, the $AUC_{last}$ divided by the therapeutically effective amount is equal to between about $1 \times 10^{-6}$ h/mL and about $1 \times 10^{-2}$ h/mL.

In some embodiments, the $AUC_{last}$ divided by the therapeutically effective amount is equal to between about $1 \times 10^{-6}$ h/mL and about $1 \times 10^{-3}$ h/mL.

In some embodiments, the $AUC_{last}$ divided by the therapeutically effective amount is equal to between about $1 \times 10^{-6}$ h/mL and about $1 \times 10^{-4}$ h/mL.

In some embodiments, the $AUC_{last}$ divided by the therapeutically effective amount is equal to between about $1 \times 10^{-6}$ h/mL and about $1 \times 10^{-5}$ h/mL.

In some embodiments, the $AUC_{last}$ divided by the therapeutically effective amount is equal to between about $1 \times 10^{-5}$ h/mL and about 0.1 h/mL.

In some embodiments, the $AUC_{last}$ divided by the therapeutically effective amount is equal to between about $1 \times 10^{-5}$ h/mL and about $1 \times 10^{-2}$ h/mL.

In some embodiments, the $AUC_{last}$ divided by the therapeutically effective amount is equal to between about $1 \times 10^{-5}$ h/mL and about $1 \times 10^{-3}$ h/mL.

In some embodiments, the $AUC_{last}$ divided by the therapeutically effective amount is equal to between about $1 \times 10^{-5}$ h/mL and about $1 \times 10^{-4}$ h/mL.

In some embodiments, the $AUC_{last}$ divided by the therapeutically effective amount is equal to between about $1\times10^{-4}$ h/mL and about 0.1 h/mL.

In some embodiments, the $AUC_{last}$ divided by the therapeutically effective amount is equal to between about $1\times10^{-4}$ h/mL and about $1\times10^{-2}$ h/mL.

In some embodiments, the $AUC_{last}$ divided by the therapeutically effective amount is equal to between about $1\times10^{-4}$ h/mL and about $1\times10^{-3}$ h/mL.

In some embodiments, the $AUC_{last}$ divided by the therapeutically effective amount is equal to between about $1\times10^{-3}$ h/mL and about 0.1 h/mL.

In some embodiments, the $AUC_{last}$ divided by the therapeutically effective amount is equal to between about $1\times10^{-3}$ h/mL and about $1\times10^{-2}$ h/mL.

In some embodiments, the $AUC_{last}$ divided by the therapeutically effective amount is equal to between about $1\times10^{-2}$ h/mL and about 0.1 h/mL.

In some embodiments, the $AUC_{last}$ divided by the $C_{max}$ is equal to at least about 5 h.

In some embodiments, the $AUC_{last}$ divided by the $C_{max}$ is equal to at least about 10 h.

In some embodiments, the $AUC_{last}$ divided by the $C_{max}$ is equal to at least about 15 h.

In some embodiments, the $AUC_{last}$ divided by the $C_{max}$ is equal to at least about 25 h.

In some embodiments, the $AUC_{last}$ divided by the $C_{max}$ is equal to between about 5 h and about 50 h.

In some embodiments, the $AUC_{last}$ divided by the $C_{max}$ is equal to between about 5 h and about 25 h.

In some embodiments, the $AUC_{last}$ divided by the $C_{max}$ is equal to between about 5 h and about 15 h.

In some embodiments, the $AUC_{last}$ divided by the $C_{max}$ is equal to between about 5 h and about 10 h.

In some embodiments, the $AUC_{last}$ divided by the $C_{max}$ is equal to between about 10 h and about 50 h.

In some embodiments, the $AUC_{last}$ divided by the $C_{max}$ is equal to between about 10 h and about 25 h.

In some embodiments, the $AUC_{last}$ divided by the $C_{max}$ is equal to between about 10 h and about 15 h.

In some embodiments, the $AUC_{last}$ divided by the $C_{max}$ is equal to between about 15 h and about 50 h.

In some embodiments, the $AUC_{last}$ divided by the $C_{max}$ is equal to between about 15 h and about 25 h.

In some embodiments, the $AUC_{last}$ divided by the $C_{max}$ is equal to between about 25 h and about 50 h.

In some embodiments, the administering results in a $C_{min}$ of at least about 5 ng/mL and a $C_{max}$ of less than about 60.

In some embodiments, the administering results in a $C_{min}$ of at least about 5 ng/mL and a $C_{max}$ of less than about 40 ng/mL.

In some embodiments, the administering results in a $C_{min}$ of at least about 5 ng/mL and a $C_{max}$ of less than about 20 ng/mL.

In some embodiments, the administering results in a $C_{min}$ of at least about 5 ng/mL and a $C_{max}$ of less than about 10 ng/mL.

In some embodiments $C_{min}$ and $C_{max}$ are averages over a plurality of treated individuals.

In some embodiments, the average peak to trough ratio of the plasma concentration of the (R)-8-chloro-1-methyl-2,3,4,5-tetrahydro-1H-3-benzazepine in the individual is less than about 3:1.

In some embodiments, the average peak to trough ratio of the plasma concentration of the (R)-8-chloro-1-methyl-2,3,4,5-tetrahydro-1H-3-benzazepine in the individual is less than about 2:1.

In some embodiments, the average peak to trough ratio of the plasma concentration of the (R)-8-chloro-1-methyl-2,3,4,5-tetrahydro-1H-3-benzazepine in the individual is less than about 1.5:1.

In some embodiments, the average peak to trough ratio of the plasma concentration of the (R)-8-chloro-1-methyl-2,3,4,5-tetrahydro-1H-3-benzazepine in the individual is less than about 1.1:1.

In any of the methods of the present invention, the peak to trough ratio of the plasma concentration of the (R)-8-chloro-1-methyl-2,3,4,5-tetrahydro-1H-3-benzazepine is an average over a plurality of treated individuals.

In some embodiments, the $C_{max}$ occurs more than 30 minutes after the administering.

In some embodiments, the $C_{max}$ occurs more than 1 hour after the administering.

In some embodiments, the $C_{max}$ occurs more than 2 hours after the administering.

In some embodiments, the $C_{max}$ occurs more than 3 hours after the administering.

In some embodiments, the $C_{max}$ occurs more than 6 hours after the administering.

In some embodiments, the $C_{max}$ occurs more than 12 hours after the administering.

In some embodiments, the $C_{max}$ occurs more than 30 minutes but less than 1 hour after the administering.

In some embodiments, the $C_{max}$ occurs more than 30 minutes but less than 2 hours after the administering.

In some embodiments, the $C_{max}$ occurs more than 30 minutes but less than 3 hours after the administering.

In some embodiments, the $C_{max}$ occurs more than 30 minutes but less than 6 hours after the administering.

In some embodiments, the $C_{max}$ occurs more than 30 minutes but less than 12 hours after the administering.

In some embodiments, the $C_{max}$ occurs more than 1 hour but less than 2 hours after the administering.

In some embodiments, the $C_{max}$ occurs more than 1 hour but less than 3 hours after the administering.

In some embodiments, the $C_{max}$ occurs more than 1 hour but less than 6 hours after the administering.

In some embodiments, the $C_{max}$ occurs more than 1 hour but less than 12 hours after the administering.

In some embodiments, the $C_{max}$ occurs more than 2 hours but less than 3 hours after the administering.

In some embodiments, the $C_{max}$ occurs more than 2 hours but less than 6 hours after the administering.

In some embodiments, the $C_{max}$ occurs more than 2 hours but less than 12 hours after the administering.

In some embodiments, the $C_{max}$ occurs more than 3 hours but less than 6 hours after the administering.

In some embodiments, the $C_{max}$ occurs more than 3 hours but less than 12 hours after the administering.

In some embodiments, the $C_{max}$ occurs more than 6 hours but less than 12 hours after the administering.

In any of the methods of the present invention, the $C_{max}$ is an average over a plurality of treated individuals.

In some embodiments, the plurality of administrations is at least about 30.

In some embodiments, the plurality of administrations is at least about 180.

In some embodiments, the plurality of administrations is at least about 365.

In some embodiments, the plurality of administrations is at least about 730.

In some embodiments, the method is more efficacious than an immediate-release method for weight management; wherein the immediate-release method for weight management comprises administering to an individual in need thereof, at the frequency, the plurality of administrations of an immediate-release dosage form comprising the therapeutically effective dose of (R)-8-chloro-1-methyl-2,3,4,5-tetrahydro-1H-3-benzazepine or a pharmaceutically acceptable salt, solvate, or hydrate thereof.

In some embodiments, the method is more efficacious than an immediate-release method for weight management; wherein the immediate-release method for weight management comprises administering to an individual in need thereof, an immediate-release dosage form comprising (R)-8-chloro-1-methyl-2,3,4,5-tetrahydro-1H-3-benzazepine or a pharmaceutically acceptable salt, solvate, or hydrate thereof; and wherein the $AUC_{last}$ of (R)-8-chloro-1-methyl-2,3,4,5-tetrahydro-1H-3-benzazepine in the immediate-release method is equal to or greater than the $AUC_{last}$ of (R)-8-chloro-1-methyl-2,3,4,5-tetrahydro-1H-3-benzazepine in the method.

In some embodiments, the weight management comprises weight loss.

In some embodiments, the weight management further comprises maintenance of weight loss.

In some embodiments, the weight management comprises decreased food consumption.

In some embodiments, the weight management comprises increasing meal-related satiety.

In some embodiments, the weight management comprises reducing pre-meal hunger.

In some embodiments, the weight management comprises reducing intra-meal food intake.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index ≥30 $kg/m^2$.

In some embodiments, the individual in need of weight management is an overweight patient with an initial body mass index ≥27 $kg/m^2$ in the presence of at least one weight related comorbid condition.

In some embodiments, the weight related co-morbid condition is selected from: hypertension, dyslipidemia, cardiovascular disease, glucose intolerance, and sleep apnea.

In some embodiments, the method further comprises administering phentermine to the individual.

In some embodiments, the individual in need of weight management has an initial body mass index ≥30 $kg/m^2$.

In some embodiments, the individual in need of weight management has an initial body mass index ≥27 $kg/m^2$.

In some embodiments, the individual in need of weight management has an initial body mass index ≥27 $kg/m^2$ in the presence of at least one weight related comorbid condition.

In some embodiments, the individual in need of weight management has an initial body mass index ≥27 $kg/m^2$ in the presence of at least one weight related comorbid condition selected from: hypertension, dyslipidemia, cardiovascular disease, glucose intolerance, and sleep apnea.

In some embodiments, the individual in need of weight management has an initial body mass index ≥25 $kg/m^2$.

In some embodiments, the individual in need of weight management has an initial body mass index ≥25 $kg/m^2$ in the presence of at least one weight related comorbid condition.

In some embodiments, the individual in need of weight management has an initial body mass index ≥25 $kg/m^2$ in the presence of at least one weight related comorbid condition selected from: hypertension, dyslipidemia, cardiovascular disease, glucose intolerance, and sleep apnea.

In some embodiments, the method for weight management further comprises administering phentermine to the individual.

One aspect of the present invention pertains to methods for the treatment of a disorder related to 5-$HT_{2C}$ receptor activity in an individual, comprising administering to an individual in need thereof, a modified-release dosage form of the present invention.

One aspect of the present invention pertains to methods for the treatment of obesity, comprising administering to an individual in need thereof, a modified-release dosage form of the present invention.

In some embodiments, the method for the treatment of obesity further comprises the administration or prescription of phentermine.

In some embodiments, the method for the treatment of obesity further comprises gastric electrical stimulation.

One aspect of the present invention pertains to methods for inducing weight loss, BMI loss, waist circumference loss or body fat percentage loss, comprising administering to an individual in need thereof, a modified-release dosage form of the present invention.

One aspect of the present invention pertains to methods for inducing weight loss, BMI loss, waist circumference loss or body fat percentage loss in an individual in preparation of the individual for bariatric surgery, comprising administering to an individual in need thereof, a modified-release dosage form of the present invention.

One aspect of the present invention pertains to methods for maintaining weight loss, BMI loss, waist circumference loss or body fat percentage loss in an individual, comprising administering to an individual in need thereof, a modified-release dosage form of the present invention.

One aspect of the present invention pertains to methods for maintaining weight loss, BMI loss, waist circumference loss or body fat percentage loss in an individual following bariatric surgery, comprising administering to an individual in need thereof, a modified-release dosage form of the present invention.

One aspect of the present invention pertains to methods for inducing satiety in an individual, comprising administering to an individual in need thereof, a modified-release dosage form of the present invention.

One aspect of the present invention pertains to methods for decreasing food intake in an individual, comprising administering to an individual in need thereof, a modified-release dosage form of the present invention.

One aspect of the present invention pertains to methods for decreasing hunger in an individual, comprising administering to an individual in need thereof, a modified-release dosage form of the present invention.

One aspect of the present invention pertains to methods for decreasing food cravings in an individual, comprising administering to an individual in need thereof, a modified-release dosage form of the present invention.

One aspect of the present invention pertains to methods for increasing intermeal interval in an individual, comprising administering to an individual in need thereof, a modified-release dosage form of the present invention.

One aspect of the present invention pertains to methods for the treatment of a disorder selected from: schizophrenia, anxiety, depression, psychoses, and alcohol addiction, comprising administering to an individual in need thereof, a modified-release dosage form of the present invention.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

In some embodiments, the modified-release dosage form comprises (R)-8-chloro-1-methyl-2,3,4,5-tetrahydro-1H-3-benzazepine hydrochloride or a pharmaceutically acceptable solvate or hydrate thereof.

In some embodiments, the modified-release dosage form comprises (R)-8-chloro-1-methyl-2,3,4,5-tetrahydro-1H-3-benzazepine hydrochloride salt hemihydrate.

In some embodiments, the modified-release dosage form comprises (R)-8-chloro-1-methyl-2,3,4,5-tetrahydro-1H-3-benzazepine hydrochloride salt hemihydrate, Form III.

In some embodiments, the modified-release dosage form further comprises an excipient selected from: (hydroxypropyl)methyl cellulose, Kollidon® SR, sodium carboxymethyl cellulose, Carbopol®, wax, and xanthan gum.

In some embodiments, the modified-release dosage form further comprises (hydroxypropyl)methyl cellulose.

In some embodiments, the (hydroxypropyl)methyl cellulose comprises Methocel® K4M.

In some embodiments, the modified-release dosage form further comprises one or more ingredients selected from: microcrystalline cellulose, mannitol, and magnesium stearate.

In some embodiments, the modified-release dosage form further comprises a film coating.

In some embodiments, the film coating comprises Opadry® II Blue.

In some embodiments, the film coating comprises ethyl cellulose, Kollicoat® SR30D, Eudragit®, or cellulose acetate.

In some embodiments, the film coating comprises ethyl cellulose.

In some embodiments, the ethyl cellulose comprises Surelease®.

In some embodiments, the film coating further comprises (hydroxypropyl)methyl cellulose.

In some embodiments, the (hydroxypropyl)methyl cellulose comprises Opadry®.

In some embodiments, the ethyl cellulose to the (hydroxypropyl)methyl cellulose is about 75:25.

In some embodiments, the ethyl cellulose to the (hydroxypropyl)methyl cellulose is about 80:20.

In some embodiments, the ethyl cellulose to the (hydroxypropyl)methyl cellulose is about 85:15.

In some embodiments, the modified-release dosage form comprises a core tablet and a coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the coating comprises Opadry® II Blue.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises Opadry® II Blue.

In some embodiments, the modified-release dosage form comprises a core tablet and a coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the coating comprises: ethyl cellulose; and (hydroxypropyl)methyl cellulose.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises: about 85% ethyl cellulose; and about 15% (hydroxypropyl)methyl cellulose.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises: about 75% ethyl cellulose; and about 25% (hydroxypropyl)methyl cellulose.

In some embodiments, the modified-release dosage form has a T80% of at least 3 h.

In some embodiments, the modified-release dosage form has a T80% of at least 6 h.

In some embodiments, the modified-release dosage form has a T80% of at least 9 h.

In some embodiments, the modified-release dosage form has a T80% of at least 12 h.

In some embodiments, the modified-release dosage form comprises a salt selected from:

a pharmaceutically acceptable salt of (R)-8-chloro-1-methyl-2,3,4,5-tetrahydro-1H-3-benzazepine and pharmaceutically acceptable solvates and hydrates thereof, wherein the salt has an aqueous solubility of less than about 200 mg/mL at about room temperature.

In some embodiments, the salt has an aqueous solubility of less than about 100 mg/mL at about room temperature.

In some embodiments, the salt has an aqueous solubility of less than about 50 mg/mL at about room temperature.

In some embodiments, the salt has an aqueous solubility of less than about 25 mg/mL at about room temperature.

In some embodiments, the salt has an aqueous solubility of less than about 10 mg/mL at about room temperature.

In some embodiments, the salt has an aqueous solubility of less than about 5 mg/mL at about room temperature.

In some embodiments, the salt has an aqueous solubility of less than about 200 mg/mL but more than about 0.0001 mg/mL at about room temperature.

In some embodiments, the salt has an aqueous solubility of less than about 100 mg/mL but more than about 0.0001 mg/mL at about room temperature.

In some embodiments, the salt has an aqueous solubility of less than about 50 mg/mL but more than about 0.0001 mg/mL at about room temperature.

In some embodiments, the salt has an aqueous solubility of less than about 25 mg/mL but more than about 0.0001 mg/mL at about room temperature.

In some embodiments, the salt has an aqueous solubility of less than about 10 mg/mL but more than about 0.0001 mg/mL at about room temperature.

In some embodiments, the salt has an aqueous solubility of less than about 5 mg/mL but more than about 0.0001 mg/mL at about room temperature.

In some embodiments, the salt is selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-4-acetamidobenzoate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; (R)-8-chloro-1-methyl-2,3,4,5-tetrahydro-1H-3-benzazepine hemipamoate salt and pharmaceutically acceptable hydrates and solvates thereof.

In some embodiments, the salt is selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; and pharmaceutically acceptable hydrates and solvates thereof.

In some embodiments, the salt is selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

In some embodiments, the salt is selected from: (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

In some embodiments, the salt is (R)-8-chloro-1-methyl-2,3,4,5-tetrahydro-1H-3-benzazepine hydroiodide salt.

In some embodiments, the salt is (R)-8-chloro-1-methyl-2,3,4,5-tetrahydro-1H-3-benzazepine maleate salt.

In some embodiments, the salt is (R)-8-chloro-1-methyl-2,3,4,5-tetrahydro-1H-3-benzazepine fumarate salt.

In some embodiments, the salt is (R)-8-chloro-1-methyl-2,3,4,5-tetrahydro-1H-3-benzazepine hemifumarate salt.

In some embodiments, the salt is (R)-8-chloro-1-methyl-2,3,4,5-tetrahydro-1H-3-benzazepine orotate salt.

In some embodiments, the salt is (R)-8-chloro-1-methyl-2,3,4,5-tetrahydro-1H-3-benzazepine orotate salt hydrate.

In some embodiments, the salt is (R)-8-chloro-1-methyl-2,3,4,5-tetrahydro-1H-3-benzazepine di-4-acetamidobenzoate salt-cocrystal methyl ethyl ketone solvate.

In some embodiments, the salt is (R)-8-chloro-1-methyl-2,3,4,5-tetrahydro-1H-3-benzazepine trans-cinnamate salt.

In some embodiments, the salt is (R)-8-chloro-1-methyl-2,3,4,5-tetrahydro-1H-3-benzazepine heminapadisilate salt.

In some embodiments, the salt is (R)-8-chloro-1-methyl-2,3,4,5-tetrahydro-1H-3-benzazepine heminapadisilate salt solvate 1.

In some embodiments, the salt is (R)-8-chloro-1-methyl-2,3,4,5-tetrahydro-1H-3-benzazepine heminapadisilate salt solvate 2.

In some embodiments, the salt is (R)-8-chloro-1-methyl-2,3,4,5-tetrahydro-1H-3-benzazepine (±)-mandelate salt hydrate.

In some embodiments, the salt is (R)-8-chloro-1-methyl-2,3,4,5-tetrahydro-1H-3-benzazepine hemipamoate salt hydrate.

Adverse Events

The safety of Compound 1 has been evaluated in three randomized, double-blind, placebo-controlled trials, one of 2 years duration ("BLOOM" trial) and two of 1 year duration ("BLOSSOM" and "BLOOM-DM" trials). A total of 3451 patients were exposed to Compound 1 10 mg twice daily for up to 1 year; 571 patients were exposed for up to 2 years; and an additional 896 patients were exposed to Compound 1 10 mg once daily for up to 1 year. The BLOOM-DM study included only patients with type 2 diabetes mellitus; BLOOM and BLOSSOM excluded patients with diabetes.

The discontinuation rate due to adverse reaction was 7.1% for non-diabetic patients and 8.6% for patients with type 2 diabetes receiving Compound 1. The most common adverse reactions leading to discontinuation more often among Compound 1 treated patients than placebo were headache (1.3% vs. 0.8%), depression (0.9% vs. 0.5%) and dizziness (0.7% vs. 0.2%).

Because clinical trials are conducted under widely varying conditions, adverse reaction rates observed in the clinical trials of a drug cannot be directly compared to rates in the clinical trials of another drug and may not reflect the rates observed in practice.

The most common adverse reactions for non-diabetic patients treated with Compound 1 compared to placebo were headache, upper respiratory tract infection, nasopharyngitis, dizziness, and nausea. The most common adverse reactions for diabetic patients were hypoglycemia, headache, back pain, nasopharyngitis, and nausea. Adverse events that were reported by ≥5% of patients and were more frequently reported by patients taking Compound 1 compared to placebo are summarized in Table A (BLOOM and BLOSSOM) and Table B (BLOOM DM).

TABLE A

Adverse Events Reported by ≥5% of Compound 1
Patients and More Commonly than
with Placebo in BLOOM and BLOSSOM

| | Number of patients (%) | |
|---|---|---|
| Adverse Event | Compound 1<br>10 mg BID<br>N = 3195 | Placebo<br>N = 3185 |
| Headache | 537 (16.8) | 321 (10.1) |
| Upper respiratory tract infection | 439 (13.7) | 391 (12.3) |
| Nasopharyngitis | 414 (13.0) | 381 (12.0) |
| Dizziness | 270 (8.5) | 122 (3.8) |
| Nausea | 264 (8.3) | 170 (5.3) |
| Fatigue | 229 (7.2) | 114 (3.6) |
| Urinary tract infection | 207 (6.5) | 171 (5.4) |
| Diarrhea | 207 (6.5) | 179 (5.6) |
| Back pain | 201 (6.3) | 178 (5.6) |
| Constipation | 186 (5.8) | 125 (3.9) |
| Dry mouth | 169 (5.3) | 74 (2.3) |

TABLE B

Adverse Events Reported by ≥5% of Compound 1
Patients and More Commonly than with Placebo
in BLOOM-DM (Patients with Type 2 Diabetes)

| | Number of patients (%) | |
|---|---|---|
| Adverse Event | Compound 1<br>10 mg BID<br>N = 3195 | Placebo<br>N = 3185 |
| Hypoglycemia (including asymptomatic) | 75 (29.3) | 53 (21.0) |
| Headache | 37 (14.5) | 18 (7.1) |
| Back pain | 30 (11.7) | 20 (7.9) |
| Nasopharyngitis | 29 (11.3) | 25 (9.9) |
| Nausea | 24 (9.4) | 20 (7.9) |
| Urinary tract infection | 23 (9.0) | 15 (6.0) |
| Cough | 21 (8.2) | 11 (4.4) |
| Hypoglycemia, symptomatic | 19 (7.4) | 16 (6.3) |
| Fatigue | 19 (7.4) | 10 (4.0) |
| Gastroenteritis viral | 18 (7.0) | 11 (4.4) |
| Dizziness | 18 (7.0) | 16 (6.3) |
| Influenza | 15 (5.9) | 13 (5.2) |
| Procedural pain | 13 (5.1) | 5 (2.0) |
| Hypertension | 13 (5.1) | 8 (3.2) |

One aspect of the present invention pertains to methods of treatment of the present invention wherein the individual to whom the modified-release dosage form of the present invention is administered experiences at least one adverse event selected from the adverse events shown in Table A and Table B.

One aspect of the present invention pertains to methods of treatment of the present invention wherein the individual to whom the salt or a pharmaceutical composition of the present invention is administered experiences at least one adverse event selected from the adverse events shown in Table A and Table B.

One aspect of the present invention pertains to the use of salts or pharmaceutical compositions of the present invention in the manufacture of a medicament for weight management in an individual, wherein the individual to whom the salt or a pharmaceutical composition of the present invention is administered experiences at least one adverse event selected from the adverse events shown in Table A and Table B.

One aspect of the present invention pertains to modified-release dosage forms, salts, or pharmaceutical composition of the present invention for use in a method of treatment, wherein the individual to whom the modified-release dosage form, salt or pharmaceutical composition of the present invention is administered experiences at least one adverse event selected from the adverse events shown in Table A and Table B.

In some embodiments, the adverse event is selected from headache, fatigue, nausea, constipation, dry mouth, and dizziness.

In some embodiments, the adverse event is headache.

In some embodiments, the adverse event is upper respiratory tract infection.

In some embodiments, the adverse event is dizziness.

In some embodiments, the adverse event is nausea.

In some embodiments, the adverse event is fatigue.

In some embodiments, the adverse event is urinary tract infection.

In some embodiments, the adverse event is diarrhea.

In some embodiments, the adverse event is back pain.

In some embodiments, the adverse event is constipation.

In some embodiments, the adverse event is dry mouth.

In some embodiments, the adverse event is nasopharyngitis.

In some embodiments, the adverse event is hypoglycemia (including asymptomatic).

In some embodiments, the adverse event is cough.

In some embodiments, the adverse event is hypoglycemia, symptomatic.

In some embodiments, the adverse event is gastroenteritis viral.

In some embodiments, the adverse event is influenza.

In some embodiments, the adverse event is procedural pain.

In some embodiments, the adverse event is hypertension.

Salts of the Present Invention

The present invention is directed, inter alia, to certain solid, stable, and readily isolable salts of (R)-8-chloro-1-methyl-2,3,4,5-tetrahydro-1H-3-benzazepine and crystalline forms thereof. The solid state properties of the crystalline forms of the present invention are summarized infra.

In the course of preparing the salts of the present invention, many counterions commonly used in the pharmaceutical industry (see e.g. Berge, et al., *Journal of Pharmaceutical Sciences,* 66:1-19 (1977)) were investigated. Acetate, DL-lactate, ascorbate, D-gluconate, besylate, napsylate, tosylate, isethionate, dichloroacetate, benzoate, esylate, gentisate, hippurate, lactobionate, xinafoate, and sebacate salts of (R)-8-chloro-1-methyl-2,3,4,5-tetrahydro-1H-3-benzazepine were prepared, but in contrast to the crystalline salts of the present invention, all of these failed to crystallize One aspect of the present invention pertains to a salt selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-4-acetamidobenzoate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; (R)-8-chloro-1-methyl-2,3,4,5-tetrahydro- 1H-3-benzazepine hemipamoate salt and pharmaceutically acceptable hydrates and solvates thereof.

One aspect of the present invention pertains to a salt selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; and pharmaceutically acceptable hydrates and solvates thereof.

One aspect of the present invention pertains to a salt selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

One aspect of the present invention pertains to (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

One aspect of the present invention pertains to (R)-8-chloro-1-methyl-2,3,4,5-tetrahydro-1H-3-benzazepine hydroiodide salt.

One aspect of the present invention pertains to (R)-8-chloro-1-methyl-2,3,4,5-tetrahydro-1H-3-benzazepine maleate salt.

One aspect of the present invention pertains to (R)-8-chloro-1-methyl-2,3,4,5-tetrahydro-1H-3-benzazepine fumarate salt.

One aspect of the present invention pertains to (R)-8-chloro-1-methyl-2,3,4,5-tetrahydro-1H-3-benzazepine hemifumarate salt.

One aspect of the present invention pertains to (R)-8-chloro-1-methyl-2,3,4,5-tetrahydro-1H-3-benzazepine orotate salt.

One aspect of the present invention pertains to (R)-8-chloro-1-methyl-2,3,4,5-tetrahydro-1H-3-benzazepine orotate salt hydrate.

One aspect of the present invention pertains to (R)-8-chloro-1-methyl-2,3,4,5-tetrahydro-1H-3-benzazepine di-4-acetamidobenzoate salt-cocrystal methyl ethyl ketone solvate.

One aspect of the present invention pertains to (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt.

One aspect of the present invention pertains to (R)-8-chloro-1-methyl-2,3,4,5-tetrahydro-1H-3-benzazepine heminapadisilate salt solvate 1.

One aspect of the present invention pertains to (R)-8-chloro-1-methyl-2,3,4,5-tetrahydro-1H-3-benzazepine heminapadisilate salt solvate 2.

One aspect of the present invention pertains to (R)-8-chloro-1-methyl-2,3,4,5-tetrahydro-1H-3-benzazepine (±)-mandelate salt hydrate.

One aspect of the present invention pertains to (R)-8-chloro-1-methyl-2,3,4,5-tetrahydro-1H-3-benzazepine hemipamoate salt hydrate.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:

(R)-8-chloro-1-methyl-2,3,4,5-tetrahydro-1H-3-benzazepine (1S)-(+)-10-camsylate salt;
(R)-8-chloro-1-methyl-2,3,4,5-tetrahydro-1H-3-benzazepine hemi-L-malate salt;
(R)-8-chloro-1-methyl-2,3,4,5-tetrahydro-1H-3-benzazepine L-glutamate salt;
(R)-8-chloro-1-methyl-2,3,4,5-tetrahydro-1H-3-benzazepine L-aspartate salt;
(R)-8-chloro-1-methyl-2,3,4,5-tetrahydro-1H-3-benzazepine hemimucate salt;
(R)-8-chloro-1-methyl-2,3,4,5-tetrahydro-1H-3-benzazepine pyroglutamate salt;
(R)-8-chloro-1-methyl-2,3,4,5-tetrahydro-1H-3-benzazepine glucuronate salt; and
(R)-8-chloro-1-methyl-2,3,4,5-tetrahydro-1H-3-benzazepine di-camphorate salt;
(R)-8-chloro-1-methyl-2,3,4,5-tetrahydro-1H-3-benzazepine bisulfate salt;
(R)-8-chloro-1-methyl-2,3,4,5-tetrahydro-1H-3-benzazepine hemisulfate salt;
(R)-8-chloro-1-methyl-2,3,4,5-tetrahydro-1H-3-benzazepine mesylate salt;
(R)-8-chloro-1-methyl-2,3,4,5-tetrahydro-1H-3-benzazepine hydrobromide salt;
(R)-8-chloro-1-methyl-2,3,4,5-tetrahydro-1H-3-benzazepine nitrate salt;
(R)-8-chloro-1-methyl-2,3,4,5-tetrahydro-1H-3-benzazepine sesqui-oxalate salt-cocrystal;
(R)-8-chloro-1-methyl-2,3,4,5-tetrahydro-1H-3-benzazepine adipate salt;
(R)-8-chloro-1-methyl-2,3,4,5-tetrahydro-1H-3-benzazepine malonate salt;
(R)-8-chloro-1-methyl-2,3,4,5-tetrahydro-1H-3-benzazepine hemimalonate salt;
(R)-8-chloro-1-methyl-2,3,4,5-tetrahydro-1H-3-benzazepine glycolate salt;
(R)-8-chloro-1-methyl-2,3,4,5-tetrahydro-1H-3-benzazepine hemi-edisylate salt;

(R)-8-chloro-1-methyl-2,3,4,5-tetrahydro-1H-3-benzazepine phosphate salt;
(R)-8-chloro-1-methyl-2,3,4,5-tetrahydro-1H-3-benzazepine citrate salt;
(R)-8-chloro-1-methyl-2,3,4,5-tetrahydro-1H-3-benzazepine hemi-oxalate salt;
(R)-8-chloro-1-methyl-2,3,4,5-tetrahydro-1H-3-benzazepine succinate salt; and
(R)-8-chloro-1-methyl-2,3,4,5-tetrahydro-1H-3-benzazepine oxoglutarate salt; and pharmaceutically acceptable solvates and hydrates thereof.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:
(R)-8-chloro-1-methyl-2,3,4,5-tetrahydro-1H-3-benzazepine (1S)-(+)-10-camsylate salt;
(R)-8-chloro-1-methyl-2,3,4,5-tetrahydro-1H-3-benzazepine hemi-L-malate salt;
(R)-8-chloro-1-methyl-2,3,4,5-tetrahydro-1H-3-benzazepine L-glutamate salt;
(R)-8-chloro-1-methyl-2,3,4,5-tetrahydro-1H-3-benzazepine L-aspartate salt;
(R)-8-chloro-1-methyl-2,3,4,5-tetrahydro-1H-3-benzazepine hemimucate salt;
(R)-8-chloro-1-methyl-2,3,4,5-tetrahydro-1H-3-benzazepine pyroglutamate salt;
(R)-8-chloro-1-methyl-2,3,4,5-tetrahydro-1H-3-benzazepine glucuronate salt;
(R)-8-chloro-1-methyl-2,3,4,5-tetrahydro-1H-3-benzazepine di-camphorate salt solvate;
(R)-8-chloro-1-methyl-2,3,4,5-tetrahydro-1H-3-benzazepine bisulfate salt;
(R)-8-chloro-1-methyl-2,3,4,5-tetrahydro-1H-3-benzazepine hemisulfate salt hydrate;
(R)-8-chloro-1-methyl-2,3,4,5-tetrahydro-1H-3-benzazepine mesylate salt;
(R)-8-chloro-1-methyl-2,3,4,5-tetrahydro-1H-3-benzazepine hydrobromide salt hemihydrate;
(R)-8-chloro-1-methyl-2,3,4,5-tetrahydro-1H-3-benzazepine nitrate salt;
(R)-8-chloro-1-methyl-2,3,4,5-tetrahydro-1H-3-benzazepine sesqui-oxalate salt-cocrystal;
(R)-8-chloro-1-methyl-2,3,4,5-tetrahydro-1H-3-benzazepine adipate salt;
(R)-8-chloro-1-methyl-2,3,4,5-tetrahydro-1H-3-benzazepine malonate salt;
(R)-8-chloro-1-methyl-2,3,4,5-tetrahydro-1H-3-benzazepine hemimalonate salt;
(R)-8-chloro-1-methyl-2,3,4,5-tetrahydro-1H-3-benzazepine glycolate salt;
(R)-8-chloro-1-methyl-2,3,4,5-tetrahydro-1H-3-benzazepine hemi-edisylate salt;
(R)-8-chloro-1-methyl-2,3,4,5-tetrahydro-1H-3-benzazepine phosphate salt;
(R)-8-chloro-1-methyl-2,3,4,5-tetrahydro-1H-3-benzazepine citrate salt hemihydrate;
(R)-8-chloro-1-methyl-2,3,4,5-tetrahydro-1H-3-benzazepine hemi-oxalate salt;
(R)-8-chloro-1-methyl-2,3,4,5-tetrahydro-1H-3-benzazepine succinate salt;
(R)-8-chloro-1-methyl-2,3,4,5-tetrahydro-1H-3-benzazepine oxoglutarate salt; and
(R)-8-chloro-1-methyl-2,3,4,5-tetrahydro-1H-3-benzazepine oxoglutarate salt solvate.

The preceding salts were prepared and characterized using the following experimental procedures and physicochemical data.

(R)-8-Chloro-1-methyl-2,3,4,5-tetrahydro-1H-3-benzazepine (1 S)-(+)-10-camsylate salt was prepared by the dropwise addition of 1 mole equivalent of ~3.6 M aqueous (1S)-(+)-10-camphorsulfonic acid to a solution of (R)-8-chloro-1-methyl-2,3,4,5-tetrahydro-1H-3-benzazepine in acetonitrile with vigorous stirring Immediate precipitation was observed and the solid was collected by filtration and washed with isopropyl alcohol. (R)-8-Chloro-1-methyl-2,3,4,5-tetrahydro-1H-3-benzazepine (1 S)-(+)-10-camsylate salt had an extrapolated melting onset temperature by DSC of about 176° C.

(R)-8-Chloro-1-methyl-2,3,4,5-tetrahydro-1H-3-benzazepine hemi-L-malate salt was prepared by the dropwise addition of L-malic acid (0.5 eq.), either in solution in hot MeOH or as a solid, to a solution of (R)-8-chloro-1-methyl-2,3,4,5-tetrahydro-1H-3-benzazepine in isopropyl acetate. The mixture was heated to ~60° C. and held at that temperature for ~1 h. The mixture was then allowed to cool to room temperature and stirred for 1-3 days. The solid product was isolated by vacuum filtration and dried on the filter or in an oven at 40° C. (R)-8-Chloro-1-methyl-2,3,4,5-tetrahydro-1H-3-benzazepine hemi-L-malate salt had an extrapolated melting onset temperature by DSC of 155-156° C.

(R)-8-Chloro-1-methyl-2,3,4,5-tetrahydro-1H-3-benzazepine L-glutamate salt was prepared by addition of L-glutamic acid (0.5-1 eq.) in hot EtOH/$H_2O$ (~2:1) to a solution of (R)-8-chloro-1-methyl-2,3,4,5-tetrahydro-1H-3-benzazepine in isopropyl acetate, followed by evaporation of the solvent overnight to produce a solid. The solid was slurried in isopropyl acetate and then isolated by filtration. Alternatively, (R)-8-Chloro-1-methyl-2,3,4,5-tetrahydro-1H-3-benzazepine L-glutamate salt was prepared by addition of a solution of L-glutamic acid (1 eq.) in hot $H_2O$ to a solution of (R)-8-chloro-1-methyl-2,3,4,5-tetrahydro-1H-3-benzazepine. The product crystallized without the need for evaporation of the solvent. (R)-8-Chloro-1-methyl-2,3,4,5-tetrahydro-1H-3-benzazepine L-glutamate salt had an extrapolated melting onset temperature by DSC of about 187° C.

(R)-8-Chloro-1-methyl-2,3,4,5-tetrahydro-1H-3-benzazepine L-aspartate salt was prepared by addition of a solution of (R)-8-chloro-1-methyl-2,3,4,5-tetrahydro-1H-3-benzazepine in either acetone or acetonitrile to one equivalent of aspartic acid solid. The mixture was heated to 50° C. then slow-cooled and stirred overnight. (R)-8-Chloro-1-methyl-2,3,4,5-tetrahydro-1H-3-benzazepine L-aspartate salt had an extrapolated melting onset temperature by DSC of about 174° C.

(R)-8-Chloro-1-methyl-2,3,4,5-tetrahydro-1H-3-benzazepine hemimucate salt was synthesized from (R)-8-chloro-1-methyl-2,3,4,5-tetrahydro-1H-3-benzazepine (2 equivalents) and mucic acid (1 equivalent) in THF, acetone or IPA (~10 mg/mL) with 4% water. (R)-8-Chloro-1-methyl-2,3,4,5-tetrahydro-1H-3-benzazepine hemimucate salt had an extrapolated melting onset temperature by DSC of about 208° C.

(R)-8-Chloro-1-methyl-2,3,4,5-tetrahydro-1H-3-benzazepine glucuronate salt was prepared by addition of a molar equivalent of D-glucuronic acid to a solution of (R)-8-chloro-1-methyl-2,3,4,5-tetrahydro-1H-3-benzazepine in isopropanol, acetonitrile, ethyl acetate, or acetone at 60° C. D-glucuronic acid, dissolved in the corresponding solvent at 60° C., was added dropwise with vigorous stirring. Precipitation occurred immediately and the suspension was allowed to cool and stir overnight. The resulting solid was recovered by filtration and dried in a fume hood overnight. (R)-8-Chloro-1-methyl-2,3,4,5-tetrahydro-1H-3-benzazepine glucuronate salt had an extrapolated melting onset temperature by DSC of about 164° C.

(R)-8-Chloro-1-methyl-2,3,4,5-tetrahydro-1H-3-benzazepine pyroglutamate salt was prepared by combining one equivalent of pyroglutamic acid with (R)-8-chloro-1-methyl-2,3,4,5-tetrahydro-1H-3-benzazepine in ethyl acetate at 60° C. then cooling slowly and stirring overnight. The resulting white solid was isolated by filtration and dried. (R)-8-Chloro-1-methyl-2,3,4,5-tetrahydro-1H-3-benzazepine pyroglutamate salt had an extrapolated melting onset temperature by DSC of about 139° C.

(R)-8-Chloro-1-methyl-2,3,4,5-tetrahydro-1H-3-benzazepine di-camphorate salt solvate was prepared by combining equal molar amounts of (R)-8-chloro-1-methyl-2,3,4,5-tetrahydro-1H-3-benzazepine and (1R,3S)-(+)-camphoric acid in ethyl acetate with 4% water. The solution was heated to 50° C. then slowly cooled. Upon cooling the sample was a clear solution and did not change after addition of MTBE. The sample was evaporated to a clear oil which formed a white solid after standing at room temperature. (R)-8-Chloro-1-methyl-2,3,4,5-tetrahydro-1H-3-benzazepine di-camphorate salt had an extrapolated melting onset temperature by DSC of about 90° C.

(R)-8-Chloro-1-methyl-2,3,4,5-tetrahydro-1H-3-benzazepine bisulfate salt was prepared by drop-wise addition of 1 mole equivalent of concentrated sulfuric acid to a solution of (R)-8-chloro-1-methyl-2,3,4,5-tetrahydro-1H-3-benzazepine free base in either isopropyl acetate or acetonitrile with vigorous stirring. Precipitation occurred immediately and the suspension was allowed to stir for 1 to 2 days. The resulting solid was recovered by filtration. (R)-8-Chloro-1-methyl-2,3,4,5-tetrahydro-1H-3-benzazepine bisulfate salt had an extrapolated melting onset temperature by DSC of about 162° C.

(R)-8-Chloro-1-methyl-2,3,4,5-tetrahydro-1H-3-benzazepine hemisulfate salt was prepared by the drop-wise addition of 0.5 mole equivalent of concentrated sulfuric acid to a solution of (R)-8-chloro-1-methyl-2,3,4,5-tetrahydro-1H-3-benzazepine free base in either isopropyl acetate or acetonitrile with vigorous stirring. Precipitation occurred immediately and the suspension was allowed to stir for 1 to 2 days. The resulting yellow solid was recovered by filtration. Acetone was added to the solid followed by sufficient water to cause dispersal (<5%). This mixture was slurried for 4 h and the solid was collected by centrifuge filtration (10,000 rpm for 1 min). The filtrate contained an oil droplet and the filter cake had a small amount of color at the bottom. The white upper portion of the filter cake was removed and air-dried overnight to leave the title salt as a white solid. (R)-8-Chloro-1-methyl-2,3,4,5-tetrahydro-1H-3-benzazepine hemisulfate salt had an extrapolated melting onset temperature by DSC of about 79° C.

(R)-8-Chloro-1-methyl-2,3,4,5-tetrahydro-1H-3-benzazepine mesylate salt was prepared by the dropwise addition of one equivalent of methanesulfonic acid (99.5%) to a solution of (R)-8-chloro-1-methyl-2,3,4,5-tetrahydro-1H-3-benzazepine free base in acetonitrile, or isopropyl acetate with vigorous stirring. Crystallization occurred either immediately or within 24 hours after the solution was heated to ~60° C. and then allowed to cool to RT while stirring. (R)-8-Chloro-1-methyl-2,3,4,5-tetrahydro-1H-3-benzazepine mesylate salt had an extrapolated melting onset temperature by DSC of about 178° C.

(R)-8-Chloro-1-methyl-2,3,4,5-tetrahydro-1H-3-benzazepine hydrobromide salt hemihydrate was prepared by the dropwise addition of one equivalent of aqueous HBr (~48%) to a solution of (R)-8-chloro-1-methyl-2,3,4,5-tetrahydro-1H-3-benzazepine free base in isopropyl acetate, acetonitrile, or ethyl acetate with vigorous stirring. The product readily precipitated from the reaction in isopropyl acetate. In acetonitrile the solvent was evaporated to near dryness to obtain a solid. In ethyl acetate, seeds were added and the reaction was allowed to stir unstoppered to initiate crystallization. The reaction was then closed and stirring was continued to afford a yellow suspension. The suspension was filtered and the solid was washed with cold ethyl acetate. The resulting white solid was under nitrogen at ~38° C., and held overnight at 25° C./75% RH. (R)-8-Chloro-1-methyl-2,3,4,5-tetrahydro-1H-3-benzazepine hydrobromide salt hemihydrate had an extrapolated dehydration onset temperature by TGA of about 72.5° C.

(R)-8-Chloro-1-methyl-2,3,4,5-tetrahydro-1H-3-benzazepine nitrate salt was prepared by dropwise addition of aqueous $HNO_3$ to a solution of (R)-8-chloro-1-methyl-2,3,4,5-tetrahydro-1H-3-benzazepine free base in isopropyl acetate or acetonitrile with vigorous stirring. (R)-8-Chloro-1-methyl-2,3,4,5-tetrahydro-1H-3-benzazepine nitrate salt had an extrapolated melting onset temperature by DSC of about 124° C.

(R)-8-Chloro-1-methyl-2,3,4,5-tetrahydro-1H-3-benzazepine sesqui-oxalate salt-cocrystal was prepared by addition of oxalic acid (0.5 eq.) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine sesqui-oxalate salt-cocrystal had an initial endotherm with an extrapolated onset temperature by DSC of about 105° C. and a second endotherm with an extrapolated melting onset temperature by DSC of about 111° C.

(R)-8-Chloro-1-methyl-2,3,4,5-tetrahydro-1H-3-benzazepine adipate salt was prepared by addition of adipic acid (0.5-1 eq.) in acetone to a solution of (R)-8-chloro-1-methyl-2,3,4,5-tetrahydro-1H-3-benzazepine at ~62° C. Precipitation occurred within 5 min and the suspension was allowed to cool to ambient temperature with stirring. (R)-8-Chloro-1-methyl-2,3,4,5-tetrahydro-1H-3-benzazepine adipate salt had multiple endothermic events by DSC starting at onset temperatures between 104° C. and 107° C.

(R)-8-Chloro-1-methyl-2,3,4,5-tetrahydro-1H-3-benzazepine malonate salt was prepared by addition of malonic acid (1 eq.) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine malonate salt had an extrapolated melting onset temperature by DSC of about 143° C.

(R)-8-Chloro-1-methyl-2,3,4,5-tetrahydro-1H-3-benzazepine hemimalonate salt was prepared by addition of malonic acid (0.5 eq.) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine hemimalonate salt had an extrapolated melting onset temperature by DSC of 135-136° C.

(R)-8-Chloro-1-methyl-2,3,4,5-tetrahydro-1H-3-benzazepine glycolate salt was prepared by the addition of one equivalent of glycolic acid to a solution of (R)-8-chloro-1-methyl-2,3,4,5-tetrahydro-1H-3-benzazepine in ethyl acetate or acetone at 60° C. Glycolic acid, at 60° C., was added dropwise, in the corresponding solvent, with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine glycolate salt had an extrapolated melting onset temperature by DSC of about 138° C.

(R)-8-Chloro-1-methyl-2,3,4,5-tetrahydro-1H-3-benzazepine hemi-edisylate salt was prepared by the dropwise addition of 0.5 equivalents of aqueous 1,2-ethanedisulfonic acid dihydrate (~3.7 M) to a solution of (R)-8-chloro-1-methyl-2,3,4,5-tetrahydro-1H-3-benzazepine free base in either acetonitrile or isopropyl acetate with vigorous stirring Immediate precipitation was observed. The solid obtained was washed with isopropyl alcohol and allowed to dry on the filter. (R)-8-Chloro-1-methyl-2,3,4,5-tetrahydro-1H-3-benzazepine hemi-edisylate salt had an extrapolated melting onset temperature by DSC of about 298° C.

(R)-8-Chloro-1-methyl-2,3,4,5-tetrahydro-1H-3-benzazepine phosphate salt was prepared by dropwise addition of ortho-phosphoric acid (85%) (0.5-1 mole equivalent) to a solution of (R)-8-chloro-1-methyl-2,3,4,5-tetrahydro-1H-3-benzazepine free base in isopropyl acetate or acetonitrile with vigorous stirring Immediate precipitation was observed in all experiments. Initially amorphous material was slurried in acetone; initially crystalline material was slurried/ripened in n-propanol for 3 days. (R)-8-Chloro-1-methyl-2,3,4,5-tetrahydro-1H-3-benzazepine phosphate salt had an extrapolated melting onset temperature by DSC of about 208° C.

(R)-8-Chloro-1-methyl-2,3,4,5-tetrahydro-1H-3-benzazepine citrate salt hemihydrate was prepared by dropwise addition of 1 mole equivalent of citric acid in hot MeOH to a solution of (R)-8-chloro-1-methyl-2,3,4,5-tetrahydro-1H-3-benzazepine in isopropyl acetate. Precipitation occurred spontaneously. (R)-8-Chloro-1-methyl-2,3,4,5-tetrahydro-1H-3-benzazepine citrate salt hemihydrate had a dehydration onset temperature by DSC of about 80° C.

(R)-8-Chloro-1-methyl-2,3,4,5-tetrahydro-1H-3-benzazepine hemi-oxalate salt was prepared by dropwise addition of 1 mole equivalent of oxalic acid as a solid or as a solution in MeOH (~2.5 M) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine hemi-oxalate salt had an extrapolated melting onset temperature by DSC of about 212° C.

(R)-8-Chloro-1-methyl-2,3,4,5-tetrahydro-1H-3-benzazepine succinate salt was prepared by the addition of succinic acid (0.5-1 eq.) in hot EtOH to a solution of (R)-8-chloro-1-methyl-2,3,4,5-tetrahydro-1H-3-benzazepine in isopropyl acetate. After overnight stirring, a solid was recovered by suction filtration and washed in isopropyl acetate. (R)-8-Chloro-1-methyl-2,3,4,5-tetrahydro-1H-3-benzazepine succinate salt had an extrapolated melting onset temperature by DSC of about 179.1° C.

(R)-8-Chloro-1-methyl-2,3,4,5-tetrahydro-1H-3-benzazepine oxoglutarate salt was prepared by addition of one equivalent of α-oxo-glutaric acid to a solution of (R)-8-chloro-1-methyl-2,3,4,5-tetrahydro-1H-3-benzazepine in ethyl acetate at 60° C. α-Oxo-glutaric acid in ethyl acetate at 60° C. was added dropwise with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine oxoglutarate salt had an extrapolated melting onset temperature by DSC of about 115° C.

(R)-8-Chloro-1-methyl-2,3,4,5-tetrahydro-1H-3-benzazepine oxoglutarate salt solvate was prepared by addition of a molar equivalent of α-oxo-glutaric acid to a solution of (R)-8-chloro-1-methyl-2,3,4,5-tetrahydro-1H-3-benzazepine in acetonitrile at 60° C. α-Oxo-glutaric acid in acetonitrile at 60° C. was added dropwise with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine oxoglutarate salt solvate had an extrapolated desolvation onset temperature by DSC of about 91° C., and a second endotherm with an extrapolated onset temperature by DSC of about 113° C.

One aspect of the present invention pertains to methods for weight management comprising administering to an individual in need thereof, a therapeutically effective amount of a salt of the present invention.

One aspect of the present invention pertains to uses of salts or pharmaceutical compositions of the present invention, in the manufacture of a medicament for weight management in an individual.

In some embodiments, the weight management comprises one or more of: weight loss, and maintenance of weight loss.

In some embodiments, the weight management comprises one or more of: weight loss, maintenance of weight loss, decreased food consumption, increasing meal-related satiety, reducing pre-meal hunger, and reducing intra-meal food intake.

In some embodiments, the medicament is used as an adjunct to diet and exercise.

In some embodiments, the individual in need of weight management is selected from: an obese patient with an initial body mass index ≥30 kg/m², an overweight patient with an initial body mass index ≥27 kg/m² in the presence of at least one weight related comorbid condition; and an overweight patient with an initial body mass index ≥27 kg/m² in the presence of at least one weight related comorbid condition; wherein the weight related co-morbid condition is selected from: hypertension, dyslipidemia, cardiovascular disease, glucose intolerance, and sleep apnea.

In some embodiments, the medicament is used in a method of the present invention.

In some embodiments, the medicament is a modified-release dosage form of the present invention.

In some embodiments, the medicament is used in combination with a second anti-obesity agent.

In some embodiments, the second anti-obesity agent is selected from: chlorphentermine, clortermine, phenpentermine, and phentermine, and pharmaceutically acceptable salts, solvates, and hydrates thereof.

In some embodiments, the medicament is used in combination with an anti-diabetes agent.

In some embodiments, the medicament is used in combination with metformin.

One aspect of the present invention pertains to the use of salts of the present invention in the manufacture of a medicament for weight management in an individual.

One aspect of the present invention pertains to salts of the present invention for use in a method of treatment of the human or animal body by therapy.

One aspect of the present invention pertains to salts of the present invention for use in a method of weight management.

One aspect of the present invention pertains to salts of the present invention for use in a method of weight loss.

One aspect of the present invention pertains to salts of the present invention for use in a method of maintenance of weight loss.

One aspect of the present invention pertains to salts of the present invention for use in a method of decreasing food consumption One aspect of the present invention pertains to salts of the present invention for use in a method of increasing meal-related satiety.

One aspect of the present invention pertains to salts of the present invention for use in a method of reducing pre-meal hunger.

One aspect of the present invention pertains to salts of the present invention for use in a method of reducing intra-meal food intake.

One aspect of the present invention pertains to salts of the present invention for use in a method of weight management further comprising a reduced-calorie diet.

One aspect of the present invention pertains to salts of the present invention for use in a method of weight management further comprising a program of regular exercise.

One aspect of the present invention pertains to salts of the present invention for use in a method of weight management further comprising a reduced-calorie diet and a program of regular exercise.

One aspect of the present invention pertains to salts of the present invention for use in a method of weight management in an obese patient with an initial body mass index ≥30 $kg/m^2$.

One aspect of the present invention pertains to salts of the present invention for use in a method of weight management in an overweight patient with an initial body mass index ≥27 $kg/m^2$ in the presence of at least one weight related co-morbid condition.

One aspect of the present invention pertains to salts of the present invention for use in a method of weight management in an overweight patient with an initial body mass index ≥27 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention for use in a method of weight management in a patient with an initial body mass index ≥30 $kg/m^2$.

One aspect of the present invention pertains to salts of the present invention for use in a method of weight management in a patient with an initial body mass index ≥27 $kg/m^2$.

One aspect of the present invention pertains to salts of the present invention for use in a method of weight management in a patient with an initial body mass index ≥27 $kg/m^2$ in the presence of at least one weight related co-morbid condition.

One aspect of the present invention pertains to salts of the present invention for use in a method of weight management in a patient with an initial body mass index ≥27 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention for use in a method of weight management in a patient with an initial body mass index ≥25 $kg/m^2$.

One aspect of the present invention pertains to salts of the present invention for use in a method of weight management in a patient with an initial body mass index ≥25 $kg/m^2$ in the presence of at least one weight related co-morbid condition.

One aspect of the present invention pertains to salts of the present invention for use in a method of weight management in a patient with an initial body mass index ≥25 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention for use in a method of weight management in combination with phentermine.

Formulation

For oral drug products, the dosing frequency can be reduced by designing a formulation that reduces the drug-release rate and thereby the rate of input of the drug into systemic circulation in order to produce the desired pharmacokinetic profile. In addition to improving patients' compliance, such modified-release dosage forms offer the advantages of enhancing therapeutic efficacy, reducing adverse effects, and enabling product differentiation. Therefore, over the past few decades, modified-release technology has been increasingly used in clinical development as an enabling technology for drug-candidate progression. It has been reported that patients' adherence to the prescribed dosing regimen is inversely related to the dosing frequency, especially for the management of chronic diseases (Saini S. D. et al. Effect Of Medication Dosing Frequency On Adherence In Chronic Diseases. *Am. J. Managed Care.* 2009; 15(6):e22-e33).

Commonly used and commercially viable modified-release technologies include hydrophilic/hydrophobic matrices; polymer-coated pellets and beads pre-loaded with API; and multilayer tablets. Osmotic pump tablets can achieve much more consistent pump-like release profiles. These may use POLYOX™ (The Dow Chemical Company) in the drug layer and push layer and may be coated with cellulose acetate and PEG.

Drug release from these technologies is controlled by one or a combination of the following mechanisms: diffusion (through the pores of a barrier coating layer or a viscous gel layer of entangled polymer chains), osmosis, and polymer swelling/erosion. Each technology is different with regard to the in vivo performance, release-controlling mechanism, development time and cost, manufacturability, applicability to the inherent biopharmaceutical properties of the API. Selection of modified-release technology for a particular drug will depend on the dose, solubility, pharmacokinetics, desired in vitro release profile, as well as clinical and marketing requirements (e.g., dosage form type, size, number of strengths).

Pharmacokinetics simulation can be used in the design and assessment of modified-release formulation development. If the therapeutic dose and human pharmacokinetics parameters are available for the drug molecule of interest, the release profile from modified-release formulation can be projected through simulation, which facilitates the selection of modified-release delivery technology, formulation, and expected release profile.

Hydrophilic Swelling Excipients

Among the modified-release technologies, the hydrophilic polymer matrix is especially widely used due to the thorough understanding of its release-control mechanism, robust formulation, conventional manufacturing process, availability of a wide range of polymers, and flexibility to tailor desired release profiles. Commonly used polymers include HPMC, high-molecular weight polyethylene oxides, polyvinylpyrrolidone, and polysaccharides of natural origin such as xanthan gum and locust bean gum.

Typically, a hydrophilic polymer matrix system consists of drug, rate-controlling polymers, and other excipients which are homogenously mixed and compressed into a tablet. Upon exposure to aqueous medium, the polymer becomes hydrated and forms a gel layer on the periphery of the tablet which modulates further water penetration and subsequent drug diffusion and release. It has been demonstrated that the drug release rate and kinetics are predominantly dependent on the rate of gel formation and erosion, gel layer thickness and strength, the solubility of added excipients, as well as the solubility of the drug to be delivered. (Siepmann J. and Peppas N. A., Modeling Of Drug Release From Delivery Systems Based On Hydroxypropyl Methylcellulose (HPMC). *Adv. Drug Deliv. Rev.,* 2001; 48, 139-157). Drug release from HMPC tablets is controlled by diffusion through the gel layer surrounding the tablet. The gel layer thickness and strength are determined by the viscosity and concentration of HPMC. Increase in HPMC level leads to the formation of a stronger gel layer, thus retarding water ingress and drug diffusion.

Tablet Coating

When exposed to aqueous medium, water penetration into hydrophilic polymer matrix tablets is modulated only by swelling of the hydrophilic polymer. The release of highly soluble APIs may not be adequately controlled by the swelling and diffusion mechanism alone. An additional mechanism may be needed to restrict water ingress into the tablet and subsequent diffusion of the API. Commonly used strategies include compression coating, multilayer tablet, and functional film coating (such as enteric coating, insoluble coating, and pH-dependent polymer coating).

Functional film coating offers the advantages of robust formulation and processing, proven in vivo performance in other commercial products (e.g., Wellbutrin XL®). The coating regulates water penetration, core tablet hydration, and API diffusion. Additives such as low-viscosity HPMC can be added to the coating as pore former. The additive dissolves and leaches out of the coating membrane when exposed to aqueous media, thus generating pores in the coating membrane. These pores allow water to penetrate through the coating and be in contact with the core tablet.

API Solubility

For active pharmaceutical ingredients (APIs) having more than adequate aqueous solubility throughout the GI-tract pH range, dissolution of the API inside a modified-release dosage form will be rapid, per the Noyes-Whitney equation:

$$\frac{dW}{dt} = \frac{DA(C_s - C)}{L}$$

where $dW/dt$ is the dissolution rate (mg/s); D is the diffusion coefficient (cm$^2$/s); A is the surface area of the API (cm$^2$); $C_s$ is the saturated concentration (or solubility) in the diffusion layer around the API; C is the bulk solvent concentration (mg/mL); and L is the diffusion layer thickness (cm). For permeable drugs, $C_s \gg C$, since drug molecules that diffuse into the GI bulk media are rapidly absorbed. In this case, C can be ignored in the Noyes-Whitney equation and dissolution rate becomes proportional to the solubility of the API.

Salt forms with high aqueous solubility may be used in modified-release dosage forms when formulated with a hydrophilic swelling excipient. A polymer coating may also be used to further modify the release of the API from these dosage forms.

In order to develop modified-release formulations of Compound 1 that do not rely on hydrophilic swelling and/or functional film coating, there is a need for new salt forms with low aqueous solubility.

Immediate Release Tablets

An immediate-release, film-coated 10-mg tablet was developed for the phase 3 clinical trials and commercialization of Compound 1 (Example 5). The solubility of the API in the immediate release tablets, Compound 1, hydrochloride salt hemihydrate, Form III (as described below), exceeds 400 mg/mL in the pH range of 1 to 7, and is classified under the Biopharmaceutics Classification System as "highly soluble". A drug substance is considered highly soluble when the highest dose strength is soluble in 250 mL or less of aqueous media over the pH range of 1-7.5. Compound 1, hydrochloride salt hemihydrate, Form III is further classified under the Biopharmaceutics Classification System as "highly permeable". In the absence of evidence suggesting instability in the gastrointestinal tract, a drug substance is considered to be highly permeable when the extent of absorption in humans is determined to be 90% or more of an administered dose based on a mass balance determination or in comparison to an intravenous reference dose.

The value of $C_{max}$ (peak plasma concentration) from the modified-release formulation should not exceed that of the immediate-release 10-mg tablet twice daily (b.i.d.), a formulation for which safety has been established in phase 3 clinical trials. Release from the modified-release formulation should be the limiting step for its absorption.

One aspect of the present invention pertains to modified-release dosage forms comprising a therapeutically effective amount of (R)-8-chloro-1-methyl-2,3,4,5-tetrahydro-1H-3-benzazepine or a pharmaceutically acceptable salt, solvate, or hydrate thereof.

In some embodiments, the modified-release dosage form is a tablet.

In some embodiments, the modified-release dosage form is for use in a method of weight management in an individual.

In some embodiments, the method comprises a plurality of administrations of the modified-release dosage form, with a frequency wherein the average interval between any two sequential the administrations is: at least about 24 hours; or about 24 hours.

In some embodiments, the plurality of administrations is: at least about 30; at least about 180; at least about 365; or at least about 730.

In some embodiments, the method is more efficacious than an immediate-release method for weight management; wherein the immediate-release method for weight management comprises administering to an individual in need thereof, at the frequency, the plurality of administrations of an immediate-release dosage form comprising the therapeutically effective amount of (R)-8-chloro-1-methyl-2,3,4,5-tetrahydro-1H-3-benzazepine or a pharmaceutically acceptable salt, solvate, or hydrate thereof.

In some embodiments, the method is more efficacious than an immediate-release method for weight management; wherein the immediate-release method for weight management comprises administering to an individual in need thereof, an immediate-release dosage form comprising (R)-8-chloro-1-methyl-2,3,4,5-tetrahydro-1H-3-benzazepine or a pharmaceutically acceptable salt, solvate, or hydrate thereof; and wherein the total plasma exposure of the individual to (R)-8-chloro-1-methyl-2,3,4,5-tetrahydro-1H-3-benzazepine over the course of the immediate-release method is equal to or greater than the total plasma exposure of the individual to (R)-8-chloro-1-methyl-2,3,4,5-tetrahydro-1H-3-benzazepine over the course of the method.

In some embodiments, the plasma concentration of the (R)-8-chloro-1-methyl-2,3,4,5-tetrahydro-1H-3-benzazepine in the individual has a $C_{max}$ of: less than about 60 ng/mL; less than about 40 ng/mL; less than about 20 ng/mL; or less than about 10 ng/mL.

In some embodiments, the $C_{max}$ divided by the therapeutically effective amount is equal to: less than about $1\times10^{-5}$ mL$^{-1}$; less than about $5\times10^{-6}$ mL$^{-1}$; less than about $1\times10^{-6}$ mL$^{-1}$; or less than about $5\times10^{-7}$ mL$^{-1}$.

In some embodiments, the $C_{max}$ occurs: more than 30 minutes after the administering; more than 1 hour after the administering; or more than 2 hours after the administering.

In some embodiments, the $C_{max}$ occurs: more than 3 hours after the administering; more than 6 hours after the administering; or more than 12 hours after the administering.

In some embodiments, the average peak to trough ratio of the plasma concentration of the (R)-8-chloro-1-methyl-2,3,4,5-tetrahydro-1H-3-benzazepine in the individual is: less than about 3:1; less than about 2:1; less than about 1.5:1; or less than about 1.1:1.

In some embodiments, the modified-release dosage form comprises a salt selected from: (R)-8-chloro-1-methyl-2,3,4,5-tetrahydro-1H-3-benzazepine hydrochloride and pharmaceutically acceptable solvates and hydrates thereof.

In some embodiments, the salt is (R)-8-chloro-1-methyl-2,3,4,5-tetrahydro-1H-3-benzazepine hydrochloride salt hemihydrate, Form III.

In some embodiments, the modified-release dosage form further comprises (hydroxypropyl)methyl cellulose.

In some embodiments, the modified-release dosage form further comprises one or more ingredients selected from: microcrystalline cellulose, mannitol, and magnesium stearate.

In some embodiments, the modified-release dosage form further comprises a film coating.

In some embodiments, the film coating comprises a water-soluble film coating.

In some embodiments, the film coating comprises ethyl cellulose.

In some embodiments, the film coating further comprises (hydroxypropyl)methyl cellulose.

In some embodiments, the ratio of the ethyl cellulose to the (hydroxypropyl)methyl cellulose is: about 75:25; about 80:20; or about 85:15.

In some embodiments, the modified-release dosage form comprises a core tablet and a film coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the film coating comprises a water-soluble film coating.

In some embodiments, the modified-release dosage form comprises a core tablet and a film coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the film coating comprises a water-soluble film coating.

In some embodiments, the modified-release dosage form comprises a core tablet and a film coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the film coating comprises: ethyl cellulose; and (hydroxypropyl)methyl cellulose.

In some embodiments, the modified-release dosage form comprises a core tablet and a film coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; the film coating comprises: about 85% ethyl cellulose; and about 15% (hydroxypropyl)methyl cellulose; or about 75% ethyl cellulose; and about 25% (hydroxypropyl)methyl cellulose.

In some embodiments, the modified-release dosage form has a T80% of: at least 3 h; at least 6 h; at least 9 h; or at least 12 h.

In some embodiments, the modified-release dosage form comprises a salt selected from: a pharmaceutically acceptable salt of (R)-8-chloro-1-methyl-2,3,4,5-tetrahydro-1H-3-benzazepine and pharmaceutically acceptable solvates and hydrates thereof, and wherein the salt has an aqueous solubility of: less than about 200 mg/mL at about room temperature; less than about 100 mg/mL at about room temperature; less than about 50 mg/mL at about room temperature; less than about 25 mg/mL at about room temperature; less than about 10 mg/mL at about room temperature; or less than about 5 mg/mL at about room temperature.

In some embodiments, the modified-release dosage form comprises a salt selected from: (R)-8-chloro-1-methyl-2,3,4,5-tetrahydro-1H-3-benzazepine hydroiodide salt; (R)-8-chloro-1-methyl-2,3,4,5-tetrahydro-1H-3-benzazepine maleate salt; (R)-8-chloro-1-methyl-2,3,4,5-tetrahydro-1H-3-benzazepine fumarate salt; and (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-acetamidobenzoate salt-cocrystal; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; and (R)-8-chloro-1-methyl-2,3,4,5-tetrahydro-1H-3-benzazepine hemipamoate salt; and pharmaceutically acceptable solvates and hydrates thereof.

One aspect of the present invention pertains to modified-release dosage forms comprising a therapeutically effective dose of (R)-8-chloro-1-methyl-2,3,4,5-tetrahydro-1H-3-benzazepine or a pharmaceutically acceptable salt, solvate, or hydrate thereof.

One aspect of the present invention pertains to modified-release dosage forms comprising a therapeutically effective dose of (R)-8-chloro-1-methyl-2,3,4,5-tetrahydro-1H-3-benzazepine or a pharmaceutically acceptable salt, solvate, or hydrate thereof, for use in a method of weight management in an individual.

One aspect of the present invention pertains to modified-release dosage forms comprising a therapeutically effective amount of (R)-8-chloro-1-methyl-2,3,4,5-tetrahydro-1H-3-benzazepine or a pharmaceutically acceptable salt, solvate, or hydrate thereof.

In some embodiments, the modified-release dosage form is a tablet.

In some embodiments, the method comprises a plurality of administrations of the modified-release dosage form, with a frequency wherein the average interval between any two sequential administrations is at least about 24 hours.

In some embodiments, the method comprises a plurality of administrations of the modified-release dosage form, with a frequency wherein the average interval between any two sequential administrations is about 24 hours.

In some embodiments, the plasma concentration of the (R)-8-chloro-1-methyl-2,3,4,5-tetrahydro-1H-3-benzazepine in the individual has a $C_{max}$ of less than about 60 ng/mL.

In some embodiments, the plasma concentration of the (R)-8-chloro-1-methyl-2,3,4,5-tetrahydro-1H-3-benzazepine in the individual has a $C_{max}$ of less than about 40 ng/mL.

In some embodiments, the plasma concentration of the (R)-8-chloro-1-methyl-2,3,4,5-tetrahydro-1H-3-benzazepine in the individual has a $C_{max}$ of less than about 20 ng/mL.

In some embodiments, the plasma concentration of the (R)-8-chloro-1-methyl-2,3,4,5-tetrahydro-1H-3-benzazepine in the individual has a $C_{max}$ of less than about 10 ng/mL.

In some embodiments, the $C_{max}$ divided by the therapeutically effective amount is equal to less than about $1 \times 10^{-5}$ mL$^{-1}$.

In some embodiments, the $C_{max}$ divided by the therapeutically effective amount is equal to less than about $5 \times 10^{-6}$ mL$^{-1}$.

In some embodiments, the $C_{max}$ divided by the therapeutically effective amount is equal to less than about $1 \times 10^{-6}$ mL$^{-1}$.

In some embodiments, the $C_{max}$ divided by the therapeutically effective amount is equal to less than about $5 \times 10^{-7}$ mL$^{-1}$.

In some embodiments, the plasma concentration of the (R)-8-chloro-1-methyl-2,3,4,5-tetrahydro-1H-3-benzazepine in the individual has a $AUC_{last}$ of at least about $1 \times 10^{-3}$ h·µg/mL.

In some embodiments, the plasma concentration of the (R)-8-chloro-1-methyl-2,3,4,5-tetrahydro-1H-3-benzazepine in the individual has a $AUC_{last}$ of at least about $1 \times 10^{-2}$ h·µg/mL.

In some embodiments, the plasma concentration of the (R)-8-chloro-1-methyl-2,3,4,5-tetrahydro-1H-3-benzazepine in the individual has a $AUC_{last}$ of at least about 0.1 h·µg/mL.

In some embodiments, the plasma concentration of the (R)-8-chloro-1-methyl-2,3,4,5-tetrahydro-1H-3-benzazepine in the individual has a $AUC_{last}$ of at least about 1 h·µg/mL. In some embodiments, the plasma concentration of the (R)-8-chloro-1-methyl-2,3,4,5-tetrahydro-1H-3-benzazepine in the individual has a $AUC_{last}$ of at least about 10 h·µg/mL.

In some embodiments, the plasma concentration of the (R)-8-chloro-1-methyl-2,3,4,5-tetrahydro-1H-3-benzazepine in the individual has a $AUC_{last}$ of at least about 100 h·µg/mL.

In any of the methods of the present invention, the $AUC_{last}$ is an average over a plurality of treated individuals.

In some embodiments, the $AUC_{last}$ divided by the therapeutically effective amount is equal to at least about $1 \times 10^{-6}$ h/mL.

In some embodiments, the $AUC_{last}$ divided by the therapeutically effective amount is equal to at least about $1 \times 10^{-5}$ h/mL.

In some embodiments, the $AUC_{last}$ divided by the therapeutically effective amount is equal to at least about $1 \times 10^{-4}$ h/mL.

In some embodiments, the $AUC_{last}$ divided by the therapeutically effective amount is equal to at least about $1 \times 10^{-3}$ h/mL.

In some embodiments, the $AUC_{last}$ divided by the therapeutically effective amount is equal to at least about $1 \times 10^{-2}$ h/mL.

In some embodiments, the $AUC_{last}$ divided by the $C_{max}$ is equal to at least about 5 h.

In some embodiments, the $AUC_{last}$ divided by the $C_{max}$ is equal to at least about 10 h.

In some embodiments, the $AUC_{last}$ divided by the $C_{max}$ is equal to at least about 15 h.

In some embodiments, the $AUC_{last}$ divided by the $C_{max}$ is equal to at least about 25 h.

In some embodiments, the administering results in a $C_{min}$ of at least about 5 ng/mL and a $C_{max}$ of less than about 60.

In some embodiments, the administering results in a $C_{min}$ of at least about 5 ng/mL and a $C_{max}$ of less than about 40 ng/mL.

In some embodiments, the administering results in a $C_{min}$ of at least about 5 ng/mL and a $C_{max}$ of less than about 20 ng/mL.

In some embodiments, the administering results in a $C_{min}$ of at least about 5 ng/mL and a $C_{max}$ of less than about 10 ng/mL.

In some embodiments $C_{min}$ and $C_{max}$ are averages over a plurality of treated individuals.

In some embodiments, the average peak to trough ratio of the plasma concentration of the (R)-8-chloro-1-methyl-2,3,4,5-tetrahydro-1H-3-benzazepine in the individual is less than about 3:1.

In some embodiments, the average peak to trough ratio of the plasma concentration of the (R)-8-chloro-1-methyl-2,3,4,5-tetrahydro-1H-3-benzazepine in the individual is less than about 2:1.

In some embodiments, the average peak to trough ratio of the plasma concentration of the (R)-8-chloro-1-methyl-2,3,4,5-tetrahydro-1H-3-benzazepine in the individual is less than about 1.5:1.

In some embodiments, the average peak to trough ratio of the plasma concentration of the (R)-8-chloro-1-methyl-2,3,4,5-tetrahydro-1H-3-benzazepine in the individual is less than about 1.1:1.

In any of the methods of the present invention, the peak to trough ratio of the plasma concentration of the (R)-8-chloro-1-methyl-2,3,4,5-tetrahydro-1H-3-benzazepine is an average over a plurality of treated individuals.

In some embodiments, the $C_{max}$ occurs more than 30 minutes after the administering.

In some embodiments, the $C_{max}$ occurs more than 1 hour after the administering.

In some embodiments, the $C_{max}$ occurs more than 2 hours after the administering.

In any of the methods of the present invention, the $C_{max}$ is an average over a plurality of treated individuals.

In some embodiments, the plurality of administrations is at least about 30.

In some embodiments, the plurality of administrations is at least about 180.

In some embodiments, the plurality of administrations is at least about 365.

In some embodiments, the plurality of administrations is at least about 730.

In some embodiments, the method is more efficacious than an immediate-release method for weight management; wherein the immediate-release method for weight management comprises administering to an individual in need thereof, at the frequency, the plurality of administrations of an immediate-release dosage form comprising the therapeutically effective dose of (R)-8-chloro-1-methyl-2,3,4,5-tetrahydro-1H-3-benzazepine or a pharmaceutically acceptable salt, solvate, or hydrate thereof.

In some embodiments, the method is more efficacious than an immediate-release method for weight management; wherein the immediate-release method for weight management comprises administering to an individual in need thereof, an immediate-release dosage form comprising (R)-8-chloro-1-methyl-2,3,4,5-tetrahydro-1H-3-benzazepine or a pharmaceutically acceptable salt, solvate, or hydrate thereof; and wherein the $AUC_{last}$ of (R)-8-chloro-1-methyl-2,3,4,5-tetrahydro-1H-3-benzazepine in the immediate-release method is equal to or greater than the $AUC_{last}$ of (R)-8-chloro-1-methyl-2,3,4,5-tetrahydro-1H-3-benzazepine in the method.

In some embodiments, the weight management comprises weight loss.

In some embodiments, the weight management further comprises maintenance of weight loss.

In some embodiments, the weight management further comprises decreasing food consumption In some embodiments, the weight management further comprises increasing meal-related satiety.

In some embodiments, the weight management further comprises reducing pre-meal hunger.

In some embodiments, the weight management further comprises reducing intra-meal food intake.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index $\geq 30$ kg/m$^2$.

In some embodiments, the individual in need of weight management is an overweight patient with an initial body mass index $\geq 27$ kg/m$^2$ in the presence of at least one weight related comorbid condition.

In some embodiments, the weight related co-morbid condition is selected from: hypertension, dyslipidemia, cardiovascular disease, glucose intolerance, and sleep apnea.

In some embodiments, the individual in need of weight management has an initial body mass index $\geq 30$ kg/m$^2$.

In some embodiments, the individual in need of weight management has an initial body mass index $\geq 27$ kg/m$^2$.

In some embodiments, the individual in need of weight management has an initial body mass index $\geq 27$ kg/m$^2$ in the presence of at least one weight related comorbid condition.

In some embodiments, the individual in need of weight management has an initial body mass index $\geq 27$ kg/m$^2$ in the presence of at least one weight related comorbid condition selected from: hypertension, dyslipidemia, cardiovascular disease, glucose intolerance, and sleep apnea.

In some embodiments, the individual in need of weight management has an initial body mass index $\geq 25$ kg/m$^2$.

In some embodiments, the individual in need of weight management has an initial body mass index $\geq 25$ kg/m$^2$ in the presence of at least one weight related comorbid condition.

In some embodiments, the individual in need of weight management has an initial body mass index $\geq 25$ kg/m$^2$ in the presence of at least one weight related comorbid condition selected from: hypertension, dyslipidemia, cardiovascular disease, glucose intolerance, and sleep apnea.

In some embodiments, the method for weight management further comprises administering phentermine to the individual.

One aspect of the present invention pertains to modified-release dosage forms of the present invention, for use in a method of treatment of a disorder related to 5-HT$_{2C}$ receptor activity in an individual.

One aspect of the present invention pertains to modified-release dosage forms of the present invention, for use in a method of treatment of obesity in an individual.

In some embodiments, the method for the treatment of obesity further comprises the administration or prescription of phentermine.

In some embodiments, the method for the treatment of obesity further comprises gastric electrical stimulation.

One aspect of the present invention pertains to modified-release dosage forms of the present invention, for use in a method for inducing weight loss, BMI loss, waist circumference loss or body fat percentage loss in an individual.

One aspect of the present invention pertains to modified-release dosage forms of the present invention, for use in a method for inducing weight loss, BMI loss, waist circumference loss or body fat percentage loss in an individual in preparation of the individual for bariatric surgery.

One aspect of the present invention pertains to modified-release dosage forms of the present invention, for use in a method for maintaining weight loss, BMI loss, waist circumference loss or body fat percentage loss in an individual.

One aspect of the present invention pertains to modified-release dosage forms of the present invention, for use in a method for maintaining weight loss, BMI loss, waist circumference loss or body fat percentage loss in an individual following bariatric surgery.

One aspect of the present invention pertains to modified-release dosage forms of the present invention, for use in a method for inducing satiety in an individual.

One aspect of the present invention pertains to modified-release dosage forms of the present invention, for use in a method for decreasing food intake in an individual.

One aspect of the present invention pertains to modified-release dosage forms of the present invention, for use in a method for decreasing hunger in an individual.

One aspect of the present invention pertains to modified-release dosage forms of the present invention, for use in a method for decreasing food cravings in an individual.

One aspect of the present invention pertains to modified-release dosage forms of the present invention, for use in a method for increasing intermeal interval in an individual.

One aspect of the present invention pertains to modified-release dosage forms of the present invention, for use in a method for the treatment of a disorder selected from: schizophrenia, anxiety, depression, psychoses, and alcohol addiction in an individual.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

In some embodiments, the modified-release dosage form comprises (R)-8-chloro-1-methyl-2,3,4,5-tetrahydro-1H-3-benzazepine hydrochloride or a pharmaceutically acceptable solvate or hydrate thereof.

In some embodiments, the modified-release dosage form comprises (R)-8-chloro-1-methyl-2,3,4,5-tetrahydro-1H-3-benzazepine hydrochloride salt hemihydrate.

In some embodiments, the modified-release dosage form comprises (R)-8-chloro-1-methyl-2,3,4,5-tetrahydro-1H-3-benzazepine hydrochloride salt hemihydrate, Form III.

In some embodiments, the modified-release dosage form further comprises an excipient selected from: (hydroxypropyl)methyl cellulose, Kollidon® SR, sodium carboxymethyl cellulose, Carbopol®, wax, and xanthan gum.

In some embodiments, the modified-release dosage form further comprises (hydroxypropyl)methyl cellulose.

In some embodiments, the (hydroxypropyl)methyl cellulose comprises Methocel® K4M.

In some embodiments, the modified-release dosage form further comprises one or more ingredients selected from: microcrystalline cellulose, mannitol, and magnesium stearate.

In some embodiments, the modified-release dosage form further comprises a film coating.

In some embodiments, the film coating comprises Opadry® II Blue.

In some embodiments, the film coating comprises ethyl cellulose, Kollicoat® SR30D, Eudragit®, or cellulose acetate.

In some embodiments, the film coating comprises ethyl cellulose.

In some embodiments, the ethyl cellulose comprises Surelease®.

In some embodiments, the film coating further comprises (hydroxypropyl)methyl cellulose.

In some embodiments, the (hydroxypropyl)methyl cellulose comprises Opadry®.

In some embodiments, the ratio of the ethyl cellulose to the (hydroxypropyl)methyl cellulose is about 75:25.

In some embodiments, the ratio of the ethyl cellulose to the (hydroxypropyl)methyl cellulose is about 80:20.

In some embodiments, the ratio of the ethyl cellulose to the (hydroxypropyl)methyl cellulose is about 85:15.

In some embodiments, the modified-release dosage form comprises a core tablet and a coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the coating comprises Opadry® II Blue.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises Opadry® II Blue.

In some embodiments, the modified-release dosage form comprises a core tablet and a coating; wherein the core tablet comprises: (R)-8-chloro-1-methyl-2,3,4,5-tetrahydro-1H-3-benzazepine hydrochloride salt hemihydrate, Form III; mannitol; (hydroxypropyl)methyl cellulose; microcrystalline cellulose; and magnesium sterate; and the coating comprises: ethyl cellulose; and (hydroxypropyl)methyl cellulose.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises: about 85% ethyl cellulose; and about 15% (hydroxypropyl)methyl cellulose.

In some embodiments, the modified-release dosage form comprises a core tablet and a coating, wherein the weight to weight ratio of the core tablet to the coating is about 20:1; and wherein the core tablet comprises: about 7% (R)-8-chloro-1-methyl-2,3,4,5-tetrahydro-1H-3-benzazepine hydrochloride salt hemihydrate, Form III; about 22.5% mannitol; about 50% (hydroxypropyl)methyl cellulose; about 20% microcrystalline cellulose; and about 0.5% magnesium sterate; and the coating comprises: about 75% ethyl cellulose; and about 25% (hydroxypropyl)methyl cellulose.

In some embodiments, the modified-release dosage form has a T80% of at least 3 h.

In some embodiments, the modified-release dosage form has a T80% of at least 6 h.

In some embodiments, the modified-release dosage form has a T80% of at least 9 h.

In some embodiments, the modified-release dosage form has a T80% of at least 12 h.

In some embodiments, the modified-release dosage form comprises a salt selected from: a pharmaceutically acceptable salt of (R)-8-chloro-1-methyl-2,3,4,5-tetrahydro-1H-3-benzazepine and pharmaceutically acceptable solvates and hydrates thereof, and wherein the salt has an aqueous solubility of less than about 200 mg/mL at about room temperature.

In some embodiments, the salt has an aqueous solubility of less than about 100 mg/mL at about room temperature.

In some embodiments, the salt has an aqueous solubility of less than about 50 mg/mL at about room temperature.

In some embodiments, the salt has an aqueous solubility of less than about 25 mg/mL at about room temperature.

In some embodiments, the salt has an aqueous solubility of less than about 10 mg/mL at about room temperature.

In some embodiments, the salt has an aqueous solubility of less than about 5 mg/mL at about room temperature.

In some embodiments, the salt is selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine di-4-acetamidobenzoate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine (±)-mandelate salt; (R)-8-chloro-1-methyl-2,3,4,5-tetrahydro-1H-3-benzazepine hemipamoate salt and pharmaceutically acceptable hydrates and solvates thereof.

In some embodiments, the salt is selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine trans-cinnamate salt; (R)-8-chloro-1-methyl-2,3,4,5-tetrahydro-1H-3- benzazepine heminapadisilate salt; and pharmaceutically acceptable hydrates and solvates thereof.

In some embodiments, the salt is selected from: (R)-8-chloro-1-methyl-2,3,4,5-tetrahydro-1H-3-benzazepine hydroiodide salt, (R)-8-chloro-1-methyl-2,3,4,5-tetrahydro-1H-3-benzazepine maleate salt, (R)-8-chloro-1-methyl-2,3,4,5-tetrahydro-1H-3-benzazepine fumarate salt; (R)-8-chloro-1-methyl-2,3,4,5-tetrahydro-1H-3-benzazepine hemifumarate salt; (R)-8-chloro-1-methyl-2,3,4,5-tetrahydro-1H-3-benzazepine orotate salt; (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine trans-cinnamate salt; (R)-8-chloro-1-methyl-2,3,4,5-tetrahydro-1H-3-benzazepine heminapadisilate salt; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

In some embodiments, the salt is selected from: (R)-8-chloro-1-methyl-2,3,4,5-tetrahydro-1H-3-benzazepine orotate salt hydrate; (R)-8-chloro-1-methyl-2,3,4,5-tetrahydro-1H-3-benzazepine di-4-acetamidobenzoate salt-cocrystal methyl ethyl ketone solvate; (R)-8-chloro-1-methyl-2,3,4,5-tetrahydro-1H-3-benzazepine heminapadisilate salt solvate 1; (R)-8-chloro-1-methyl-2,3,4,5-tetrahydro-1H-3-benzazepine heminapadisilate salt solvate 2; (R)-8-chloro-1-methyl-2,3,4,5-tetrahydro-1H-3-benzazepine (±)-mandelate salt hydrate; (R)-8-chloro-1-methyl-2,3,4,5-tetrahydro-1H-3-benzazepine hemipamoate salt hydrate.

In some embodiments, the salt is (R)-8-chloro-1-methyl-2,3,4,5-tetrahydro-1H-3-benzazepine hydroiodide salt.

In some embodiments, the salt is (R)-8-chloro-1-methyl-2,3,4,5-tetrahydro-1H-3-benzazepine maleate salt.

In some embodiments, the salt is (R)-8-chloro-1-methyl-2,3,4,5-tetrahydro-1H-3-benzazepine fumarate salt.

In some embodiments, the salt is (R)-8-chloro-1-methyl-2,3,4,5-tetrahydro-1H-3-benzazepine hemifumarate salt.

In some embodiments, the salt is (R)-8-chloro-1-methyl-2,3,4,5-tetrahydro-1H-3-benzazepine orotate salt hydrate.

In some embodiments, the salt is (R)-8-chloro-1-methyl-2,3,4,5-tetrahydro-1H-3-benzazepine orotate salt.

In some embodiments, the salt is (R)-8-chloro-1-methyl-2,3,4,5-tetrahydro-1H-3-benzazepine orotate salt hydrate.

In some embodiments, the salt is (R)-8-chloro-1-methyl-2,3,4,5-tetrahydro-1H-3-benzazepine di-4-acetamidobenzoate salt-cocrystal methyl ethyl ketone solvate.

In some embodiments, the salt is (R)-8-chloro-1-methyl-2,3,4,5-tetrahydro-1H-3-benzazepine trans-cinnamate salt.

In some embodiments, the salt is (R)-8-chloro-1-methyl-2,3,4,5-tetrahydro-1H-3-benzazepine heminapadisilate salt.

In some embodiments, the salt is (R)-8-chloro-1-methyl-2,3,4,5-tetrahydro-1H-3-benzazepine heminapadisilate salt solvate 1.

In some embodiments, the salt is (R)-8-chloro-1-methyl-2,3,4,5-tetrahydro-1H-3-benzazepine heminapadisilate salt solvate 2.

In some embodiments, the salt is (R)-8-chloro-1-methyl-2,3,4,5-tetrahydro-1H-3-benzazepine (±)-mandelate salt hydrate.

In some embodiments, the salt is (R)-8-chloro-1-methyl-2,3,4,5-tetrahydro-1H-3-benzazepine hemipamoate salt hydrate.

In some embodiments, the modified-release dosage form further comprises one or more pharmaceutically acceptable excipients.

In some embodiments, the modified-release dosage form is for oral administration to an individual.

In some embodiments, the modified-release dosage form is selected from the group consisting of: tablets, capsules, pills, cachets, and lozenges.

In some embodiments, the modified-release dosage form is a tablet.

In some embodiments, the modified-release dosage form is for administration in combination with phentermine.

One aspect of the present invention pertains to methods of manufacturing a modified-release dosage form comprising: providing a compound selected from: (R)-8-chloro-1-methyl-2,3,4,5-tetrahydro-1H-3-benzazepine, and pharmaceutically acceptable salts, solvates, and hydrates thereof; and formulating the compound into a modified-release dosage form.

In some embodiments, the method of manufacturing a modified-release dosage form of the present invention comprises, for example, one or more of the following: dispersing a compound selected from: (R)-8-chloro-1-methyl-2,3,4,5-tetrahydro-1H-3-benzazepine, and pharmaceutically acceptable solvates and hydrates thereof, in a rate-controlling polymer matrix; coating a tablet comprising a compound selected from: (R)-8-chloro-1-methyl-2,3,4,5-tetrahydro-1H-3-benzazepine, and pharmaceutically acceptable solvates and hydrates thereof, with a functional coating; alternating layers comprising a compound selected from: (R)-8-chloro-1-methyl-2,3,4,5-tetrahydro-1H-3-benzazepine, and pharmaceutically acceptable solvates and hydrates thereof, with layers of functional coating; loading a bead with a compound selected from: (R)-8-chloro-1-methyl-2,3,4,5-tetrahydro-1H-3-benzazepine, and pharmaceutically acceptable solvates and hydrates thereof; binding a compound selected from: (R)-8-chloro-1-methyl-2,3,4,5-tetrahydro-1H-3-benzazepine, and pharmaceutically acceptable solvates and hydrates thereof, to a water-insoluble polymer resin; and surrounding a reservoir comprising a compound selected from: (R)-8-chloro-1-methyl-2,3,4,5-tetrahydro-1H-3-benzazepine, and pharmaceutically acceptable solvates and hydrates thereof, with a rate-controlling membrane.

Any of the modified-release dosage forms of the present invention can be further limited by any of the specific formulation characteristics anywhere in this application.

Modified-Release Mechanisms

Drug release from a swellable hydrophilic matrix is a complex phenomenon involving a number of physical processes, such as water or biological fluid penetration into the matrix, polymer chain relaxation and disentanglement, matrix geometry variation, and polymer gel dissolution/erosion (Hopfenberg H B, Hsu K C *Swelling-controlled, constant rate delivery systems* Polym. Eng. Sci. 1978; 18(15):1186-1191; Lee P I *Diffusional release of a solute from a polymeric matrix—approximate analytical solutions* J. Membrane Sci. 1980; 7(3):255-275; Lee P I, Peppas N A *Prediction of polymer dissolution in swellable controlled-release systems* J. Control. Release. 1987; 6(1):207-215; Harland R S, Gazzaniga A, Sangalli M E, Colombo P, Peppas N A *Drug/polymer matrix swelling and dissolution* Pharm. Res. 1988; 5(8):488-494). Upon exposure to an aqueous solution or gastrointestinal fluids, the surface of a tablet is wetted and the polymer hydrates form a gel layer around the matrix due to swelling. This gel layer slows down water ingress into the tablet. Simultaneously, the drug inside the gel layer dissolves and diffuses out. In case of a highly soluble drug, this usually leads to an initial burst release due to the presence of drug on the surface of the matrix tablet. The gel layer grows with time as water permeates continuously into the core of the matrix, thereby increasing the thickness of the gel layer and providing a diffusion barrier to drug release. When the periphery of the gel layer becomes fully hydrated, the polymer chains become completely relaxed and can no longer maintain the integrity of the gel layer, which leads to disentanglement and erosion of the surface of the matrix. It is well established that concentration gradient-driven diffusion and polymer relaxation are the most important rate-limiting steps in regulating drug release, although the presence of drugs and additional excipients may enhance or suppress the swelling osmotic pressure at the swelling front and thus modify the mechanical integrity of polymer gel depending on the solubility of the additives. Essentially, diffusion and polymer relaxation compete in controlling drug release, leading to the usually observed non-Fickian release kinetics.

Over the past few decades, great efforts have been made in attempts to generalize the swelling and dissolution of polymers in general, and to quantify the drug-release process from the swellable hydrophilic matrices in particular (Fan L T, Singh S K *Controlled release, a quantitative treatment* New York, N.Y.: Springer-Verlag, 1989; Siepmann J, Peppas N A *Modeling of drug release from delivery systems based on hydroxypropyl methylcellulose (HPMC)* Adv. Drug Deliv. Rev. 2001; 48(2-3):139-157; Costa P, Lobo J M S *Modeling and comparison of dissolution profiles* Eur. J. Pharm. Sci. 2001; 13(2):123-133). Because of the synchronous occurrence of numerous phenomena during dissolution of a swellable hydrophilic matrix, the developed mathematical models are rather sophisticated, and in most cases have to be solved by numerical algorithms or finite element methods, which limits the routine application of those models (Paul D R, McSpadden S K *Diffusional release of a solute from a polymeric matrix* J. Membrane Sci. 1976; 1:33-48; Tu Y O *A multi-phase Stefan problem describing the swelling and the dissolution of glassy polymer* Quar. Appl. Math. 1977; XXXV:269-285; Siepmann J, Streubel A, Peppas N A *Understanding and predicting drug delivery from hydrophilic matrix tablets using the "sequential layer" model* Pharm. Res. 2002; 19(3):306-314). Equation 1 is one of the most widely used equations in modeling drug release from a swellable hydrophilic matrix:

$$\frac{M_t}{M_\infty} = k \cdot t^n \quad \text{Equation 1}$$

wherein $M_t$ is the amount of drug released at time t, $M_\infty$ is the total drug loading, and $M_t/M_\infty$ is the fraction of drug released at time t (Korsmeyer R W, Gurny R, Doelker E, Buri P, Peppas N A *Mechanisms of solute release from porous hydrophilic polymers*. Int. J. Pharm. 1983; 15(1):25-35; Ritger P L, Peppas N A *A simple equation for description of solute release I. Fickian and non-fickian release from non-swellable devices in the form of slabs, spheres, cylinders or discs* J. Control. Release. 1987; 5(1):23-36). In Equation 1, k is a constant incorporating the structural and geometric characteristic of a matrix system, and n is an exponent that characterizes the release mechanism. Generally, this equation is only applicable for $M_t/M_\infty \leq 80\%$. In the case of cylindrical matrix tablets, the drug-release mechanism is Fickian diffusion if n=0.45. If 0.45<n<0.89, the mechanism is non-Fickian or anomalous diffusion. If n≥0.89, release is indicative of Case-II transport or commonly referred to as zero-order release. If n≥1, release is considered to be super Case-II transport.

Crystalline Forms

Polymorphism is the ability of a substance to exist as two or more crystalline phases that have different arrangements and/or conformations of the molecules in the crystal lattice. Polymorphs show the same properties in the liquid or gaseous state but they may behave differently in the solid state.

Besides single-component polymorphs, drugs can also exist as salts and other multicomponent crystalline phases. For example, solvates and hydrates may contain an active pharmaceutical ingredient (API) host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily. Recently, polymorph screens of 245 compounds revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

The present invention is directed, inter alia, to crystalline forms of salts of (R)-8-chloro-1-methyl-2,3,4,5-tetrahydro-1H-3-benzazepine and hydrates and solvates thereof. The crystalline forms of the present invention can be identified by unique solid state signatures with respect to, for example, differential scanning calorimetry (DSC), X-ray powder diffraction (PXRD), and other solid state methods. Further characterization with respect to water or solvent content of the crystalline forms of the present invention can be gauged by any of the following methods for example, thermogravimetric analysis (TGA), DSC and the like. For DSC, it is known that the temperatures observed will depend upon sample purity, the rate of temperature change, as well as sample preparation technique and the particular instrument employed. Thus, the values reported herein relating to DSC thermograms can vary by about ±6° C. The values reported herein relating to DSC thermograms can also vary by about ±20 joules per gram. For PXRD, the relative intensities of the peaks can vary, depending upon the sample preparation technique, the sample mounting procedure and the particular instrument employed. Moreover, instrument variation and other factors can often affect the 20 values. Therefore, the peak assignments of diffraction patterns can vary by about ±0.2°2θ. The relative intensities of the reported peaks can also vary. For TGA, the features reported herein can vary by about ±5° C. The TGA features reported herein can also vary by about ±2% weight change due to, for example, sample variation. Further characterization with respect to hygroscopicity of the crystalline form can be gauged by, for example, dynamic moisture sorption (DMS). The DMS features reported herein can vary by about ±5% relative humidity. The DMS features reported herein can also vary by about ±5% weight change. The deliquescence relative humidity (DRH) measurements by water activity meter are sensitive to sample quality and quantity. The DRH measurements reported herein can vary by about ±5% RH.

Compound 1 Hydrochloride Salt Hemihydrate

The physical properties of Form III of Compound 1 hydrochloride salt hemihydrate are summarized in Table 1 below.

TABLE 1

Figure 2:
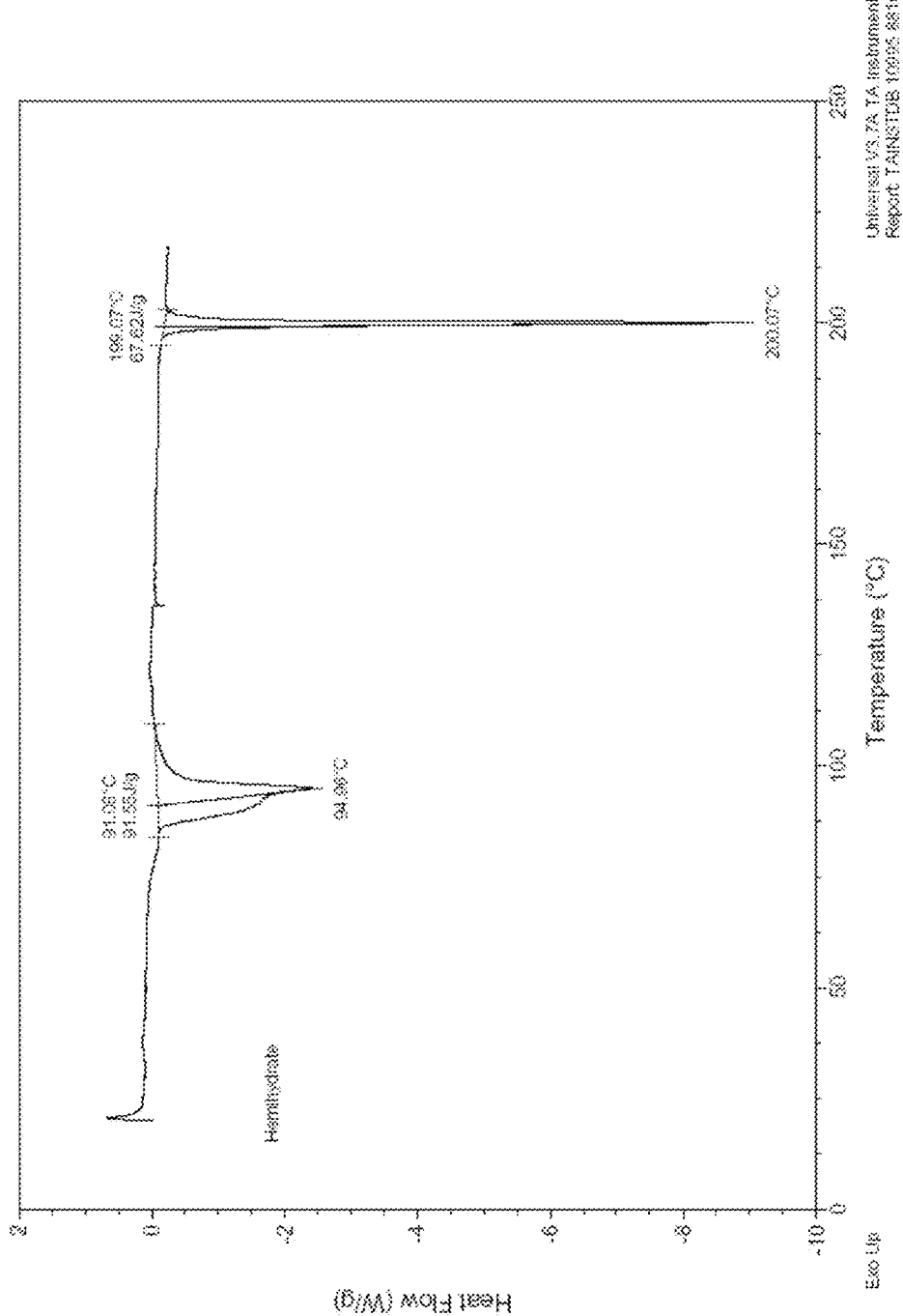
FIG. 2: DSC of Compound 1 Hydrochloride Salt, Hemihydrate Form III.
Figure 3:
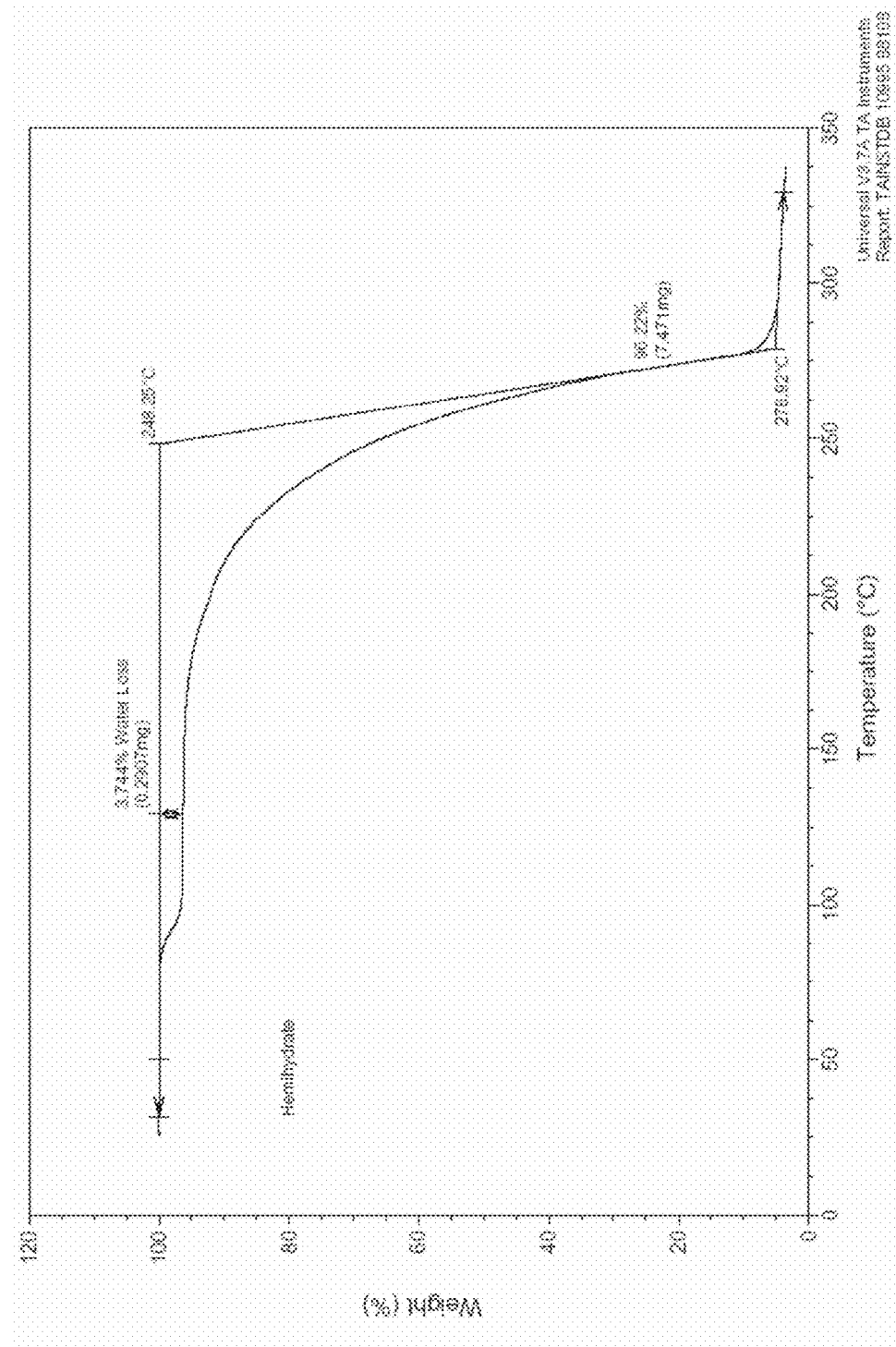
FIG. 3: TGA of Compound 1 Hydrochloride Salt, Hemihydrate Form III.
Figure 4:
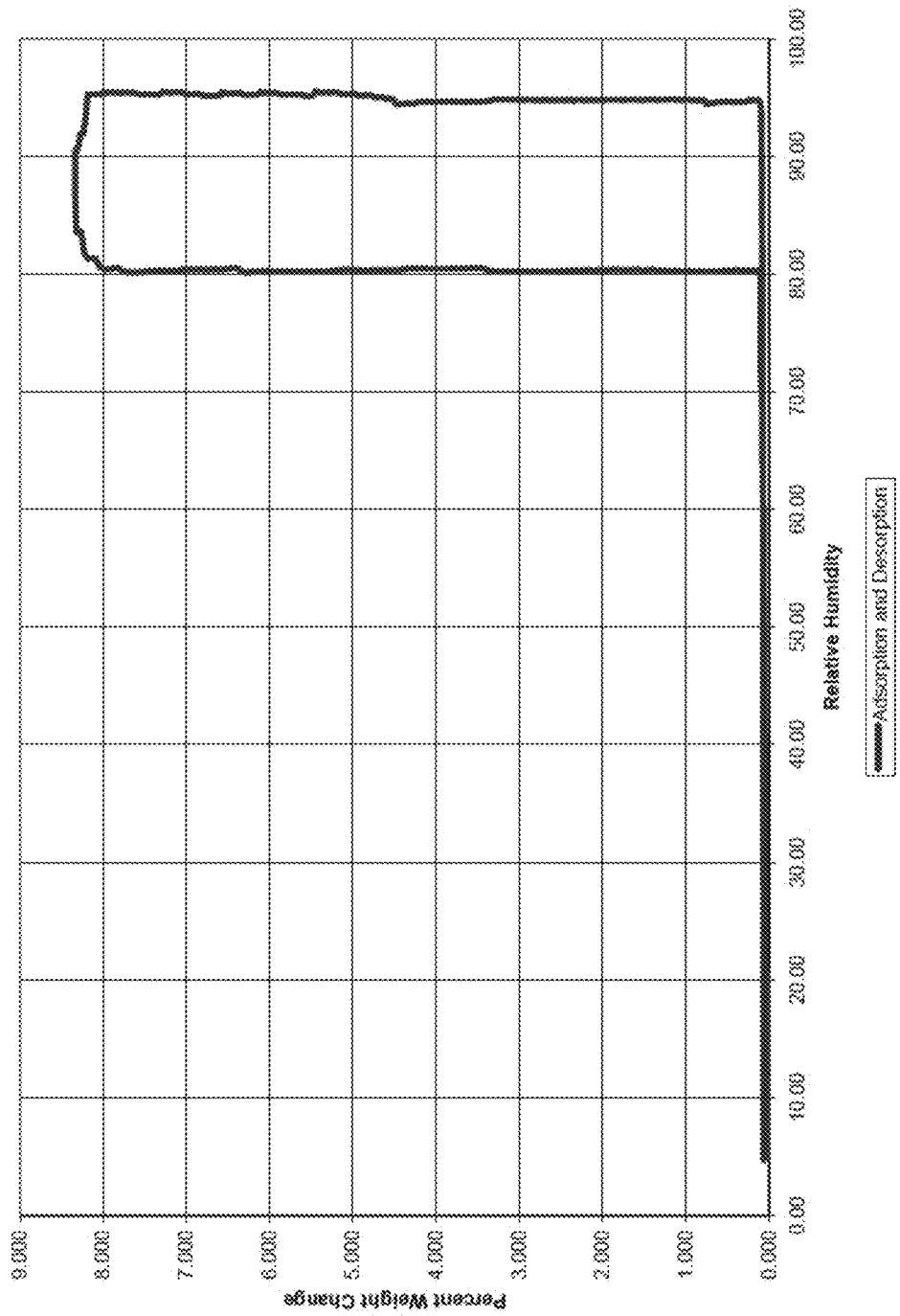
FIG. 4: DMS of Compound 1 Hydrochloride Salt, Hemihydrate Form III.

| | Compound 1 Hydrochloride Salt Hemihydrate, Form III |
|---|---|
| PXRD | FIG. 1: Peaks at 13.7°, 14.9°, 15.4°, 15.8°, 16.7°, 18.9 °2θ |
| DSC | FIG. 2: 95° C. (dehydration); 200° C. (melt) |
| TGA | FIG. 3: 3.7% water loss |
| DMS | FIG. 4: non-hygroscopic |

Compound 1 hydrochloride salt hemihydrate, Form III displays a dehydration feature calculated as a 3.7% weight loss which is consistent with the theoretical weight loss of 3.7% for a hemihydrate. Analysis by DSC further confirms the TGA results, where Compound 1 hydrochloride salt hemihydrate, Form III shows a dehydration event at about 95° C. and a melting/decomposition endotherm at about 200-201° C.

DMS data shows that Compound 1 hydrochloride salt hemihydrate, Form III is substantially non-hygroscopic, adsorbing less than 0.5 wt % water out to and including the 90% RH hold at 25° C. and the XRPD pattern showed no change in crystalline form after the DMS cycle.

Certain X-ray powder diffraction peaks for Compound 1 hydrochloride salt hemihydrate, Form III are shown in Table 2 below.

TABLE 2

| Pos. (°2θ) | Pos. (°2θ) | Pos. (°2θ) |
|---|---|---|
| 10.2 | 26.0 | 24.7 |
| 12.7 | 26.5 | 29.0 |
| 13.7 | 26.9 | 30.0 |
| 14.9 | 27.6 | 30.3 |
| 15.4 | 28.2 | 30.8 |
| 15.8 | 20.5 | 31.1 |
| 16.7 | 21.4 | 32.0 |
| 18.5 | 22.8 | 32.3 |
| 18.9 | 23.2 | 32.7 |
| 19.2 | 23.5 | 33.3 |
| 20.1 | 24.0 | 33.8 |
| 25.3 | 24.2 | 35.8 |
| 25.7 | | |

Form III of Compound 1 hydrochloride salt hemihydrate can be prepared as described in Example 4.

Compound 1 Hydroiodide Salt

One aspect of the present invention pertains to a crystalline form of (R)-8-chloro-1-methyl-2,3,4,5-tetrahydro-1H-3-benzazepine hydroiodide salt (Compound 1 hydroiodide salt). In some embodiments, the crystalline form of (R)-8-chloro-1-methyl-2,3,4,5-tetrahydro-1H-3-benzazepine hydroiodide salt is Form I (Compound 1 hydroiodide salt, Form I). The physical properties of Form I of Compound 1 hydroiodide salt are summarized in Table 3 below.

TABLE 3

Figure 5:
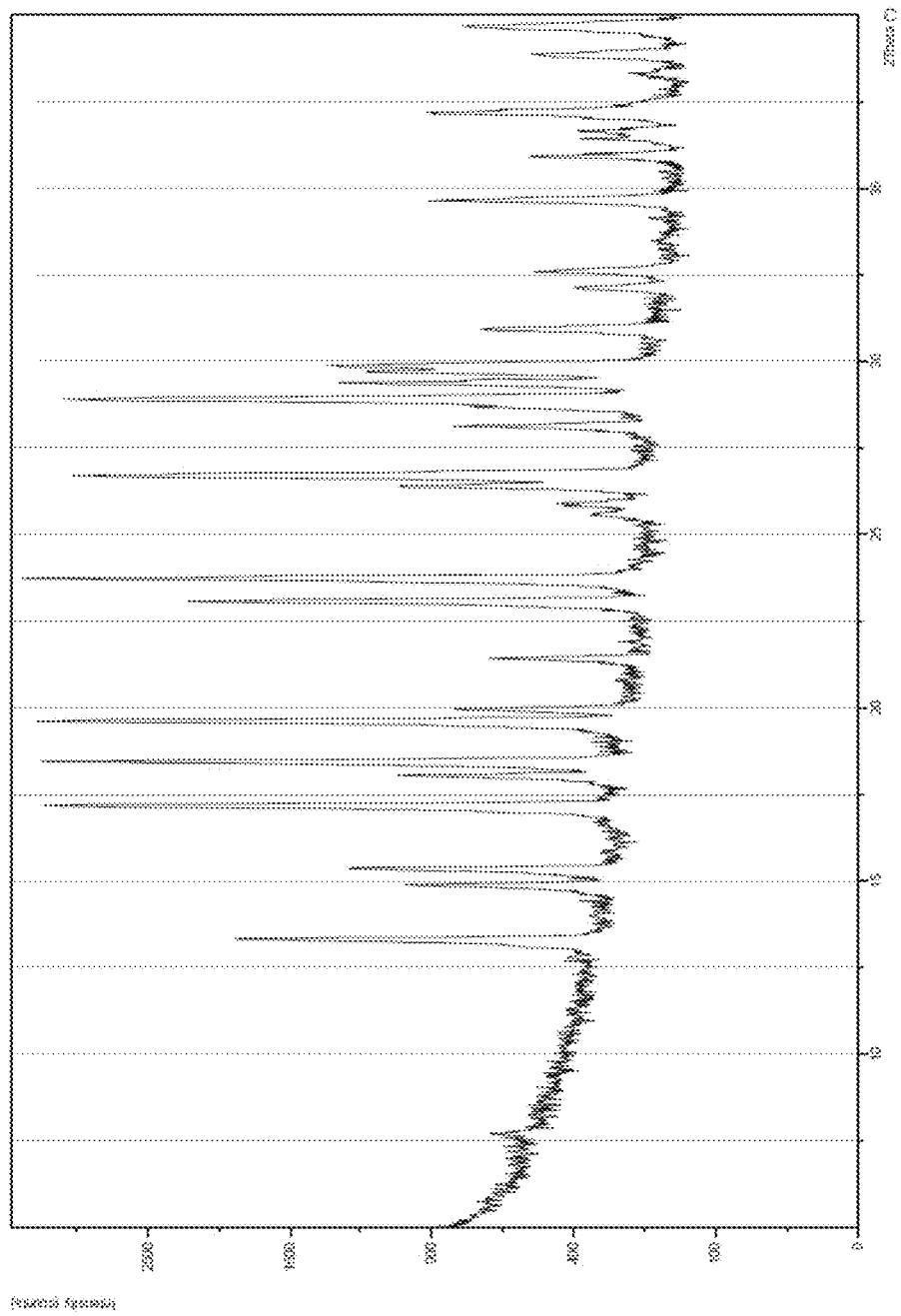
FIG. 5: PXRD of Compound 1 Hydroiodide Salt, Form I.

| | Compound 1 Hydroiodide Salt, Form I |
|---|---|
| PXRD | FIG. 5: Peaks of ≥30% relative intensity at 13.32, 15.35, 17.19, 18.46, 19.62, 23.07, 23.73, 26.70, 28.91, 29.37, 29.70, and 29.87 °2θ |
| TGA | FIG. 6: anhydrous with significant weight loss after melting |
| DSC | FIG. 6: extrapolated onset temperature about 121° C.; enthalpy of fusion 88 J/g |
| DMS | FIG. 7: non-hygroscopic |

The TGA showed Compound 1 hydroiodide salt to be anhydrous, which was confirmed by Karl Fischer analysis. Melting onset by DSC was 121° C.; melting was accompanied by the beginning of large weight loss (>30%) out to about 200° C.

DMS analysis showed that the title salt was non-hygroscopic. Based on water activity measurement of a saturated aqueous solution with excess solid, the DRH was 99% RH at 25° C.

Certain X-ray powder diffraction peaks for Form I of Compound 1 hydroiodide salt are shown in Table 4 below.

TABLE 4

| Pos. (°2θ) | Rel. Int. (%) |
|---|---|
| 7.69 | 5.14 |
| 13.32 | 49.45 |
| 14.88 | 21.72 |
| 15.35 | 30.89 |
| 17.19 | 92.91 |
| 18.05 | 24.11 |
| 18.46 | 94.03 |
| 19.62 | 94.85 |
| 19.96 | 17.75 |
| 21.42 | 12.98 |
| 23.07 | 62.26 |
| 23.73 | 100.00 |
| 25.60 | 4.89 |
| 25.90 | 8.24 |
| 26.40 | 26.59 |
| 26.70 | 89.53 |
| 28.13 | 19.48 |
| 28.67 | 15.75 |
| 28.91 | 89.32 |
| 29.37 | 35.62 |
| 29.70 | 31.97 |
| 29.87 | 36.93 |
| 30.93 | 16.46 |
| 32.11 | 7.39 |
| 32.60 | 11.00 |
| 34.65 | 23.37 |
| 35.92 | 11.58 |
| 36.43 | 7.12 |
| 36.65 | 7.39 |
| 37.17 | 23.25 |
| 38.30 | 2.88 |
| 38.85 | 11.23 |
| 39.66 | 19.10 |

One aspect of the present invention is directed to a crystalline form of Compound 1 hydroiodide salt having an X-ray powder diffraction pattern comprising a peak, in terms of 2θ, at about 23.73°. In some embodiments, the crystalline form has an X-ray powder diffraction pattern comprising a peak, in terms of 2θ, at about 19.62°. In some embodiments, the crystalline form has an X-ray powder diffraction pattern comprising peaks, in terms of 2θ, at about 23.73° and about 19.62°. In some embodiments, the crystalline form has an X-ray powder diffraction pattern comprising peaks, in terms of 2θ, at about 23.73° and about 18.46°. In some embodiments, the crystalline form has an X-ray powder diffraction pattern comprising peaks, in terms of 2θ, at about 23.73°, about 19.62° and about 18.46°. In some embodiments, the crystalline form has an X-ray powder diffraction pattern comprising peaks, in terms of 2θ, at about 23.73°, about 19.62°, about 18.46°, about 17.19°, about 26.70°, about 28.91°, and about 23.07°. In some embodiments, the crystalline form has an X-ray powder diffraction pattern comprising peaks, in terms of 2θ, at about 23.73°, about 19.62°, about 18.46°, about 17.19°, about 26.70°, about 28.91°, about 23.07°, about 13.32°, about 29.87°, and about 29.37°. One aspect of the present invention is directed to a crystalline form of Compound 1 hydroiodide salt having an X-ray powder diffraction pattern comprising one or more peaks listed in Table 4. In some embodiments, the crystalline form has an X-ray powder diffraction pattern substantially as shown in FIG. 5, wherein by "substantially" is meant that the reported peaks can vary by about ±0.2°2θ, and also that the relative intensities of the reported peaks can vary.

In some embodiments, the crystalline form of Compound 1 hydroiodide salt has a differential scanning calorimetry thermogram comprising an endotherm with an extrapolated onset temperature between about 105° C. and about 135° C. In some embodiments, the crystalline form of Compound 1 hydroiodide salt has a differential scanning calorimetry thermogram comprising an endotherm with an extrapolated onset temperature at about 121° C. In some embodiments, the crystalline form of Compound 1 hydroiodide salt has a differential scanning calorimetry thermogram comprising an endotherm with an associated heat flow of about 88 joules per gram. In some embodiments, the crystalline form of Compound 1 hydroiodide salt has a thermogravimetric analysis profile substantially as shown in FIG. 6, wherein by "substantially" is meant that the reported TGA features can vary by about ±5° C. and by about ±2% weight change.

Figure 6:
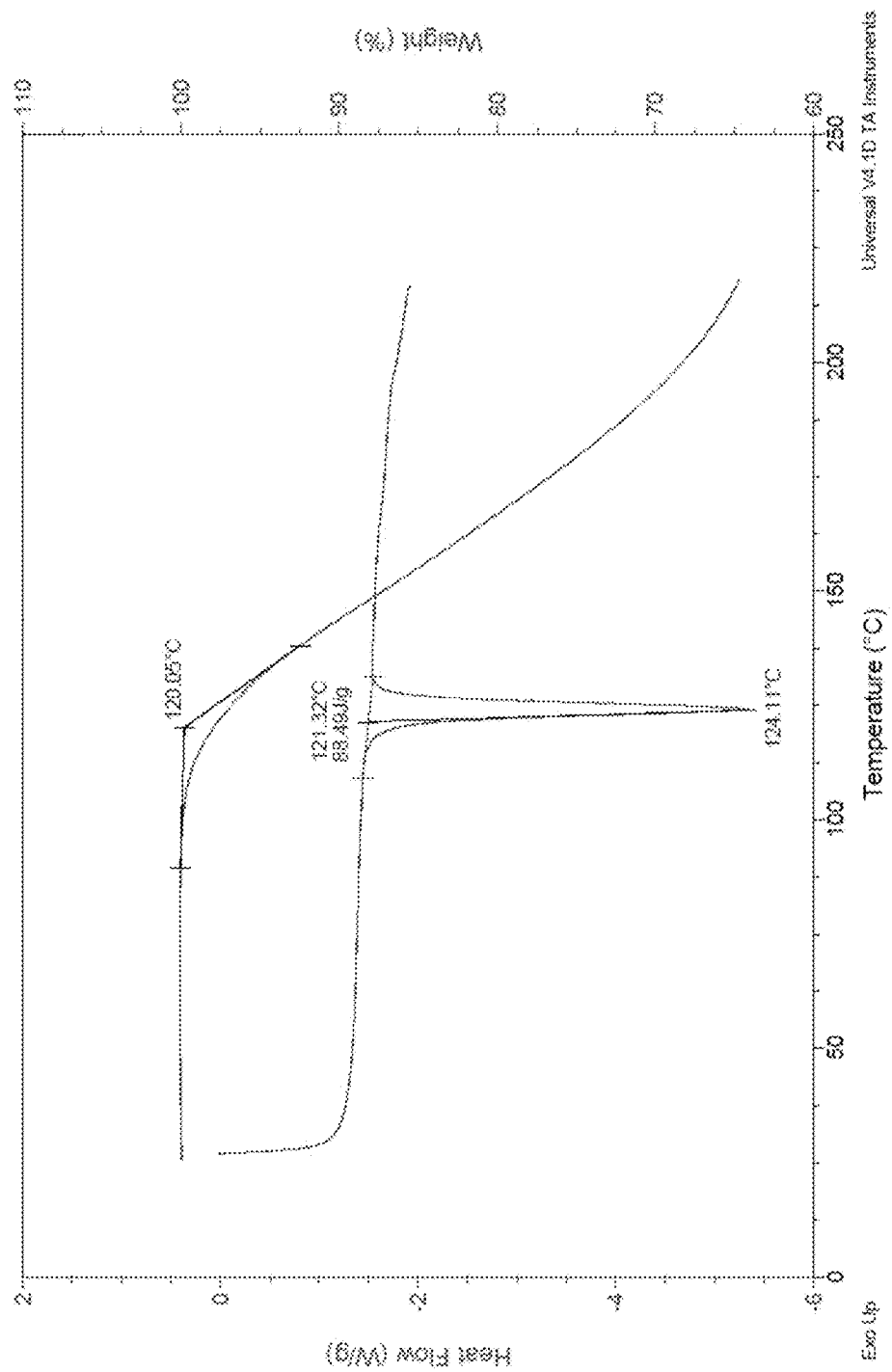
FIG. 6: DSC and TGA of Compound 1 Hydroiodide Salt, Form I.

In some embodiments, the crystalline form of Compound 1 hydroiodide salt has a differential scanning calorimetry thermogram substantially as shown in FIG. 6, wherein by "substantially" is meant that the reported DSC features can vary by about ±6° C. and by about ±20 joules per gram.

Figure 7:
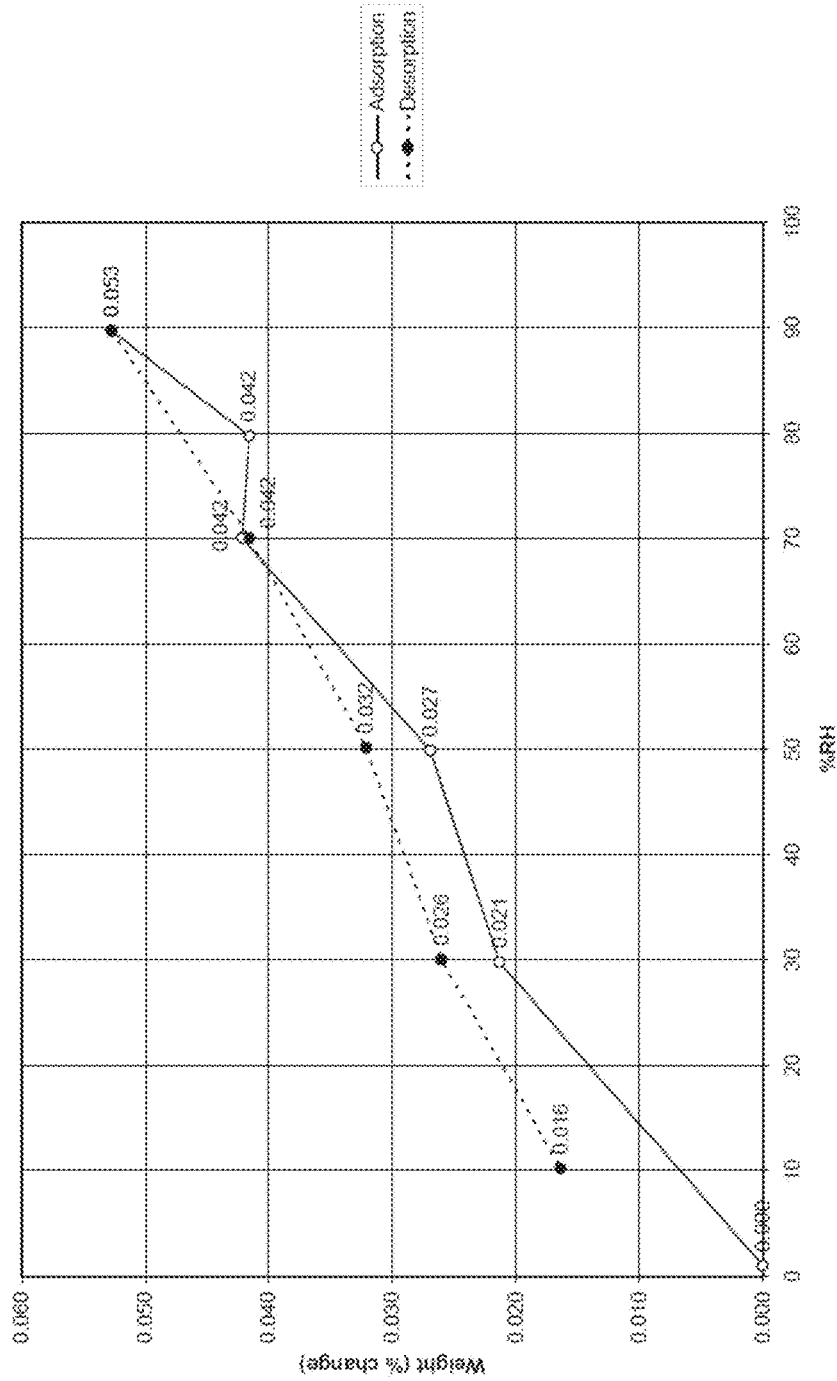
FIG. 7: DMS of Compound 1 Hydroiodide Salt, Form I.

In some embodiments, the crystalline form of Compound 1 hydroiodide salt has a dynamic moisture sorption profile substantially as shown in FIG. 7, wherein by "substantially" is meant that the reported DMS features can vary by about ±5% relative humidity and by about ±5% weight change.

Form I of Compound 1 hydroiodide salt can be prepared by any of the suitable procedures known in the art for preparing crystalline polymorphs. In some embodiments Form I of Compound 1 hydroiodide salt can be prepared as described in Example 3.1. In some embodiments, Form I of Compound 1 hydroiodide salt can be prepared by slurrying crystalline Compound 1 hydroiodide salt containing one or more crystalline forms other than Form I. In some embodiments, the crystalline form of Compound 1 hydroiodide salt can be prepared by recrystallizing crystalline Compound 1 hydroiodide salt containing one or more crystalline forms other than Form I.

Compound 1 Maleate Salt

One aspect of the present invention pertains to a crystalline form of (R)-8-chloro-1-methyl-2,3,4,5-tetrahydro-1H-3-benzazepine maleate salt (Compound 1 maleate salt). In some embodiments, the crystalline form of (R)-8-chloro-1-methyl-2,3,4,5-tetrahydro-1H-3-benzazepine maleate salt is Form I (Compound 1 maleate salt, Form I). The physical properties of Form I of Compound 1 maleate salt are summarized in Table 5 below.

TABLE 5

Figure 8:
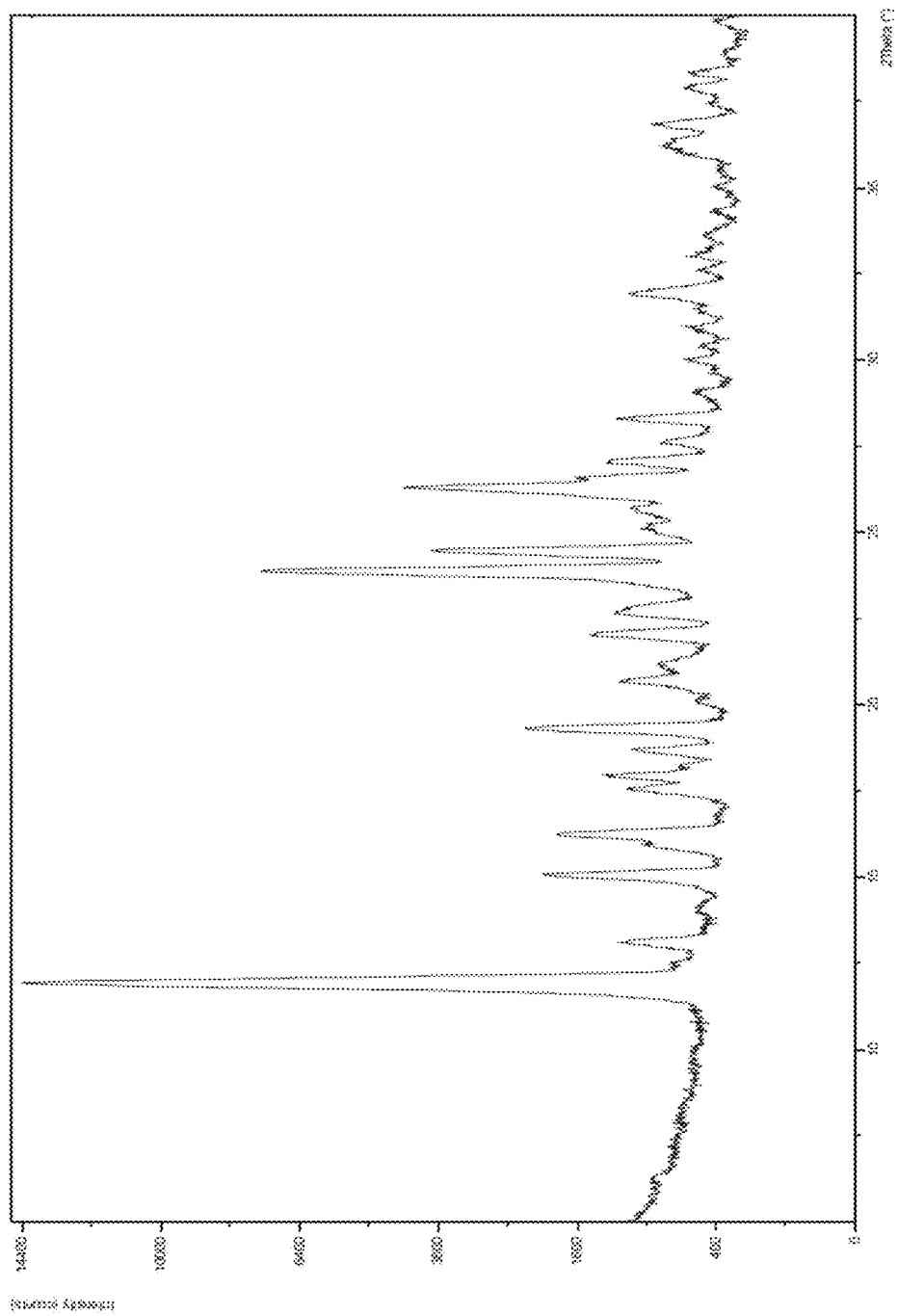
FIG. 8: PXRD of Compound 1 Maleate Salt, Form I.

| Compound 1 Maleate Salt, Form I | |
|---|---|
| PXRD | FIG. 8: Peaks of ≥6% relative intensity at 11.93, 15.07, 16.23, 17.95, 19.32, 22.04, 23.88, 24.46, 26.31, 26.58, 27.07, and 28.29 °2θ |
| TGA | FIG. 9: <0.2% weight loss up to about 150° C. |
| DSC | FIG. 9: extrapolated onset temperature about 166° C.; enthalpy of fusion 81 J/g |
| DMS | FIG. 10: 0.15% weight gain at 90% RH |

Form I of Compound 1 maleate salt had a melting onset temperature about 166° C. The TGA was consistent with an anhydrous salt. It was not hygroscopic, picking up just 0.15% weight out to and including the 90% RH hold at 25° C.

Certain X-ray powder diffraction peaks for Form I of Compound 1 maleate salt are shown in Table 6 below.

TABLE 6

| Pos. (°2θ) | Rel. Int. (%) |
|---|---|
| 6.27 | 1.11 |
| 9.75 | 0.37 |
| 11.93 | 100.00 |
| 13.10 | 5.17 |
| 14.08 | 0.80 |
| 15.07 | 11.71 |
| 15.87 | 3.43 |
| 16.23 | 10.63 |
| 17.56 | 5.14 |
| 17.95 | 7.04 |
| 18.23 | 2.16 |
| 18.70 | 4.99 |
| 19.32 | 13.61 |
| 20.08 | 1.21 |
| 20.68 | 5.64 |
| 21.16 | 3.12 |
| 22.04 | 7.58 |
| 22.66 | 5.78 |
| 22.86 | 4.49 |
| 23.88 | 49.41 |
| 24.46 | 23.70 |
| 25.14 | 3.79 |
| 25.69 | 4.62 |
| 26.31 | 27.36 |
| 26.58 | 9.01 |
| 27.07 | 6.57 |
| 27.61 | 3.09 |
| 28.29 | 6.17 |
| 29.06 | 1.62 |
| 30.00 | 2.08 |
| 30.40 | 1.34 |
| 30.93 | 1.95 |
| 31.40 | 1.55 |
| 31.90 | 5.47 |
| 32.60 | 1.53 |
| 33.03 | 2.00 |
| 33.63 | 1.35 |
| 34.32 | 0.98 |
| 35.02 | 0.94 |
| 36.22 | 3.42 |
| 36.42 | 2.93 |
| 36.84 | 4.04 |
| 37.43 | 1.23 |
| 37.90 | 2.36 |
| 38.31 | 2.07 |
| 38.88 | 0.70 |

One aspect of the present invention is directed to a crystalline form of Compound 1 maleate salt having an X-ray powder diffraction pattern comprising a peak, in terms of 2θ, at about 11.93°. In some embodiments, the crystalline form has an X-ray powder diffraction pattern comprising a peak, in terms of 2θ, at about 23.88°. In some embodiments, the crystalline form has an X-ray powder diffraction pattern comprising peaks, in terms of 2θ, at about 11.93° and about 23.88°. In some embodiments, the crystalline form has an X-ray powder diffraction pattern comprising peaks, in terms of 2θ, at about 11.93° and about 26.31°. In some embodiments, the crystalline form has an X-ray powder diffraction pattern comprising peaks, in terms of 2θ, at about 11.93°, about 23.88°, and about 26.31°. In some embodiments, the crystalline form has an X-ray powder diffraction pattern comprising peaks, in terms of 2θ, at about 11.93°, about 23.88°, about 26.31°, about 24.46°, about 19.32°, about 15.07°, and about 16.23°. In some embodiments, the crystalline form has an X-ray powder diffraction pattern comprising peaks, in terms of 2θ, at about 11.93°, about 23.88°, about 26.31°, about 24.46°, about 19.32°, about 15.07°, about 16.23°, about 26.58°, about 22.04°, and about 17.95°. One aspect of the present invention is directed to a crystalline form of Compound 1 maleate salt having an X-ray powder diffraction pattern comprising one or more peaks listed in Table 6. In some embodiments, the crystalline form has an X-ray powder diffraction pattern substantially as shown in FIG. 8, wherein by "substantially" is meant that the reported peaks can vary by about ±0.2°2θ, and also that the relative intensities of the reported peaks can vary.

In some embodiments, the crystalline form of Compound 1 maleate salt has a differential scanning calorimetry thermogram comprising an endotherm with an extrapolated onset temperature between about 150° C. and about 180° C. In some embodiments, the crystalline form of Compound 1 maleate salt has a differential scanning calorimetry thermogram comprising an endotherm with an extrapolated onset temperature at about 166° C. In some embodiments, the crystalline form of Compound 1 maleate salt has a differential scanning calorimetry thermogram comprising an endotherm with an associated heat flow of about 81 joules per gram. In some embodiments, the crystalline form of Compound 1 maleate salt has a thermogravimetric analysis profile substantially as shown in FIG. 9, wherein by "substantially" is meant that the reported TGA features can vary by about ±5° C. and by about ±2% weight change.

Figure 9:
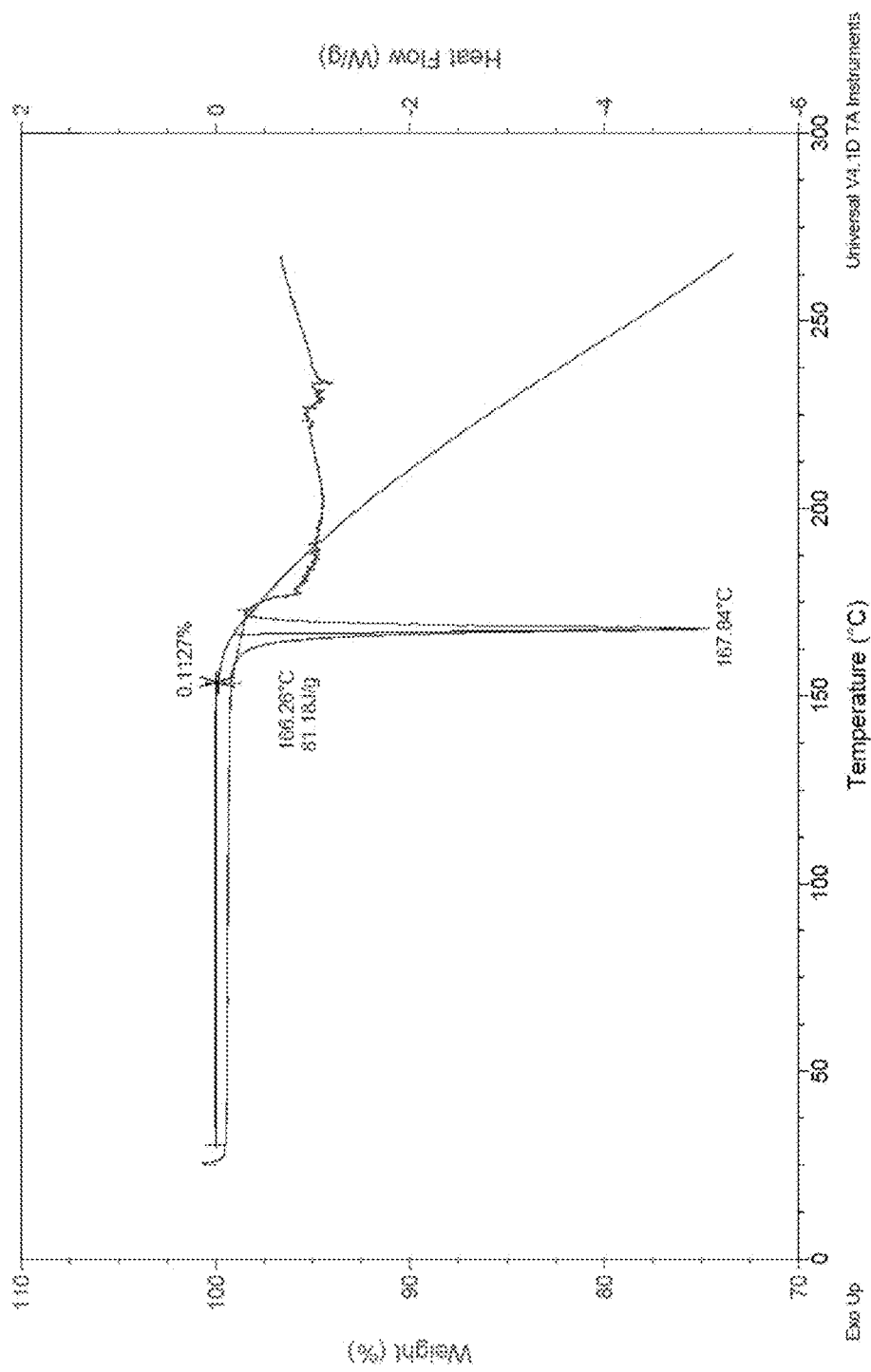
FIG. 9: DSC and TGA of Compound 1 Maleate Salt, Form I.

In some embodiments, the crystalline form of Compound 1 maleate salt has a differential scanning calorimetry thermogram substantially as shown in FIG. 9, wherein by "substantially" is meant that the reported DSC features can vary by about ±6° C. and by about ±20 joules per gram.

Figure 10:
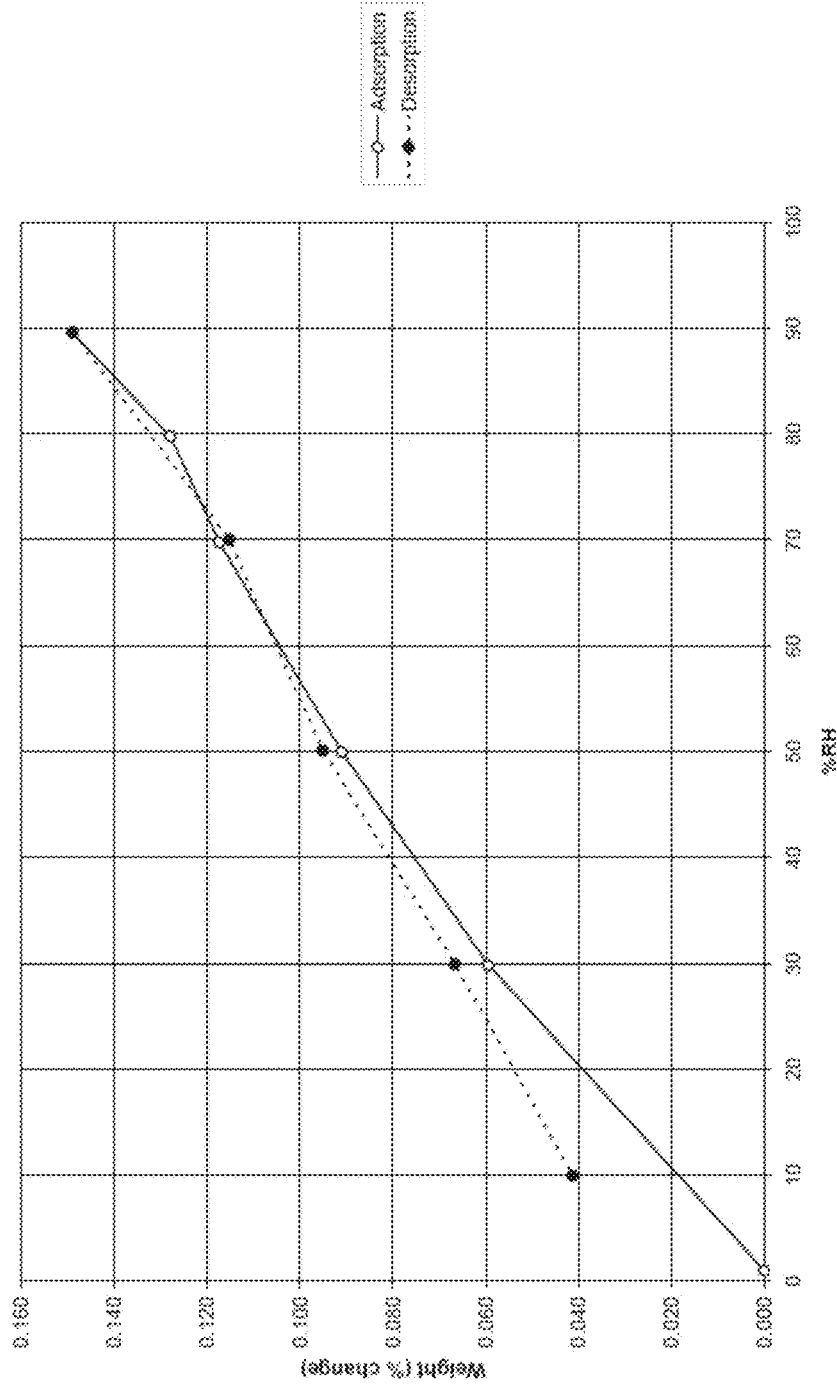
FIG. 10: DMS of Compound 1 Maleate Salt, Form I.

In some embodiments, the crystalline form of Compound 1 maleate salt has a dynamic moisture sorption profile substantially as shown in FIG. 10, wherein by "substantially" is meant that the reported DMS features can vary by about ±5% relative humidity and by about ±5% weight change.

Form I of Compound 1 maleate salt can be prepared by any of the suitable procedures known in the art for preparing crystalline polymorphs. In some embodiments Form I of Compound 1 maleate salt can be prepared as described in Example 3.2. In some embodiments, Form I of Compound 1 maleate salt can be prepared by slurrying crystalline Compound 1 maleate salt containing one or more crystalline forms other than Form I. In some embodiments, the crystalline form of Compound 1 maleate salt can be prepared by recrystallizing crystalline Compound 1 maleate salt containing one or more crystalline forms other than Form I.

Compound 1 Fumarate Salt

One aspect of the present invention pertains to a crystalline form of (R)-8-chloro-1-methyl-2,3,4,5-tetrahydro-1H-3-benzazepine fumarate salt (Compound 1 fumarate salt). In some embodiments, the crystalline form of (R)-8-chloro-1-methyl-2,3,4,5-tetrahydro-1H-3-benzazepine fumarate salt is Form I (Compound 1 fumarate salt, Form I). The physical properties of Form I of Compound 1 fumarate salt are summarized in Table 7 below.

TABLE 7

Figure 11:
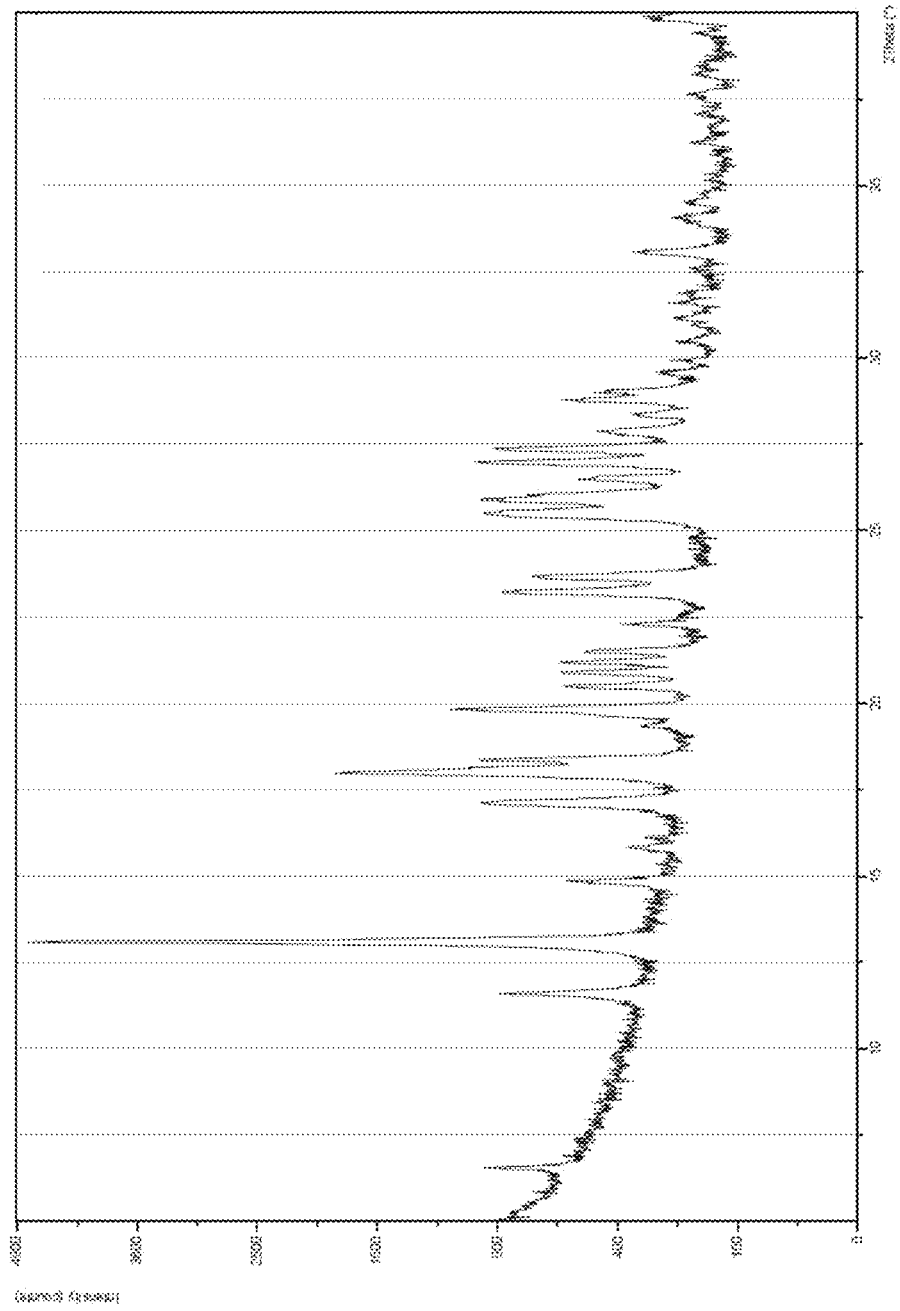
FIG. 11: PXRD of Compound 1 Fumarate Salt, Form I.

| | Compound 1 Fumarate Salt, Form I |
|---|---|
| PXRD | FIG. 11: Peaks of ≥10% relative intensity at 11.59, 13.08, 17.11, 17.99, 18.36, 19.82, 23.21, 23.67, 25.40, 25.50, 25.89, 26.98, 27.36, and 28.78 °2θ |
| TGA | FIG. 12: No significant weight loss up to about 150° C.; 16.85% weight between about 147° C. and about 210° C., prior to the melt onset |
| DSC | FIG. 12: extrapolated onset temperature about 219° C. |
| DMS | FIG. 13: non-hygroscopic up to 90% RH |

Compound 1 fumarate salt, Form I showed a very high melting onset of 218-219° C. depending on the sample analyzed. TGA showed the salt to be anhydrous, with significant weight loss prior to the melting onset, likely due to vaporization of the salt of components thereof. Compound 1 fumarate salt, Form I was non-hygroscopic by DMS analysis out to and including the 90% RH hold at 25° C. and the DRH by water activity meter was 99% RH at 25° C.

Certain X-ray powder diffraction peaks for Form I of Compound 1 fumarate salt are shown in Table 8 below.

TABLE 8

| Pos. (°2θ) | Rel. Int. (%) |
|---|---|
| 5.21 | 1.52 |
| 6.54 | 8.43 |
| 11.59 | 12.41 |
| 13.08 | 100.00 |
| 14.83 | 6.90 |
| 15.82 | 2.85 |
| 16.10 | 1.59 |
| 17.11 | 16.74 |
| 17.99 | 37.47 |
| 18.36 | 17.64 |
| 19.34 | 2.94 |
| 19.82 | 21.63 |
| 20.49 | 9.18 |
| 20.89 | 9.65 |
| 21.18 | 9.82 |
| 21.50 | 7.76 |
| 22.28 | 4.79 |
| 23.21 | 15.98 |
| 23.67 | 13.08 |
| 25.40 | 15.12 |
| 25.50 | 18.21 |
| 25.89 | 18.50 |
| 26.50 | 8.01 |
| 26.98 | 18.69 |
| 27.36 | 16.46 |
| 27.86 | 6.57 |
| 28.36 | 4.33 |
| 28.78 | 10.03 |
| 29.03 | 6.71 |
| 29.56 | 2.87 |
| 29.91 | 1.62 |
| 30.49 | 1.74 |
| 31.14 | 2.15 |
| 31.61 | 2.14 |
| 31.86 | 1.78 |
| 33.06 | 5.03 |
| 34.06 | 2.59 |
| 34.50 | 2.02 |
| 36.24 | 1.65 |
| 36.64 | 0.86 |
| 37.09 | 1.36 |
| 37.64 | 1.82 |
| 38.24 | 1.51 |
| 39.40 | 1.38 |

One aspect of the present invention is directed to a crystalline form of Compound 1 fumarate salt having an X-ray powder diffraction pattern comprising a peak, in terms of 2θ, at about 13.08°. In some embodiments, the crystalline form has an X-ray powder diffraction pattern comprising a peak, in terms of 2θ, at about 17.99°. In some embodiments, the crystalline form has an X-ray powder diffraction pattern comprising peaks, in terms of 2θ, at about 13.08° and about 17.99°. In some embodiments, the crystalline form has an X-ray powder diffraction pattern comprising peaks, in terms of 2θ, at about 13.08° and about 19.82°. In some embodiments, the crystalline form has an X-ray powder diffraction pattern comprising peaks, in terms of 2θ, at about 13.08°, about 17.99°, and about 19.82°. In some embodiments, the crystalline form has an X-ray powder diffraction pattern comprising peaks, in terms of 2θ, at about 13.08°, about 17.99°, about 19.82°, about 26.98°, about 25.89°, about 25.50°, and about 18.36°. In some embodiments, the crystalline form has an X-ray powder diffraction pattern comprising peaks, in terms of 2θ, at about 13.08°, about 17.99°, about 19.82°, about 26.98°, about 25.89°, about 25.50°, about 18.36°, about 17.11°, about 27.36°, and about 23.21°. One aspect of the present invention is directed to a crystalline form of Compound 1 fumarate salt having an X-ray powder diffraction pattern comprising one or more peaks listed in Table 8. In some embodiments, the crystalline form has an X-ray powder diffraction pattern substantially as shown in FIG. 11, wherein by "substantially" is meant that the reported peaks can vary by about ±0.2° 2θ, and also that the relative intensities of the reported peaks can vary.

In some embodiments, the crystalline form of Compound 1 fumarate salt has a differential scanning calorimetry thermogram comprising an endotherm with an extrapolated onset temperature between about 205° C. and about 235° C. In some embodiments, the crystalline form of Compound 1 fumarate salt has a differential scanning calorimetry thermogram comprising an endotherm with an extrapolated onset temperature at about 219° C.

Figure 12:
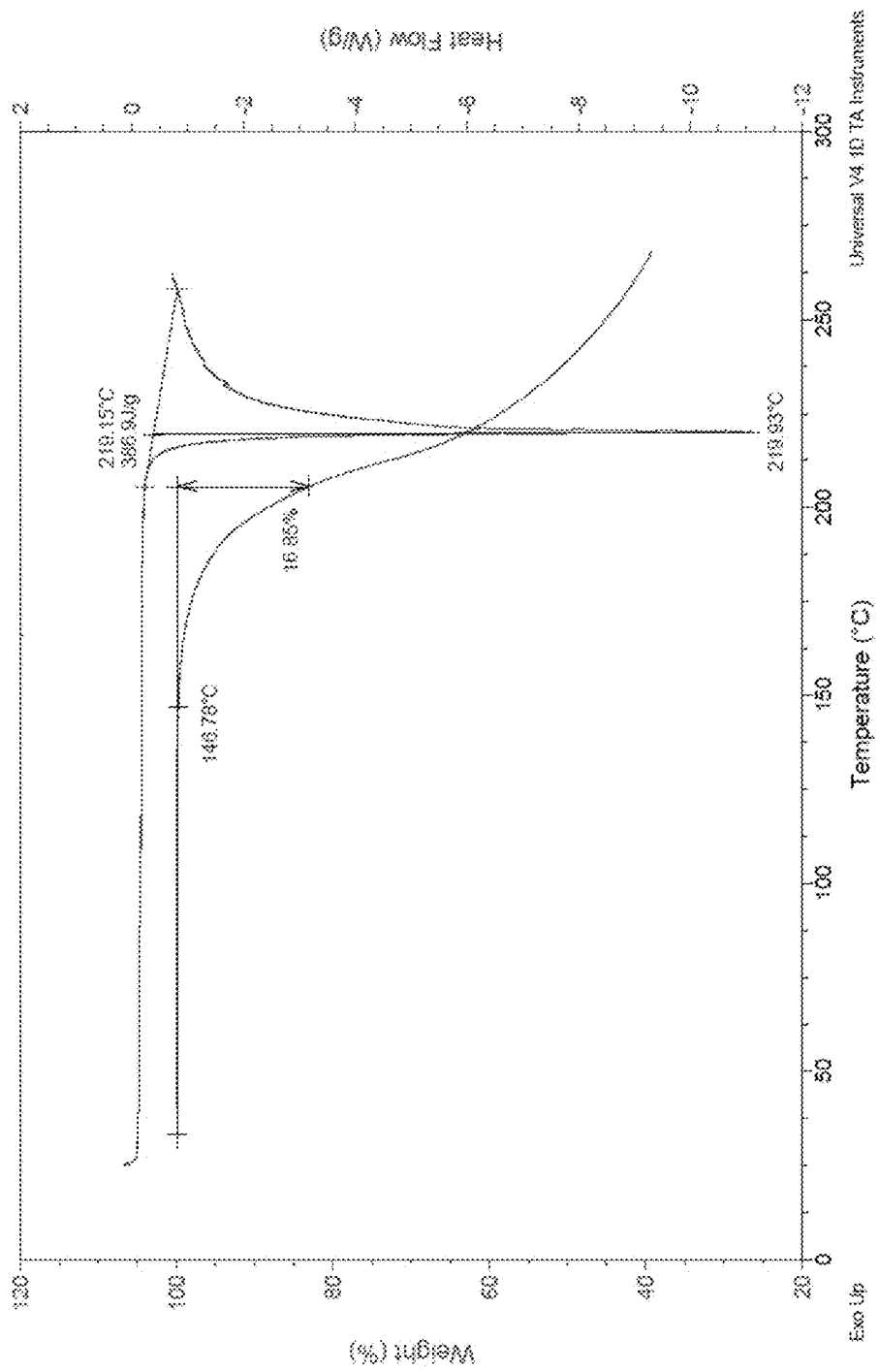
FIG. 12: DSC and TGA of Compound 1 Fumarate Salt, Form I.

In some embodiments, the crystalline form of Compound 1 fumarate salt has a thermogravimetric analysis profile substantially as shown in FIG. 12, wherein by "substantially" is meant that the reported TGA features can vary by about ±5° C. and by about ±2% weight change.

In some embodiments, the crystalline form of Compound 1 fumarate salt has a differential scanning calorimetry thermogram substantially as shown in FIG. 12, wherein by "substantially" is meant that the reported DSC features can vary by about ±6° C. and by about ±20 joules per gram.

Figure 13:
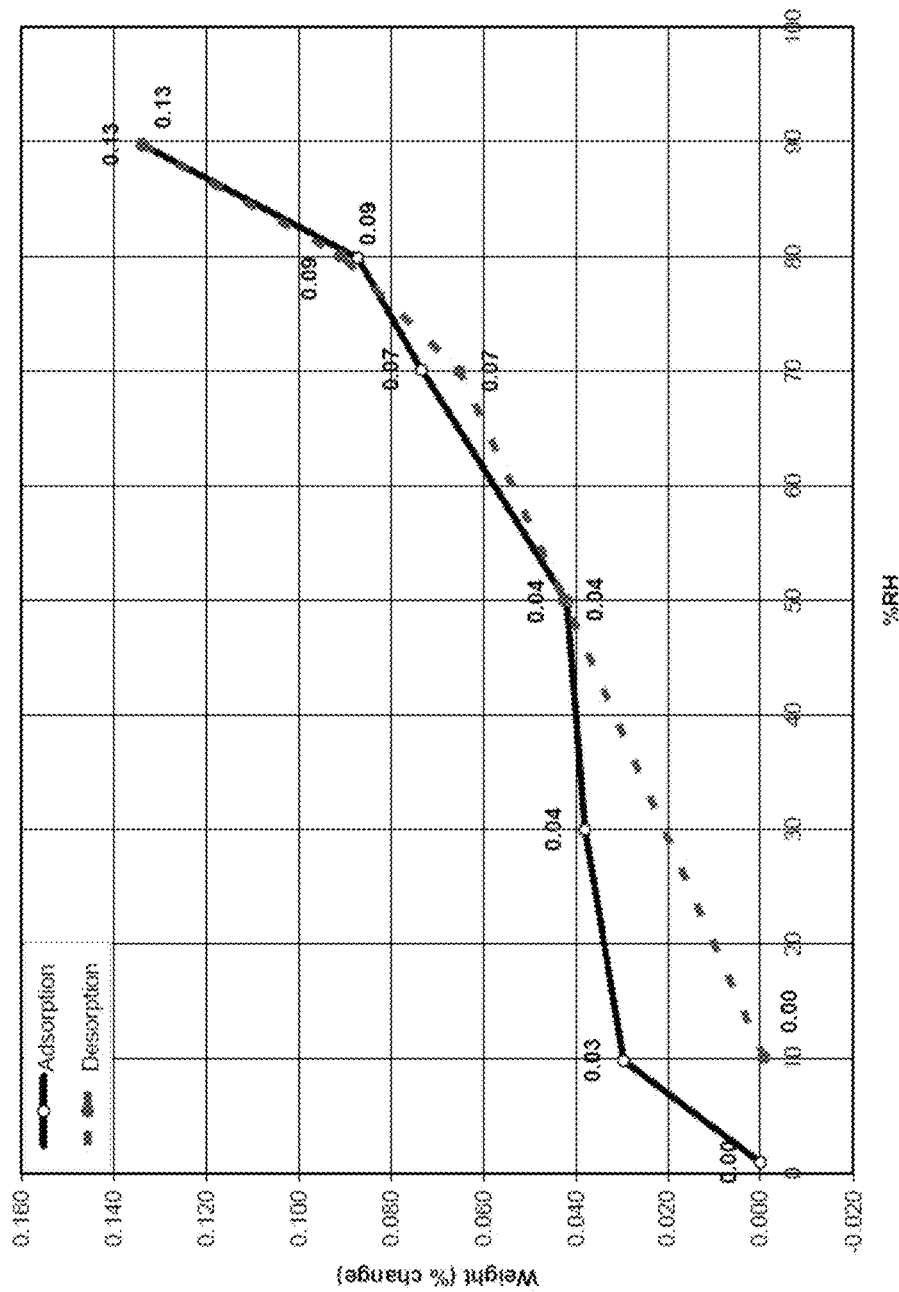
FIG. 13: DMS of Compound 1 Fumarate Salt, Form I.

In some embodiments, the crystalline form of Compound 1 fumarate salt has a dynamic moisture sorption profile substantially as shown in FIG. 13, wherein by "substantially" is meant that the reported DMS features can vary by about ±5% relative humidity and by about ±5% weight change.

Form I of Compound 1 fumarate salt can be prepared by any of the suitable procedures known in the art for preparing crystalline polymorphs. In some embodiments Form I of Compound 1 fumarate salt can be prepared as described in Example 3.3. In some embodiments, Form I of Compound 1 fumarate salt can be prepared by slurrying crystalline Compound 1 fumarate salt containing one or more crystalline forms other than Form I. In some embodiments, the crystalline form of Compound 1 fumarate salt can be prepared by recrystallizing crystalline Compound 1 fumarate salt containing one or more crystalline forms other than Form I.

Compound 1 Hemifumarate Salt

One aspect of the present invention pertains to a crystalline form of (R)-8-chloro-1-methyl-2,3,4,5-tetrahydro-1H-3-benzazepine hemifumarate salt (Compound 1 hemifumarate salt). In some embodiments, the crystalline form of (R)-8-chloro-1-methyl-2,3,4,5-tetrahydro-1H-3-benzazepine hemifumarate salt is Form I (Compound 1 hemifumarate salt, Form I). The physical properties of Form I of Compound 1 hemifumarate salt are summarized in Table 9 below.

TABLE 9

Figure 14:
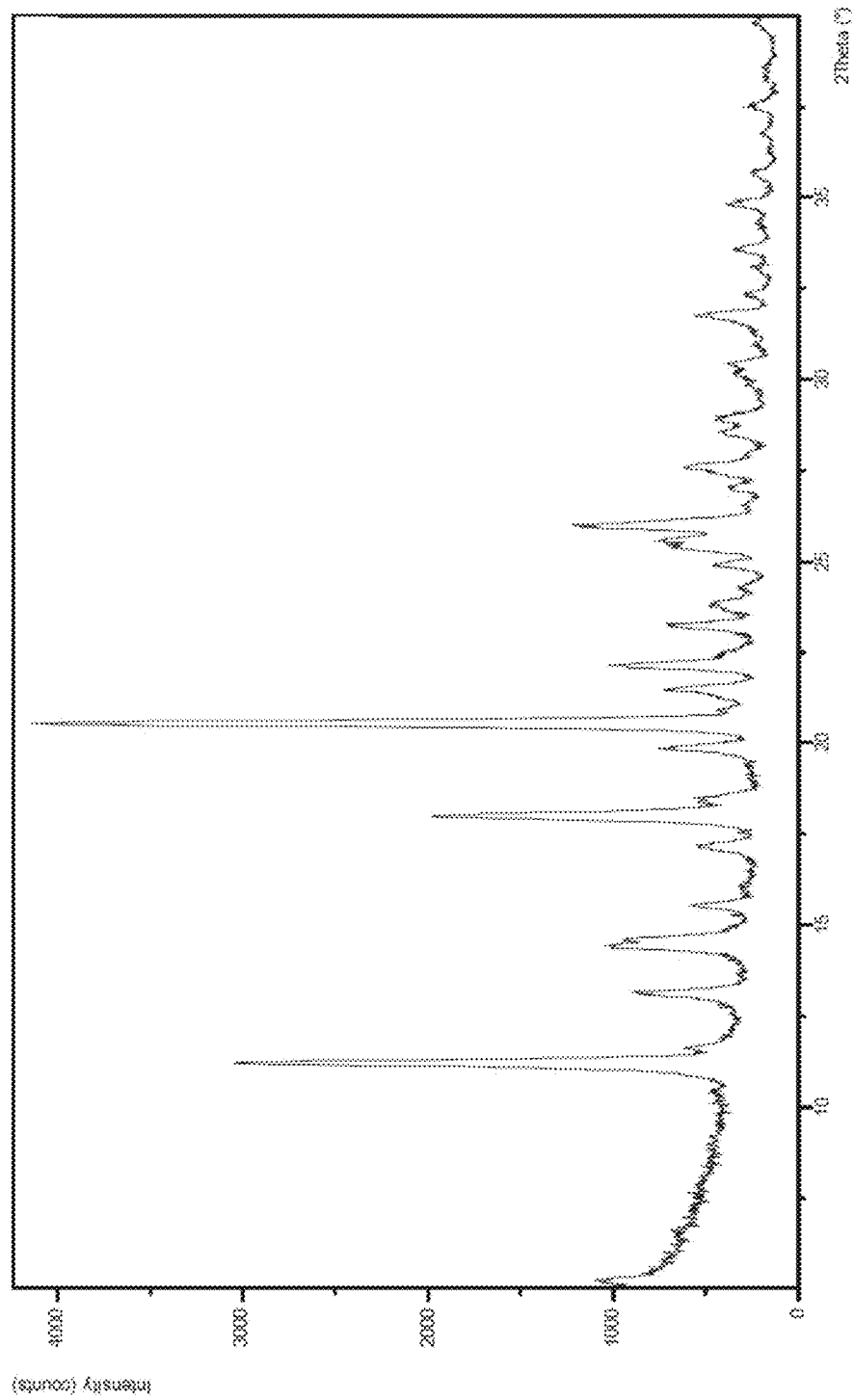
FIG. 14: PXRD of Compound 1 Hemifumarate Salt, Form I.

| | Compound 1 Hemifumarate Salt, Form I |
|---|---|
| PXRD | FIG. 14: Peaks of ≥10% relative intensity at 11.21, 13.12, 14.41, 14.60, 18.00, 19.85, 20.54, 21.47, 22.15, 23.24, 25.34, 25.57, 25.98, and 27.60 °2θ |
| TGA | FIG. 15: about 27% weight loss up to about 160° C. |
| DSC | FIG. 15: extrapolated onset temperature about 158° C.; enthalpy of fusion 51 J/g |
| DMS | FIG. 16: ~8% weight gain at about 50% RH |

Compound 1 hemifumarate salt, Form I had a melting onset of 158° C. by DSC, however, significant weight loss occurred prior to this melting onset based on TGA data. The weight loss was slightly more than the theoretical amount of fumaric acid for an anhydrous hemifumarate salt (27.0% vs. 22.9%).

Compound 1 hemifumarate salt, Form I formed a hydrate during DMS analysis, which was labile enough to lose the water upon desorption to 5% RH at 25° C. The ~8% weight gain is slightly higher than the theoretical % weight gain (7.1%) for a monohydrate.

Certain X-ray powder diffraction peaks for Form I of Compound 1 hemifumarate salt are shown in Table 10 below.

TABLE 10

| Pos. (°2θ) | Rel. Int. (%) |
|---|---|
| 5.22 | 7.76 |
| 11.21 | 68.97 |
| 11.62 | 6.75 |
| 13.12 | 14.50 |
| 14.41 | 18.42 |
| 14.60 | 16.63 |
| 15.53 | 8.04 |
| 17.17 | 7.72 |
| 18.00 | 44.75 |
| 18.45 | 7.42 |
| 19.85 | 13.99 |
| 20.54 | 100.00 |
| 21.47 | 12.45 |
| 22.15 | 20.83 |
| 23.24 | 12.38 |
| 23.82 | 6.64 |
| 24.26 | 2.82 |
| 24.92 | 6.64 |
| 25.34 | 11.01 |
| 25.57 | 14.60 |
| 25.98 | 24.15 |
| 27.02 | 4.46 |
| 27.60 | 10.77 |
| 28.55 | 6.21 |
| 28.92 | 6.45 |
| 30.41 | 5.52 |
| 31.75 | 9.94 |
| 32.34 | 3.42 |
| 33.06 | 2.05 |
| 33.58 | 4.55 |
| 34.82 | 6.53 |
| 35.67 | 2.88 |

TABLE 10-continued

| Pos. (°2θ) | Rel. Int. (%) |
|---|---|
| 36.77 | 1.82 |
| 37.51 | 3.33 |
| 38.46 | 1.55 |

One aspect of the present invention is directed to a crystalline form of Compound 1 hemifumarate salt having an X-ray powder diffraction pattern comprising a peak, in terms of 2θ, at about 20.54°. In some embodiments, the crystalline form has an X-ray powder diffraction pattern comprising a peak, in terms of 2θ, at about 11.21°. In some embodiments, the crystalline form has an X-ray powder diffraction pattern comprising peaks, in terms of 2θ, at about 20.54° and about 11.21°. In some embodiments, the crystalline form has an X-ray powder diffraction pattern comprising peaks, in terms of 2θ, at about 20.54° and about 18.00°. In some embodiments, the crystalline form has an X-ray powder diffraction pattern comprising peaks, in terms of 2θ, at about 20.54°, about 11.21°, and about 18.00°. In some embodiments, the crystalline form has an X-ray powder diffraction pattern comprising peaks, in terms of 2θ, at about 20.54°, about 11.21°, about 18.00°, about 25.98°, about 22.15°, about 14.41°, and about 14.60°. In some embodiments, the crystalline form has an X-ray powder diffraction pattern comprising peaks, in terms of 2θ, at about 20.54°, about 11.21°, about 18.00°, about 25.98°, about 22.15°, about 14.41°, about 14.60°, about 25.57°, about 13.12°, and about 19.85°. One aspect of the present invention is directed to a crystalline form of Compound 1 hemifumarate salt having an X-ray powder diffraction pattern comprising one or more peaks listed in Table 10. In some embodiments, the crystalline form has an X-ray powder diffraction pattern substantially as shown in FIG. 14, wherein by "substantially" is meant that the reported peaks can vary by about ±0.2°2θ, and also that the relative intensities of the reported peaks can vary.

In some embodiments, the crystalline form of Compound 1 hemifumarate salt has a differential scanning calorimetry thermogram comprising an endotherm with an extrapolated onset temperature between about 140° C. and about 170° C. In some embodiments, the crystalline form of Compound 1 hemifumarate salt has a differential scanning calorimetry thermogram comprising an endotherm with an extrapolated onset temperature at about 158° C. In some embodiments, the crystalline form of Compound 1 hemifumarate salt has a differential scanning calorimetry thermogram comprising an endotherm with an associated heat flow of about 51 joules per gram. In some embodiments, the crystalline form of Compound 1 hemifumarate salt has a thermogravimetric analysis profile substantially as shown in FIG. 15, wherein by "substantially" is meant that the reported TGA features can vary by about ±5° C. and by about ±2% weight change.

Figure 15:
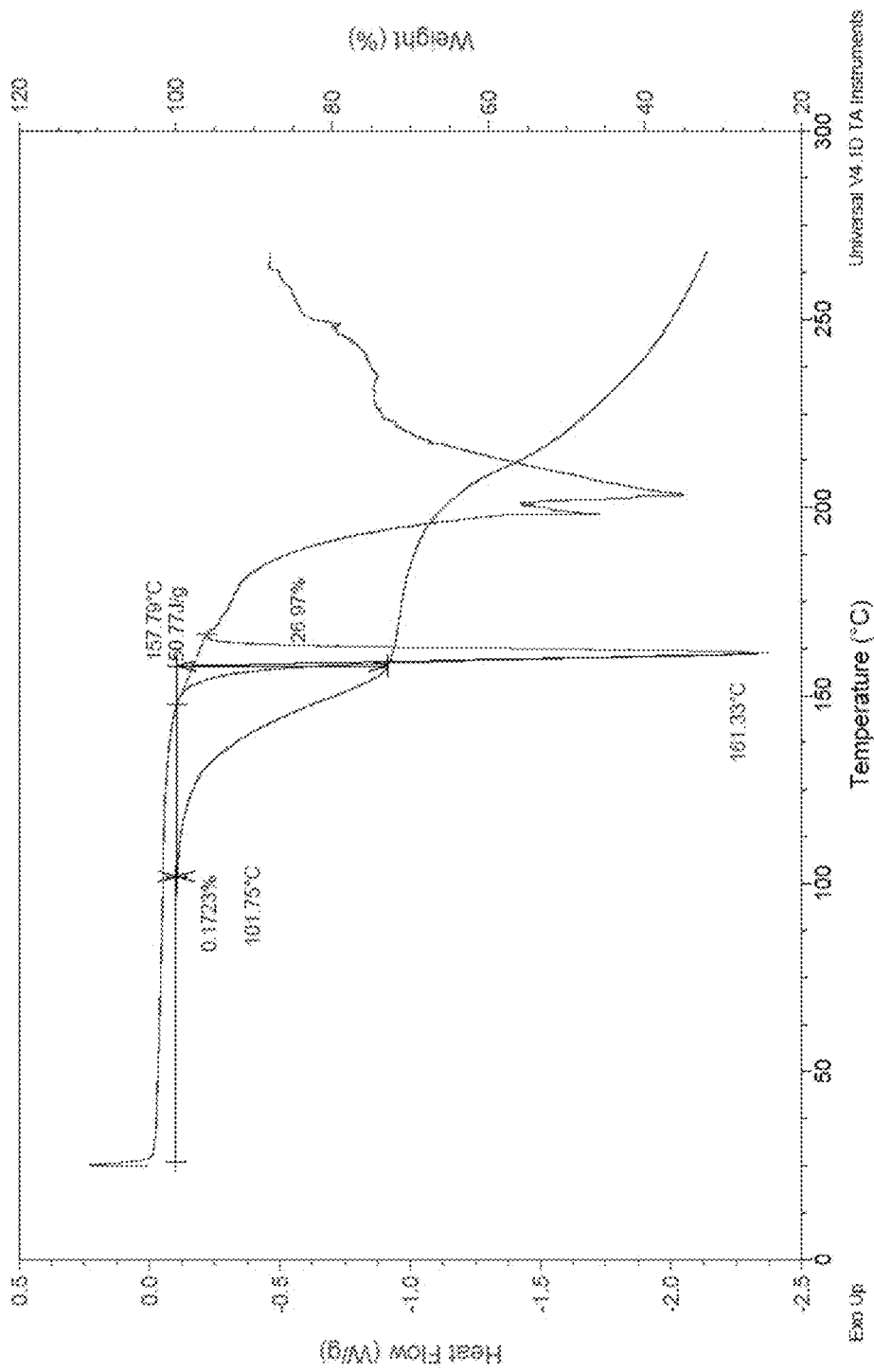
FIG. 15: DSC and TGA of Compound 1 Hemifumarate Salt, Form I.

In some embodiments, the crystalline form of Compound 1 hemifumarate salt has a differential scanning calorimetry thermogram substantially as shown in FIG. 15, wherein by "substantially" is meant that the reported DSC features can vary by about ±6° C. and by about ±20 joules per gram.

Figure 16:
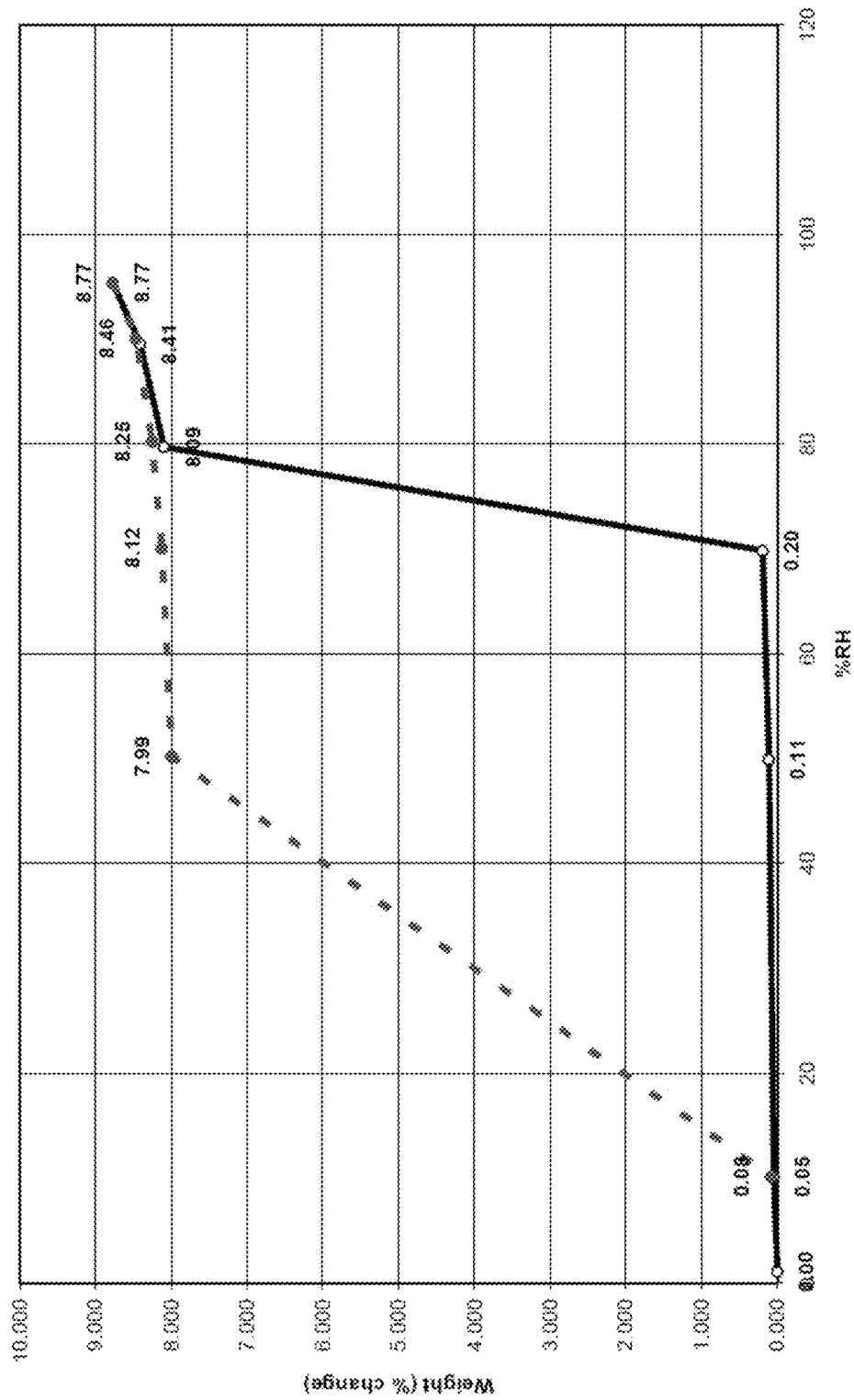
FIG. 16: DMS of Compound 1 Hemifumarate Salt, Form I.

In some embodiments, the crystalline form of Compound 1 hemifumarate salt has a dynamic moisture sorption profile substantially as shown in FIG. 16, wherein by "substantially" is meant that the reported DMS features can vary by about ±5% relative humidity and by about ±5% weight change.

Form I of Compound 1 hemifumarate salt can be prepared by any of the suitable procedures known in the art for preparing crystalline polymorphs. In some embodiments Form I of Compound 1 hemifumarate salt can be prepared as described in Example 3.4. In some embodiments, Form I of Compound 1 hemifumarate salt can be prepared by slurrying crystalline Compound 1 hemifumarate salt containing one or more crystalline forms other than Form I. In some embodiments, the crystalline form of Compound 1 hemifumarate salt can be prepared by recrystallizing crystalline Compound 1 hemifumarate salt containing one or more crystalline forms other than Form I.

Compound 1 Orotate Salt

One aspect of the present invention pertains to a crystalline form of (R)-8-chloro-1-methyl-2,3,4,5-tetrahydro-1H-3-benzazepine orotate salt (Compound 1 orotate salt). In some embodiments, the crystalline form of (R)-8-chloro-1-methyl-2,3,4,5-tetrahydro-1H-3-benzazepine orotate salt is Form I (Compound 1 orotate salt, Form I). The physical properties of Form I of Compound 1 orotate salt are summarized in Table 11 below.

TABLE 11

Figure 17:
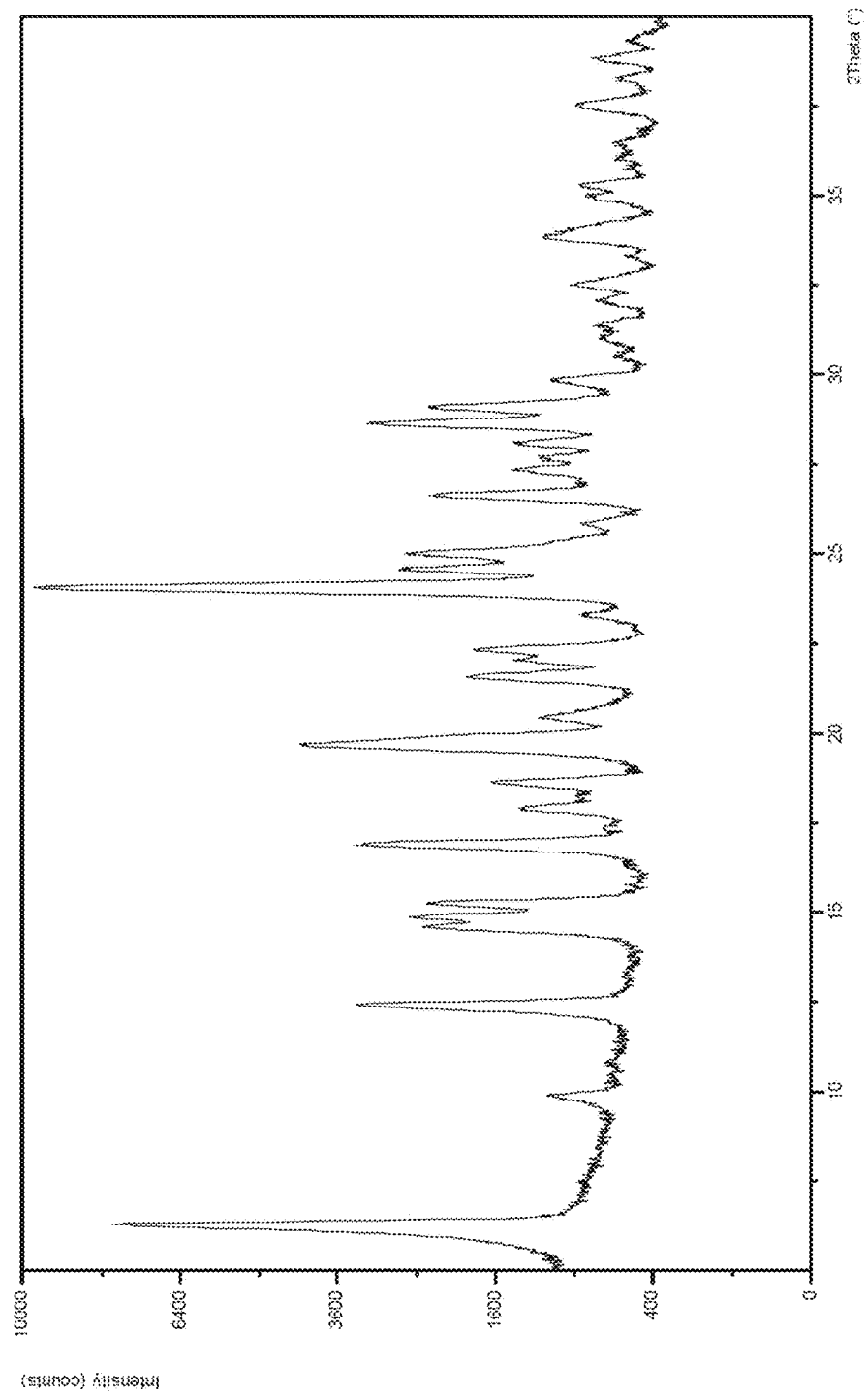
FIG. 17: PXRD of Compound 1 Orotate Salt, Form I.

| Compound 1 Orotate Salt, Form I | |
|---|---|
| PXRD | FIG. 17: Peaks of ≥20% relative intensity at 6.30, 12.44, 14.59, 14.86, 16.96, 19.62, 19.71, 24.07, 24.55, 25.02, 26.64, and 28.64 °2θ |
| TGA | FIG. 18: no significant weight loss up to about 200° C. |
| DSC | FIG. 18: extrapolated onset temperature for initial endotherm about 236° C., followed by multiple thermal events |
| DMS | FIG. 19: ~0.15% weight gain at about 90% RH |

Compound 1 orotate salt, Form I was an anhydrous salt by TGA. The initial melting onset by DSC was 236° C. However, the initial endotherm was small and followed immediately by a small exotherm which was followed immediately by larger endothermic events. Based on TGA results, there was significant weight loss occurring throughout these thermal events, indicating that the salt melted with decomposition. Compound 1 orotate salt was non-hygroscopic by DMS analysis, picking up about 0.15% out to and including the 90% RH hold at 25° C.

Certain X-ray powder diffraction peaks for Form I of Compound 1 orotate salt are shown in Table 12 below.

TABLE 12

| Pos. (°2θ) | Rel. Int. (%) |
|---|---|
| 6.30 | 73.29 |
| 9.91 | 4.94 |
| 12.44 | 29.14 |
| 14.59 | 20.96 |
| 14.86 | 22.50 |
| 15.29 | 18.32 |
| 16.96 | 27.39 |
| 17.89 | 9.67 |
| 18.63 | 12.70 |
| 19.62 | 37.19 |
| 19.71 | 39.63 |
| 19.93 | 18.27 |
| 20.44 | 7.74 |
| 21.57 | 15.75 |
| 22.03 | 10.37 |
| 22.35 | 14.64 |
| 23.29 | 4.21 |
| 24.07 | 100.00 |
| 24.55 | 23.57 |
| 25.02 | 23.70 |

TABLE 12-continued

| Pos. (°2θ) | Rel. Int. (%) |
|---|---|
| 25.84 | 4.42 |
| 26.64 | 20.04 |
| 27.36 | 11.06 |
| 27.74 | 8.30 |
| 28.09 | 10.48 |
| 28.64 | 28.74 |
| 29.14 | 19.54 |
| 29.85 | 6.78 |
| 31.40 | 3.45 |
| 32.04 | 3.34 |
| 32.53 | 5.46 |
| 33.80 | 8.09 |
| 34.97 | 4.19 |
| 35.33 | 4.53 |
| 36.48 | 2.29 |
| 37.55 | 5.27 |
| 38.25 | 2.26 |
| 38.82 | 3.95 |
| 39.34 | 1.66 |

One aspect of the present invention is directed to a crystalline form of Compound 1 orotate salt having an X-ray powder diffraction pattern comprising a peak, in terms of 2θ, at about 24.07°. In some embodiments, the crystalline form has an X-ray powder diffraction pattern comprising a peak, in terms of 2θ, at about 6.30°. In some embodiments, the crystalline form has an X-ray powder diffraction pattern comprising peaks, in terms of 2θ, at about 24.07° and about 6.30°. In some embodiments, the crystalline form has an X-ray powder diffraction pattern comprising peaks, in terms of 2θ, at about 24.07° and about 19.71°. In some embodiments, the crystalline form has an X-ray powder diffraction pattern comprising peaks, in terms of 2θ, at about 24.07°, about 6.30°, and about 19.71°. In some embodiments, the crystalline form has an X-ray powder diffraction pattern comprising peaks, in terms of 2θ, at about 24.07°, about 6.30°, about 19.71°, about 19.62°, about 12.44°, about 28.64°, and about 16.96°. In some embodiments, the crystalline form has an X-ray powder diffraction pattern comprising peaks, in terms of 2θ, at about 24.07°, about 6.30°, about 19.71°, about 19.62°, about 12.44°, about 28.64°, about 16.96°, about 25.02°, about 24.55°, and about 14.86°. One aspect of the present invention is directed to a crystalline form of Compound 1 orotate salt having an X-ray powder diffraction pattern comprising one or more peaks listed in Table 12. In some embodiments, the crystalline form has an X-ray powder diffraction pattern substantially as shown in FIG. 17, wherein by "substantially" is meant that the reported peaks can vary by about ±0.2°2θ, and also that the relative intensities of the reported peaks can vary.

In some embodiments, the crystalline form of Compound 1 orotate salt has a differential scanning calorimetry thermogram comprising an endotherm with an extrapolated onset temperature between about 220° C. and about 250° C. In some embodiments, the crystalline form of Compound 1 orotate salt has a differential scanning calorimetry thermogram comprising an endotherm with an extrapolated onset temperature at about 236° C. In some embodiments, the crystalline form of Compound 1 orotate salt has a thermogravimetric analysis profile substantially as shown in FIG. 18, wherein by "substantially" is meant that the reported TGA features can vary by about ±5° C. and by about ±2% weight change.

Figure 18:
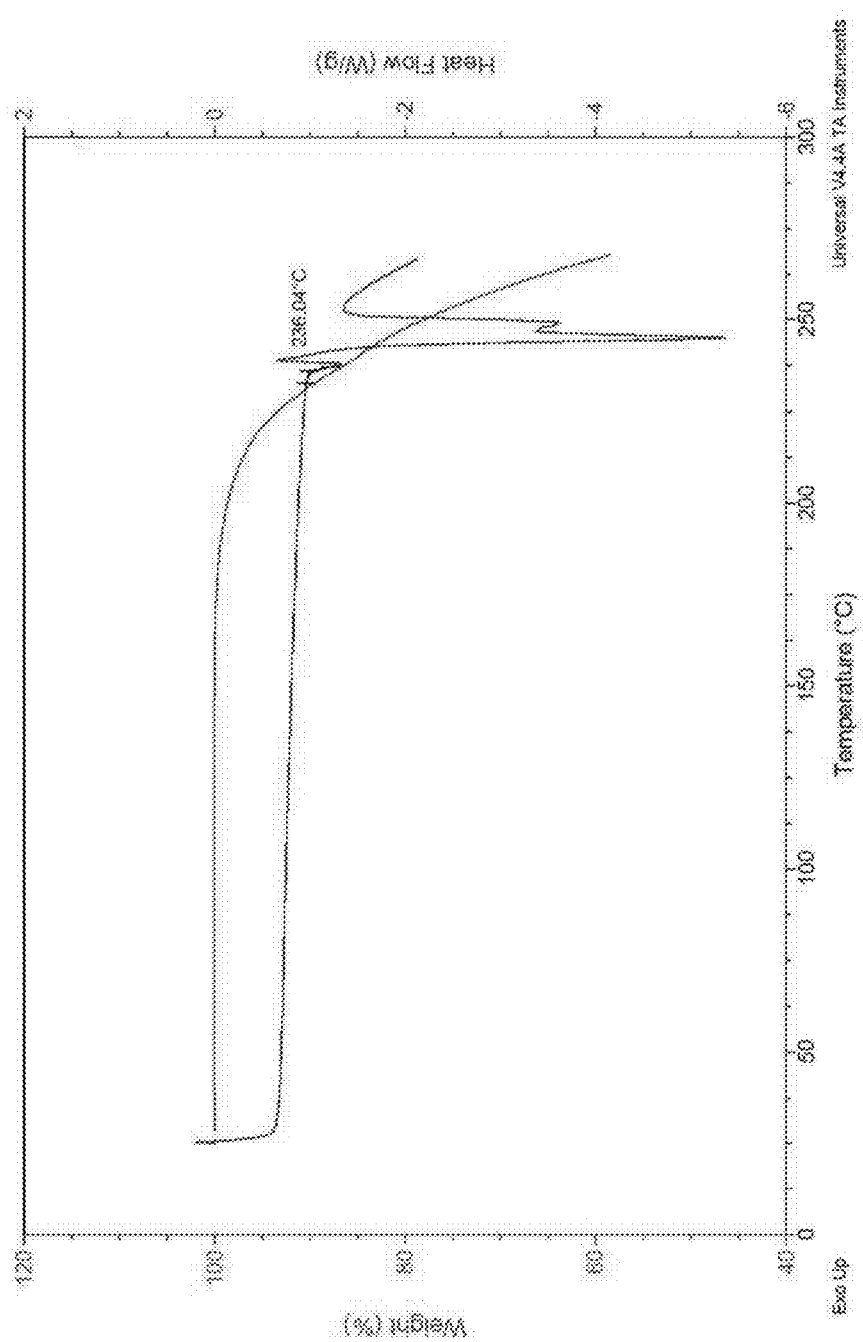
FIG. 18: DSC and TGA of Compound 1 Orotate Salt, Form I.

In some embodiments, the crystalline form of Compound 1 orotate salt has a differential scanning calorimetry thermogram substantially as shown in FIG. 18, wherein by "substantially" is meant that the reported DSC features can vary by about ±6° C. and by about ±20 joules per gram.

Figure 19:
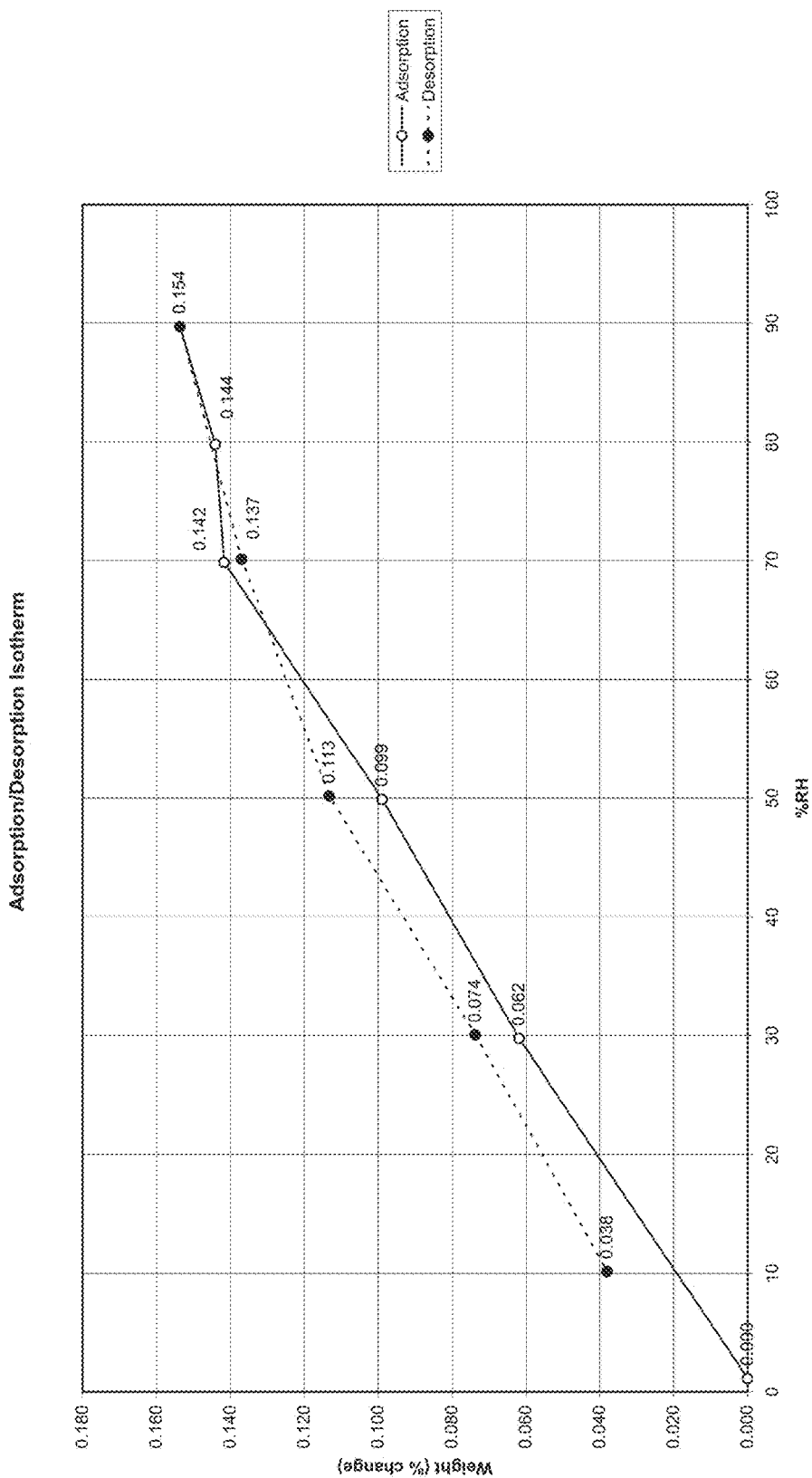
FIG. 19: DMS of Compound 1 Orotate Salt, Form I.

In some embodiments, the crystalline form of Compound 1 orotate salt has a dynamic moisture sorption profile substantially as shown in FIG. 19, wherein by "substantially" is meant that the reported DMS features can vary by about ±5% relative humidity and by about ±5% weight change.

Form I of Compound 1 orotate salt can be prepared by any of the suitable procedures known in the art for preparing crystalline polymorphs. In some embodiments Form I of Compound 1 orotate salt can be prepared as described in Example 3.5. In some embodiments, Form I of Compound 1 orotate salt can be prepared by slurrying crystalline Compound 1 orotate salt containing one or more crystalline forms other than Form I. In some embodiments, the crystalline form of Compound 1 orotate salt can be prepared by recrystallizing crystalline Compound 1 orotate salt containing one or more crystalline forms other than Form I.

Compound 1 Orotate Salt Hydrate

One aspect of the present invention pertains to a crystalline form of (R)-8-chloro-1-methyl-2,3,4,5-tetrahydro-1H-3-benzazepine orotate salt hydrate (Compound 1 orotate salt hydrate). In some embodiments, the crystalline form of (R)-8-chloro-1-methyl-2,3,4,5-tetrahydro-1H-3-benzazepine orotate salt hydrate is Form I (Compound 1 orotate salt hydrate, Form I). The physical properties of Form I of Compound 1 orotate salt hydrate are summarized in Table 13 below.

TABLE 13

Figure 20:
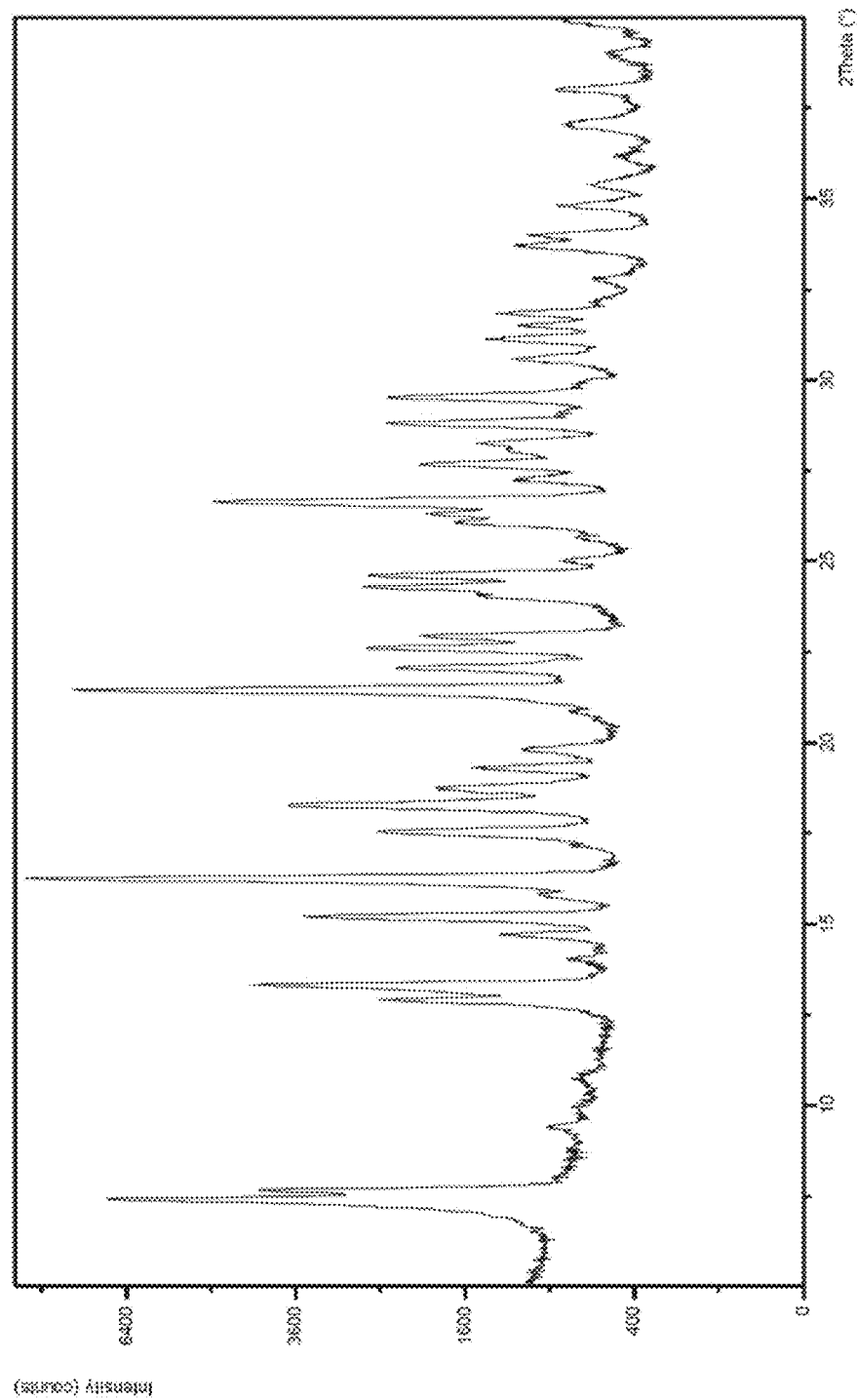
FIG. 20: PXRD of Compound 1 Orotate Salt Hydrate, Form I.

| | Compound 1 Orotate Salt Hydrate, Form I |
|---|---|
| PXRD | FIG. 20: Peaks of ≥28% relative intensity at 7.43, 7.6774, 13.35, 15.25, 16.28, 18.31, 21.47, 22.60, 24.31, 24.61, and 26.67 °2θ |
| TGA | FIG. 21: about 2.7% weight loss up to about 147° C. and about 0.9% between about 147° C. and about 179° C. |
| DSC | FIG. 21: extrapolated onset temperature about 173° C. corresponding to a melt/recrystallization; extrapolated onset temperature about 234° C. corresponding to a melt decomposition |
| DMS | FIG. 22: ~0.14% weight gain at about 90% RH |

Compound 1 orotate salt hydrate had weight loss observed in two steps, the first (2.7%) measured out to ~147° C., and the second (0.9%) occurring out to ~179° C. The total weight loss (~3.6%) was close to the theoretical amount for a 0.75 (3:4) hydrate (3.7%). The two step weight loss was consistent with two H$_2$O molecules having similar binding energies that are different than the third H$_2$O molecule in the crystal lattice. A melting onset of ~234° C. by DSC scanned at 10° C./min followed an endotherm/exotherm melt/crystallization at ~173° C. These thermal events are consistent with conversion of the hydrated lattice to the anhydrous lattice and melting/decomposition of anhydrous Compound 1 orotate, which was confirmed by removing a sample from TGA after scanning to 200° C. and then running PXRD.

Compound 1 orotate salt hydrate, Form I was non-hygroscopic by DMS analysis, picking up about 0.14% out to and including the 90% RH hold at 25°.

Certain X-ray powder diffraction peaks for Form I of Compound 1 orotate salt hydrate are shown in Table 14 below.

TABLE 14

| Pos. (°2θ) | Rel. Int. (%) |
|---|---|
| 7.43 | 78.01 |
| 7.68 | 42.82 |
| 9.43 | 2.77 |
| 10.77 | 1.07 |
| 12.91 | 25.56 |
| 13.35 | 45.76 |
| 14.05 | 2.50 |
| 14.71 | 10.30 |
| 15.25 | 35.49 |
| 15.79 | 5.69 |
| 16.28 | 100.00 |
| 17.58 | 25.45 |
| 18.31 | 41.37 |
| 18.78 | 17.59 |
| 19.33 | 12.83 |
| 19.85 | 7.03 |
| 21.47 | 91.69 |
| 22.08 | 24.23 |
| 22.60 | 28.39 |
| 22.95 | 20.91 |
| 23.99 | 11.59 |
| 24.31 | 29.32 |
| 24.61 | 29.10 |
| 25.02 | 4.66 |
| 25.63 | 3.12 |
| 26.06 | 16.10 |
| 26.30 | 19.78 |
| 26.67 | 56.52 |
| 27.21 | 8.79 |
| 27.67 | 21.48 |
| 28.25 | 13.60 |
| 28.84 | 26.07 |
| 29.52 | 26.20 |
| 30.57 | 9.68 |
| 31.13 | 13.31 |
| 31.51 | 9.71 |
| 31.81 | 11.19 |
| 32.79 | 2.68 |
| 33.74 | 9.94 |
| 34.00 | 8.50 |
| 34.77 | 5.13 |
| 35.37 | 3.39 |
| 36.11 | 1.06 |
| 37.01 | 5.26 |
| 38.01 | 6.71 |
| 39.05 | 2.24 |

One aspect of the present invention is directed to a crystalline form of Compound 1 orotate salt hydrate having an X-ray powder diffraction pattern comprising a peak, in terms of 2θ, at about 16.28°. In some embodiments, the crystalline form has an X-ray powder diffraction pattern comprising a peak, in terms of 2θ, at about 21.47°. In some embodiments, the crystalline form has an X-ray powder diffraction pattern comprising peaks, in terms of 2θ, at about 16.28° and about 21.47°. In some embodiments, the crystalline form has an X-ray powder diffraction pattern comprising peaks, in terms of 2θ, at about 16.28° and about 7.43°. In some embodiments, the crystalline form has an X-ray powder diffraction pattern comprising peaks, in terms of 2θ, at about 16.28°, about 21.47°, and about 7.43°. In some embodiments, the crystalline form has an X-ray powder diffraction pattern comprising peaks, in terms of 2θ, at about 16.28°, about 21.47°, about 7.43°, about 26.67°, about 13.35°, about 7.6774°, and about 18.31°. In some embodiments, the crystalline form has an X-ray powder diffraction pattern comprising peaks, in terms of 2θ, at about 16.28°, about 21.47°, about 7.43°, about 26.67°, about 13.35°, about 7.6774°, about 18.31°, about 15.25°, about 24.31°, and about 24.61°. One aspect of the present invention is directed to a crystalline form of Compound 1 orotate salt hydrate having an X-ray powder diffraction pattern comprising one or more peaks listed in Table 14. In some embodiments, the crystalline form has an X-ray powder diffraction pattern substantially as shown in FIG. 20, wherein by "substantially" is meant that the reported peaks can vary by about ±0.2°2θ, and also that the relative intensities of the reported peaks can vary.

In some embodiments, the crystalline form of Compound 1 orotate salt hydrate has a differential scanning calorimetry thermogram comprising an endotherm with an extrapolated onset temperature between about 160° C. and about 190° C. In some embodiments, the crystalline form of Compound 1 orotate salt hydrate has a differential scanning calorimetry thermogram comprising an endotherm with an extrapolated onset temperature at about 173° C. In some embodiments, the crystalline form of Compound 1 orotate salt hydrate has a differential scanning calorimetry thermogram comprising an endotherm with an extrapolated onset temperature between about 220° C. and about 250° C. In some embodiments, the crystalline form of Compound 1 orotate salt hydrate has a differential scanning calorimetry thermogram comprising an endotherm with an extrapolated onset temperature at about 234° C. In some embodiments, the crystalline form of Compound 1 orotate salt hydrate has a thermogravimetric analysis profile substantially as shown in FIG. 21, wherein by "substantially" is meant that the reported TGA features can vary by about ±5° C. and by about ±2% weight change.

Figure 21:
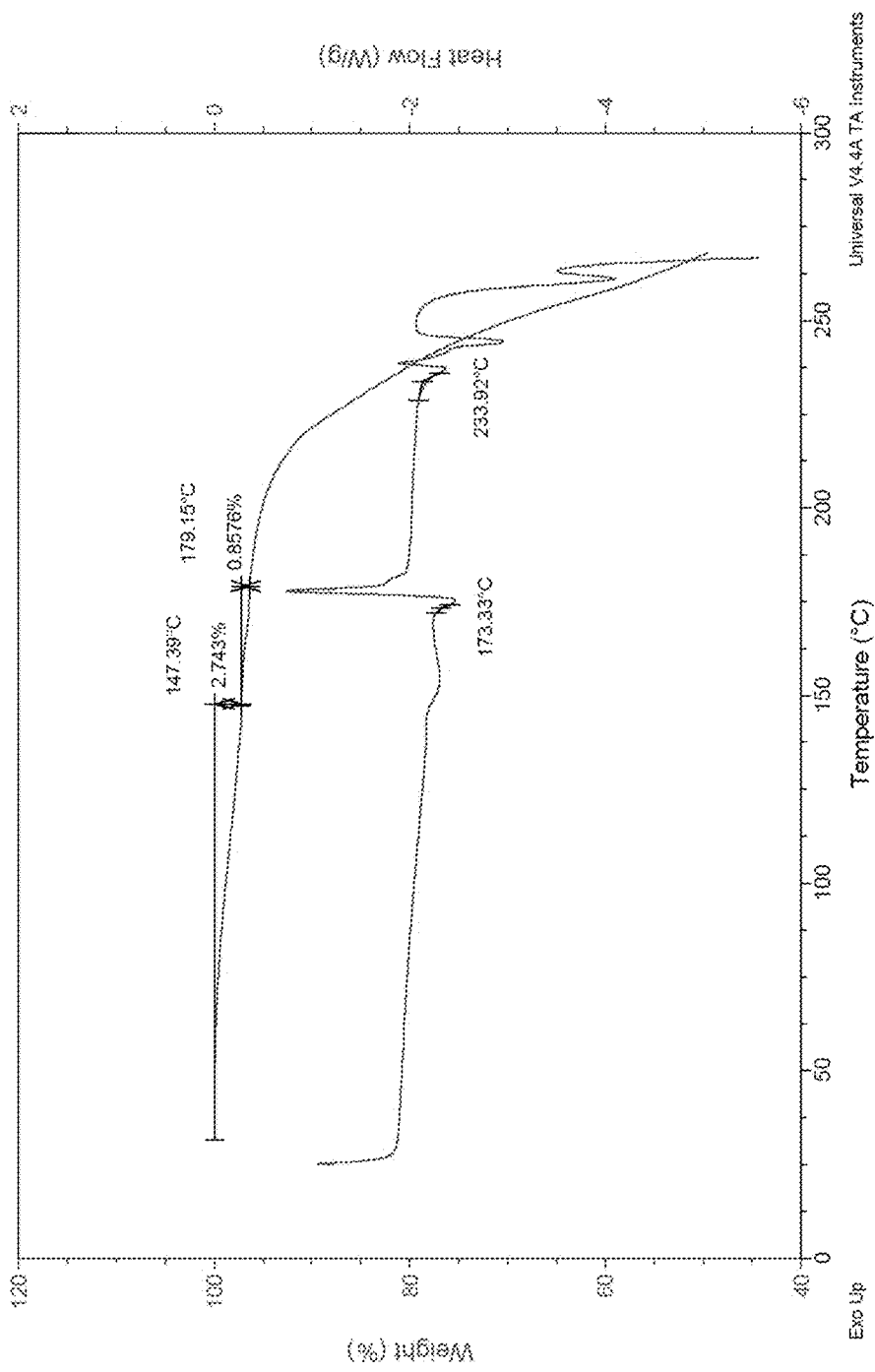
FIG. 21: DSC and TGA of Compound 1 Orotate Salt Hydrate, Form I.

In some embodiments, the crystalline form of Compound 1 orotate salt hydrate has a differential scanning calorimetry thermogram substantially as shown in FIG. 21, wherein by "substantially" is meant that the reported DSC features can vary by about ±6° C. and by about ±20 joules per gram.

Figure 22:
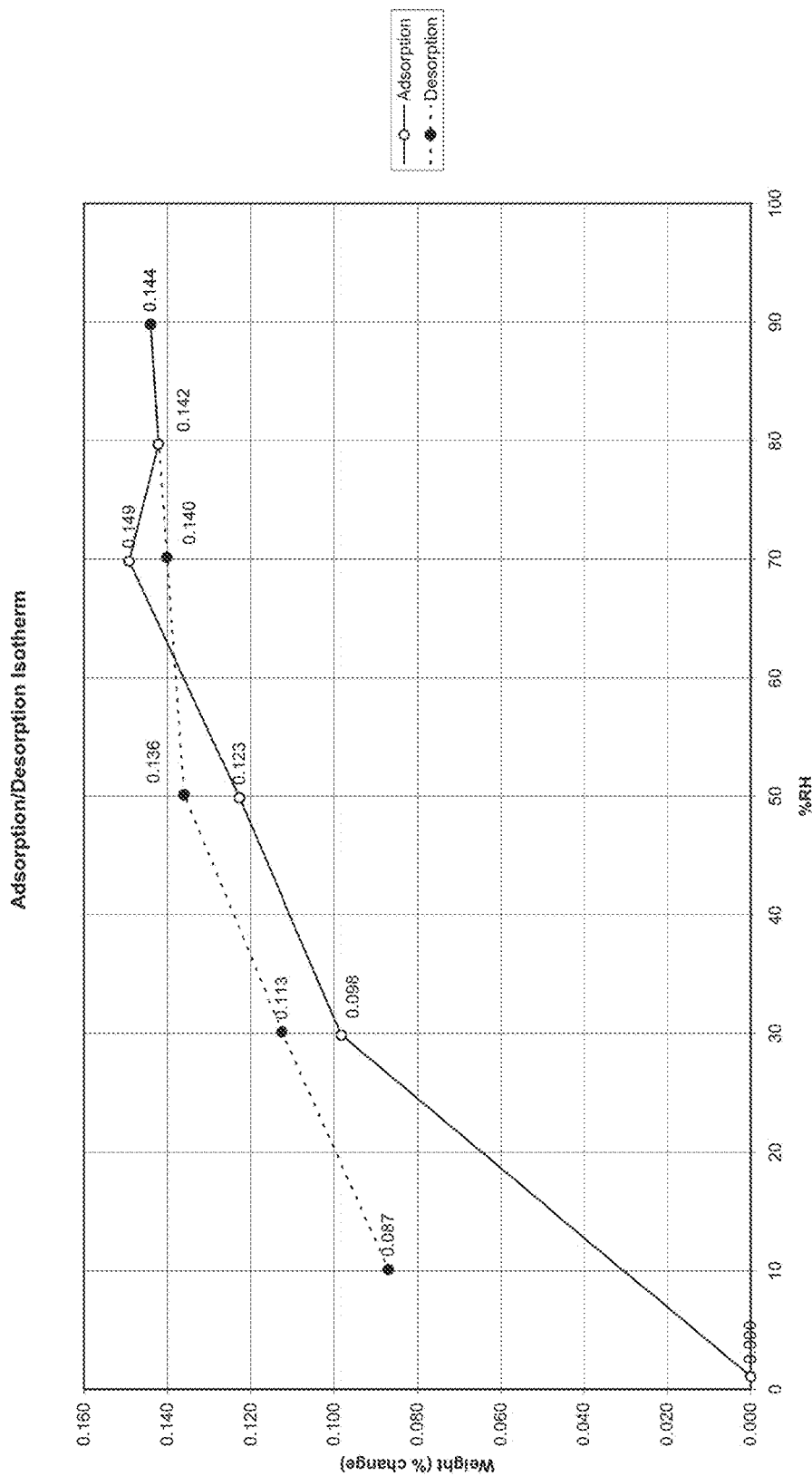
FIG. 22: DMS of Compound 1 Orotate Salt Hydrate, Form I.

In some embodiments, the crystalline form of Compound 1 orotate salt hydrate has a dynamic moisture sorption profile substantially as shown in FIG. 22, wherein by "substantially" is meant that the reported DMS features can vary by about ±5% relative humidity and by about ±5% weight change.

Form I of Compound 1 orotate salt hydrate can be prepared by any of the suitable procedures known in the art for preparing crystalline polymorphs. In some embodiments Form I of Compound 1 orotate salt hydrate can be prepared as described in Example 3.6. In some embodiments, Form I of Compound 1 orotate salt hydrate can be prepared by slurrying crystalline Compound 1 orotate salt hydrate containing one or more crystalline forms other than Form I. In some embodiments, the crystalline form of Compound 1 orotate salt hydrate can be prepared by recrystallizing crystalline Compound 1 orotate salt hydrate containing one or more crystalline forms other than Form I.

Compound 1 Di-4-Acetamidobenzoate Salt-Cocrystal Methyl Ethyl Ketone Solvate

One aspect of the present invention pertains to a crystalline form of (R)-8-chloro-1-methyl-2,3,4,5-tetrahydro-1H-3-benzazepine di-4-acetamidobenzoate salt-cocrystal methyl ethyl ketone solvate (Compound 1 di-4-acetamidobenzoate salt-cocrystal methyl ethyl ketone solvate). In some embodiments, the crystalline form of (R)-8-chloro-1-methyl-2,3,4,5-tetrahydro-1H-3-benzazepine di-4-acetamidobenzoate salt-cocrystal methyl ethyl ketone solvate is Form I (Compound 1 di-4-acetamidobenzoate salt-cocrystal methyl ethyl ketone solvate, Form I). The physical properties of Form I of Compound 1 di-4-acetamidobenzoate salt-cocrystal methyl ethyl ketone solvate are summarized in Table 15 below.

TABLE 15

Figure 23:
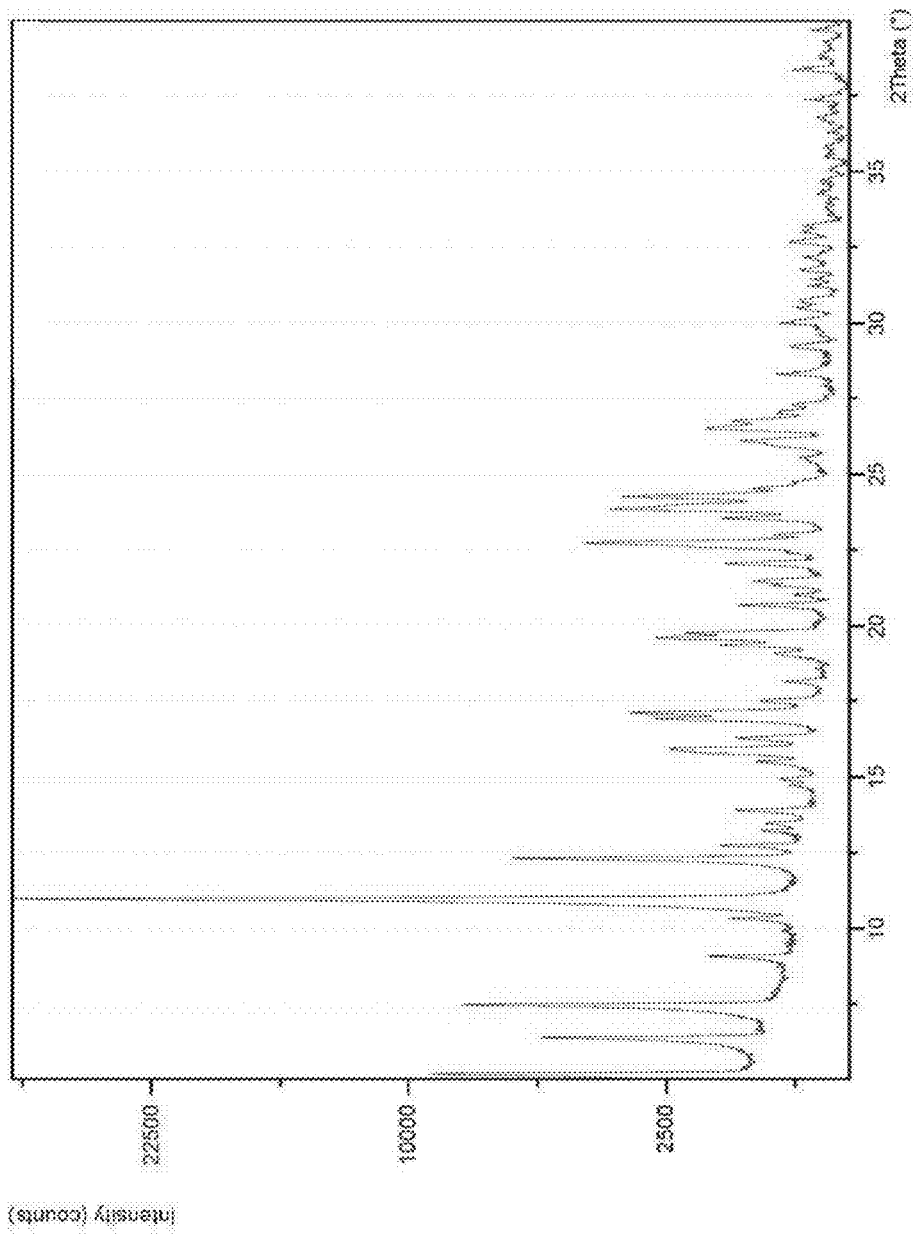
FIG. 23: PXRD of Compound 1 Di-4-acetamidobenzoate Salt-Cocrystal Methyl Ethyl Ketone Solvate, Form I.

| | Compound 1 Di-4-acetamidobenzoate Salt-Cocrystal Methyl Ethyl Ketone Solvate, Form I |
|---|---|
| PXRD | FIG. 23: Peaks of ≥7% relative intensity at 5.19, 6.38, 7.46, 10.98, 12.31, 15.92, 16.92, 17.11, 19.60, 22.73, 23.84, and 24.26 °2θ |
| TGA | FIG. 24: about 2.7% weight loss up to about 115° C. |
| DSC | FIG. 24: extrapolated melting/desolvation onset temperature about 113° C.; enthalpy of fusion 89 J/g |
| DMS | FIG. 25: ~9% weight gain at about 90% RH |

DSC analysis of Compound 1 di-4-acetamidobenzoate salt-cocrystal methyl ethyl ketone solvate showed a melting/desolvation onset temperature of 113° C. and an enthalpy of fusion of 89 J/g. By TGA the sample lost approximately 2.7% by weight during melting and continued to lose weight after the melt.

Compound 1 di-4-acetamidobenzoate salt-cocrystal methyl ethyl ketone solvate, Form I did not pick up significant weight below 70% RH. The sample was hygroscopic above this point and picked up 2.6% weight at 80% RH and over 9% weight out to and including the 90% RH hold at 25° C. Hysteresis on the desorption isotherm indicated a possible solid phase transition.

The sample lost over 2.4% weight upon completion of the desorption phase, which had not been removed during the drying step at 40° C. and ~1% RH. This is consistent with the weight loss seen in the TGA upon melting suggesting that solvate solvent was lost during the DMS experiment. After DMS analysis the sample remained a white solid, however the PXRD pattern showed significant amorphous character and crystalline peaks consistent with 4-acetamidobenzoic acid rather than Compound 1 di-4-acetamidobenzoate salt.

Certain X-ray powder diffraction peaks for Form I of Compound 1 di-4-acetamidobenzoate salt-cocrystal methyl ethyl ketone solvate are shown in Table 16 below.

TABLE 16

| Pos. (°2θ) | Rel. Int. (%) |
|---|---|
| 5.19 | 28.81 |
| 6.38 | 16.51 |
| 6.65 | 2.56 |
| 7.46 | 24.99 |
| 9.07 | 4.73 |
| 9.92 | 1.52 |
| 10.33 | 3.77 |
| 10.98 | 100.00 |
| 12.31 | 19.40 |
| 12.73 | 4.03 |
| 13.22 | 2.33 |
| 13.46 | 2.20 |
| 13.90 | 3.44 |
| 14.73 | 1.33 |
| 14.93 | 1.57 |
| 15.22 | 0.99 |
| 15.49 | 2.52 |
| 15.77 | 5.13 |
| 15.92 | 7.04 |
| 16.27 | 3.30 |
| 16.92 | 7.80 |
| 17.11 | 9.58 |
| 17.51 | 2.41 |
| 18.14 | 1.45 |
| 19.06 | 1.85 |
| 19.35 | 4.07 |
| 19.60 | 7.82 |
| 19.76 | 6.14 |
| 20.69 | 3.37 |
| 21.02 | 1.10 |
| 21.34 | 1.94 |
| 21.48 | 2.63 |
| 22.06 | 3.89 |
| 22.40 | 1.36 |
| 22.58 | 4.80 |
| 22.73 | 13.36 |
| 22.99 | 1.91 |
| 23.54 | 4.05 |
| 23.84 | 11.04 |
| 23.99 | 6.46 |
| 24.26 | 10.06 |
| 24.53 | 2.77 |
| 24.76 | 1.13 |
| 25.55 | 1.01 |
| 25.93 | 1.90 |
| 26.10 | 3.17 |
| 26.51 | 4.92 |
| 26.57 | 4.03 |
| 26.75 | 3.49 |
| 27.02 | 1.74 |
| 27.29 | 1.24 |
| 27.54 | 0.36 |
| 27.93 | 0.29 |
| 28.29 | 1.76 |
| 29.23 | 1.26 |
| 29.60 | 0.49 |
| 30.00 | 1.69 |
| 30.10 | 1.23 |
| 30.50 | 1.00 |
| 30.73 | 1.02 |
| 31.22 | 0.76 |
| 31.44 | 0.69 |
| 31.71 | 0.84 |
| 31.78 | 0.90 |
| 32.16 | 0.90 |
| 32.39 | 0.43 |
| 32.67 | 1.35 |
| 33.00 | 0.85 |
| 33.21 | 0.84 |
| 33.78 | 0.28 |
| 34.26 | 0.52 |
| 34.59 | 0.38 |
| 34.72 | 0.42 |
| 35.04 | 0.22 |
| 35.48 | 0.37 |
| 35.79 | 0.32 |
| 36.28 | 0.29 |
| 36.56 | 0.22 |
| 36.79 | 0.55 |
| 37.37 | 0.87 |
| 37.48 | 0.34 |
| 38.07 | 0.09 |
| 38.35 | 1.26 |
| 38.45 | 0.78 |
| 38.73 | 0.44 |
| 39.30 | 0.37 |
| 39.67 | 0.69 |

One aspect of the present invention is directed to a crystalline form of Compound 1 di-4-acetamidobenzoate salt-cocrystal methyl ethyl ketone solvate having an X-ray powder diffraction pattern comprising a peak, in terms of 2θ, at about 10.98°. In some embodiments, the crystalline form has an X-ray powder diffraction pattern comprising a peak, in terms of 2θ, at about 5.19°. In some embodiments, the crystalline form has an X-ray powder diffraction pattern comprising peaks, in terms of 2θ, at about 10.98° and about 5.19°. In some embodiments, the crystalline form has an X-ray powder diffraction pattern comprising peaks, in terms of 2θ, at about 10.98° and about 7.46°. In some embodiments, the crystalline form has an X-ray powder diffraction pattern comprising peaks, in terms of 2θ, at about 10.98°, about 5.19°, and about 7.46°. In some embodiments, the crystalline form has an X-ray powder diffraction pattern comprising peaks, in terms of 2θ, at about 10.98°, about 5.19°, about 7.46°, about 12.31°, about 6.38°, about 22.73°, and about 23.84°. In some embodiments, the crystalline form has an X-ray powder diffraction pattern comprising peaks, in terms of 2θ, at about 10.98°, about 5.19°, about 7.46°, about 12.31°, about 6.38°, about 22.73°, about 23.84°, about 24.26°, about 17.11°, and about 19.60°. One aspect of the present invention is directed to a crystalline form of Compound 1 di-4-acetamidobenzoate salt-cocrystal methyl ethyl ketone solvate having an X-ray powder diffraction pattern comprising one or more peaks listed in Table 16. In some embodiments, the crystalline form has an X-ray powder diffraction pattern substantially as shown in FIG. 23, wherein by "substantially" is meant that the reported peaks can vary by about ±0.2°2θ, and also that the relative intensities of the reported peaks can vary.

In some embodiments, the crystalline form of Compound 1 di-4-acetamidobenzoate salt-cocrystal methyl ethyl ketone solvate has a differential scanning calorimetry thermogram comprising an endotherm with an extrapolated onset temperature between about 100° C. and about 130° C. In some embodiments, the crystalline form of Compound 1 di-4-acetamidobenzoate salt-cocrystal methyl ethyl ketone solvate has a differential scanning calorimetry thermogram comprising an endotherm with an extrapolated onset temperature at about 113° C. In some embodiments, the crystalline form of Compound 1 di-4-acetamidobenzoate salt-cocrystal methyl ethyl ketone solvate has a differential scanning calorimetry thermogram comprising an endotherm with an associated heat flow of about 89 joules per gram. In some embodiments, the crystalline form of Compound 1 di-4-acetamidobenzoate salt-cocrystal methyl ethyl ketone solvate has a thermogravimetric analysis profile substantially as shown in FIG. 24, wherein by "substantially" is meant that the reported TGA features can vary by about ±5° C. and by about ±2% weight change.

Figure 24:
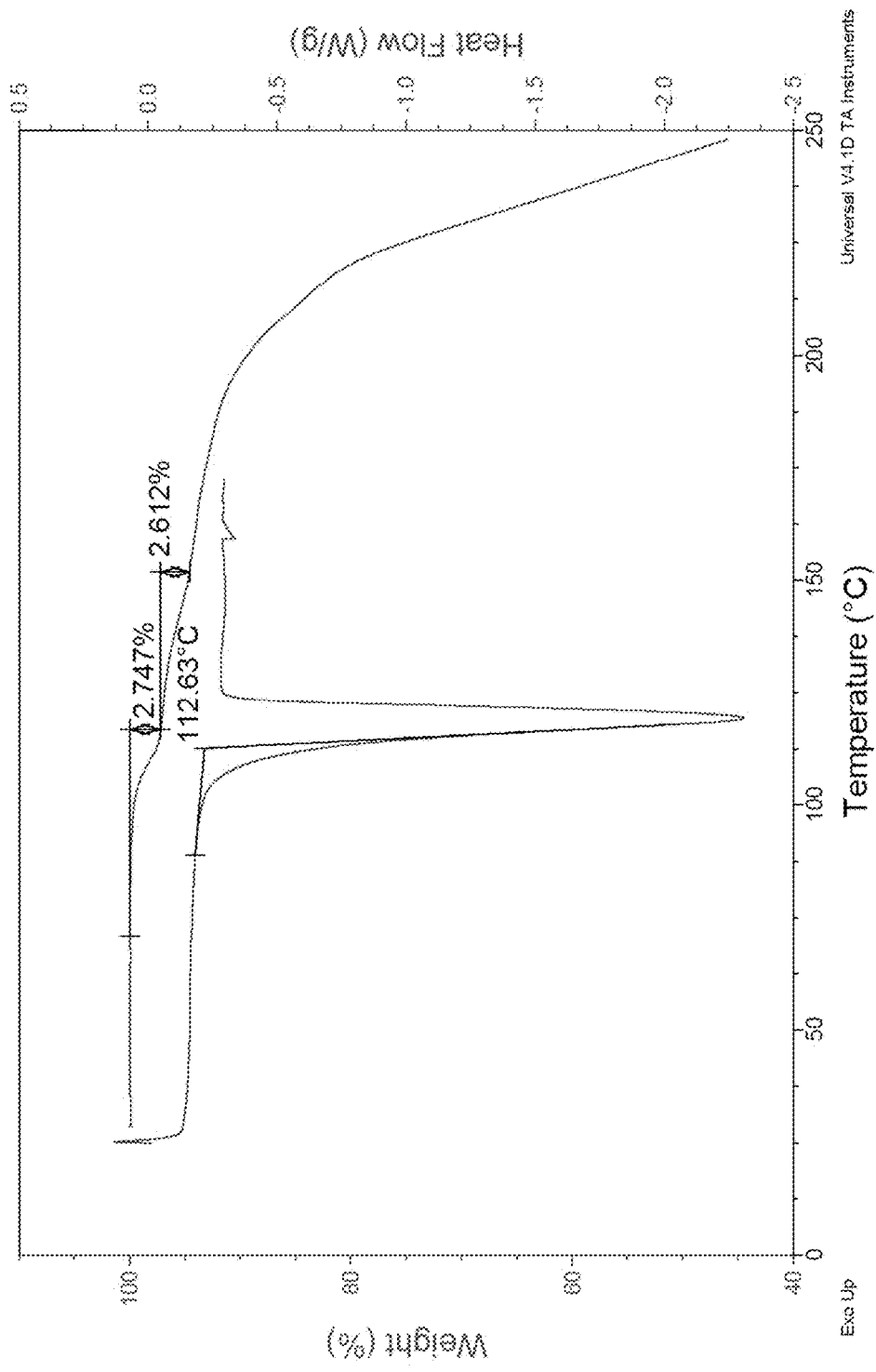
FIG. 24: DSC and TGA of Compound 1 Di-4-acetamidobenzoate Salt-Cocrystal Methyl Ethyl Ketone Solvate, Form I.

In some embodiments, the crystalline form of Compound 1 di-4-acetamidobenzoate salt-cocrystal methyl ethyl ketone solvate has a differential scanning calorimetry thermogram substantially as shown in FIG. 24, wherein by "substantially" is meant that the reported DSC features can vary by about ±6° C. and by about ±20 joules per gram.

Figure 25:
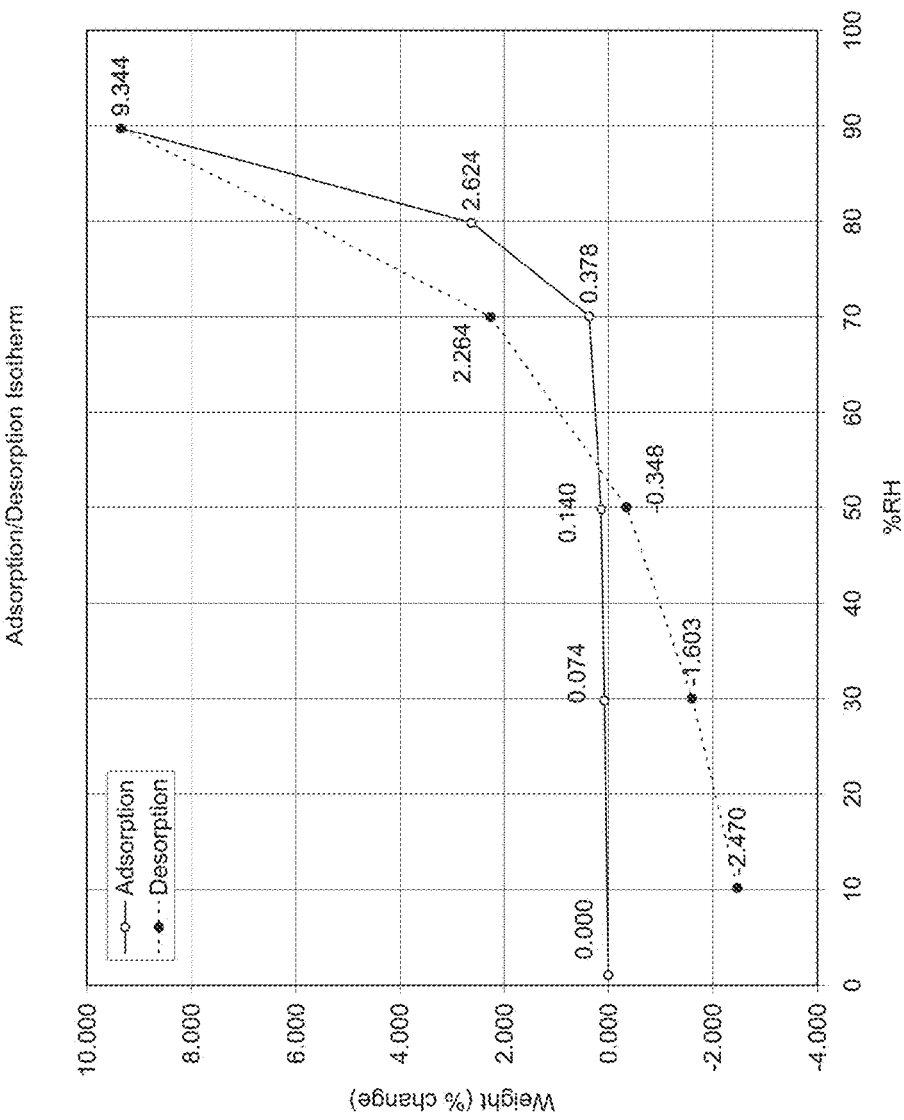
FIG. 25: DMS of Compound 1 Di-4-acetamidobenzoate Salt-Cocrystal Methyl Ethyl Ketone Solvate, Form I.

In some embodiments, the crystalline form of Compound 1 di-4-acetamidobenzoate salt-cocrystal methyl ethyl ketone solvate has a dynamic moisture sorption profile substantially as shown in FIG. 25, wherein by "substantially" is meant that the reported DMS features can vary by about ±5% relative humidity and by about ±5% weight change.

Form I of Compound 1 di-4-acetamidobenzoate salt-cocrystal methyl ethyl ketone solvate can be prepared by any of the suitable procedures known in the art for preparing crystalline polymorphs. In some embodiments Form I of Compound 1 di-4-acetamidobenzoate salt-cocrystal methyl ethyl ketone solvate can be prepared as described in Example 3.7. In some embodiments, Form I of Compound 1 di-4-acetamidobenzoate salt-cocrystal methyl ethyl ketone solvate can be prepared by slurrying crystalline Compound 1 di-4-acetamidobenzoate salt-cocrystal methyl ethyl ketone solvate containing one or more crystalline forms other than Form I. In some embodiments, the crystalline form of Compound 1 di-4-acetamidobenzoate salt-cocrystal methyl ethyl ketone solvate can be prepared by recrystallizing crystalline Compound 1 di-4-acetamidobenzoate salt-cocrystal methyl ethyl ketone solvate containing one or more crystalline forms other than Form I.

Compound 1 Trans-Cinnamate Salt

One aspect of the present invention pertains to a crystalline form of (R)-8-chloro-1-methyl-2,3,4,5-tetrahydro-1H-3-benzazepine trans-cinnamate salt (Compound 1 trans-cinnamate salt). In some embodiments, the crystalline form of (R)-8-chloro-1-methyl-2,3,4,5-tetrahydro-1H-3-benzazepine trans-cinnamate salt is Form I (Compound 1 trans-cinnamate salt, Form I). The physical properties of Form I of Compound 1 trans-cinnamate salt are summarized in Table 17 below.

TABLE 17

Figure 26:
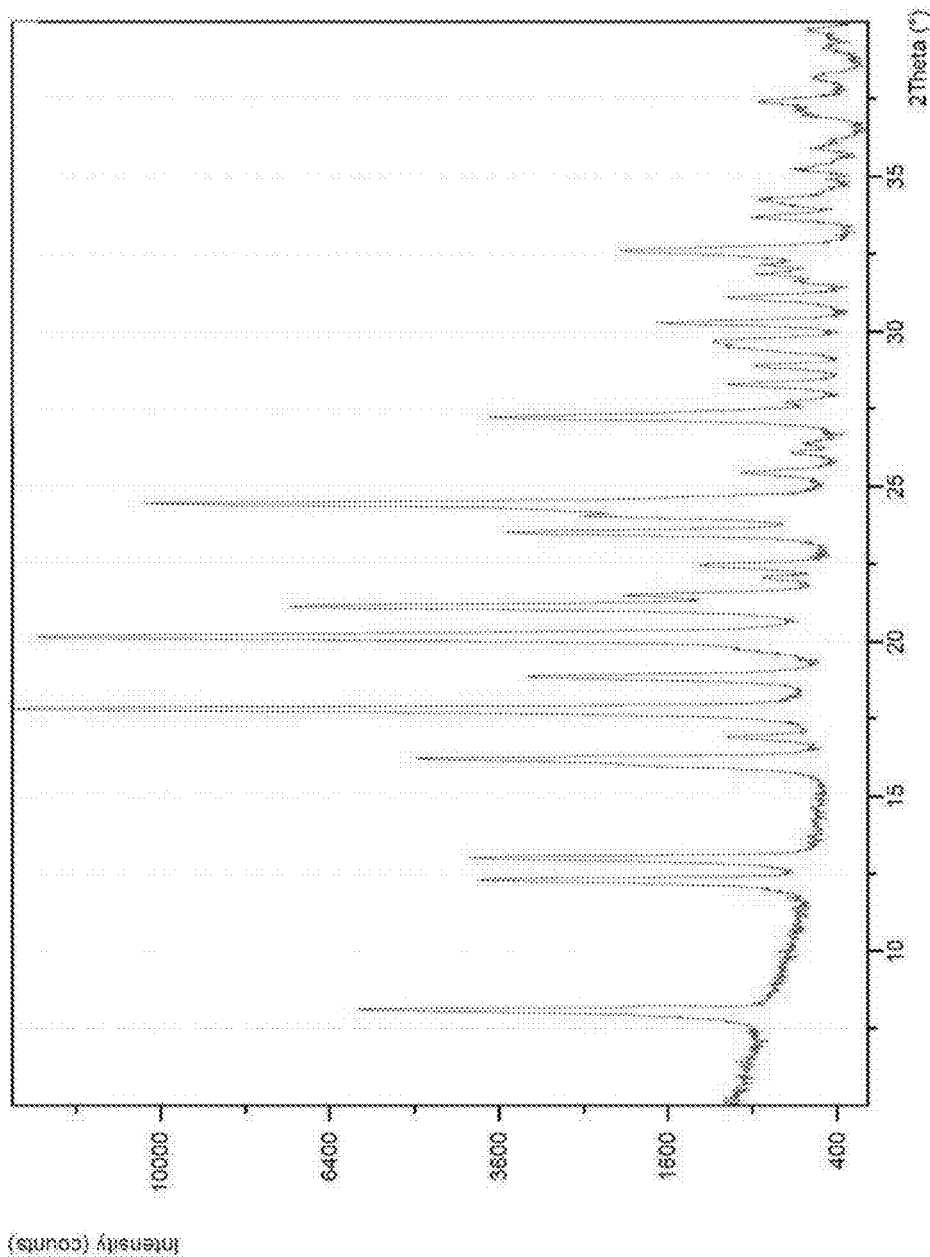
FIG. 26: PXRD of Compound 1 trans-Cinnamate Salt, Form I.

| Compound 1 trans-Cinnamate Salt, Form I | |
|---|---|
| PXRD | FIG. 26: Peaks of ≥15% relative intensity at 8.10, 12.30, 13.02, 16.20, 17.81, 18.85, 20.14, 21.13, 23.51, 24.05, 24.44, and 27.21 °2θ |
| TGA | FIG. 27 minimal weight loss below about 106° C. |
| DSC | FIG. 27: extrapolated onset temperature about 106° C.; enthalpy of fusion 106 J/g |
| DMS | FIG. 28: ~1.2% weight gain at about 90% RH |

Compound 1 trans-cinnamate salt, Form I exhibited a melting onset at 106° C. and a heat of fusion of 106 J/g. Prior to the melting onset there was minimal weight loss and upon melting there was a gradual and complete weight loss, indicating the isolated crystal phase is not solvated.

Compound 1 trans-cinnamate salt was non-hygroscopic up to 80% RH and picked up only 1.2% water out to and including the 90% RH hold at 25° C., although it was still picking up water after 2 h at 90% RH. The sample subsequently lost nearly all of the absorbed water at 80% RH.

Certain X-ray powder diffraction peaks for Form I of Compound 1 trans-cinnamate salt are shown in Table 18 below.

TABLE 18

| Pos. (°2θ) | Rel. Int. (%) |
|---|---|
| 5.13 | 3.06 |
| 8.10 | 38.71 |
| 11.38 | 0.30 |
| 12.30 | 24.89 |
| 13.02 | 25.86 |
| 13.69 | 0.17 |
| 15.97 | 10.33 |
| 16.20 | 32.67 |
| 16.91 | 4.68 |
| 17.81 | 100.00 |
| 18.85 | 20.63 |
| 19.74 | 4.46 |
| 20.14 | 94.56 |
| 21.13 | 50.39 |
| 21.49 | 11.51 |
| 22.06 | 2.95 |
| 22.45 | 6.58 |
| 23.51 | 23.10 |
| 24.05 | 15.29 |
| 24.44 | 74.03 |
| 24.67 | 7.75 |
| 25.44 | 4.22 |
| 26.07 | 1.82 |
| 26.40 | 1.21 |
| 27.21 | 24.86 |
| 27.70 | 2.29 |
| 28.27 | 5.25 |
| 28.88 | 3.69 |
| 29.53 | 5.40 |
| 29.70 | 6.11 |
| 30.27 | 9.55 |
| 31.09 | 5.39 |
| 31.63 | 1.98 |
| 31.86 | 3.98 |

TABLE 18-continued

| Pos. (°2θ) | Rel. Int. (%) |
|---|---|
| 32.15 | 3.41 |
| 32.62 | 12.95 |
| 33.69 | 4.14 |
| 34.22 | 3.82 |
| 34.30 | 3.39 |
| 34.89 | 0.83 |
| 35.18 | 1.87 |
| 35.24 | 2.17 |
| 35.90 | 1.54 |
| 36.17 | 0.77 |
| 36.98 | 1.79 |
| 37.42 | 3.71 |
| 38.17 | 1.47 |
| 39.13 | 1.23 |
| 39.67 | 1.56 |
| 39.74 | 1.76 |

One aspect of the present invention is directed to a crystalline form of Compound 1 trans-cinnamate salt having an X-ray powder diffraction pattern comprising a peak, in terms of 2θ, at about 17.81°. In some embodiments, the crystalline form has an X-ray powder diffraction pattern comprising a peak, in terms of 2θ, at about 20.14°. In some embodiments, the crystalline form has an X-ray powder diffraction pattern comprising peaks, in terms of 2θ, at about 17.81° and about 20.14°. In some embodiments, the crystalline form has an X-ray powder diffraction pattern comprising peaks, in terms of 2θ, at about 17.81° and about 24.44°. In some embodiments, the crystalline form has an X-ray powder diffraction pattern comprising peaks, in terms of 2θ, at about 17.81°, about 20.14°, and about 24.44°. In some embodiments, the crystalline form has an X-ray powder diffraction pattern comprising peaks, in terms of 2θ, at about 17.81°, about 20.14°, about 21.13°, about 8.10°, about 24.44°, about 16.20°, and about 13.02°. In some embodiments, the crystalline form has an X-ray powder diffraction pattern comprising peaks, in terms of 2θ, at about 17.81°, about 20.14°, about 24.44°, about 21.13°, about 8.10°, about 16.20°, about 13.02°, about 12.30°, about 27.21°, and about 23.51°. One aspect of the present invention is directed to a crystalline form of Compound 1 trans-cinnamate salt having an X-ray powder diffraction pattern comprising one or more peaks listed in Table 18. In some embodiments, the crystalline form has an X-ray powder diffraction pattern substantially as shown in FIG. 26, wherein by "substantially" is meant that the reported peaks can vary by about ±0.2°2θ, and also that the relative intensities of the reported peaks can vary.

In some embodiments, the crystalline form of Compound 1 trans-cinnamate salt has a differential scanning calorimetry thermogram comprising an endotherm with an extrapolated onset temperature between about 90° C. and about 120° C. In some embodiments, the crystalline form of Compound 1 trans-cinnamate salt has a differential scanning calorimetry thermogram comprising an endotherm with an extrapolated onset temperature at about 106° C. In some embodiments, the crystalline form of Compound 1 trans-cinnamate salt has a differential scanning calorimetry thermogram comprising an endotherm with an associated heat flow of about 106 joules per gram. In some embodiments, the crystalline form of Compound 1 trans-cinnamate salt has a thermogravimetric analysis profile substantially as shown in FIG. 27, wherein by "substantially" is meant that the reported TGA features can vary by about ±5° C. and by about ±2% weight change.

Figure 27:
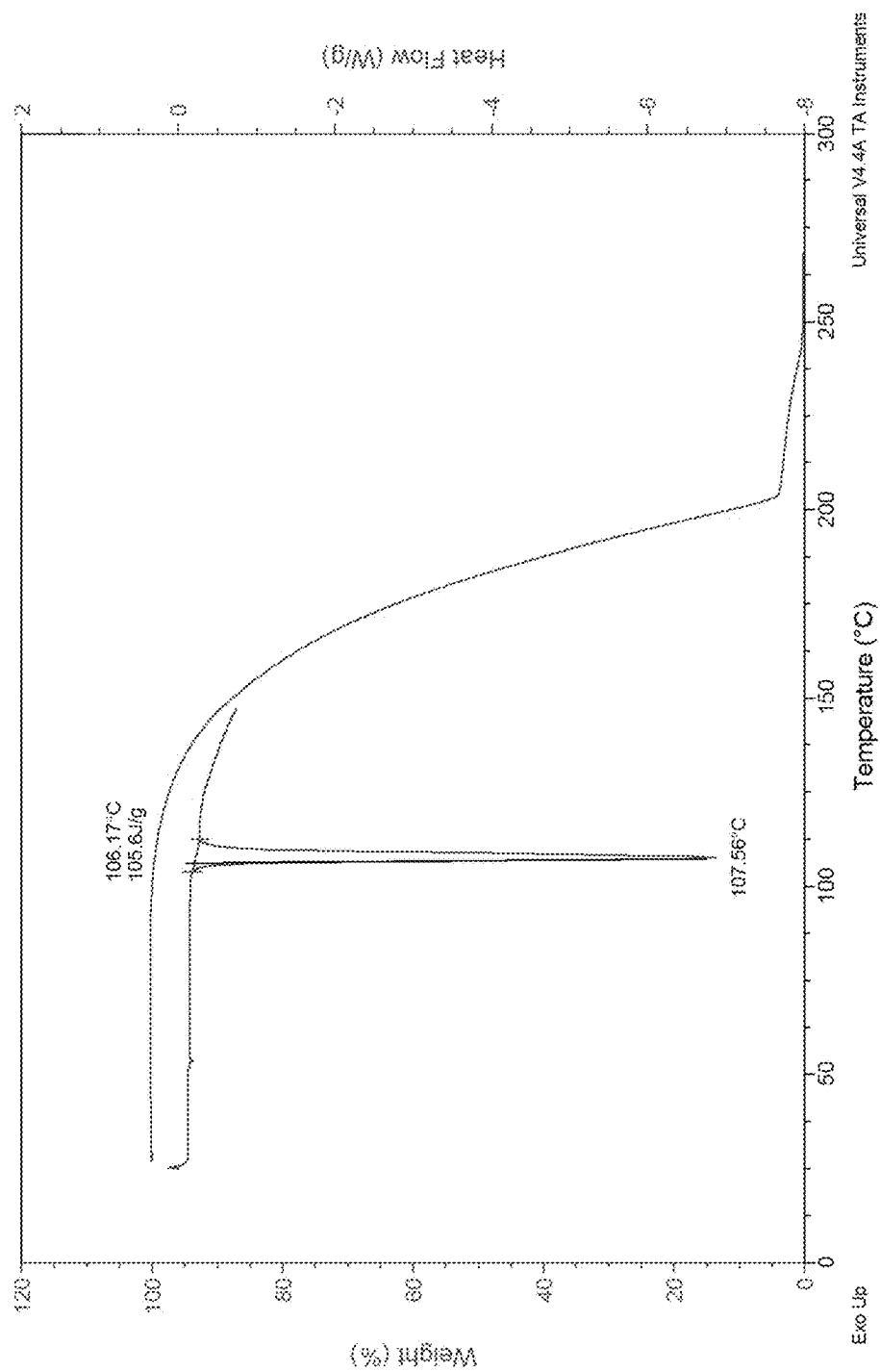
FIG. 27: DSC and TGA of Compound 1 trans-Cinnamate Salt, Form I.

In some embodiments, the crystalline form of Compound 1 trans-cinnamate salt has a differential scanning calorimetry thermogram substantially as shown in FIG. 27, wherein by "substantially" is meant that the reported DSC features can vary by about ±6° C. and by about ±20 joules per gram.

Figure 28:
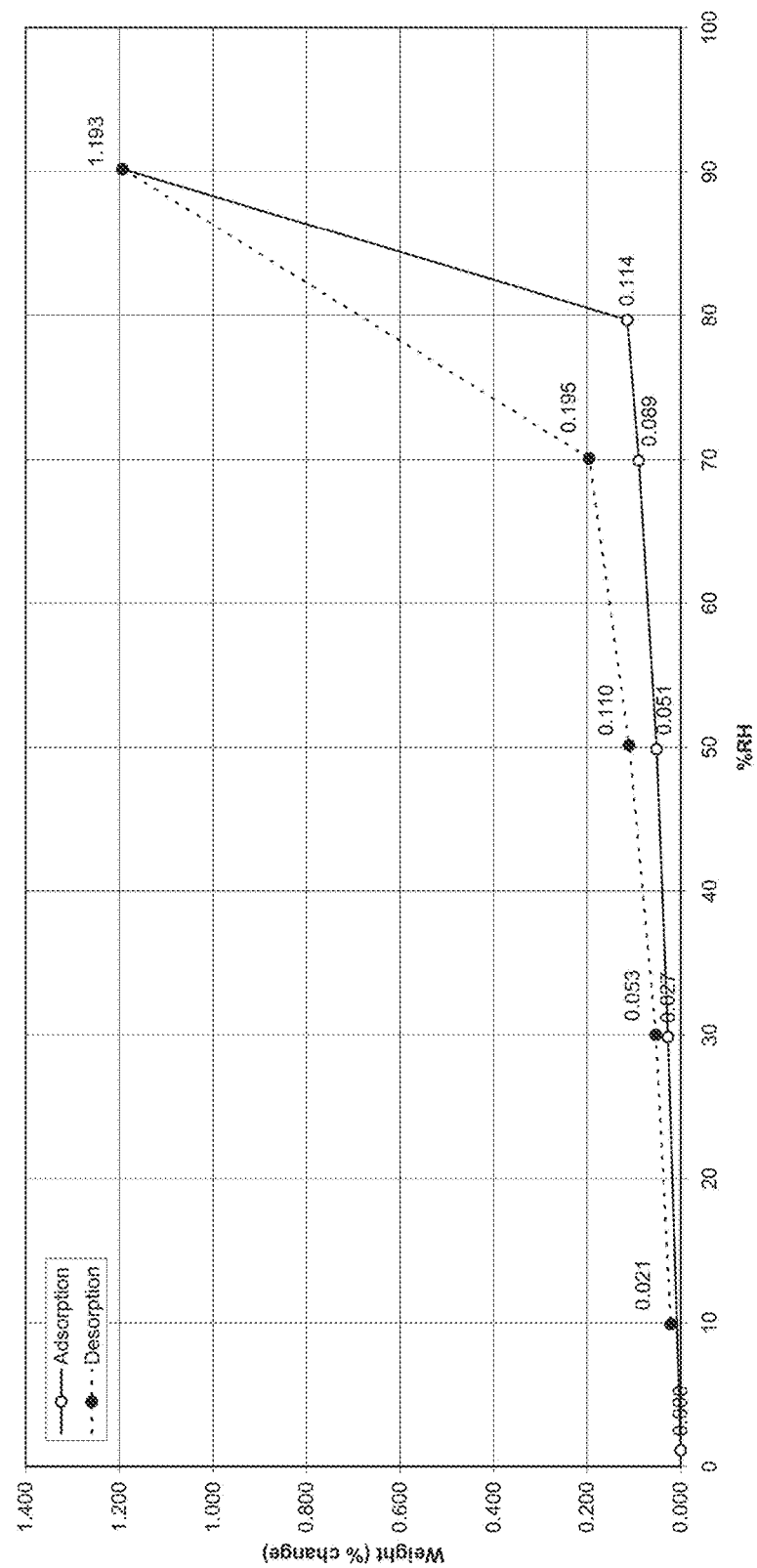
FIG. 28: DMS of Compound 1 trans-Cinnamate Salt, Form I.

In some embodiments, the crystalline form of Compound 1 trans-cinnamate salt has a dynamic moisture sorption profile substantially as shown in FIG. 28, wherein by "substantially" is meant that the reported DMS features can vary by about ±5% relative humidity and by about ±5% weight change.

Form I of Compound 1 trans-cinnamate salt can be prepared by any of the suitable procedures known in the art for preparing crystalline polymorphs. In some embodiments Form I of Compound 1 trans-cinnamate salt can be prepared as described in Example 3.8. In some embodiments, Form I of Compound 1 trans-cinnamate salt can be prepared by slurrying crystalline Compound 1 trans-cinnamate salt containing one or more crystalline forms other than Form I. In some embodiments, the crystalline form of Compound 1 trans-cinnamate salt can be prepared by recrystallizing crystalline Compound 1 trans-cinnamate salt containing one or more crystalline forms other than Form I.

Compound 1 Heminapadisilate Salt

One aspect of the present invention pertains to a crystalline form of (R)-8-chloro-1-methyl-2,3,4,5-tetrahydro-1H-3-benzazepine heminapadisilate salt (Compound 1 heminapadisilate salt). In some embodiments, the crystalline form of (R)-8-chloro-1-methyl-2,3,4,5-tetrahydro-1H-3-benzazepine heminapadisilate salt is Form I (Compound 1 heminapadisilate salt, Form I). The physical properties of Form I of Compound 1 heminapadisilate salt are summarized in Table 19 below.

TABLE 19

Figure 29:
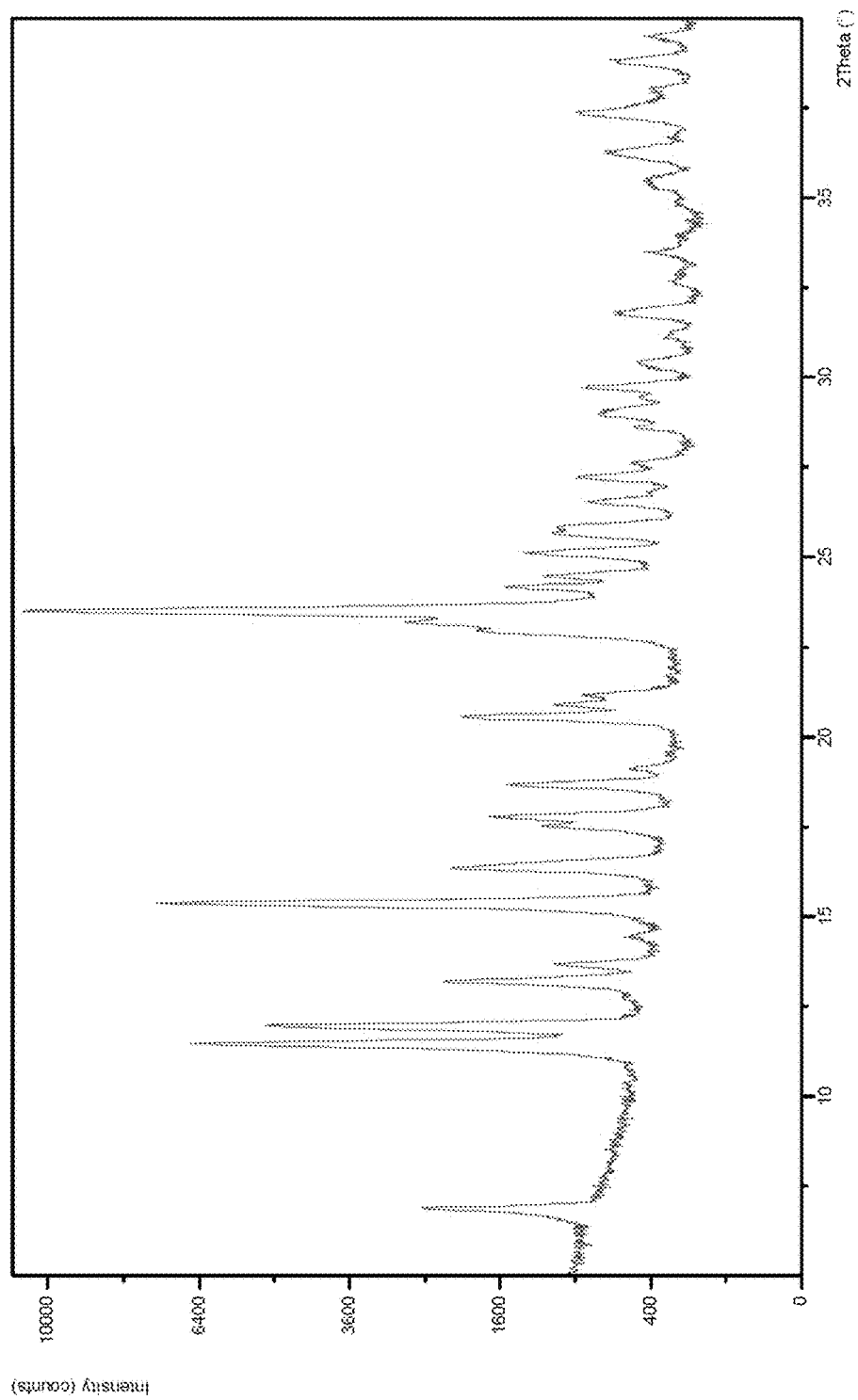
FIG. 29: PXRD of Compound 1 Heminapadisilate Salt, Form I.

| Compound 1 Heminapadisilate Salt, Form I | |
|---|---|
| PXRD | FIG. 29: Peaks of ≥12% relative intensity at 6.89, 11.47, 11.96, 13.20, 15.37, 16.35, 17.79, 20.56, 22.96, 23.19, 23.50, and 24.16 °2θ |
| TGA | FIG. 30: negligible weight loss up to about 250° C. |
| DSC | FIG. 30: extrapolated onset temperature about 266° C.; enthalpy of fusion 90 J/g |
| DMS | FIG. 31: ~0.68% weight gain at about 90% RH |

Compound 1 heminapadisilate, Form I was an anhydrous salt by TGA. The melting onset by DSC was 266° C.

Compound 1 heminapadisilate was non-hygroscopic by DMS analysis, picking up about 0.68% out to and including the 90% RH hold at 25° C. A small amount of hysteresis was observed.

Certain X-ray powder diffraction peaks for Form I of Compound 1 heminapadisilate salt are shown in Table 20 below.

TABLE 20

| Pos. (°2θ) | Rel. Int. (%) |
|---|---|
| 6.89 | 16.97 |
| 11.47 | 57.56 |
| 11.96 | 43.61 |
| 13.20 | 17.14 |
| 13.68 | 6.08 |
| 14.43 | 0.91 |
| 15.37 | 64.85 |
| 16.35 | 17.19 |
| 17.53 | 8.12 |
| 17.79 | 13.21 |

TABLE 20-continued

| Pos. (°2θ) | Rel. Int. (%) |
|---|---|
| 18.67 | 11.73 |
| 19.12 | 1.98 |
| 20.56 | 16.78 |
| 20.90 | 7.39 |
| 21.15 | 5.32 |
| 22.96 | 15.05 |
| 23.19 | 23.64 |
| 23.50 | 100.00 |
| 24.16 | 12.32 |
| 24.47 | 8.64 |
| 25.13 | 10.31 |
| 25.68 | 8.00 |
| 25.87 | 7.23 |
| 26.55 | 5.56 |
| 27.23 | 6.00 |
| 27.61 | 2.56 |
| 28.62 | 2.47 |
| 28.98 | 4.60 |
| 29.73 | 5.45 |
| 30.41 | 2.29 |
| 31.18 | 0.78 |
| 31.77 | 3.36 |
| 33.48 | 1.68 |
| 35.43 | 1.87 |
| 36.25 | 4.01 |
| 37.35 | 6.37 |
| 37.96 | 1.62 |
| 38.79 | 3.63 |
| 39.48 | 1.86 |
| 25.13 | 10.31 |

One aspect of the present invention is directed to a crystalline form of Compound 1 heminapadisilate salt having an X-ray powder diffraction pattern comprising a peak, in terms of 2θ, at about 23.50°. In some embodiments, the crystalline form has an X-ray powder diffraction pattern comprising a peak, in terms of 2θ, at about 15.37°. In some embodiments, the crystalline form has an X-ray powder diffraction pattern comprising peaks, in terms of 2θ, at about 23.50° and about 15.37°. In some embodiments, the crystalline form has an X-ray powder diffraction pattern comprising peaks, in terms of 2θ, at about 23.50° and about 11.47°. In some embodiments, the crystalline form has an X-ray powder diffraction pattern comprising peaks, in terms of 2θ, at about 23.50°, about 15.37°, and about 11.47°. In some embodiments, the crystalline form has an X-ray powder diffraction pattern comprising peaks, in terms of 2θ, at about 23.50°, about 15.37°, about 11.47°, about 11.96°, about 23.19°, about 16.35°, and about 13.20°. In some embodiments, the crystalline form has an X-ray powder diffraction pattern comprising peaks, in terms of 2θ, at about 23.50°, about 15.37°, about 11.47°, about 11.96°, about 23.19°, about 16.35°, about 13.20°, about 6.89°, about 20.56°, and about 22.96°. One aspect of the present invention is directed to a crystalline form of Compound 1 heminapadisilate salt having an X-ray powder diffraction pattern comprising one or more peaks listed in Table 20. In some embodiments, the crystalline form has an X-ray powder diffraction pattern substantially as shown in FIG. 29, wherein by "substantially" is meant that the reported peaks can vary by about ±0.2°2θ, and also that the relative intensities of the reported peaks can vary.

In some embodiments, the crystalline form of Compound 1 heminapadisilate salt has a differential scanning calorimetry thermogram comprising an endotherm with an extrapolated onset temperature between about 250° C. and about 280° C. In some embodiments, the crystalline form of Compound 1 heminapadisilate salt has a differential scanning calorimetry thermogram comprising an endotherm with an extrapolated onset temperature at about 266° C. In some embodiments, the crystalline form of Compound 1 heminapadisilate salt has a differential scanning calorimetry thermogram comprising an endotherm with an associated heat flow of about 90 joules per gram. In some embodiments, the crystalline form of Compound 1 heminapadisilate salt has a thermogravimetric analysis profile substantially as shown in FIG. 30, wherein by "substantially" is meant that the reported TGA features can vary by about ±5° C. and by about ±2% weight change.

Figure 30:
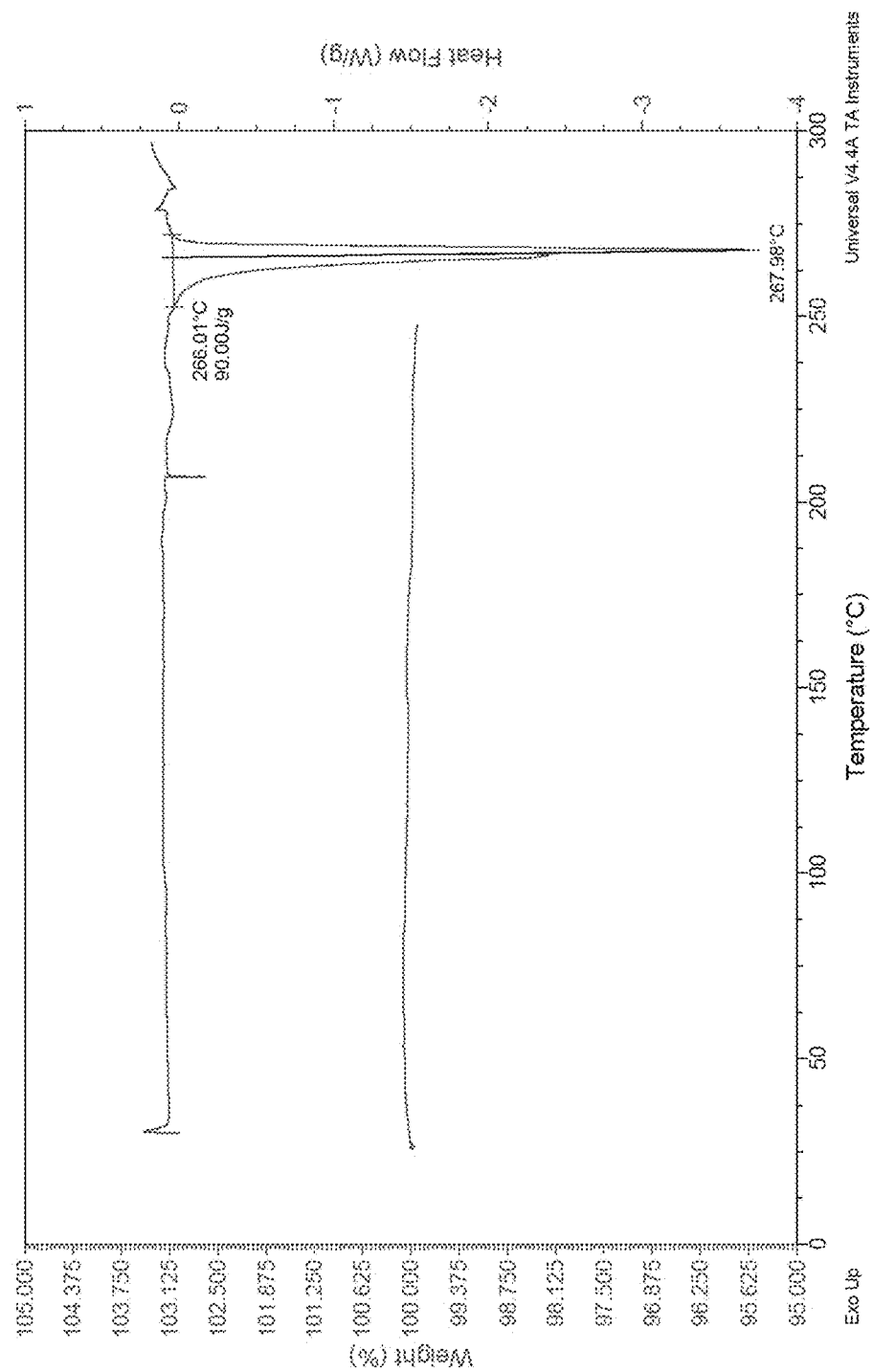
FIG. 30: DSC and TGA of Compound 1 Heminapadisilate Salt, Form I.

In some embodiments, the crystalline form of Compound 1 heminapadisilate salt has a differential scanning calorimetry thermogram substantially as shown in FIG. 30, wherein by "substantially" is meant that the reported DSC features can vary by about ±6° C. and by about ±20 joules per gram.

Figure 31:
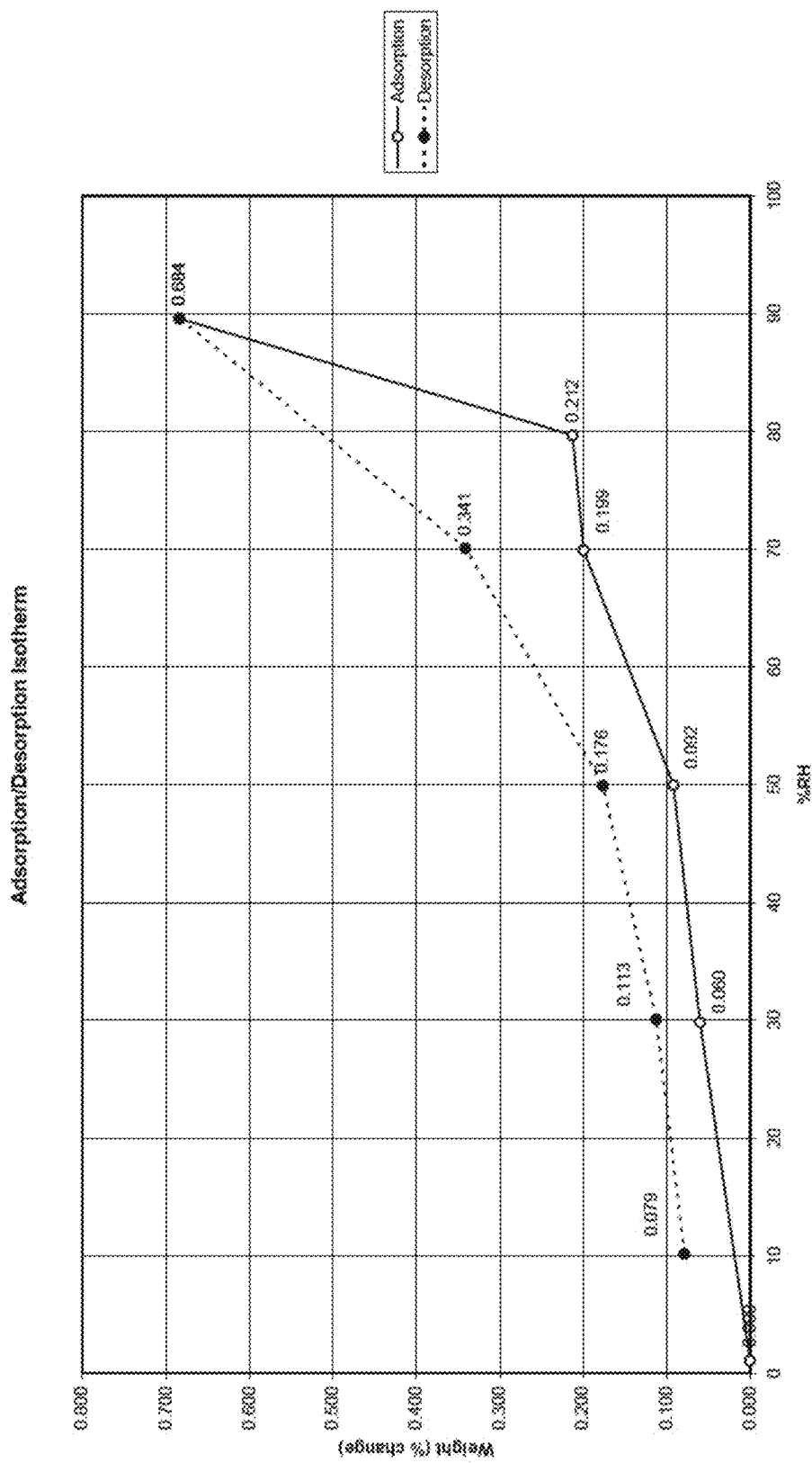
FIG. 31: DMS of Compound 1 Heminapadisilate Salt, Form I.

In some embodiments, the crystalline form of Compound 1 heminapadisilate salt has a dynamic moisture sorption profile substantially as shown in FIG. 31, wherein by "substantially" is meant that the reported DMS features can vary by about ±5% relative humidity and by about ±5% weight change.

Form I of Compound 1 heminapadisilate salt can be prepared by any of the suitable procedures known in the art for preparing crystalline polymorphs. In some embodiments Form I of Compound 1 heminapadisilate salt can be prepared as described in Example 3.9. In some embodiments, Form I of Compound 1 heminapadisilate salt can be prepared by slurrying crystalline Compound 1 heminapadisilate salt containing one or more crystalline forms other than Form I. In some embodiments, the crystalline form of Compound 1 heminapadisilate salt can be prepared by recrystallizing crystalline Compound 1 heminapadisilate salt containing one or more crystalline forms other than Form I.

Compound 1 Heminapadisilate Salt Solvate 1

One aspect of the present invention pertains to a crystalline form of (R)-8-chloro-1-methyl-2,3,4,5-tetrahydro-1H-3-benzazepine heminapadisilate salt solvate 1 (Compound 1 heminapadisilate salt solvate 1). In some embodiments, the crystalline form of (R)-8-chloro-1-methyl-2,3,4,5-tetrahydro-1H-3-benzazepine heminapadisilate salt solvate 1 is Form I (Compound 1 heminapadisilate salt solvate 1, Form I). The physical properties of Form I of Compound 1 heminapadisilate salt solvate 1 are summarized in Table 21 below.

TABLE 21

Figure 32:
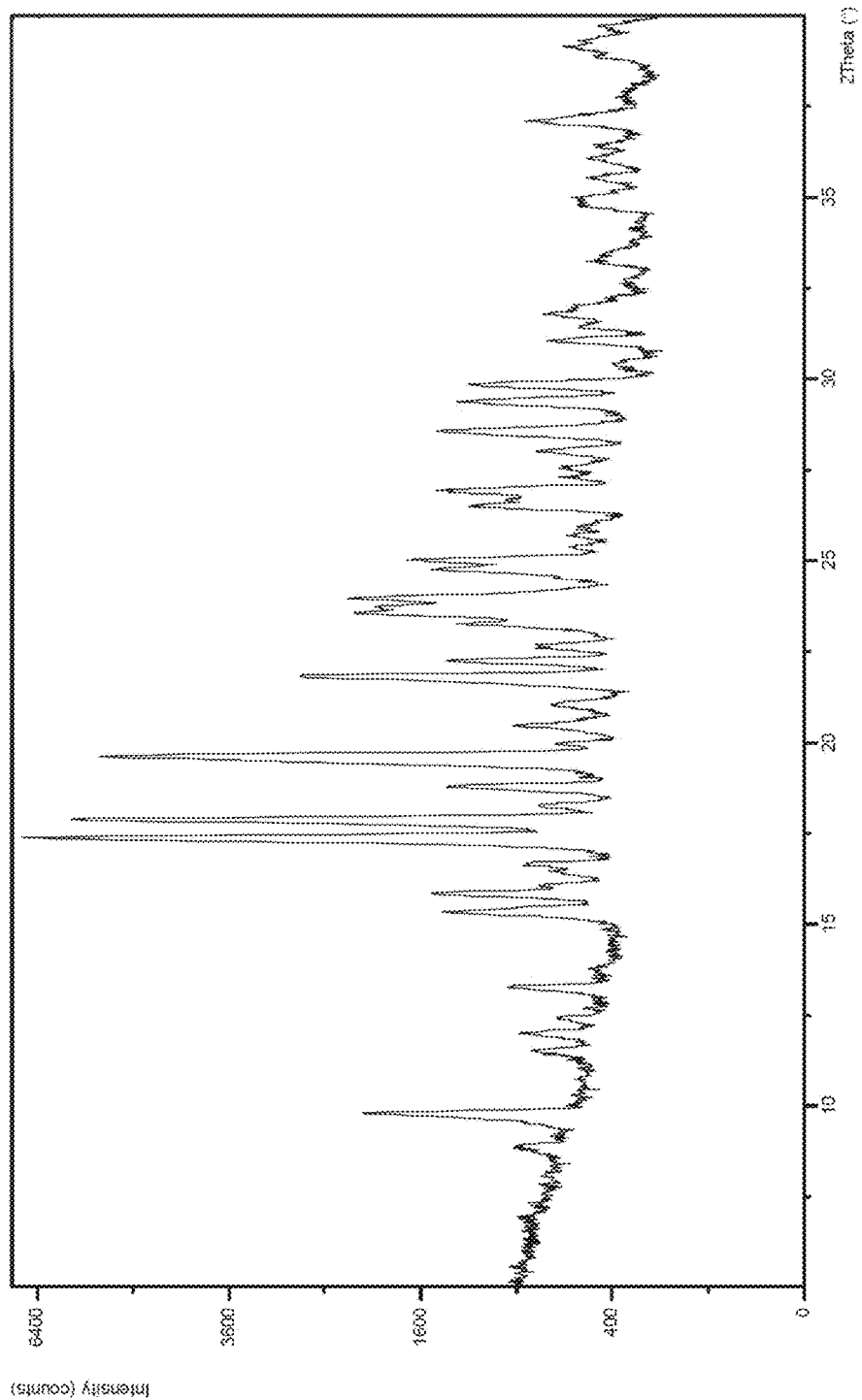
FIG. 32: PXRD of Compound 1 Heminapadisilate Salt Solvate 1, Form I.

| | Compound 1 Heminapadisilate Salt Solvate 1, Form I |
|---|---|
| PXRD | FIG. 32: Peaks of ≥18% relative intensity at 9.81, 17.39, 17.89, 19.62, 21.82, 23.56, 23.72, 23.96, 24.77, 25.03, and 28.56 °2θ |
| TGA | FIG. 33: about 5.7% weight loss up to about 140° C. |
| DSC | FIG. 33: extrapolated desolvation onset temperature about 101° C. |

Compound 1 heminapadisilate salt solvate 1, Form I was a solvated crystalline material with desolvation onset of ~101° C. by DSC.

Compound 1 heminapadisilate salt solvate 1 had a weight loss of ~5.7% by TGA scanned at 10° C./min out to ~140° C. This weight loss was slightly lower than the theoretical value (6.1%) for a 0.25 ethyl acetate solvate. The desolvation was followed by further weight loss due to degradation.

Certain X-ray powder diffraction peaks for Form I of Compound 1 heminapadisilate salt solvate 1 are shown in Table 22 below.

TABLE 22

| Pos. (°2θ) | Rel. Int. (%) |
|---|---|
| 8.88 | 4.39 |
| 9.81 | 24.81 |
| 11.52 | 4.97 |
| 12.00 | 6.53 |
| 12.41 | 3.09 |
| 13.27 | 8.22 |
| 13.72 | 0.84 |
| 15.33 | 16.21 |
| 15.85 | 17.98 |
| 16.64 | 7.18 |
| 17.39 | 100.00 |
| 17.89 | 88.70 |
| 18.27 | 6.29 |
| 18.79 | 16.55 |
| 19.62 | 81.41 |
| 19.97 | 4.91 |
| 20.46 | 9.13 |
| 21.05 | 5.44 |
| 21.82 | 38.90 |
| 22.24 | 16.71 |
| 22.64 | 6.90 |
| 23.26 | 15.31 |
| 23.56 | 30.08 |
| 23.72 | 26.89 |
| 23.96 | 29.50 |
| 24.77 | 19.08 |
| 25.03 | 21.97 |
| 25.38 | 4.20 |
| 25.70 | 4.25 |
| 26.51 | 14.39 |
| 26.93 | 17.74 |
| 27.31 | 4.58 |
| 27.56 | 5.06 |
| 28.02 | 7.12 |
| 28.56 | 18.80 |
| 29.38 | 15.96 |
| 29.84 | 14.47 |
| 30.40 | 1.54 |
| 31.05 | 6.52 |
| 31.43 | 4.11 |
| 31.78 | 6.89 |
| 32.66 | 0.84 |
| 33.26 | 2.72 |
| 34.82 | 4.07 |
| 35.53 | 3.34 |
| 36.07 | 3.41 |
| 36.41 | 2.75 |
| 37.09 | 8.05 |
| 39.12 | 5.16 |
| 39.68 | 2.65 |

One aspect of the present invention is directed to a crystalline form of Compound 1 heminapadisilate salt solvate 1 having an X-ray powder diffraction pattern comprising a peak, in terms of 2θ, at about 17.39°. In some embodiments, the crystalline form has an X-ray powder diffraction pattern comprising a peak, in terms of 2θ, at about 17.89°. In some embodiments, the crystalline form has an X-ray powder diffraction pattern comprising peaks, in terms of 2θ, at about 17.39° and about 17.89°. In some embodiments, the crystalline form has an X-ray powder diffraction pattern comprising peaks, in terms of 2θ, at about 17.39° and about 19.62°. In some embodiments, the crystalline form has an X-ray powder diffraction pattern comprising peaks, in terms of 2θ, at about 17.39°, about 17.89°, and about 19.62°. In some embodiments, the crystalline form has an X-ray powder diffraction pattern comprising peaks, in terms of 2θ, at about 17.39°, about 17.89°, about 19.62°, about 21.82°, about 23.56°, about 23.96°, and about 23.72°. In some embodiments, the crystalline form has an X-ray powder diffraction pattern comprising peaks, in terms of 2θ, at about 17.39°, about 17.89°, about 19.62°, about 21.82°, about 23.56°, about 23.96°, about 23.72°, about 9.81°, about 25.03°, and about 24.77°. One aspect of the present invention is directed to a crystalline form of Compound 1 heminapadisilate salt solvate 1 having an X-ray powder diffraction pattern comprising one or more peaks listed in Table 22. In some embodiments, the crystalline form has an X-ray powder diffraction pattern substantially as shown in FIG. 32, wherein by "substantially" is meant that the reported peaks can vary by about ±0.2°2θ, and also that the relative intensities of the reported peaks can vary.

In some embodiments, the crystalline form of Compound 1 heminapadisilate salt solvate 1 has a differential scanning calorimetry thermogram comprising an endotherm with an extrapolated onset temperature between about 85° C. and about 115° C. In some embodiments, the crystalline form of Compound 1 heminapadisilate salt solvate 1 has a differential scanning calorimetry thermogram comprising an endotherm with an extrapolated onset temperature at about 101° C. In some embodiments, the crystalline form of Compound 1 heminapadisilate salt solvate 1 has a thermogravimetric analysis profile substantially as shown in FIG. 33, wherein by "substantially" is meant that the reported TGA features can vary by about ±5° C. and by about ±2% weight change.

Figure 33:
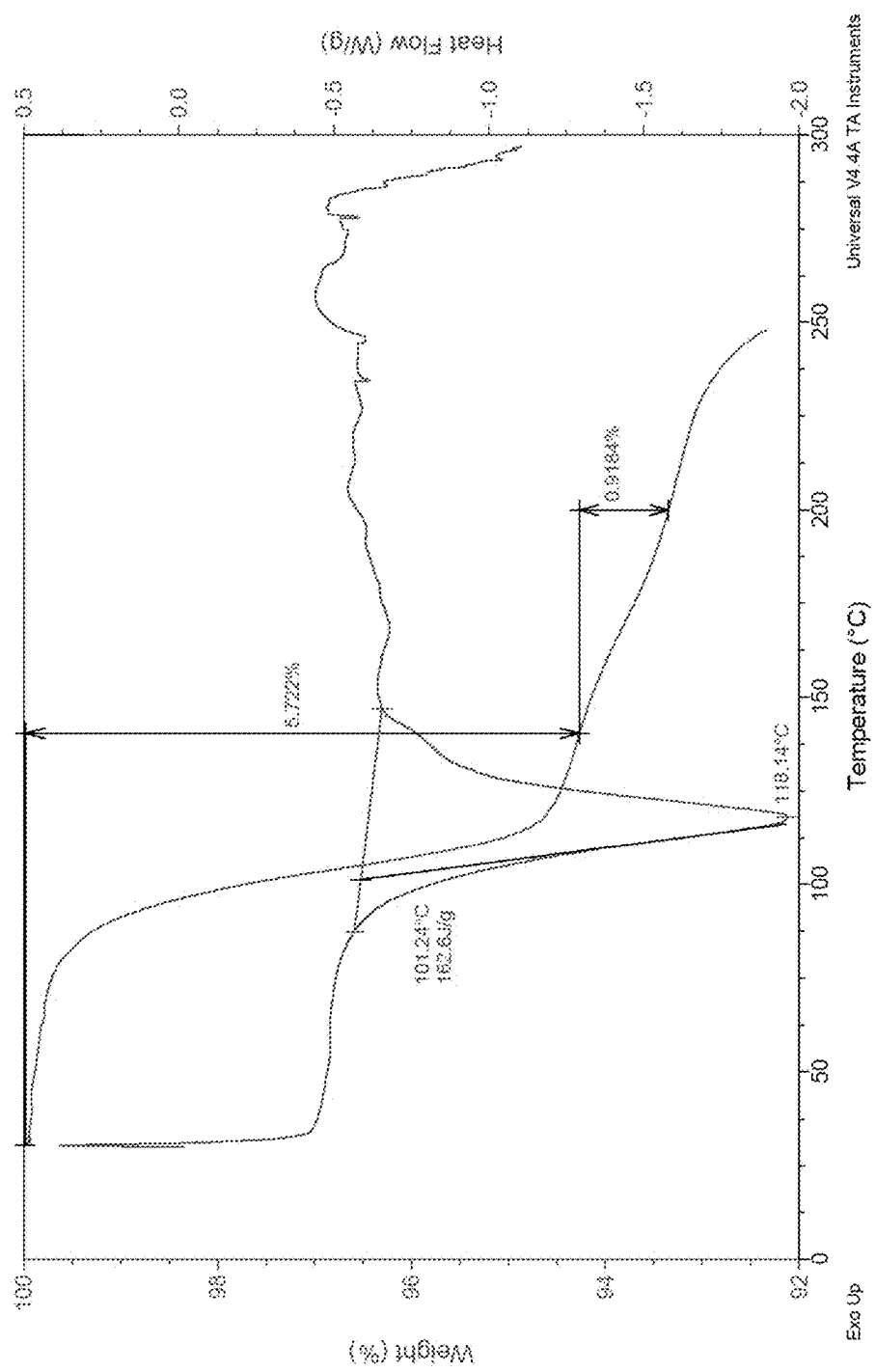
FIG. 33: DSC and TGA of Compound 1 Heminapadisilate Salt Solvate 1, Form I.

In some embodiments, the crystalline form of Compound 1 heminapadisilate salt solvate 1 has a differential scanning calorimetry thermogram substantially as shown in FIG. 33, wherein by "substantially" is meant that the reported DSC features can vary by about ±6° C. and by about ±20 joules per gram.

Form I of Compound 1 heminapadisilate salt solvate 1 can be prepared by any of the suitable procedures known in the art for preparing crystalline polymorphs. In some embodiments Form I of Compound 1 heminapadisilate salt solvate 1 can be prepared as described in Example 3.10. In some embodiments, Form I of Compound 1 heminapadisilate salt solvate 1 can be prepared by slurrying crystalline Compound 1 heminapadisilate salt solvate 1 containing one or more crystalline forms other than Form I. In some embodiments, the crystalline form of Compound 1 heminapadisilate salt solvate 1 can be prepared by recrystallizing crystalline Compound 1 heminapadisilate salt solvate 1 containing one or more crystalline forms other than Form I.

Compound 1 Heminapadisilate Salt Solvate 2

One aspect of the present invention pertains to a crystalline form of (R)-8-chloro-1-methyl-2,3,4,5-tetrahydro-1H-3-benzazepine heminapadisilate salt solvate 2 (Compound 1 heminapadisilate salt solvate 2). In some embodiments, the crystalline form of (R)-8-chloro-1-methyl-2,3,4,5-tetrahydro-1H-3-benzazepine heminapadisilate salt solvate 2 is Form I (Compound 1 heminapadisilate salt solvate 2, Form I). The physical properties of Form I of Compound 1 heminapadisilate salt solvate 2 are summarized in Table 23 below.

TABLE 23

Figure 34:
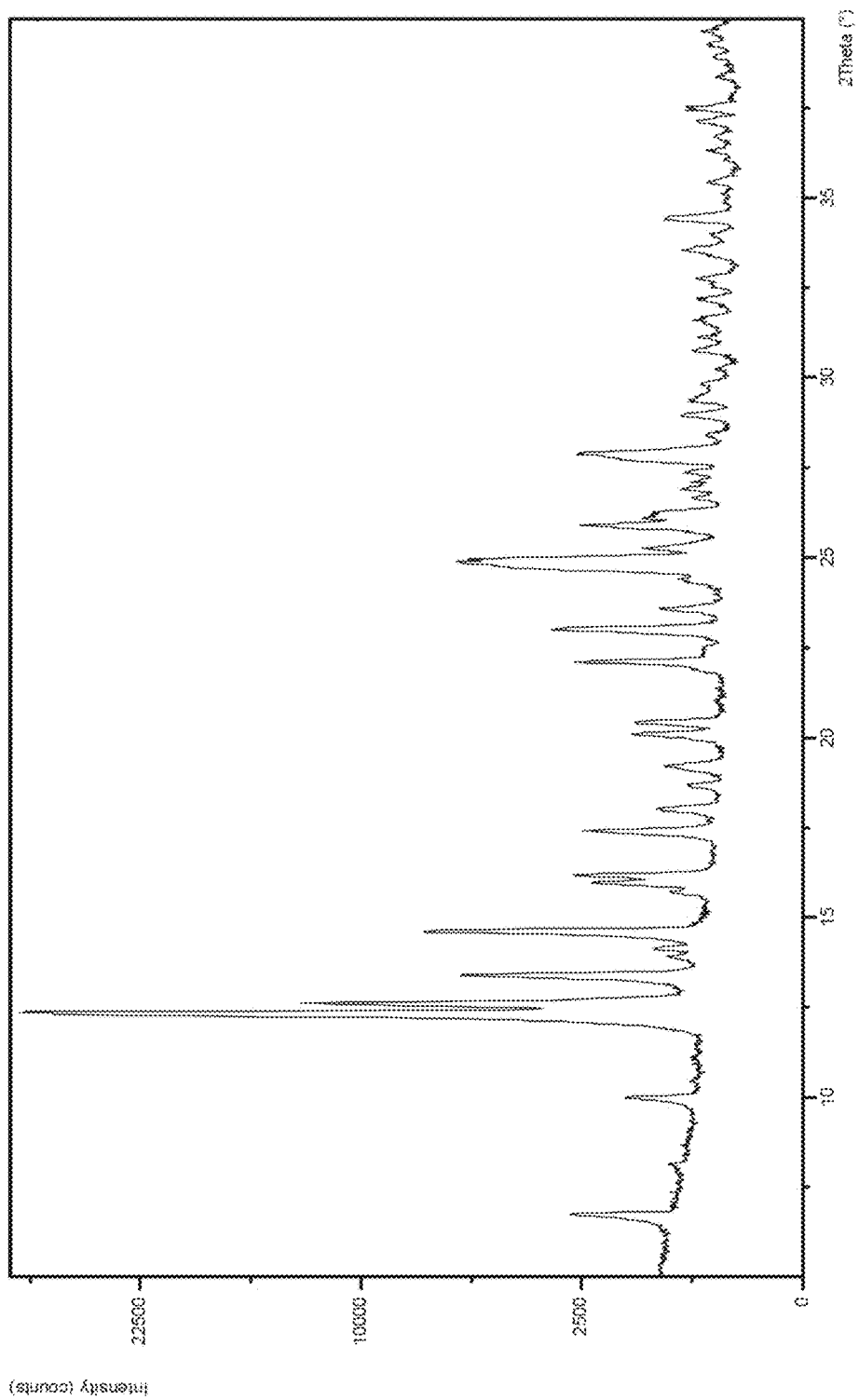
FIG. 34: PXRD of Compound 1 Heminapadisilate Salt Solvate 2, Form I.

| Compound 1 Heminapadisilate Salt Solvate 2, Form I | |
|---|---|
| PXRD | FIG. 34: Peaks of ≥7% relative intensity at 12.35, 12.62, 13.40, 14.61, 16.17, 22.10, 23.01, 24.65, 24.72, 24.87, 24.99, 25.90, and 27.89 °2θ |
| TGA | FIG. 35: about 4.6% weight loss up to about 175° C. |
| DSC | FIG. 35: extrapolated desolvation onset temperature about 129° C.; extrapolated melt onset temperature about 264° C., approximately matching that of the non-solvated salt |

Compound 1 heminapadisilate salt solvate 2, Form I had a weight loss of ~4.6% (desolvation onset ~129° C.) out to ~175° C. This weight loss was slightly higher than the theoretical value (4.1%) for a 0.25 solvate 2. The desolvation was followed by a melt onset of ~264° C., which approximately matched that of the non-solvated salt.

Certain X-ray powder diffraction peaks for Form I of Compound 1 heminapadisilate salt solvate 2 are shown in Table 24 below.

TABLE 24

| Pos. (°2θ) | Rel. Int. (%) |
|---|---|
| 6.74 | 6.31 |
| 8.11 | 0.52 |
| 10.00 | 3.40 |
| 12.35 | 100.00 |
| 12.62 | 41.09 |
| 13.40 | 18.53 |
| 13.91 | 1.60 |
| 14.13 | 2.10 |
| 14.61 | 23.26 |
| 15.70 | 1.60 |
| 15.96 | 6.21 |
| 16.17 | 7.52 |
| 17.41 | 6.74 |
| 18.01 | 2.21 |
| 18.7116 | 0.98 |
| 19.2120 | 2.07 |
| 20.1031 | 3.73 |
| 20.4188 | 3.55 |
| 22.10 | 7.57 |
| 23.01 | 9.64 |
| 23.5671 | 2.44 |
| 24.3864 | 1.44 |
| 24.65 | 8.48 |
| 24.72 | 13.74 |
| 24.87 | 19.13 |
| 24.99 | 15.06 |
| 25.2689 | 3.31 |
| 25.90 | 7.13 |
| 26.1036 | 3.34 |
| 26.26 | 2.82 |
| 26.66 | 1.02 |
| 26.92 | 1.46 |
| 27.37 | 1.31 |
| 27.69 | 4.44 |
| 27.89 | 7.47 |
| 28.42 | 0.61 |
| 28.95 | 1.54 |
| 29.37 | 1.07 |
| 29.83 | 0.79 |
| 30.24 | 0.31 |
| 30.75 | 1.14 |
| 31.12 | 0.95 |
| 31.62 | 0.88 |
| 32.19 | 0.92 |
| 32.77 | 1.02 |
| 33.54 | 1.64 |
| 33.97 | 0.52 |
| 34.42 | 2.41 |
| 34.48 | 2.28 |
| 35.45 | 0.61 |
| 36.32 | 0.73 |
| 36.69 | 0.49 |
| 37.13 | 1.03 |
| 37.42 | 1.17 |
| 38.37 | 0.41 |
| 38.92 | 0.52 |
| 39.26 | 0.66 |
| 39.63 | 0.87 |

One aspect of the present invention is directed to a crystalline form of Compound 1 heminapadisilate salt solvate 2 having an X-ray powder diffraction pattern comprising a peak, in terms of 2θ, at about 12.35°. In some embodiments, the crystalline form has an X-ray powder diffraction pattern comprising a peak, in terms of 2θ, at about 12.62°. In some embodiments, the crystalline form has an X-ray powder diffraction pattern comprising peaks, in terms of 2θ, at about 12.35° and about 12.62°. In some embodiments, the crystalline form has an X-ray powder diffraction pattern comprising peaks, in terms of 2θ, at about 12.35° and about 14.61°. In some embodiments, the crystalline form has an X-ray powder diffraction pattern comprising peaks, in terms of 2θ, at about 12.35°, about 12.62°, and about 14.61°. In some embodiments, the crystalline form has an X-ray powder diffraction pattern comprising peaks, in terms of 2θ, at about 12.35°, about 12.62°, about 14.61°, about 24.87°, about 13.40°, about 24.99°, and about 24.72°. In some embodiments, the crystalline form has an X-ray powder diffraction pattern comprising peaks, in terms of 2θ, at about 12.35°, about 12.62°, about 14.61°, about 24.87°, about 13.40°, about 24.99°, about 24.72°, about 23.01°, about 24.65°, and about 22.10°. One aspect of the present invention is directed to a crystalline form of Compound 1 heminapadisilate salt solvate 2 having an X-ray powder diffraction pattern comprising one or more peaks listed in Table 24. In some embodiments, the crystalline form has an X-ray powder diffraction pattern substantially as shown in FIG. 34, wherein by "substantially" is meant that the reported peaks can vary by about ±0.2°2θ, and also that the relative intensities of the reported peaks can vary.

In some embodiments, the crystalline form of Compound 1 heminapadisilate salt solvate 2 has a differential scanning calorimetry thermogram comprising an endotherm with an extrapolated onset temperature between about 110° C. and about 140° C. In some embodiments, the crystalline form of Compound 1 heminapadisilate salt solvate 2 has a differential scanning calorimetry thermogram comprising an endotherm with an extrapolated onset temperature at about 129° C. In some embodiments, the crystalline form of Compound 1 heminapadisilate salt solvate 2 has a differential scanning calorimetry thermogram comprising an endotherm with an extrapolated onset temperature between about 250° C. and about 280° C. In some embodiments, the crystalline form of Compound 1 heminapadisilate salt solvate 2 has a differential scanning calorimetry thermogram comprising an endotherm with an extrapolated onset temperature at about 264° C. In some embodiments, the crystalline form of Compound 1 heminapadisilate salt solvate 2 has a differential scanning calorimetry thermogram comprising an endotherm with an extrapolated onset temperature between about 110° C. and about 140° C., and an endotherm with an extrapolated onset temperature between about 250° C. and about 280° C. In some embodiments, the crystalline form of Compound 1 heminapadisilate salt solvate 2 has a differential scanning calorimetry thermogram comprising an endotherm with an extrapolated onset temperature at about 129° C., and an endotherm with an extrapolated onset temperature at about 264° C. In some embodiments, the crystalline form of Compound 1 heminapadisilate salt solvate 2 has a thermogravimetric analysis profile substantially as shown in FIG. 35, wherein by "substantially" is meant that the reported TGA features can vary by about ±5° C. and by about ±2% weight change.

Figure 35:
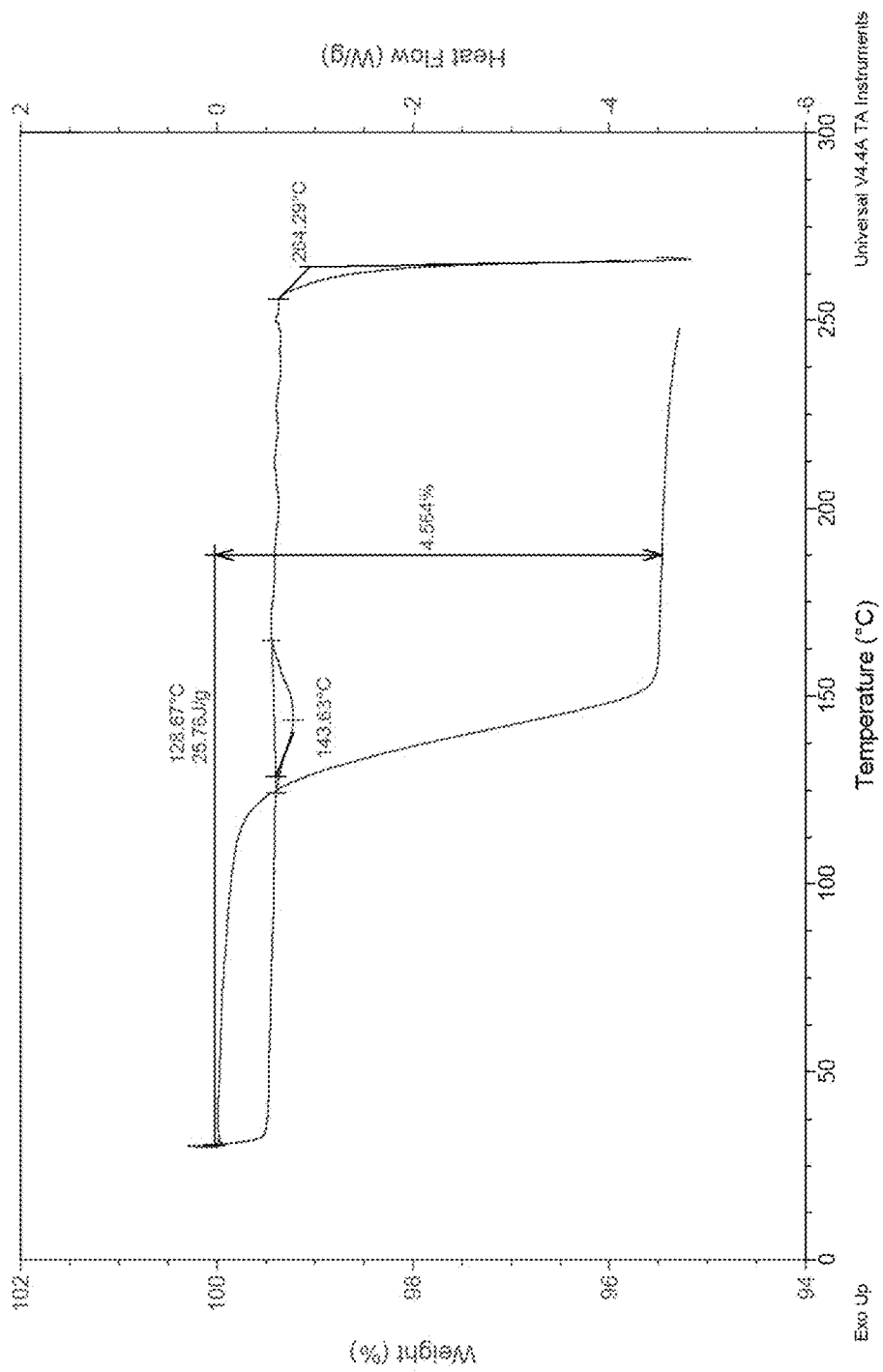
FIG. 35: DSC and TGA of Compound 1 Heminapadisilate Salt Solvate 2, Form I.

In some embodiments, the crystalline form of Compound 1 heminapadisilate salt solvate 2 has a differential scanning calorimetry thermogram substantially as shown in FIG. 35, wherein by "substantially" is meant that the reported DSC features can vary by about ±6° C. and by about ±20 joules per gram.

Form I of Compound 1 heminapadisilate salt solvate 2 can be prepared by any of the suitable procedures known in the art for preparing crystalline polymorphs. In some embodiments Form I of Compound 1 heminapadisilate salt solvate 2 can be prepared as described in Example 3.11. In some embodiments, Form I of Compound 1 heminapadisilate salt solvate 2 can be prepared by slurrying crystalline Compound 1 heminapadisilate salt solvate 2 containing one or more crystalline forms other than Form I. In some embodiments, the crystalline form of Compound 1 heminapadisilate salt solvate 2 can be prepared by recrystallizing crystalline Compound 1 heminapadisilate salt solvate 2 containing one or more crystalline forms other than Form I.

Compound 1 (±)-Mandelate Salt Hydrate

One aspect of the present invention pertains to a crystalline form of (R)-8-chloro-1-methyl-2,3,4,5-tetrahydro-1H-3-benzazepine (±)-mandelate salt hydrate (Compound 1 (±)-mandelate salt hydrate). In some embodiments, the crystalline form of (R)-8-chloro-1-methyl-2,3,4,5-tetrahydro-1H-3-benzazepine (±)-mandelate salt hydrate is Form I (Compound 1 (±)-mandelate salt hydrate, Form I). The physical properties of Form I of Compound 1 (±)-mandelate salt hydrate are summarized in Table 25 below.

TABLE 25

Figure 36:
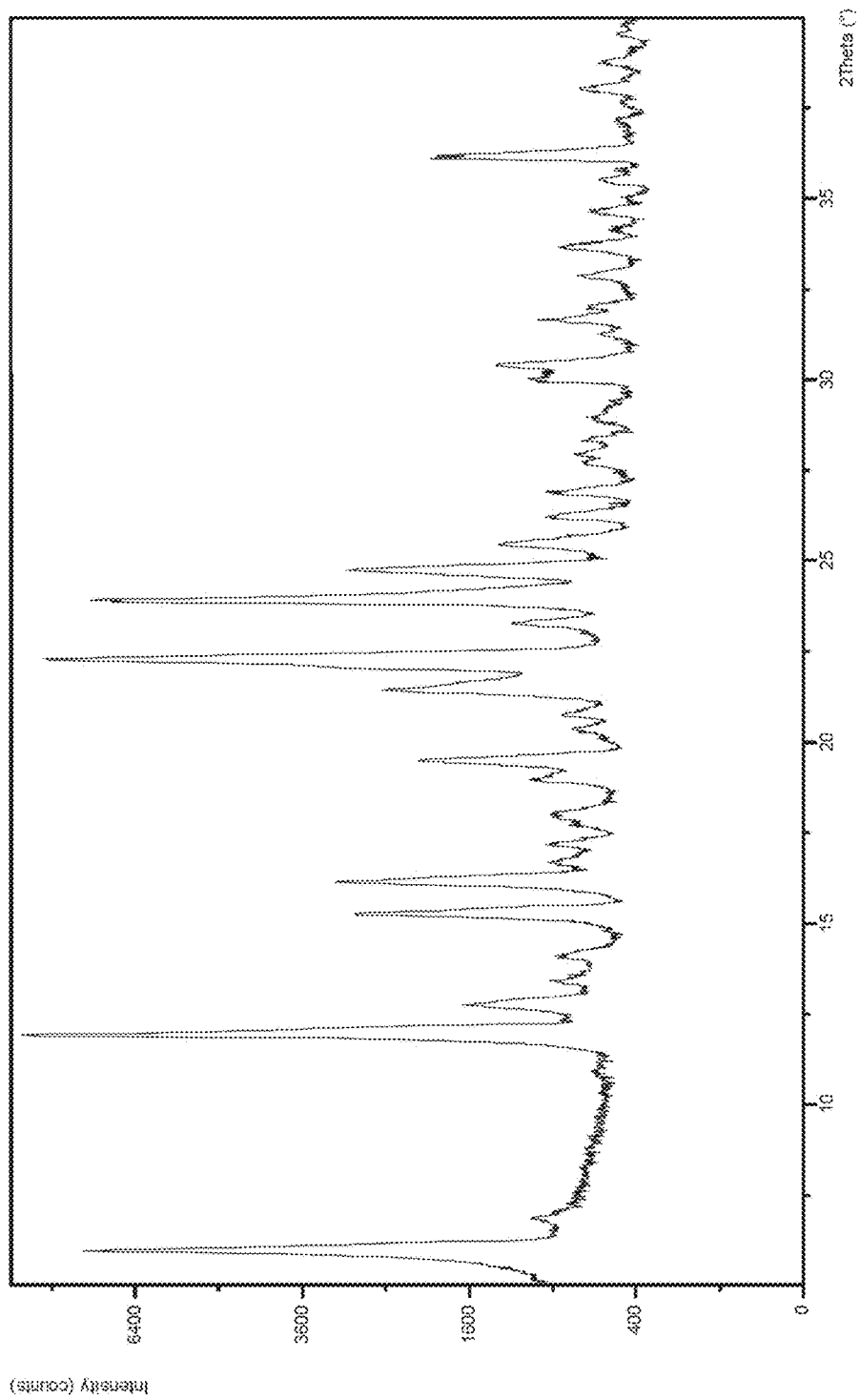
FIG. 36: PXRD of Compound 1 (±)-Mandelate Salt Hydrate, Form I.

| | Compound 1 (±)-Mandelate Salt Hydrate, Form I |
|---|---|
| PXRD | FIG. 36: Peaks of ≥18% relative intensity at 5.97, 11.91, 12.13, 15.26, 16.15, 19.49, 21.45, 22.06, 22.29, 23.90, 24.76, 36.13, and 36.21 °2θ |
| TGA | FIG. 37: about 4.8% weight loss up to about 100° C. |
| DSC | FIG. 37: extrapolated desolvation onset temperature about 74° C. |
| DMS | FIG. 38: Non-hygroscopic |

Compound 1 (±)-mandelate salt hydrate, Form I had a weight loss of ~4.8% (desolvation onset ~74° C.) out to ~100° C. This weight loss was in good agreement with the theoretical value (4.9%) for a monohydrate. The DSC desolvation endotherm overlapped with another endotherm that immediately followed it, corresponding to melting of an anhydrous form of Compound 1 mandelate prior to degradation of the salt.

Compound 1 (±)-mandelate salt hydrate was non-hygroscopic by DMS analysis, picking up about 0.039% out to and including the 90% RH hold at 25° C.

Certain X-ray powder diffraction peaks for Form I of Compound 1 (±)-mandelate salt hydrate are shown in Table 26 below.

TABLE 26

| Pos. (°2θ) | Rel. Int. (%) |
|---|---|
| 5.97 | 81.75 |
| 6.85 | 4.55 |
| 11.91 | 100.00 |
| 12.13 | 27.08 |
| 12.74 | 12.67 |
| 13.41 | 4.20 |
| 14.10 | 3.89 |
| 15.26 | 28.44 |
| 16.15 | 31.10 |
| 16.69 | 4.64 |
| 17.18 | 4.92 |
| 17.97 | 4.50 |
| 18.96 | 6.57 |
| 19.49 | 19.57 |
| 20.35 | 3.21 |
| 20.77 | 4.12 |
| 21.45 | 24.21 |
| 22.06 | 30.36 |
| 22.29 | 93.53 |
| 23.28 | 8.78 |
| 23.90 | 76.41 |
| 24.76 | 30.51 |

TABLE 26-continued

| Pos. (°2θ) | Rel. Int. (%) |
|---|---|
| 25.46 | 10.29 |
| 26.23 | 5.55 |
| 26.89 | 5.65 |
| 28.37 | 2.71 |
| 28.96 | 2.42 |
| 30.01 | 7.29 |
| 30.41 | 11.01 |
| 31.66 | 6.38 |
| 32.02 | 2.79 |
| 32.87 | 3.64 |
| 33.66 | 5.17 |
| 34.64 | 2.83 |
| 35.51 | 2.20 |
| 36.13 | 18.33 |
| 36.21 | 18.07 |
| 38.04 | 3.60 |
| 38.77 | 1.69 |

One aspect of the present invention is directed to a crystalline form of Compound 1 (±)-mandelate salt hydrate having an X-ray powder diffraction pattern comprising a peak, in terms of 2θ, at about 11.91°. In some embodiments, the crystalline form has an X-ray powder diffraction pattern comprising a peak, in terms of 2θ, at about 22.29°. In some embodiments, the crystalline form has an X-ray powder diffraction pattern comprising peaks, in terms of 2θ, at about 11.91° and about 22.29°. In some embodiments, the crystalline form has an X-ray powder diffraction pattern comprising peaks, in terms of 2θ, at about 11.91° and about 5.97°. In some embodiments, the crystalline form has an X-ray powder diffraction pattern comprising peaks, in terms of 2θ, at about 11.91°, about 22.29°, and about 5.97°. In some embodiments, the crystalline form has an X-ray powder diffraction pattern comprising peaks, in terms of 2θ, at about 11.91°, about 22.29°, about 5.97°, about 23.90°, about 16.15°, about 24.76°, and about 22.06°. In some embodiments, the crystalline form has an X-ray powder diffraction pattern comprising peaks, in terms of 2θ, at about 11.91°, about 22.29°, about 5.97°, about 23.90°, about 16.15°, about 24.76°, about 22.06°, about 15.26°, about 12.13°, and about 21.45°. One aspect of the present invention is directed to a crystalline form of Compound 1 (±)-mandelate salt hydrate having an X-ray powder diffraction pattern comprising one or more peaks listed in Table 26. In some embodiments, the crystalline form has an X-ray powder diffraction pattern substantially as shown in FIG. 36, wherein by "substantially" is meant that the reported peaks can vary by about ±0.2°2θ, and also that the relative intensities of the reported peaks can vary.

In some embodiments, the crystalline form of Compound 1 (±)-mandelate salt hydrate has a differential scanning calorimetry thermogram comprising an endotherm with an extrapolated onset temperature between about 60° C. and about 90° C. In some embodiments, the crystalline form of Compound 1 (±)-mandelate salt hydrate has a differential scanning calorimetry thermogram comprising an endotherm with an extrapolated onset temperature at about 74° C. In some embodiments, the crystalline form of Compound 1 (±)-mandelate salt hydrate has a thermogravimetric analysis profile substantially as shown in FIG. 37, wherein by "substantially" is meant that the reported TGA features can vary by about ±5° C. and by about ±2% weight change.

Figure 37:
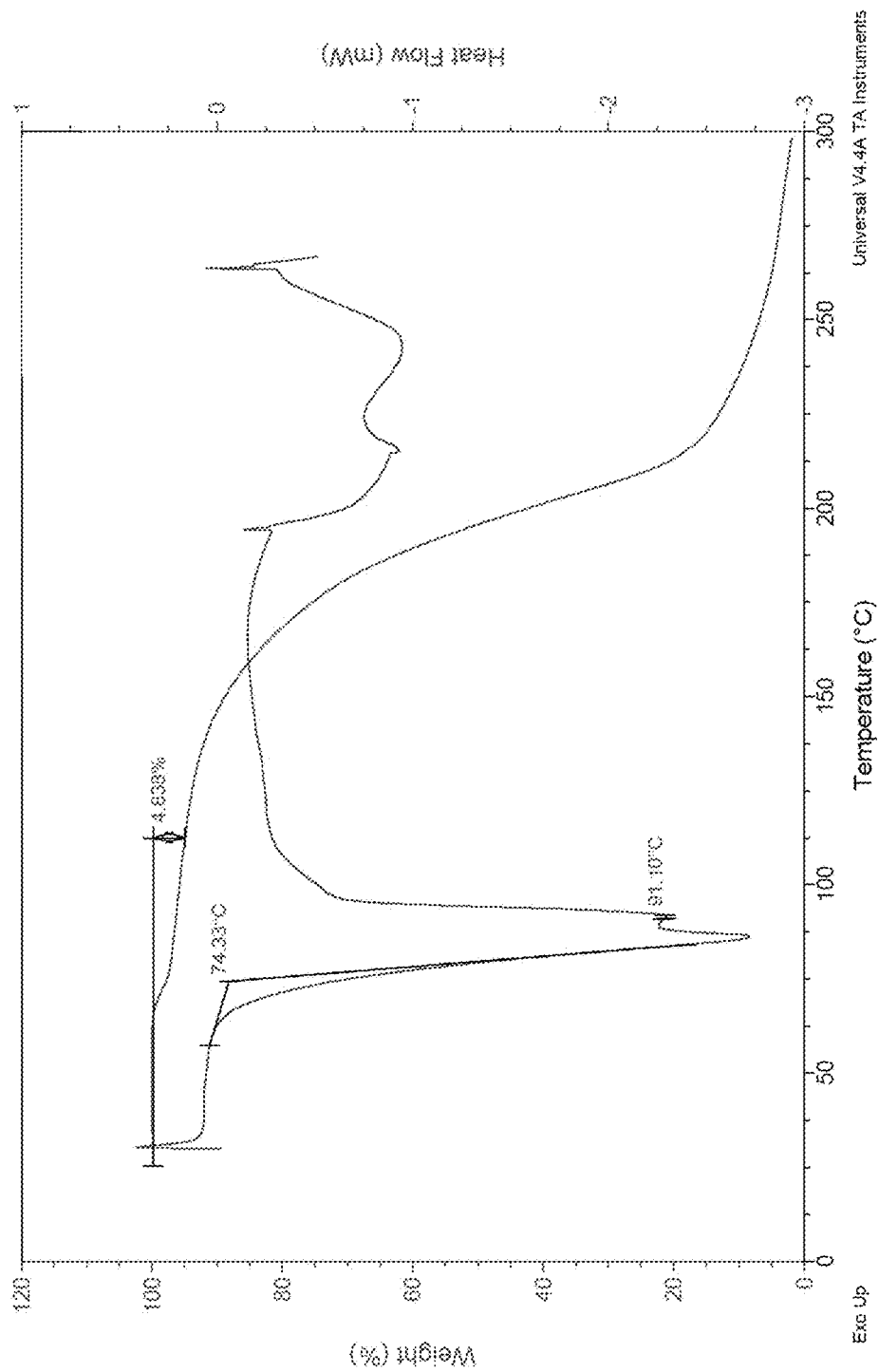
FIG. 37: DSC and TGA of Compound 1 (±)-Mandelate Salt Hydrate, Form I.

In some embodiments, the crystalline form of Compound 1 (±)-mandelate salt hydrate has a differential scanning calorimetry thermogram substantially as shown in FIG. 37, wherein by "substantially" is meant that the reported DSC features can vary by about ±6° C. and by about ±20 joules per gram.

Figure 38:
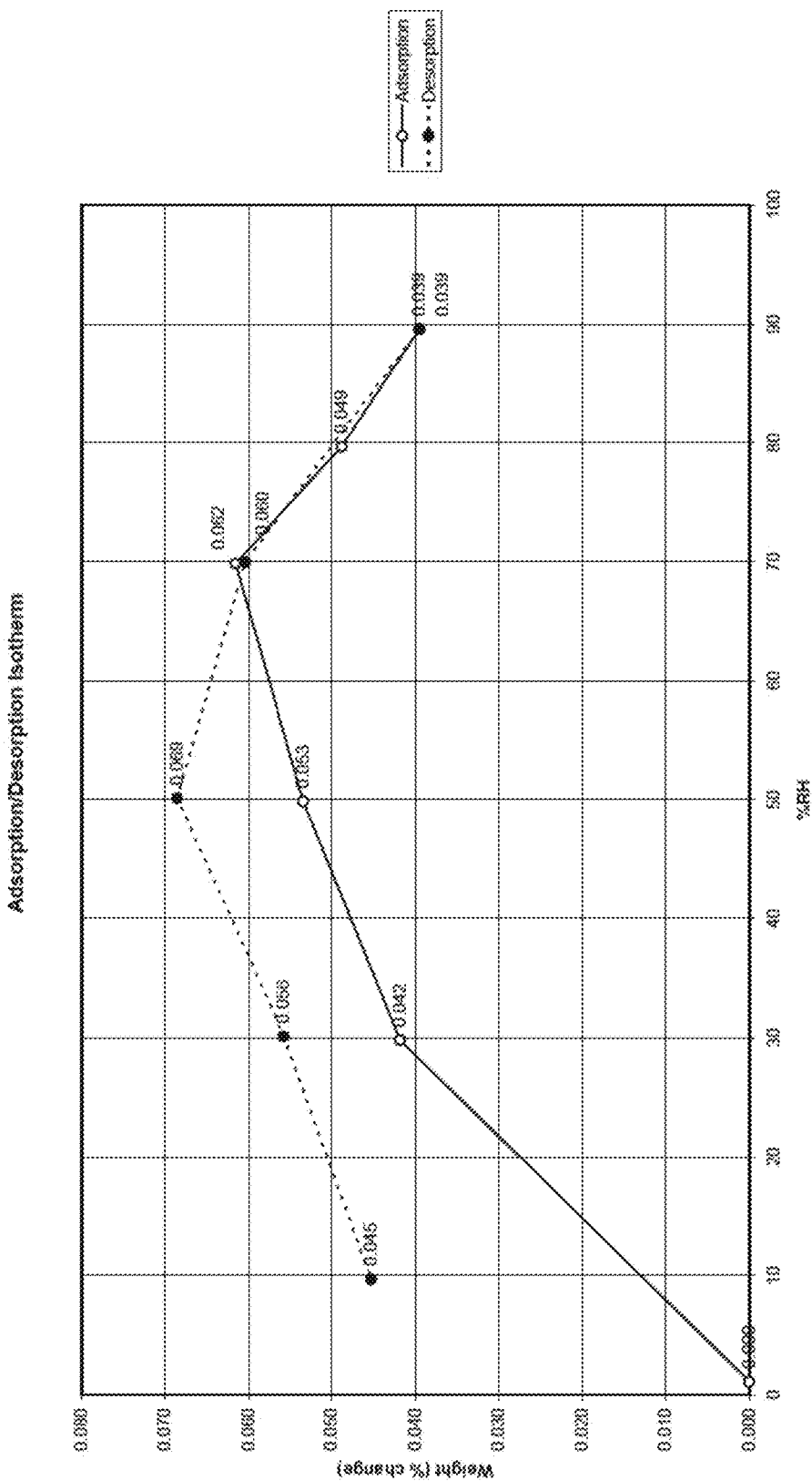
FIG. 38: DMS of Compound 1 (±)-Mandelate Salt Hydrate, Form I.

In some embodiments, the crystalline form of Compound 1 (±)-mandelate salt hydrate has a dynamic moisture sorption profile substantially as shown in FIG. 38, wherein by "substantially" is meant that the reported DMS features can vary by about ±5% relative humidity and by about ±5% weight change.

Form I of Compound 1 (±)-mandelate salt hydrate can be prepared by any of the suitable procedures known in the art for preparing crystalline polymorphs. In some embodiments Form I of Compound 1 (±)-mandelate salt hydrate can be prepared as described in Example 3.12. In some embodiments, Form I of Compound 1 (±)-mandelate salt hydrate can be prepared by slurrying crystalline Compound 1 (±)-mandelate salt hydrate containing one or more crystalline forms other than Form I. In some embodiments, the crystalline form of Compound 1 (±)-mandelate salt hydrate can be prepared by recrystallizing crystalline Compound 1 (±)-mandelate salt hydrate containing one or more crystalline forms other than Form I.

Compound 1 Hemipamoate Salt Hydrate

One aspect of the present invention pertains to a crystalline form of (R)-8-chloro-1-methyl-2,3,4,5-tetrahydro-1H-3-benzazepine hemipamoate salt hydrate (Compound 1 hemipamoate salt hydrate). In some embodiments, the crystalline form of (R)-8-chloro-1-methyl-2,3,4,5-tetrahydro-1H-3-benzazepine hemipamoate salt hydrate is Form I (Compound 1 hemipamoate salt hydrate, Form I). The physical properties of Form I of Compound 1 hemipamoate salt hydrate are summarized in Table 27 below.

TABLE 27

Compound 1 Hemipamoate Salt Hydrate, Form I

Figure 39:
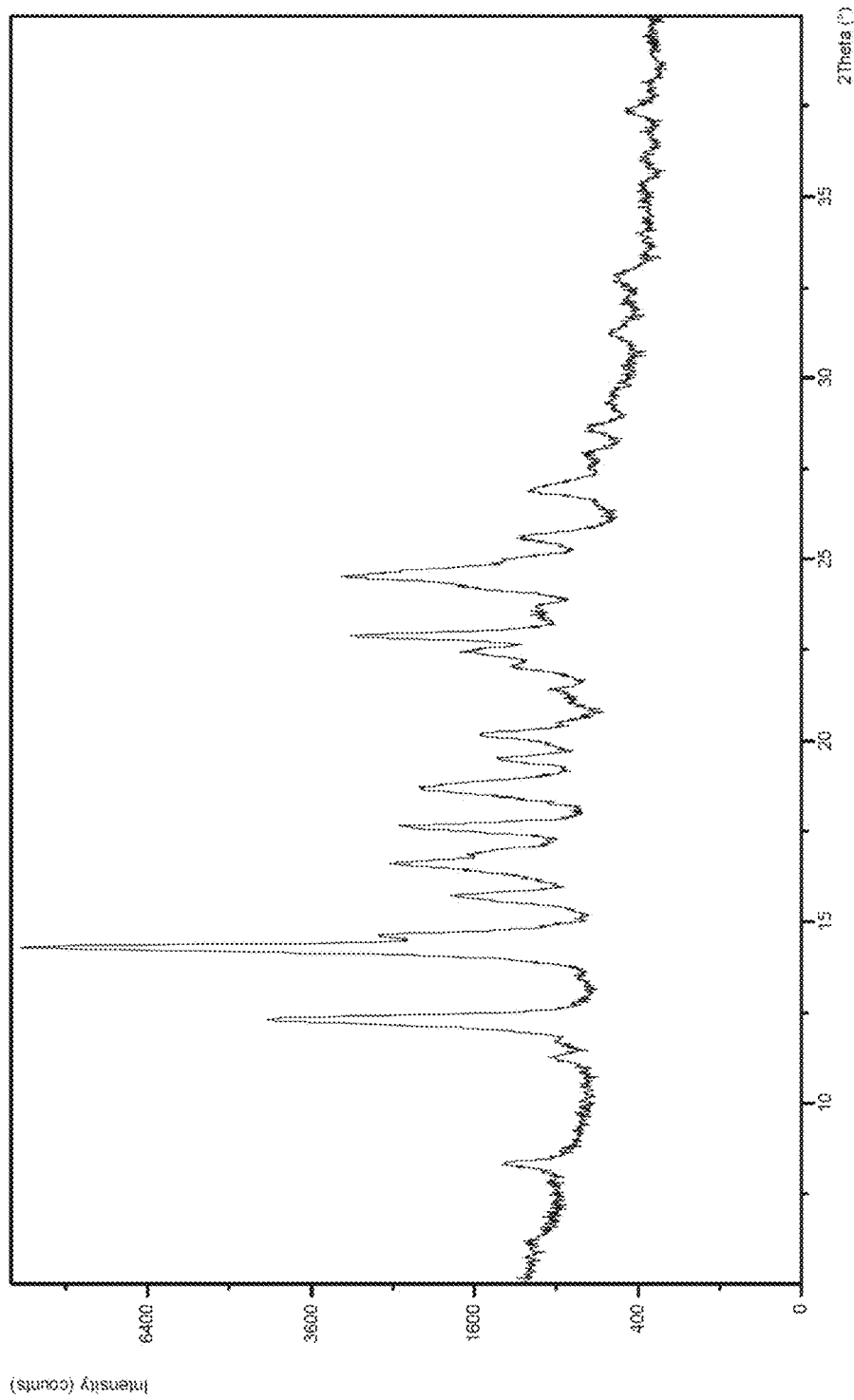
FIG. 39: PXRD of Compound 1 Hemipamoate Salt Hydrate, Form I.

| | |
|---|---|
| PXRD | FIG. 39: Peaks of ≥11% relative intensity at 12.30, 14.29, 14.61, 15.70, 16.60, 17.63, 18.68, 20.16, 22.46, 22.88, 24.19, and 24.52 °2θ |
| TGA | FIG. 40: about 5.3% weight loss below about 160° C.; extrapolated desolvation onset temperature about 101° C.; |
| DSC | FIG. 40: extrapolated melt/decomposition onset temperature about 244° C. |
| DMS | FIG. 41: ~1.472% weight gain at about 90% RH |

Compound 1 hemipamoate salt hydrate, Form I had a weight loss of ~5.3% (desolation onset ~101° C. by TGA) out to ~160° C. This weight loss was slightly higher than, but in fair agreement with the theoretical value (4.4%) for a monohydrate. The desolvation was followed by degradation. The melting/decomposition onset was ~244° C. by DSC.

Compound 1 hemipamoate salt hydrate, Form I was slightly hygroscopic by DMS analysis, picking up about 1.472% out to and including the 90% RH hold at 25° C.

Certain X-ray powder diffraction peaks for Form I of Compound 1 hemipamoate salt hydrate are shown in Table 28 below.

TABLE 28

| Pos. (°2θ) | Rel. Int. (%) |
|---|---|
| 8.31 | 5.94 |
| 11.26 | 3.08 |
| 12.30 | 42.58 |
| 14.29 | 100.00 |
| 14.61 | 24.16 |
| 15.70 | 14.34 |

TABLE 28-continued

| Pos. (°2θ) | Rel. Int. (%) |
|---|---|
| 16.60 | 22.83 |
| 16.93 | 10.48 |
| 17.63 | 20.47 |
| 18.68 | 19.14 |
| 19.50 | 9.81 |
| 20.16 | 11.73 |
| 21.40 | 4.74 |
| 22.05 | 8.63 |
| 22.46 | 13.98 |
| 22.88 | 29.20 |
| 23.62 | 6.41 |
| 24.19 | 13.17 |
| 24.52 | 31.09 |
| 25.04 | 9.19 |
| 25.61 | 8.43 |
| 26.90 | 7.69 |
| 27.87 | 3.00 |
| 28.60 | 2.92 |
| 29.31 | 1.55 |
| 31.23 | 1.82 |
| 32.76 | 1.57 |
| 37.38 | 1.47 |

One aspect of the present invention is directed to a crystalline form of Compound 1 hemipamoate salt hydrate having an X-ray powder diffraction pattern comprising a peak, in terms of 2θ, at about 14.29°. In some embodiments, the crystalline form has an X-ray powder diffraction pattern comprising a peak, in terms of 2θ, at about 12.30°. In some embodiments, the crystalline form has an X-ray powder diffraction pattern comprising peaks, in terms of 2θ, at about 14.29° and about 12.30°. In some embodiments, the crystalline form has an X-ray powder diffraction pattern comprising peaks, in terms of 2θ, at about 14.29° and about 24.52°. In some embodiments, the crystalline form has an X-ray powder diffraction pattern comprising peaks, in terms of 2θ, at about 14.29°, about 12.30°, and about 24.52°. In some embodiments, the crystalline form has an X-ray powder diffraction pattern comprising peaks, in terms of 2θ, at about 14.29°, about 12.30°, about 24.52°, about 22.88°, about 14.61°, about 16.60°, and about 17.63°. In some embodiments, the crystalline form has an X-ray powder diffraction pattern comprising peaks, in terms of 2θ, at about 14.29°, about 12.30°, about 24.52°, about 22.88°, about 14.61°, about 16.60°, about 17.63°, about 18.68°, about 15.70°, and about 22.46°. One aspect of the present invention is directed to a crystalline form of Compound 1 hemipamoate salt hydrate having an X-ray powder diffraction pattern comprising one or more peaks listed in Table 28. In some embodiments, the crystalline form has an X-ray powder diffraction pattern substantially as shown in FIG. 39, wherein by "substantially" is meant that the reported peaks can vary by about ±0.2°2θ, and also that the relative intensities of the reported peaks can vary.

In some embodiments, the crystalline form of Compound 1 hemipamoate salt hydrate has a differential scanning calorimetry thermogram comprising an endotherm with an extrapolated onset temperature between about 85° C. and about 115° C. In some embodiments, the crystalline form of Compound 1 hemipamoate salt hydrate has a differential scanning calorimetry thermogram comprising an endotherm with an extrapolated onset temperature at about 101° C. In some embodiments, the crystalline form of Compound 1 hemipamoate salt hydrate has a differential scanning calorimetry thermogram comprising an endotherm with an extrapolated onset temperature between about 230° C. and about 260° C. In some embodiments, the crystalline form of Compound 1 hemipamoate salt hydrate has a differential scanning calorimetry thermogram comprising an endotherm with an extrapolated onset temperature at about 244° C. In some embodiments, the crystalline form of Compound 1 hemipamoate salt hydrate has a differential scanning calorimetry thermogram comprising an endotherm with an extrapolated onset temperature between about 85° C. and about 115° C., and an endotherm with an extrapolated onset temperature between about 230° C. and about 260° C. In some embodiments, the crystalline form of Compound 1 hemipamoate salt hydrate has a differential scanning calorimetry thermogram comprising an endotherm with an extrapolated onset temperature at about 101° C. and an endotherm with an extrapolated onset temperature at about 244° C. In some embodiments, the crystalline form of Compound 1 hemipamoate salt hydrate has a thermogravimetric analysis profile substantially as shown in FIG. 40, wherein by "substantially" is meant that the reported TGA features can vary by about ±5° C. and by about ±2% weight change.

Figure 40:
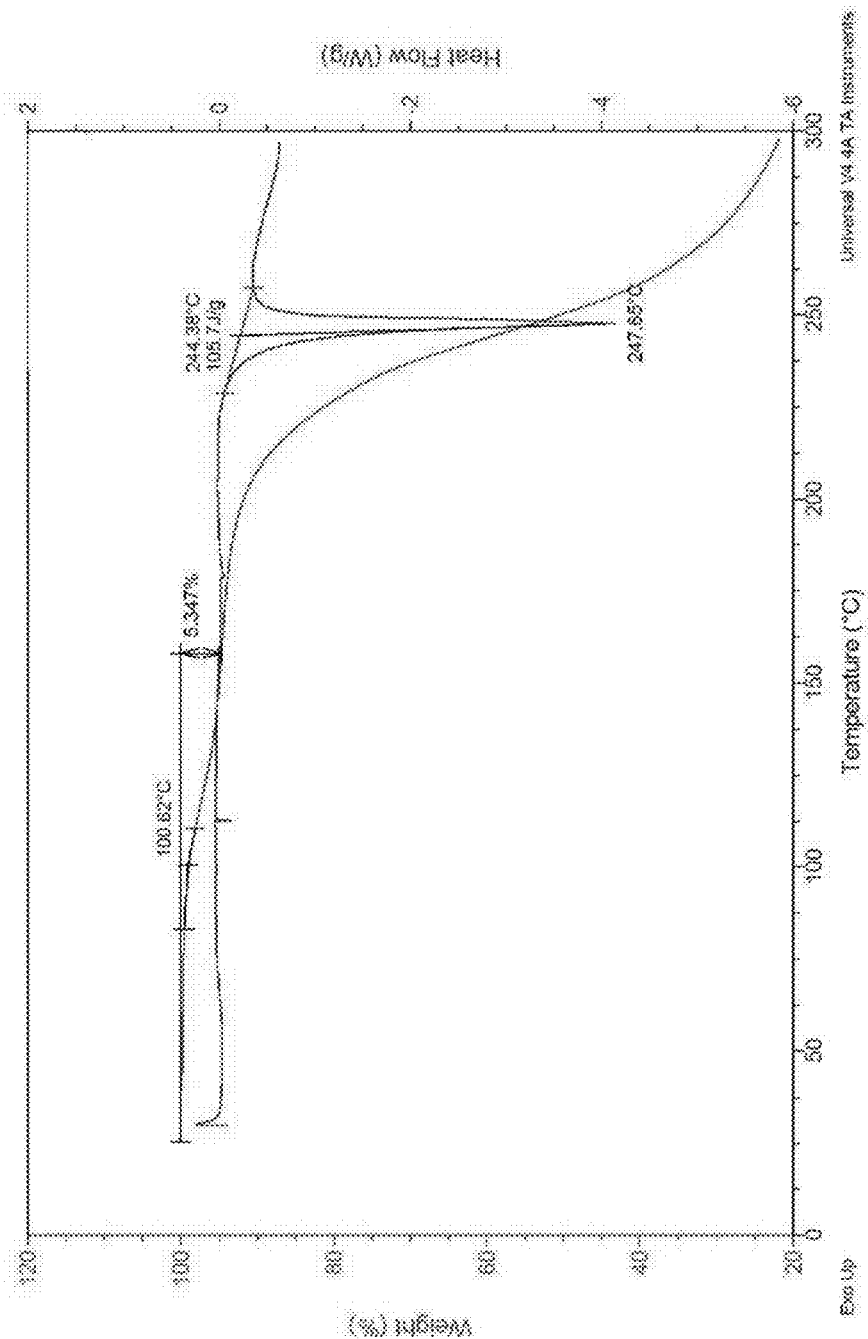
FIG. 40: DSC and TGA of Compound 1 Hemipamoate Salt Hydrate, Form I.

In some embodiments, the crystalline form of Compound 1 hemipamoate salt hydrate has a differential scanning calorimetry thermogram substantially as shown in FIG. 40, wherein by "substantially" is meant that the reported DSC features can vary by about ±6° C. and by about ±20 joules per gram.

Figure 41:
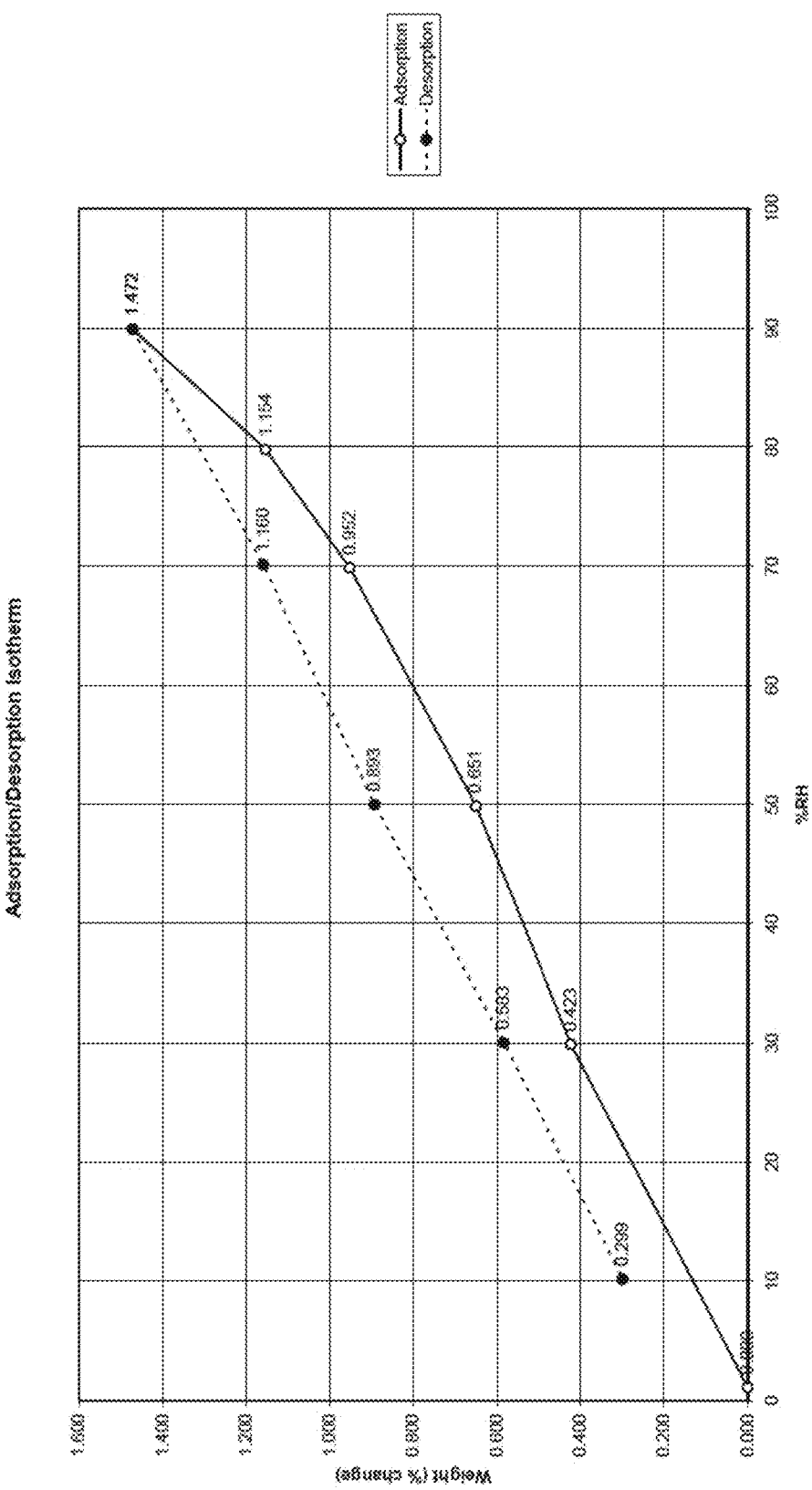
FIG. 41: DMS of Compound 1 Hemipamoate Salt Hydrate, Form I.

In some embodiments, the crystalline form of Compound 1 hemipamoate salt hydrate has a dynamic moisture sorption profile substantially as shown in FIG. 41, wherein by "substantially" is meant that the reported DMS features can vary by about ±5% relative humidity and by about ±5% weight change.

Form I of Compound 1 hemipamoate salt hydrate can be prepared by any of the suitable procedures known in the art for preparing crystalline polymorphs. In some embodiments Form I of Compound 1 hemipamoate salt hydrate can be prepared as described in Example 3.13. In some embodiments, Form I of Compound 1 hemipamoate salt hydrate can be prepared by slurrying crystalline Compound 1 hemipamoate salt hydrate containing one or more crystalline forms other than Form I. In some embodiments, the crystalline form of Compound 1 hemipamoate salt hydrate can be prepared by recrystallizing crystalline Compound 1 hemipamoate salt hydrate containing one or more crystalline forms other than Form I.

One aspect of the present invention pertains to pharmaceutical compositions comprising a crystalline form of the present invention, and a pharmaceutically acceptable carrier.

One aspect of the present invention pertains to processes for preparing a pharmaceutical composition comprising admixing a crystalline form of the present invention, and a pharmaceutically acceptable carrier.

One aspect of the present invention pertains to modified-release dosage forms comprising a crystalline form of the present invention.

One aspect of the present invention pertains to methods for weight management comprising administering to an individual in need thereof a crystalline form of the present invention.

One aspect of the present invention pertains to the use of crystalline forms of the present invention in the manufacture of a medicament for weight management in an individual.

One aspect of the present invention pertains to crystalline forms of the present invention for use in a method of treatment of the human or animal body by therapy.

One aspect of the present invention pertains to crystalline forms of the present invention for use in a method of weight management.

One aspect of the present invention pertains to crystalline forms of the present invention for use in a method of weight loss.

One aspect of the present invention pertains to crystalline forms of the present invention for use in a method of maintenance of weight loss.

One aspect of the present invention pertains to crystalline forms of the present invention for use in a method of decreasing food consumption One aspect of the present invention pertains to crystalline forms of the present invention for use in a method of increasing meal-related satiety.

One aspect of the present invention pertains to crystalline forms of the present invention for use in a method of reducing pre-meal hunger.

One aspect of the present invention pertains to crystalline forms of the present invention for use in a method of reducing intra-meal food intake.

One aspect of the present invention pertains to crystalline forms of the present invention for use in a method of weight management further comprising a reduced-calorie diet.

One aspect of the present invention pertains to crystalline forms of the present invention for use in a method of weight management further comprising a program of regular exercise.

One aspect of the present invention pertains to crystalline forms of the present invention for use in a method of weight management further comprising a reduced-calorie diet and a program of regular exercise.

One aspect of the present invention pertains to crystalline forms of the present invention for use in a method of weight management in an obese patient with an initial body mass index ≥30 kg/m$^2$.

One aspect of the present invention pertains to crystalline forms of the present invention for use in a method of weight management in an overweight patient with an initial body mass index ≥27 kg/m$^2$ in the presence of at least one weight related co-morbid condition.

One aspect of the present invention pertains to crystalline forms of the present invention for use in a method of weight management in an overweight patient with an initial body mass index ≥27 kg/m$^2$ in the presence of at least one weight related co-morbid condition selected from: hypertension, dyslipidemia, cardiovascular disease, glucose intolerance, and sleep apnea.

One aspect of the present invention pertains to crystalline forms of the present invention for use in a method of weight management in a patient with an initial body mass index ≥30 kg/m$^2$.

One aspect of the present invention pertains to crystalline forms of the present invention for use in a method of weight management in a patient with an initial body mass index ≥27 kg/m$^2$.

One aspect of the present invention pertains to crystalline forms of the present invention for use in a method of weight management in a patient with an initial body mass index ≥27 kg/m$^2$ in the presence of at least one weight related co-morbid condition.

One aspect of the present invention pertains to crystalline forms of the present invention for use in a method of weight management in a patient with an initial body mass index ≥27 kg/m$^2$ in the presence of at least one weight related co-morbid condition selected from: hypertension, dyslipidemia, cardiovascular disease, glucose intolerance, and sleep apnea.

One aspect of the present invention pertains to crystalline forms of the present invention for use in a method of weight management in a patient with an initial body mass index ≥25 kg/m².

One aspect of the present invention pertains to crystalline forms of the present invention for use in a method of weight management in a patient with an initial body mass index ≥25 kg/m² in the presence of at least one weight related co-morbid condition.

One aspect of the present invention pertains to crystalline forms of the present invention for use in a method of weight management in a patient with an initial body mass index ≥25 kg/m² in the presence of at least one weight related co-morbid condition selected from: hypertension, dyslipidemia, cardiovascular disease, glucose intolerance, and sleep apnea.

Pharmaceutical Compositions

A further aspect of the present invention pertains to pharmaceutical compositions comprising one or more salts according to any of the salt embodiments disclosed herein and one or more pharmaceutically acceptable carriers. Some embodiments pertain to pharmaceutical compositions comprising a salt according to any of the salt embodiments disclosed herein and a pharmaceutically acceptable carrier. Some embodiments pertain to pharmaceutical compositions comprising any subcombination of salts according to any of the salt embodiments disclosed herein.

Another aspect of the present invention pertains to methods of producing pharmaceutical compositions comprising admixing one or more salts according to any of the salt embodiments disclosed herein and one or more pharmaceutically acceptable carriers. Some embodiments pertain to a method of producing a pharmaceutical composition comprising admixing a salt according to any of the salt embodiments disclosed herein and a pharmaceutically acceptable carrier. Some embodiments pertain to a methods of producing pharmaceutical compositions comprising admixing any subcombination of salts according to any of the salt embodiments disclosed herein and a pharmaceutically acceptable carrier.

One aspect of the present invention pertains to methods of manufacturing a pharmaceutical composition comprising: admixing a compound selected from: a salt of the present invention and pharmaceutically acceptable solvates and hydrates thereof, with a pharmaceutically acceptable excipient.

The salts and crystalline forms of the present invention can be used as active ingredients in pharmaceutical compositions, specifically as 5-HT$_{2C}$-receptor modulators. The term "active ingredient" as defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the salts of the present invention can vary within wide limits and as is customary and is known to the physician, it is to be tailored to the individual conditions in each individual case. It depends, for example, on the nature and severity of the illness to be treated, on the condition of the patient, on the salt employed or on whether an acute or chronic disease state is treated or prophylaxis conducted or on whether further active compounds are administered in addition to the salts of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

Some embodiments of the present invention include a method of producing a pharmaceutical composition for "combination-therapy" comprising admixing at least one salt according to any of the salt embodiments disclosed herein, together with at least one known pharmaceutical agent as described herein and a pharmaceutically acceptable carrier.

It is noted that when the salts of the present invention are utilized as active ingredients in a pharmaceutical composition, these are not intended for use only in humans, but in other non-human mammals as well. Indeed, recent advances in the area of animal health-care mandate that consideration be given for the use of active agents, such as 5-HT$_{2C}$-receptor modulators, for the treatment of a 5-HT$_{2C}$-receptor-associated disease or disorders in companionship animals (e.g., cats, dogs, etc.) and in livestock animals (e.g., cows, chickens, fish, etc.). Those of ordinary skill in the art are readily credited with understanding the utility of such salts in such settings.

One aspect of the present invention pertains to pharmaceutical compositions comprising a salt of the present invention.

One aspect of the present invention pertains to processes for preparing pharmaceutical compositions comprising admixing a salt of the present invention, and a pharmaceutically acceptable carrier One aspect of the present invention pertains to pharmaceutical compositions of the present invention for use in a method of treatment of the human or animal body by therapy.

One aspect of the present invention pertains to pharmaceutical compositions of the present invention for use in a method of weight management.

One aspect of the present invention pertains to pharmaceutical compositions of the present invention for use in a method of weight loss.

One aspect of the present invention pertains to pharmaceutical compositions of the present invention for use in a method of maintenance of weight loss.

One aspect of the present invention pertains to pharmaceutical compositions of the present invention for use in a method of decreasing food consumption One aspect of the present invention pertains to pharmaceutical compositions of the present invention for use in a method of increasing meal-related satiety.

One aspect of the present invention pertains to pharmaceutical compositions of the present invention for use in a method of reducing pre-meal hunger.

One aspect of the present invention pertains to pharmaceutical compositions of the present invention for use in a method of reducing intra-meal food intake.

One aspect of the present invention pertains to pharmaceutical compositions of the present invention for use in a method of weight management further comprising a reduced-calorie diet.

One aspect of the present invention pertains to pharmaceutical compositions of the present invention for use in a method of weight management further comprising a program of regular exercise.

One aspect of the present invention pertains to pharmaceutical compositions of the present invention for use in a method of weight management further comprising a reduced-calorie diet and a program of regular exercise.

One aspect of the present invention pertains to pharmaceutical compositions of the present invention for use in a method of weight management in an obese patient with an initial body mass index ≥30 kg/m$^2$.

One aspect of the present invention pertains to pharmaceutical compositions of the present invention for use in a method of weight management in an overweight patient with an initial body mass index ≥27 kg/m$^2$ in the presence of at least one weight related co-morbid condition.

One aspect of the present invention pertains to pharmaceutical compositions of the present invention for use in a method of weight management in an overweight patient with an initial body mass index ≥27 kg/m$^2$ in the presence of at least one weight related co-morbid condition selected from: hypertension, dyslipidemia, cardiovascular disease, glucose intolerance, and sleep apnea.

One aspect of the present invention pertains to pharmaceutical compositions of the present invention for use in a method of weight management in a patient with an initial body mass index ≥30 kg/m$^2$.

One aspect of the present invention pertains to pharmaceutical compositions of the present invention for use in a method of weight management in a patient with an initial body mass index ≥27 kg/m$^2$.

One aspect of the present invention pertains to pharmaceutical compositions of the present invention for use in a method of weight management in a patient with an initial body mass index ≥27 kg/m$^2$ in the presence of at least one weight related co-morbid condition.

One aspect of the present invention pertains to pharmaceutical compositions of the present invention for use in a method of weight management in a patient with an initial body mass index ≥27 kg/m$^2$ in the presence of at least one weight related co-morbid condition selected from: hypertension, dyslipidemia, cardiovascular disease, glucose intolerance, and sleep apnea.

One aspect of the present invention pertains to pharmaceutical compositions of the present invention for use in a method of weight management in a patient with an initial body mass index ≥25 kg/m$^2$.

One aspect of the present invention pertains to pharmaceutical compositions of the present invention for use in a method of weight management in a patient with an initial body mass index ≥25 kg/m$^2$ in the presence of at least one weight related co-morbid condition.

One aspect of the present invention pertains to pharmaceutical compositions of the present invention for use in a method of weight management in a patient with an initial body mass index ≥25 kg/m$^2$ in the presence of at least one weight related co-morbid condition selected from: hypertension, dyslipidemia, cardiovascular disease, glucose intolerance, and sleep apnea.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to compounds described herein that are salts, it embraces pharmaceutically acceptable solvates and/or hydrates of such salts.

It will be apparent to those skilled in the art that the dosage forms described herein may comprise, as the active component, either a salts or crystalline form thereof as described herein, or a solvate or hydrate thereof. Moreover, various hydrates and solvates of the salts or crystalline form thereof described herein will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999.

Accordingly, one aspect of the present invention pertains to methods of administering hydrates and solvates of salts or crystalline forms thereof described herein and/or their pharmaceutically acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Isotopes

The present disclosure includes all isotopes of atoms occurring in the present salts and crystalline forms thereof. Isotopes include those atoms having the same atomic number but different mass numbers. One aspect of the present invention includes every combination of one or more atoms in the present salts and crystalline forms thereof that is replaced with an atom having the same atomic number but a different mass number. One such example is the replacement of an atom that is the most naturally abundant isotope, such as $^1$H or $^{12}$C, found in one the present salts and crystalline forms thereof, with a different atom that is not the most naturally abundant isotope, such as $^2$H or $^3$H (replacing $^1$H), or $^{11}$C, $^{13}$C, or $^{14}$C (replacing $^{12}$C). A salt wherein such a replacement has taken place is commonly referred to as being isotopically-labeled. Isotopic-labeling of the present salts and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$C. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present salts and crystalline forms thereof, wherein the naturally occurring distribution of the isotopes in the composition is perturbed. Another aspect of the present invention includes compositions and pharmaceutical compositions comprising salts and crystalline forms thereof as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Indications

Obesity is a life-threatening disorder in which there is an increased risk of morbidity and mortality arising from concomitant diseases such as, but not limited to, type II diabetes, hypertension, stroke, certain forms of cancers and gallbladder disease.

Obesity has become a major healthcare issue in the Western World and increasingly in some third world countries. The increase in the number of obese people is due largely to the increasing preference for high fat content foods but also, and this can be a more important factor, the decrease in activity in most people's lives. In spite of the growing awareness of the health concerns linked to obesity the percentage of individuals that are overweight or obese continues to increase. The most significant concern, from a public health perspective, is that children who are overweight grow up to be overweight or obese adults, and accordingly are at greater risk for major health problems. Therefore, it appears that the number of individuals that are overweight or obese will continue to increase.

Whether someone is classified as overweight or obese is generally determined on the basis of his or her body mass index (BMI) which is calculated by dividing body weight (kg) by height squared (m$^2$). Thus, the units for BMI are kg/m$^2$. BMI is more highly correlated with body fat than any other indicator of height and weight. A person is considered overweight when they have a BMI in the range of 25-30 kg/m$^2$, whereas a person with a BMI over 30 kg/m$^2$ is classified as obese. Obesity is further divided into three classes: Class I (BMI of about 30 to about 34.9 kg/m$^2$), Class II (BMI of about 35 to 39.9 kg/m$^2$) and Class III (about 40 kg/m$^2$ or greater); see Table below for complete classifications.

| Classification Of Weight By Body Mass Index (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases for an individual there is an increased risk of morbidity and mortality relative to an individual with normal BMI. Accordingly, overweight and obese individuals (BMI of about 25 kg/m$^2$ and above) are at increased risk for physical ailments such as, but not limited to, high blood pressure, cardiovascular disease (particularly hypertension), high blood cholesterol, dyslipidemia, type II (non-insulin dependent) diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), diseases of reproduction (such as sexual dysfunction, both male and female, including male erectile dysfunction), bladder control problems (such as stress incontinence), uric acid nephrolithiasis, psychological disorders (such as depression, eating disorders, distorted body image, and low self esteem). Research has shown that even a modest reduction in body weight can correspond to a significant reduction in the risk of developing other ailments, such as, but not limited to, coronary heart disease.

As mentioned above, obesity increases the risk of developing cardiovascular diseases. Coronary insufficiency, atheromatous disease, and cardiac insufficiency are at the forefront of the cardiovascular complications induced by obesity. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for type 2 diabetes and coronary heart disease and the potential value of an integrated approach to the prevention of these conditions based on the prevention of obesity [Perry, I. J., et al. *BMJ* 310, 560-564 (1995)]. It is estimated that if the entire population had an ideal weight, the risk of coronary insufficiency would decrease by 25% and the risk of cardiac insufficiency and of cerebral vascular accidents by 35%.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina and increases the risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment for individuals that are overweight or obese is to offer diet and life style advice, such as, reducing the fat content of their diet and increasing their physical activity. However many patients find these difficult to maintain and need additional help from drug therapy to sustain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of the patient population led to its withdrawal by the FDA in 1998.

The 5-HT$_{2C}$ receptor is recognized as a well-accepted receptor target for the treatment of obesity, psychiatric, and other disorders. See, for example, Halford et al., *Serotonergic Drugs Effects on Appetite Expression and Use for the Treatment of Obesity*, Drugs 2007; 67 (1): 27-55; Naughton et al., *A Review Of The Role Of Serotonin Receptors In Psychiatric Disorders.* Human Psychopharmacology (2000), 15(6), 397-415.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In a phase 3 human clinical trial evaluating the safety and efficacy of lorcaserin for weight management, statistical significance (p<0.0001) was achieved on all three of the hierarchically ordered co-primary endpoints for patients treated with lorcaserin versus placebo. Treatment with lorcaserin was generally very well tolerated. An assessment of echocardiograms indicated no apparent drug-related effect on the development of US Food and Drug Administration (FDA)-defined valvulopathy over the two-year treatment period. The hierarchically ordered endpoints were the proportion of patients achieving 5% or greater weight loss after 12 months, the difference in mean weight loss compared to placebo after 12 months, and the proportion of patients achieving 10% or greater weight loss after 12 months. Compared to placebo, using an intent-to-treat last observation carried forward (ITT-LOCF) analysis, treatment with lorcaserin was associated with highly statistically significant (p<0.0001) categorical and average weight loss from baseline after 12 months: 47.5% of lorcaserin patients lost greater than or equal to 5% of their body weight from baseline compared to 20.3% in the placebo group. This result satisfied the efficacy benchmark in the most recent FDA draft guidance. Average weight loss of 5.8% of body weight, or 12.7 pounds, was achieved in the lorcaserin group, compared to 2.2% of body weight, or 4.7 pounds, in the placebo group. Statistical separation from placebo was observed by Week 2, the first post-baseline measurement. 22.6% of lorcaserin patients lost greater than or equal to 10% of their body weight from baseline, compared to 7.7% in the placebo group. Lorcaserin patients who completed 52 weeks of treatment according to the protocol lost an average of 8.2% of body weight, or 17.9 pounds, compared to 3.4%, or 7.3 pounds, in the placebo group (p<0.0001).

In addition to obesity, the 5-HT$_{2C}$ receptor is also involved in other diseases, conditions and disorders, such as, obsessive compulsive disorder, some forms of depression, and epilepsy. Accordingly, 5-HT$_{2C}$ receptor agonists can have anti-panic properties, and properties useful for the treatment of sexual dysfunction. In addition, 5-HT$_{2C}$ receptor agonists are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. What the individual is doing with regard to food and weight is neither normal nor healthy.

The 5-HT$_{2C}$ receptor plays a role in Alzheimer Disease (AD). Therapeutic agents currently prescribed for Alzheimer's disease (AD) are cholinomimetic agents that act by inhibiting the enzyme acetylcholinesterase. The resulting effect is increased levels of acetylcholine, which modestly improves neuronal function and cognition in patients with AD. Although, dysfunction of cholinergic brain neurons is an early manifestation of AD, attempts to slow the progression of the disease with these agents have had only modest success, perhaps because the doses that can be administered are limited by peripheral cholinergic side effects, such as tremors, nausea, vomiting, and dry mouth. In addition, as AD progresses, these agents tend to lose their effectiveness due to continued cholinergic neuronal loss.

Therefore, there is a need for agents that have beneficial effects in AD, particularly in alleviating symptoms by improving cognition and slowing or inhibiting disease progression, without the side effects observed with current therapies. Therefore, serotonin 5-HT$_{2C}$ receptors, which are exclusively expressed in brain, are attractive targets.

Another disease, disorder or condition that can is associated with the function of the 5-HT$_{2C}$ receptor is erectile dysfunction (ED). Erectile dysfunction is the inability to achieve or maintain an erection sufficiently rigid for intercourse, ejaculation, or both. An estimated 20-30 million men in the United States have this condition at some time in their lives. The prevalence of the condition increases with age. Five percent of men 40 years of age report ED. This rate increases to between 15% and 25% by the age of 65, and to 55% in men over the age of 75 years.

Erectile dysfunction can result from a number of distinct problems. These include loss of desire or libido, the inability to maintain an erection, premature ejaculation, lack of emission, and inability to achieve an orgasm. Frequently, more than one of these problems presents themselves simultaneously. The conditions may be secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems. Erectile dysfunction, when organic, is primarily due to vascular irregularities associated with atherosclerosis, diabetes, and hypertension.

There is evidence for use of a serotonin 5-HT$_{2C}$ agonist for the treatment of sexual dysfunction in males and females. The serotonin 5-HT$_{2C}$ receptor is involved with the processing and integration of sensory information, regulation of central monoaminergic systems, and modulation of neuroendocrine responses, anxiety, feeding behavior, and cerebrospinal fluid production [Tecott, L. H., et al. Nature 374: 542-546 (1995)]. In addition, the serotonin 5-HT$_{2C}$ receptor has been implicated in the mediation of penile erections in rats, monkeys, and humans.

In summary, the 5-HT$_{2C}$ receptor is a validated and well-accepted receptor target for the prophylaxis and/or treatment of 5-HT$_{2C}$ mediated receptor diseases and disorders, such as, obesity, eating disorders, psychiatric disorders, Alzheimer Disease, sexual dysfunction and disorders related thereto. It can be seen that there exists a need for selective 5-HT$_{2C}$ receptor agonists that can safely address these needs. The present invention is directed to these, as well as other, important ends.

One aspect of the present invention pertains to methods for weight management, comprising administering to an individual in need thereof, a therapeutically effective amount of a salt, or a pharmaceutical composition of the present invention.

In some embodiments, the weight management comprises one or more of: weight loss and maintenance of weight loss.

In some embodiments, the weight management comprises one or more of: weight loss, maintenance of weight loss, decreasing food consumption, increasing meal-related satiety, reducing pre-meal hunger, and reducing intra-meal food intake.

In some embodiments, the weight loss is as an adjunct to diet and exercise.

In some embodiments, the individual in need of weight management is selected from: an obese patient with an initial body mass index ≥30 kg/m², an overweight patient with an initial body mass index ≥27 kg/m² in the presence of at least one weight related comorbid condition; an overweight patient with an initial body mass index ≥27 kg/m² in the presence of at least one weight related comorbid condition; wherein the weight related co-morbid condition is selected from: hypertension, dyslipidemia, cardiovascular disease, glucose intolerance, and sleep apnea.

In some embodiments, the method further comprises administering a second anti-obesity agent to the individual.

In some embodiments, the second anti-obesity agent is selected from: chlorphentermine, clortermine, phenpentermine, and phentermine, and pharmaceutically acceptable salts, solvates, and hydrates thereof.

In some embodiments, the method further comprises administering an anti-diabetes agent to the individual.

In some embodiments, the anti-diabetes agent is metformin.

In some embodiments, the weight management comprises weight loss.

In some embodiments, the weight management further comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index ≥30 kg/m².

In some embodiments, the individual in need of weight management is an overweight patient with an initial body mass index ≥27 kg/m² in the presence of at least one weight related comorbid condition.

In some embodiments, the individual in need of weight management is an overweight patient with an initial body mass index ≥27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥30 kg/m².

In some embodiments, the individual in need of weight management has an initial body mass index ≥27 kg/m².

In some embodiments, the individual in need of weight management has an initial body mass index ≥27 kg/m² in the presence of at least one weight related comorbid condition.

In some embodiments, the individual in need of weight management has an initial body mass index ≥27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥25 kg/m².

In some embodiments, the individual in need of weight management has an initial body mass index ≥25 kg/m² in the presence of at least one weight related comorbid condition.

In some embodiments, the individual in need of weight management has an initial body mass index ≥25 kg/m² in the presence of at least one weight related comorbid condition selected from: hypertension, dyslipidemia, cardiovascular disease, glucose intolerance, and sleep apnea.

In some embodiments, the method for weight management further comprises administering phentermine to the individual.

One aspect of the present invention pertains to methods for the treatment of a disorder related to 5-HT$_{2C}$ receptor activity in an individual, comprising administering to an individual in need thereof, a therapeutically effective amount of a salt, or a pharmaceutical composition of the present invention.

One aspect of the present invention pertains to methods for the treatment of obesity, comprising administering to an individual in need thereof, a therapeutically effective amount of a salt, or a pharmaceutical composition of the present invention.

In some embodiments, the method for the treatment of obesity further comprises the administration or prescription of phentermine.

In some embodiments, the method for the treatment of obesity further comprises gastric electrical stimulation.

One aspect of the present invention pertains to methods for inducing weight loss, BMI loss, waist circumference loss or body fat percentage loss, comprising administering to an individual in need thereof, a therapeutically effective amount of a salt, or a pharmaceutical composition of the present invention.

One aspect of the present invention pertains to methods for inducing weight loss, BMI loss, waist circumference loss or body fat percentage loss in an individual in preparation of the individual for bariatric surgery, comprising administering to an individual in need thereof, a therapeutically effective amount of a salt, or a pharmaceutical composition of the present invention.

One aspect of the present invention pertains to methods for maintaining weight loss, BMI loss, waist circumference loss or body fat percentage loss in an individual, comprising administering to an individual in need thereof, a therapeutically effective amount of a salt, or a pharmaceutical composition of the present invention.

One aspect of the present invention pertains to methods for maintaining weight loss, BMI loss, waist circumference loss or body fat percentage loss in an individual following bariatric surgery, comprising administering to an individual in need thereof, a therapeutically effective amount of a salt, or a pharmaceutical composition of the present invention.

One aspect of the present invention pertains to methods for inducing satiety in an individual, comprising administering to an individual in need thereof, a therapeutically effective amount of a salt, or a pharmaceutical composition of the present invention.

One aspect of the present invention pertains to methods for decreasing food intake in an individual, comprising administering to an individual in need thereof, a therapeutically effective amount of a salt, or a pharmaceutical composition of the present invention.

One aspect of the present invention pertains to methods for decreasing hunger in an individual, comprising administering to an individual in need thereof, a therapeutically effective amount of a salt, or a pharmaceutical composition of the present invention.

One aspect of the present invention pertains to methods for decreasing food cravings in an individual, comprising administering to an individual in need thereof, a therapeutically effective amount of a salt, or a pharmaceutical composition of the present invention.

One aspect of the present invention pertains to methods for increasing intermeal interval in an individual, comprising administering to an individual in need thereof, a therapeutically effective amount of a salt, or a pharmaceutical composition of the present invention.

One aspect of the present invention pertains to methods for the treatment of a disorder selected from: schizophrenia, anxiety, depression, psychoses, and alcohol addiction, comprising administering to an individual in need thereof, a therapeutically effective amount of a salt, or a pharmaceutical composition of the present invention.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

One aspect of the present invention pertains to the use of salts of the present invention, in the manufacture of a medicament for weight management in an individual.

In some embodiments, the weight management comprises weight loss.

In some embodiments, the weight management further comprises maintenance of weight loss.

In some embodiments, the weight management comprises decreasing food consumption.

In some embodiments, the weight management comprises increasing meal-related satiety.

In some embodiments, the weight management comprises reducing pre-meal hunger.

In some embodiments, the weight management comprises reducing intra-meal food intake.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual is an obese patient with an initial body mass index $\geq 30$ kg/m$^2$.

In some embodiments, the individual is an overweight patient with an initial body mass index $\geq 27$ kg/m$^2$ in the presence of at least one weight related comorbid condition.

In some embodiments, the individual is an overweight patient with an initial body mass index $\geq 27$ kg/m$^2$ in the presence of at least one weight related comorbid condition selected from: hypertension, dyslipidemia, cardiovascular disease, glucose intolerance, and sleep apnea.

In some embodiments, the individual has an initial body mass index $\geq 30$ kg/m$^2$.

In some embodiments, the individual has an initial body mass index $\geq 27$ kg/m$^2$.

In some embodiments, the individual has an initial body mass index $\geq 27$ kg/m$^2$ in the presence of at least one weight related comorbid condition.

In some embodiments, the individual has an initial body mass index $\geq 27$ kg/m$^2$ in the presence of at least one weight related comorbid condition selected from: hypertension, dyslipidemia, cardiovascular disease, glucose intolerance, and sleep apnea.

In some embodiments, the individual has an initial body mass index $\geq 25$ kg/m$^2$.

In some embodiments, the individual has an initial body mass index $\geq 25$ kg/m$^2$ in the presence of at least one weight related comorbid condition.

In some embodiments, the individual has an initial body mass index $\geq 25$ kg/m$^2$ in the presence of at least one weight related comorbid condition selected from: hypertension, dyslipidemia, cardiovascular disease, glucose intolerance, and sleep apnea.

In some embodiments, the medicament for weight management is used in combination with phentermine.

One aspect of the present invention pertains to the use of salts of the present invention, in the manufacture of a medicament for a disorder related to 5-HT$_{2C}$ receptor activity in an individual.

One aspect of the present invention pertains to the use of salts of the present invention, in the manufacture of a medicament for the treatment of obesity in an individual.

In some embodiments, the treatment of obesity further comprises the administration or prescription of phentermine.

In some embodiments, the treatment of obesity further comprises gastric electrical stimulation.

One aspect of the present invention pertains to the use of salts of the present invention, in the manufacture of a medicament for inducing weight loss, BMI loss, waist circumference loss or body fat percentage loss in an individual.

One aspect of the present invention pertains to the use of salts of the present invention, in the manufacture of a medicament for inducing weight loss, BMI loss, waist circumference loss or body fat percentage loss in an individual in preparation of the individual for bariatric surgery.

One aspect of the present invention pertains to the use of salts of the present invention, in the manufacture of a medicament for maintaining weight loss, BMI loss, waist circumference loss or body fat percentage loss in an individual.

One aspect of the present invention pertains to the use of salts of the present invention, in the manufacture of a medicament for maintaining weight loss, BMI loss, waist circumference loss or body fat percentage loss in an individual following bariatric surgery.

One aspect of the present invention pertains to the use of salts of the present invention, in the manufacture of a medicament for inducing satiety in an individual.

One aspect of the present invention pertains to the use of salts of the present invention, in the manufacture of a medicament for decreasing food intake in an individual.

One aspect of the present invention pertains to the use of salts of the present invention, in the manufacture of a medicament for decreasing hunger in an individual.

One aspect of the present invention pertains to the use of salts of the present invention, in the manufacture of a medicament for decreasing food cravings in an individual.

One aspect of the present invention pertains to the use of salts of the present invention, in the manufacture of a medicament for increasing intermeal interval in an individual.

One aspect of the present invention pertains to the use of salts of the present invention, in the manufacture of a medicament for the treatment of a disorder selected from: schizophrenia, anxiety, depression, psychoses, and alcohol addiction in an individual.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

One aspect of the present invention pertains to salts of the present invention, for use in a method of treatment of the human or animal body by therapy.

One aspect of the present invention pertains to salts of the present invention, for use in a method of weight management.

One aspect of the present invention pertains to salts of the present invention, for use in a method of weight loss.

One aspect of the present invention pertains to salts of the present invention, for use in a method of maintenance of weight loss.

One aspect of the present invention pertains to salts of the present invention, for use in a method of decreasing food consumption.

One aspect of the present invention pertains to salts of the present invention, for use in a method of increasing meal-related satiety.

One aspect of the present invention pertains to salts of the present invention, for use in a method of reducing pre-meal hunger.

One aspect of the present invention pertains to salts of the present invention, for use in a method of reducing intra-meal food intake.

One aspect of the present invention pertains to salts of the present invention, for use in a method of weight management further comprising a reduced-calorie diet.

One aspect of the present invention pertains to salts of the present invention, for use in a method of weight management further comprising a program of regular exercise.

One aspect of the present invention pertains to salts of the present invention, for use in a method of weight management further comprising a reduced-calorie diet and a program of regular exercise.

One aspect of the present invention pertains to salts of the present invention, for use in a method of weight management in an obese patient with an initial body mass index ≥30 $kg/m^2$.

One aspect of the present invention pertains to salts of the present invention, for use in a method of weight management in an overweight patient with an initial body mass index ≥27 $kg/m^2$ in the presence of at least one weight related co-morbid condition.

One aspect of the present invention pertains to salts of the present invention, for use in a method of weight management in an overweight patient with an initial body mass index ≥27 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention, for use in a method of weight management in an individual with an initial body mass index ≥30 $kg/m^2$.

One aspect of the present invention pertains to salts of the present invention, for use in a method of weight management in an individual with an initial body mass index ≥27 $kg/m^2$.

One aspect of the present invention pertains to salts of the present invention, for use in a method of weight management in an individual with an initial body mass index ≥27 $kg/m^2$ in the presence of at least one weight related co-morbid condition.

One aspect of the present invention pertains to salts of the present invention, for use in a method of weight management in an individual with an initial body mass index ≥27 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention, for use in a method of weight management in an individual with an initial body mass index ≥25 $kg/m^2$.

One aspect of the present invention pertains to salts of the present invention, for use in a method of weight management in an individual with an initial body mass index ≥25 $kg/m^2$ in the presence of at least one weight related co-morbid condition.

One aspect of the present invention pertains to salts of the present invention, for use in a method of weight management in an individual with an initial body mass index ≥25 $kg/m^2$ in the presence of at least one weight related co-morbid condition selected from: hypertension, dyslipidemia, cardiovascular disease, glucose intolerance, and sleep apnea.

One aspect of the present invention pertains to salts of the present invention, for use in a method of weight management in combination with phentermine.

One aspect of the present invention pertains to salts and pharmaceutical compositions of the present invention, for use in a method of treatment of the human or animal body by therapy.

One aspect of the present invention pertains to salts and pharmaceutical compositions of the present invention, for use in a method of weight management.

One aspect of the present invention pertains to salts and pharmaceutical compositions of the present invention, for use in a method of weight loss.

One aspect of the present invention pertains to salts and pharmaceutical compositions of the present invention, for use in a method of maintenance of weight loss.

One aspect of the present invention pertains to salts and pharmaceutical compositions of the present invention, for use in a method of decreasing food consumption.

One aspect of the present invention pertains to salts and pharmaceutical compositions of the present invention, for use in a method of increasing meal-related satiety.

One aspect of the present invention pertains to salts and pharmaceutical compositions of the present invention, for use in a method of reducing pre-meal hunger.

One aspect of the present invention pertains to salts and pharmaceutical compositions of the present invention, for use in a method of reducing intra-meal food intake.

One aspect of the present invention pertains to salts and pharmaceutical compositions of the present invention, for use in a method of weight management further comprising a reduced-calorie diet.

One aspect of the present invention pertains to salts and pharmaceutical compositions of the present invention, for use in a method of weight management further comprising a program of regular exercise.

One aspect of the present invention pertains to salts and pharmaceutical compositions of the present invention, for use in a method of weight management further comprising a reduced-calorie diet and a program of regular exercise.

One aspect of the present invention pertains to salts and pharmaceutical compositions of the present invention, for use in a method of weight management in an obese patient with an initial body mass index ≥30 $kg/m^2$.

One aspect of the present invention pertains to salts and pharmaceutical compositions of the present invention, for use in a method of weight management in an overweight patient with an initial body mass index ≥27 $kg/m^2$ in the presence of at least one weight related co-morbid condition.

One aspect of the present invention pertains to salts and pharmaceutical compositions of the present invention, for use in a method of weight management in an overweight patient with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to salts and pharmaceutical compositions of the present invention, for use in a method of weight management in an individual with an initial body mass index ≥30 kg/m².

One aspect of the present invention pertains to salts and pharmaceutical compositions of the present invention, for use in a method of weight management in an individual with an initial body mass index ≥27 kg/m².

One aspect of the present invention pertains to salts and pharmaceutical compositions of the present invention, for use in a method of weight management in an individual with an initial body mass index ≥27 kg/m² in the presence of at least one weight related co-morbid condition.

One aspect of the present invention pertains to salts and pharmaceutical compositions of the present invention, for use in a method of weight management in an individual with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to salts and pharmaceutical compositions of the present invention, for use in a method of weight management in an individual with an initial body mass index ≥25 kg/m².

One aspect of the present invention pertains to salts and pharmaceutical compositions of the present invention, for use in a method of weight management in an individual with an initial body mass index ≥25 kg/m² in the presence of at least one weight related co-morbid condition.

One aspect of the present invention pertains to salts and pharmaceutical compositions of the present invention, for use in a method of weight management in an individual with an initial body mass index ≥25 kg/m² in the presence of at least one weight related co-morbid condition selected from: hypertension, dyslipidemia, cardiovascular disease, glucose intolerance, and sleep apnea.

In some embodiments, the individual in need of weight management has an initial body mass index ≥about 20 kg/m² in the presence of at least one weight related comorbid condition.

In some embodiments, the individual in need of weight management has an initial body mass index ≥about 20 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 21 kg/m² in the presence of at least one weight related comorbid condition.

In some embodiments, the individual in need of weight management has an initial body mass index ≥about 21 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 22 kg/m² in the presence of at least one weight related comorbid condition.

In some embodiments, the individual in need of weight management has an initial body mass index ≥about 22 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 23 kg/m² in the presence of at least one weight related comorbid condition.

In some embodiments, the individual in need of weight management has an initial body mass index ≥about 23 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 24 kg/m² in the presence of at least one weight related comorbid condition.

In some embodiments, the individual in need of weight management has an initial body mass index ≥about 24 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 25 kg/m² in the presence of at least one weight related comorbid condition.

In some embodiments, the individual in need of weight management has an initial body mass index ≥about 25 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 26 kg/m² in the presence of at least one weight related comorbid condition.

In some embodiments, the individual in need of weight management has an initial body mass index ≥about 26 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 27 kg/m² in the presence of at least one weight related comorbid condition.

In some embodiments, the individual in need of weight management has an initial body mass index ≥about 27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 28 kg/m² in the presence of at least one weight related comorbid condition.

In some embodiments, the individual in need of weight management has an initial body mass index ≥about 28 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 29 kg/m² in the presence of at least one weight related comorbid condition.

In some embodiments, the individual in need of weight management has an initial body mass index ≥about 29 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 30 kg/m² in the presence of at least one weight related comorbid condition.

In some embodiments, the individual in need of weight management has an initial body mass index ≥about 30 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 31 kg/m² in the presence of at least one weight related comorbid condition.

In some embodiments, the individual in need of weight management has an initial body mass index ≥about 31 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 32 kg/m² in the presence of at least one weight related comorbid condition.

In some embodiments, the individual in need of weight management has an initial body mass index ≥about 32 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 33 kg/m² in the presence of at least one weight related comorbid condition.

In some embodiments, the individual in need of weight management has an initial body mass index ≥about 33 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 34 kg/m² in the presence of at least one weight related comorbid condition.

In some embodiments, the individual in need of weight management has an initial body mass index ≥about 34 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 35 kg/m² in the presence of at least one weight related comorbid condition.

In some embodiments, the individual in need of weight management has an initial body mass index ≥about 35 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 36 kg/m² in the presence of at least one weight related comorbid condition.

In some embodiments, the individual in need of weight management has an initial body mass index ≥about 36 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 37 kg/m² in the presence of at least one weight related comorbid condition.

In some embodiments, the individual in need of weight management has an initial body mass index ≥about 37 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 38 kg/m² in the presence of at least one weight related comorbid condition.

In some embodiments, the individual in need of weight management has an initial body mass index ≥about 38 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 39 kg/m² in the presence of at least one weight related comorbid condition.

In some embodiments, the individual in need of weight management has an initial body mass index ≥about 39 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 40 kg/m² in the presence of at least one weight related comorbid condition.

In some embodiments, the individual in need of weight management has an initial body mass index ≥about 40 kg/m² in the presence of at least one weight related comorbid condition selected from: hypertension, dyslipidemia, cardiovascular disease, glucose intolerance, and sleep apnea.

One aspect of the present invention pertains to salts and pharmaceutical compositions of the present invention, for use in a method of weight management in combination with phentermine.

One aspect of the present invention pertains to salts and pharmaceutical compositions of the present invention, for use in a method of treatment of a disorder related to 5-HT$_{2C}$ receptor activity in an individual.

One aspect of the present invention pertains to salts and pharmaceutical compositions of the present invention, for use in a method of treatment of obesity in an individual.

In some embodiments, the method of treatment of obesity further comprises the administration or prescription of phentermine.

In some embodiments, the method of treatment of obesity further comprises gastric electrical stimulation.

One aspect of the present invention pertains to salts and pharmaceutical compositions of the present invention, for use in a method of inducing weight loss, BMI loss, waist circumference loss or body fat percentage loss in an individual.

One aspect of the present invention pertains to salts and pharmaceutical compositions of the present invention, for use in a method of inducing weight loss, BMI loss, waist circumference loss or body fat percentage loss in an individual in preparation of the individual for bariatric surgery.

One aspect of the present invention pertains to salts and pharmaceutical compositions of the present invention, for use in a method of maintaining weight loss, BMI loss, waist circumference loss or body fat percentage loss in an individual.

One aspect of the present invention pertains to salts and pharmaceutical compositions of the present invention, for use in a method of maintaining weight loss, BMI loss, waist circumference loss or body fat percentage loss in an individual following bariatric surgery.

One aspect of the present invention pertains to salts and pharmaceutical compositions of the present invention, for use in a method of inducing satiety in an individual.

One aspect of the present invention pertains to salts and pharmaceutical compositions of the present invention, for use in a method of decreasing food intake in an individual.

One aspect of the present invention pertains to salts and pharmaceutical compositions of the present invention, for use in a method of decreasing hunger in an individual.

One aspect of the present invention pertains to salts and pharmaceutical compositions of the present invention, for use in a method of decreasing food cravings in an individual.

One aspect of the present invention pertains to salts and pharmaceutical compositions of the present invention, for use in a method of increasing intermeal interval in an individual.

One aspect of the present invention pertains to salts and pharmaceutical compositions of the present invention, for use in a method of treatment of a disorder selected from: schizophrenia, anxiety, depression, psychoses, and alcohol addiction in an individual.

In some embodiments, the disorder is schizophrenia.
In some embodiments, the disorder is anxiety.
In some embodiments, the disorder is depression.
In some embodiments, the disorder is psychoses.
In some embodiments, the disorder is alcohol addiction.

Combination Therapies

The modified-release dosage-forms of the present invention can be used in combination with suitable pharmaceutical agents.

In some embodiments the modified-release dosage-forms of the present invention can be used in combination with a second anti-obesity agent. Anti-obesity agents include, for example, adrenergic reuptake inhibitors, apolipoprotein-B secretion/microsomal triglyceride transfer protein inhibitors, β3 adrenergic receptor agonists, bombesin agonists, cannabinoid 1 receptor antagonists, cholescystokinin-A agonists, ciliary neutrotrophic factors, dopamine agonists, galanin antagonists, ghrelin receptor antagonists, glucagon-like peptide-1 receptor agonists, glucocorticoid receptor agonists or antagonists, histamine-3 receptor antagonists or reverse agonists, human agouti-related proteins, leptin receptor agonists, lipase inhibitors, MCR-4 agonists, melanin concentrating hormone antagonists, melanocyte-stimulating hormone receptor analogs, monoamine reuptake inhibitors, neuromedin U receptor agonists, neuropeptide-Y antagonists, orexin receptor antagonists, stimulants, sympathomimetic agents, thyromimetic agents, and urocortin binding protein antagonists.

In some embodiments, the second anti-obesity agent is selected from: 4-methylamphetamine, 5-HTP, amfecloral, amfepentorex, amfepramone, aminorex, amphetamine, amphetaminil, atomoxetine, benfluorex, benzphetamine, bromocriptine, bupropion, cathine, cathinone, cetilistat, chlorphentermine, ciclazindol, clobenzorex, cloforex, clominorex, clortermine, dapiclermin, dehydroepiandrosterone, dehydroepiandrosterone analogues, dexmethylphenidate, dextroamphetamine, dextromethamphetamine, difemetorex, dimethylcathinone, dinitrophenol, diphemethoxidine, ephedra, ephedrine, ethylamphetamine, etolorex, fenbutrazate, fencamfamine, fenethylline, fenproporex, fludorex, fluminorex, furfenorex, galactomannan, glucomannan, ibipinabant, indanorex, khat, L-dopa, leptin, a leptin analog, levopropylhexedrine, lisdexamfetamine, L-phenylalanine, L-tryptophan, L-tyrosine, N-[[trans-4-[(4,5-dihydro[1]ben-zothiepino[5,4-d]thiazol-2-yl)amino]cyclohexyl]methyl]methanesulfonamide, manifaxine, mazindol, mefenorex, metformin, methamphetamine, methylphenidate, naloxone, naltrexone, oleoyl-estrone, orlistat, otenabant, oxyntomodulin, P57, pemoline, peptide YY, phendimetrazine, phenethylamine, phenmetrazine, phenpentermine, phentermine, phenylpropanolamine, pipradrol, prolintane, propylhexedrine, pseudoephedrine, pyrovalerone, radafaxine, reboxetine, rimonabant, setazindol, sibutramine, simmondsin, sterculia, surinabant, synephrine, taranabant, tesofensine, topiramate, viloxazine, xylopropamine, yohimbine, zonisamide, and zylofuramine, and pharmaceutically acceptable salts, solvates, and hydrates thereof.

In some embodiments, the second anti-obesity agent is selected from: 4-methylamphetamine, amfecloral, amfepentorex, amfepramone, aminorex, amphetamine, amphetaminil, atomoxetine, benfluorex, benzphetamine, bupropion, cathine, cathinone, chlorphentermine, ciclazindol, clobenzorex, cloforex, clominorex, clortermine, dexmethylphenidate, dextroamphetamine, dextromethamphetamine, difemetorex, dimethylcathinone, diphemethoxidine, ephedra, ephedrine, ethylamphetamine, etolorex, fenbutrazate, fencamfamine, fenethylline, fenproporex, fludorex, fluminorex, furfenorex, indanorex, khat, levopropylhexedrine, lisdexamfetamine, manifaxine, mazindol, mefenorex, methamphetamine, methylphenidate, pemoline, phendimetrazine, phenethylamine, phenmetrazine, phenpentermine, phentermine, phenylpropanolamine, pipradrol, prolintane, propylhexedrine, pseudoephedrine, pyrovalerone, radafaxine, reboxetine, setazindol, sibutramine, synephrine, taranabant, tesofensine, viloxazine, xylopropamine, and zylofuramine, and pharmaceutically acceptable salts, solvates, and hydrates thereof.

In some embodiments, the second anti-obesity agent is selected from: chlorphentermine, clortermine, phenpentermine, and phentermine, and pharmaceutically acceptable salts, solvates, and hydrates thereof.

In some embodiments the modified-release dosage-forms of the present invention can be used in combination with an anti-diabetes agent. Anti-diabetes agents include, for example, DPP-IV inhibitors, biguanides, alpha-glucosidase inhibitors, insulin analogues, sulfonylureas, SGLT2 inhibitors, meglitinides, thiazolidinediones, anti-diabetic peptide analogues, and GPR119 agonists.

In some embodiments, the anti-diabetes agent is selected from: sitagliptin, vildagliptin, saxagliptin, alogliptin, linagliptin, phenformin, metformin, buformin, proguanil, acarbose, miglitol, voglibose, tolbutamide, acetohexamide, tolazamide, chlorpropamide, glipizide, glibenclamide, glimepiride, gliclazide, dapagliflozin, remigliflozin, sergliflozin, and 4-[6-(6-methanesulfonyl-2-methyl-pyridin-3-ylamino)-5-methoxy-pyrimidin-4-yloxy]-piperidine-1-carboxylic acid isopropyl ester.

In some embodiments, the anti-diabetes agent is a DPP-IV inhibitor selected from the following compounds and pharmaceutically acceptable salts, solvates, and hydrates thereof: 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one; 1-[2-(3-hydroxyadamant-1-ylamino)acetyl]pyrrolidine-2(S)-carbonitrile; (1S,3S,5S)-2-[2(S)-amino-2-(3-hydroxyadamantan-1-yl)acetyl]-2-azabicyclo[3.1.0]hexane-3-carbonitrile; 2-[6-[3(R)-aminopiperidin-1-yl]-3-methyl-2,4-dioxo-1,2,3,4-tetrahydropyrimidin-1-ylmethyl]benzonitrile; 8-[3(R)-aminopiperidin-1-yl]-7-(2-butynyl)-3-methyl-1-(4-methylquinazolin-2-ylmethyl)xanthine; 1-[N-[3(R)-pyrrolidinyl]glycyl]pyrrolidin-2(R)-yl boronic acid; 4(S)-fluoro-1-[2-[(1R,3S)-3-(1H-1,2,4-triazol-1-ylmethyl)cyclopentylamino]acetyl]pyrrolidine-2(S)-carbonitrile; 1-[(2S,3S,11bS)-2-amino-9,10-dimethoxy-2,3,4, 6,7,11b-hexahydro-1H-pyrido [2,1-a]isoquinolin-3-yl]-4 (S)-(fluoromethyl)pyrrolidin-2-one; (2S,4S)-2-cyano-4-fluoro-1-[(2-hydroxy-1,1-dimethyl)ethylamino] acetylpyrrolidine; 8-(cis-hexahydro-pyrrolo [3,2-b]pyrrol-1-yl)-3-methyl-7-(3-methyl-but-2-enyl)-1-(2-oxo-2-phenylethyl)-3,7-dihydro-purine-2,6-dione; 1-((3S,4S)-4-amino-1-(4-(3,3-difluoropyrrolidin-1-yl)-1,3,5-triazin-2-yl) pyrrolidin-3-yl)-5,5difluoropiperidin-2-one; (R)-2-((6-(3-aminopiperidin-1-yl)-3-methyl-2,4-dioxo-3,4-dihydropyrimidin-1(2H)-yl)methyl)-4-fluorobenzonitrile; 5-{(S)-2-[2-((S)-2-cyano-pyrrolidin-1-yl)-2-oxo-ethylamino]-propyl}-5-(1H-tetrazol-5-yl)10,11-dihydro-5H-dibenzo [a,d]cycloheptene-2,8-dicarboxylic acid bis-dimethylamide; ((2S,4S)-4-(4-(3-methyl-1-phenyl-1H-pyrazol-5-yl)piperazin-1-yl)pyrrolidin-2-yl)(thiazolidin-3-yl) methanone; (2S,4S)-1-[2-[(4-ethoxycarbonylbicyclo [2.2.2] oct-1-yl)amino]acetyl]-4-fluoropyrrolidine-2-carbonitrile; 6-[(3R)-3-amino-piperidin-1-yl]-5-(2-chloro-5-fluoro-benzyl)-1,3-dimethyl-1,5dihydro-pyrrolo [3,2-d]pyrimidine-2,4-dione; 2-({6-[(3R)-3-amino-3-methylpiperidin-1-yl]-1,3-dimethyl-2,4-dioxo-1,2,3,4-tetrahydro-5H-pyrrolo [3,2-d] pyrimidin-5-yl}methyl)-4-fluorobenzonitrile; (2S)-1-{[2-(5-methyl-2-phenyl-oxazol-4-yl)-ethylamino]-acetyl}-pyrrolidine-2-carbonitrile; (2S)-1-{[1,1-dimethyl-3-(4-pyridin-3-yl-imidazol-1-yl)-propylamino]-acetyl}-pyrrolidine-2-carbonitrile; (3,3-difluoropyrrolidin-1-yl)-((2S,4S)-4-(4-(pyrimidin-2-yl)piperazin-1-yl)pyrrolidin-2-yl)methanone; (2S,4S)-1-[(2S)-2-amino-3,3-bis(4-fluorophenyl)propanoyl]-4-fluoropyrrolidine-2-carbonitrile; (2S,5R)-5-ethynyl-1-{N-(4-methyl-1-(4-carboxy-pyridin-2-yl)piperidin-4-yl)glycyl}pyrrolidine-2-carbonitrile; and (1S,6R)-3-{[3-(trifluoromethyl)-5,6-dihydro [1,2,4]triazolo [4,3-a]pyrazin-7(8H)-yl]carbonyl}-6-(2,4,5-trifluorophenyl)cyclohex-3-en-1-amine.

In some embodiments, the anti-diabetes agent is an alpha-glucosidase inhibitor selected from the following compounds and pharmaceutically acceptable salts, solvates, and hydrates thereof: (2R,3R,4R,5R)-4-((2R,3R,4R,5S,6R)-5-((2R,3R,4S,5S,6R)-3,4-dihydroxy-6-methyl-5-((1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal; (2R,3R,4R,5S)-1-(2-hydroxyethyl)-2-(hydroxymethyl)piperidine-3,4,5-triol; and (1S,2S,3R,4S,5S)-5-(1,3-dihydroxypropan-2-ylamino)-1-(hydroxymethyl)cyclohexane-1,2,3,4-tetraol.

In some embodiments, the anti-diabetes agent is a sulfonylurea selected from the following compounds and pharmaceutically acceptable salts, solvates, and hydrates thereof: N-(4-(N-(cyclohexylcarbamoyl)sulfamoyl)phenethyl)-5-methylpyrazine-2-carboxamide); 5-chloro-N-(4-(N-(cyclohexylcarbamoyl)sulfamoyl)phenethyl)-2-methoxybenzamide; and 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide.

In some embodiments, the anti-diabetes agent is an SGLT2 inhibitor selected from the following compounds and pharmaceutically acceptable salts, solvates, and hydrates thereof: (2S,3R,4R,5S,6R)-2-(4-chloro-3-(4-ethoxybenzyl)phenyl)-6-(hydroxymethyl)tetrahydro-2H-pyran-3,4,5-triol; ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl)methyl carbonate; and ethyl ((2R,3S,4S,5R,6S)-3,4,5-trihydroxy-6-(2-(4-methoxybenzyl)phenoxy)tetrahydro-2H-pyran-2-yl) methyl carbonate.

In some embodiments, the anti-diabetes agent is a meglitinide selected from the following compounds and pharmaceutically acceptable salts, solvates, and hydrates thereof: (S)-2-ethoxy-4-(2-(3-methyl-1-(2-(piperidin-1-yl)phenyl) butylamino)-2-oxoethyl)benzoic acid; (R)-2-((1r,4R)-4-isopropylcyclohexanecarboxamido)-3-phenylpropanoic acid; and (S)-2-benzyl-4-((3aR,7aS)-1H-isoindol-2(3H,3aH,4H,5H,6H,7H,7aH)-yl)-4-oxobutanoic acid.

In some embodiments, the anti-diabetes agent is a biguanide selected from the following compounds and pharmaceutically acceptable salts, solvates, and hydrates thereof: metformin, phenformin, buformin, and proguanil.

In some embodiments, the anti-diabetes agent is metformin.

In some embodiments, the anti-diabetes agent is a GPR119 agonist selected from the GPR119 agonists disclosed in the following PCT applications: WO2006083491, WO 2008081204, WO2009123992, WO2010008739, WO2010029089, and WO2010149684.

In some embodiments, the anti-diabetes agent is 446-(6-methanesulfonyl-2-methyl-pyridin-3-ylamino)-5-methoxy-pyrimidin-4-yloxyl-piperidine-1-carboxylic acid isopropyl ester.

In some embodiments, the anti-diabetes agent is 5-(4-(4-(3-fluoro-4-(methylsulfonyl)phenoxy)butan-2-yl)piperidin-1-yl)-3-isopropyl-1,2,4-oxadiazole.

Other anti-obesity agents, and anti-diabetes agents including the agents set forth infra, are well known, or will be readily apparent in light of the instant disclosure, to one of ordinary skill in the art. It will be understood that the scope of combination therapy of the modified-release dosage forms of the present invention with other anti-obesity agents and with anti-diabetes agents is not limited to those listed above, but includes in principle any combination with any pharmaceutical agent or pharmaceutical composition useful for the treatment of overweight, obese, and diabetic individuals.

One aspect of the present invention pertains to modified-release dosage forms of the present invention, characterized in that the modified-release dosage form is administered in conjunction with a second anti-obesity agent as described herein.

One aspect of the present invention pertains to modified-release dosage forms of the present invention, characterized in that the modified-release dosage form is administered in conjunction with an anti-diabetes agent as described herein.

One aspect of the present invention pertains to modified-release dosage forms of the present invention for use in combination with a second anti-obesity agent for use in weight management.

One aspect of the present invention pertains to modified-release dosage forms of the present invention for use in combination with an anti-diabetes agent for use in weight management and the treatment of diabetes.

One aspect of the present invention pertains to methods of weight management in an individual in need thereof, comprising administering to the individual a modified-release dosage form of the present invention and a second anti-obesity agent wherein the modified-release dosage form and the second anti-obesity agent are administered to the individual simultaneously, separately, or sequentially.

One aspect of the present invention pertains to methods of weight management and treating diabetes in an individual in need thereof, comprising administering to the individual a modified-release dosage form of the present invention and an anti-diabetes agent wherein the modified-release dosage form and the anti-diabetes agent are administered to the individual simultaneously, separately, or sequentially.

One aspect of the present invention pertains to methods of weight management in an individual in need thereof, wherein the individual has been or is being treated with a second anti-obesity agent, the method comprising administering to the individual a therapeutically effective amount of a modified-release dosage form of the present invention.

One aspect of the present invention pertains to methods of weight management and treatment of diabetes in an individual in need thereof, wherein the individual has been or is being treated with an anti-diabetes agent, the method comprising administering to the individual a therapeutically effective amount of a modified-release dosage form of the present invention.

One aspect of the present invention pertains to anti-obesity agents, characterized in that the anti-obesity agent is administered in conjunction with a modified-release dosage form of the present invention.

One aspect of the present invention pertains to anti-diabetes agents, characterized in that the anti-diabetes agent is administered in conjunction with a modified-release dosage form of the present invention.

One aspect of the present invention pertains to anti-obesity agents for use in combination with a modified-release dosage form of the present invention for use in weight management.

One aspect of the present invention pertains to anti-diabetes agents for use in combination with a modified-release dosage form of the present invention for use in weight management and the treatment of diabetes.

One aspect of the present invention pertains to methods of weight management in an individual in need thereof, comprising administering to the individual an anti-obesity agent and a modified-release dosage form of the present invention wherein the anti-obesity agent and the modified-release dosage form are administered to the individual simultaneously, separately, or sequentially.

One aspect of the present invention pertains to methods of weight management and treating diabetes in an individual in need thereof, comprising administering to the individual an anti-diabetes agent and a modified-release dosage form of the present invention wherein the anti-diabetes agent and the modified-release dosage form are administered to the individual simultaneously, separately, or sequentially.

One aspect of the present invention pertains to methods of weight management in an individual in need thereof, wherein the individual has been or is being treated with a modified-release dosage form of the present invention, the method comprising administering to the individual a therapeutically effective amount of a second anti-obesity agent.

One aspect of the present invention pertains to methods of weight management and treatment of diabetes in an individual in need thereof, wherein the individual has been or is being treated with a modified-release dosage form of the present invention, the method comprising administering to the individual a therapeutically effective amount of an anti-diabetes agent.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Examples

The following examples are provided to further define the invention without, however, limiting the invention to the particulars of these examples. The compounds and salts thereof described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Powder X-ray Diffraction (PXRD) studies were conducted using an X'Pert PRO MPD powder diffractometer (PANalytical, Inc.; EQ0233) with a Cu source set at 45 kV and 40 mA, Cu(Kα) radiation and an X'Celerator detector. Samples were placed on a PXRD sample plate either as-is or ground slightly to reduce the size of large particles or crystals. Data were collected with the samples spinning from 5° to 40°2θ. Data were analyzed by X'Pert Data Viewer software, version 1.0a, to determine crystallinity and/or crystal form, and by X'Pert HighScore software, version 1.0b, to generate the tables of PXRD peaks.

Differential scanning calorimetry (DSC) studies were conducted using a TA Instruments, Q2000 (EQ1980) at heating rate 10° C./min. The instruments were calibrated by the vendor for temperature and energy using the melting point and enthalpy of fusion of an indium standard.

Thermogravimetric analyses (TGA) were conducted using a TA Instruments TGA Q5000 (EQ1982) at heating rate 10° C./min. The instrument was calibrated by the vendor using Alumel and Nickel Curie points for the furnace temperature and a standard weight for the balance.

Dynamic moisture-sorption (DMS) studies were conducted using a dynamic moisture-sorption analyzer, VTI Corporation, SGA-100, equipment #0228. Samples were prepared for DMS analysis by placing 5 mg to 20 mg of a sample in a tared sample holder. The sample was placed on the hang-down wire of the VTI balance. A drying step was run, typically at 40° C. and 0.5-1% RH for 1-2 h. The isotherm temperature is 25° C. Defined % RH holds typically ranged from 10% RH to 90% RH or 95% RH, with intervals of 10 to 20% RH. A % weight change smaller than 0.010% over a specified number of minutes (typically 10-20), or up to 2 h, whichever occurs first, is required before continuing to the next % RH hold. The water content of the sample equilibrated as described above was determined at each % RH hold.

If saturated in water with excess solid, a deliquescing compound or salt thereof equilibrated in a closed system at a given temperature produces a % RH in that closed system that is equal to its deliquescing % RH (DRH) at that temperature. Fractional relative humidity is equal to water activity ($a_w$) in the vapor phase and at equilibrium in a closed system, the $a_w$ in an aqueous solution is equal to the aw in the vapor phase above the solution (see Equation 1).

$$\frac{DRH}{100\%} = \frac{\% RH}{100\%} \text{(above enclosed } sat\ aq\ sol'n \text{ at } equil) =$$

$$a_w(\text{vapor}) = a_w(\text{liquid})$$

Equation 1

A water activity meter was used to measure DRH for selected salts described herein. The instrument used for this study is a Decagon Devices AquaLab 4TE water activity meter, equipment #2169. This instrument is designed with temperature control and a small headspace above the enclosed sample to establish equilibrium between solution and vapor phases quickly. Measured $a_w$ values at 25° C. for samples of aqueous-saturated lorcaserin salts with excess solid were multiplied by 100% to get DRH values in % RH.

Acquity ultra performance liquid chromatography (UPLC) from Waters was used for solubility and stoichiometry determination. Instrument number is SY-EQ 1889. UPLC was equipped with Acquity PDA detector. UPLC mobile phase solvent A was 0.1% TFA in DI-water, solvent B was 0.1% TFA in acetonitrile. The mobile phase gradient as shown in the table below:

| Time (min) | Flow (mL/min) | % A | % B | Curve |
|---|---|---|---|---|
|  | 0.600 | 95.0 | 5.0 |  |
| 2.00 | 0.600 | 5.0 | 95.0 | 6 |
| 2.50 | 0.600 | 5.0 | 95.0 | 6 |
| 2.75 | 0.600 | 95.0 | 5.0 | 1 |
| 5.00 | 0.000 | 95.0 | 5.0 | 11 |

Column temperature was 40±5° C. Acquity UPLC® HSS T3 1.8 µm, 2.1×50 mm column was used.

A known amount of sample was dissolved in water and analyzed by UPLC. The weight percent of Compound 1 in the salt samples was determined by comparing the UV signal to that of a standard, Compound 1 hydrochloride salt hemihydrate, or Compound 1 free base. The percentage of Compound 1 or the percentage of the counterion determined was compared to the theoretical values to establish the stoichiometry.

Example 1: Modified-Release Tablets Comprising (R)-8-Chloro-1-methyl-2,3,4,5-tetrahydro-1H-3-benzazepine Hydrochloride Salt Hemihydrate, Form III Modified-release tablet formulations of (R)-8-chloro-1-methyl-2,3,4,5-tetrahydro-1H-3-benzazepine hydrochloride salt hemihydrate, Form III were prepared. The upper limit of the desired release profile as established by pharmacokinetics simulation was defined as a $C_{max}$ not more than the $C_{max}$ observed when dosing 10-mg immediate-release tablets b.i.d.

Reagents and Materials
  (R)-8-chloro-1-methyl-2,3,4,5-tetrahydro-1H-3-benzazepine hydrochloride salt hemihydrate, Form III
  Hydroxypropyl methyl cellulose K4M, Colorcon
Microcrystalline cellulose (Avicel PH102), FMC
Mannitol, Pearlitol 200SD, Roquette
Mannitol, Mannogem EZ, SPI Pharma
Mannitol, Mannogem 2080, SPI Pharma
Magnesium stearate, vegetable grade, Mallinckrodt
Surelease® (ethyl cellulose dispersion), Colorcon
Opadry® (YS-1-7472), Colorcon
Opadry® II Blue (89F90951), Colorcon
Manufacturing
  The following batches were manufactured:

All modified-release tablets were manufactured with a direct compression process at a batch size of 300 g to 500 gas follows. (R)-8-chloro-1-methyl-2,3,4,5-tetrahydro-1H-3-benzazepine hydrochloride salt hemihydrate, HPMC, mannitol and MCC were blended in a 2-quart V blender (Globe Pharma MaxiBlend®) for 12 min. The mixture was screened through a sieve (#20). The sieved mixture was blended for a further 5-10 min, magnesium sterate was added and blending was continued for a further 5 min. The mixture was compressed into tablets using a Piccola PLC rotary tablet press (10-20 rpm; 10 kp) and the tablets were coated using a Vector LDCS Hi-Coater® with an 11.5"-diameter pan.

Dissolution Testing

Dissolution testing was performed using USP apparatus I (basket method) in 900 mL 0.1 N HCl solution at 37° C. and 100 rpm. The concentration of (R)-8-chloro-1-methyl-2,3,4,5-tetrahydro-1H-3-benzazepine was analyzed using an HPLC method. The time needed to achieve 80% cumulative release (T80%) was estimated from the dissolution profiles.

Establishment of the Upper Limit of the Release Profile

Figure 42:
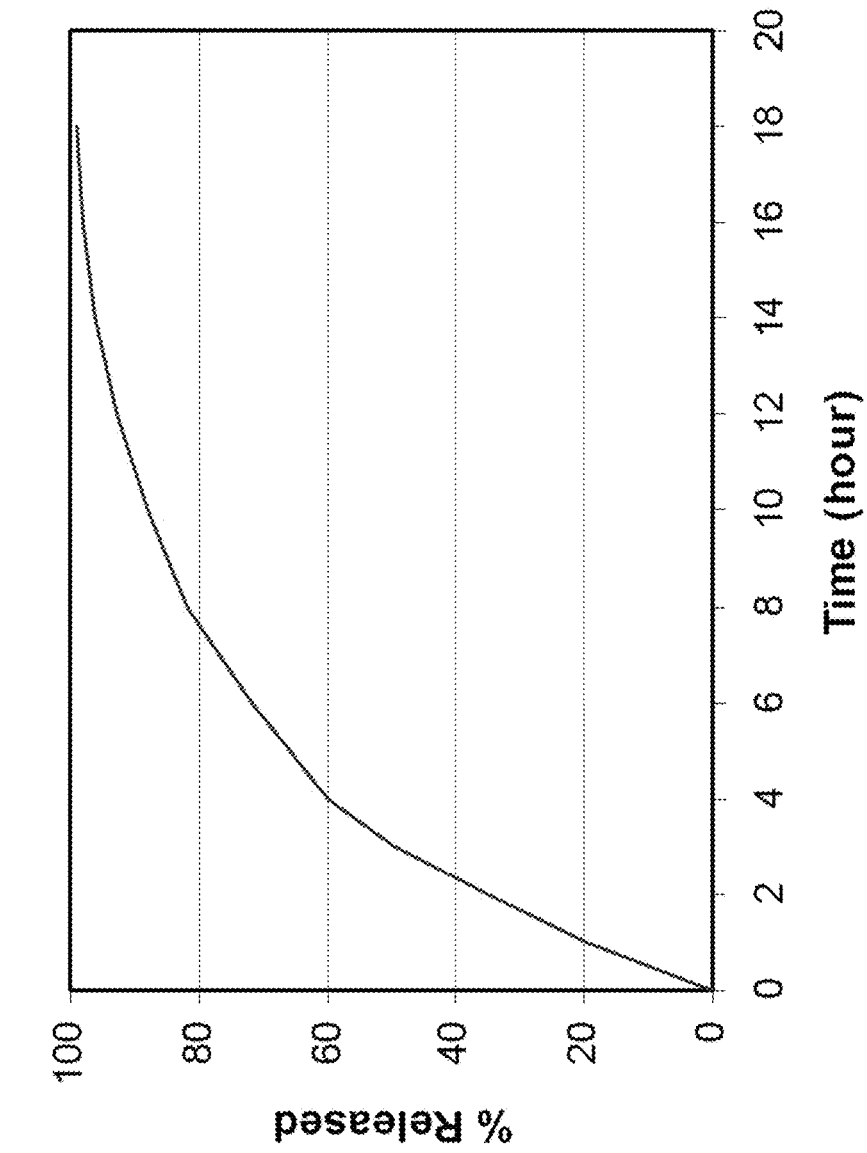
FIG. 42: Upper Limit of Release of Compound 1 Hydrochloride Salt Hemihydrate, Form III from Modified-release Formulation.
Figure 43:
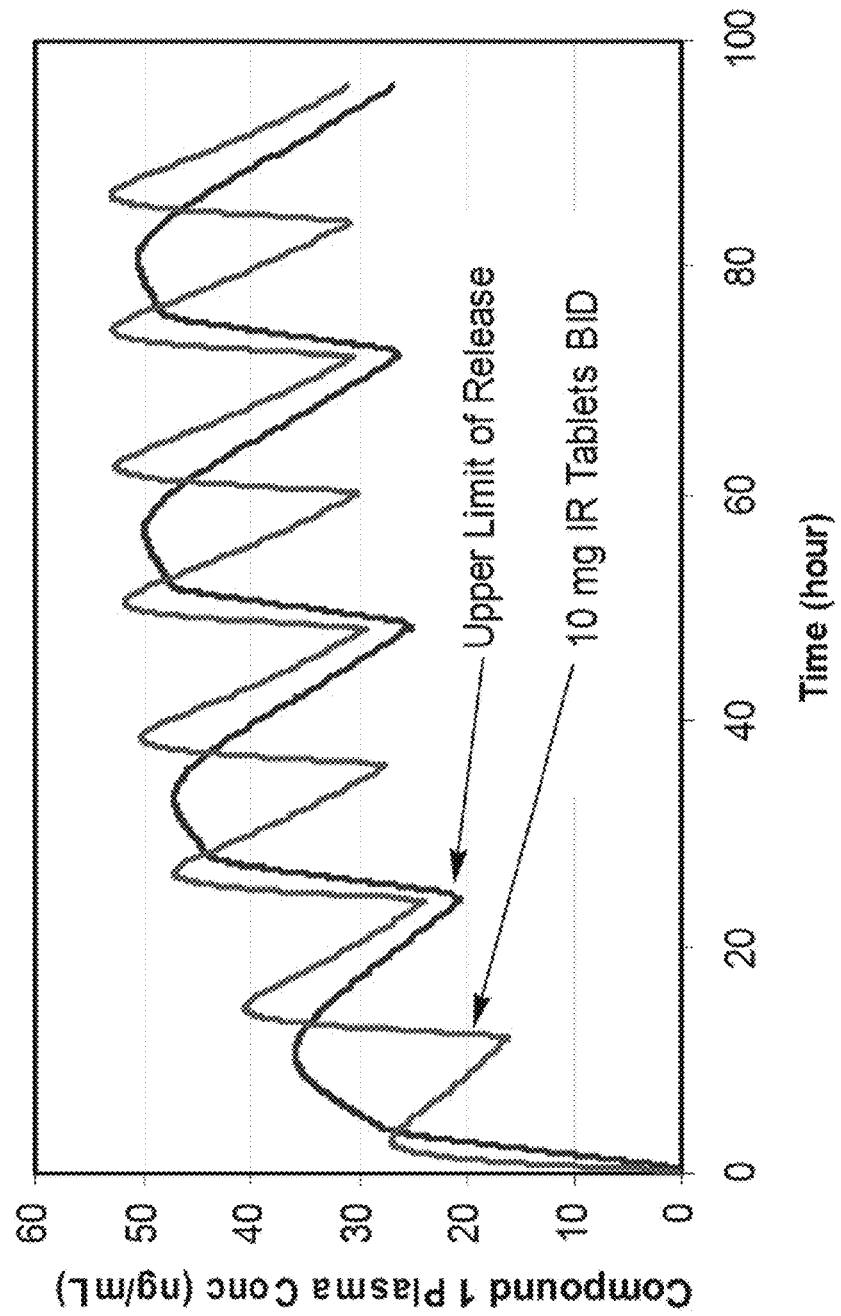
FIG. 43: Pharmacokinetics Simulation of 20-mg Modified-release Formulation and 10-mg Immediate-release (IR) Tablets of Compound 1 Hydrochloride Salt Hemihydrate, Form III.

The GastroPlus™ software (Simulations Plus, Inc., Lancaster, Calif.) was used to simulate the pharmacokinetics of Compound 1 from immediate-release and modified-release tablets. Through pharmacokinetics simulation, the upper limit of the release profile was established as shown in FIG. 42. The corresponding pharmacokinetics simulation is shown in FIG. 43. The release profile follows first order release kinetics and T80% is approximately 8 hours. The lower limit was not defined. Pharmacokinetics parameters of Compound 1 were obtained from an open-label, single-dose, cross-over clinical study in the fed and fasted state. Input variables and default values for GastroPlus™ simulation were as follows Compound 1 Parameters
  LogP: 2.56
  pKa: 9.53
  Dosage form: a) controller release tablet with 20-mg q.d. dosing or b) immediate-release tablet of 10-mg b.i.d dosing
  Solubility: 400 mg/mL
  Particle density: 1.2 g/mL
  Effective permeability: $3.54 \times 10^{-6}$ cm/s
Physiological Parameters (Default Values)
  Stomach retention time: 0.25 h
  Dose volume: 250 mL

| Ingredient | Batch 1 | 2 | 3 | 4 | 5 | 6 | 7 | 8 | 9 | 10 | 11 |
|---|---|---|---|---|---|---|---|---|---|---|---|
| Core Tablet (mg) | | | | | | | | | | | |
| Compound 1 Hydrochloride Salt Hemihydrate, Form III | 20.8 | 20.8 | 20.8 | 20.8 | 20.8 | 20.8 | 20.8 | 20.8 | 20.8 | 31.2 | 31.2 |
| Mannitol | 67.7 | 67.7 | 67.7 | 67.7 | 67.7 | 97.7 | 97.7 | 67.7 | 67.7 | 57.3 | 57.3 |
| HPMC K4M | 150 | 150 | 150 | 150 | 150 | 120 | 120 | 150 | 150 | 150 | 150 |
| Avicel PH102 | 60 | 60 | 60 | 60 | 60 | 60 | 60 | 60 | 60 | 60 | 60 |
| Magnesium stearate | 1.5 | 1.5 | 1.5 | 1.5 | 1.5 | 1.5 | 1.5 | 1.5 | 1.5 | 1.5 | 1.5 |
| Coating (mg) | | | | | | | | | | | |
| Opadry ® II Blue | 15.1 | 0 | 0 | 0 | 0 | 0 | 0 | 0 | 0 | 0 | 0 |
| Surelease ®/Opadry ® 85/15 | 0 | 7.8 | 13.7 | 0 | 0 | 8.7 | 15.5 | 0 | 0 | 8.7 | 15.4 |
| Surelease ®/Opadry ® 80/20 | 0 | 0 | 0 | 0 | 14.9 | 0 | 0 | 0 | 0 | 0 | 0 |
| Surelease ®/Opadry ® 75/25 | 0 | 0 | 0 | 16.2 | 0 | 0 | 0 | 7.5 | 29.7 | 0 | 0 |

Figure 44:
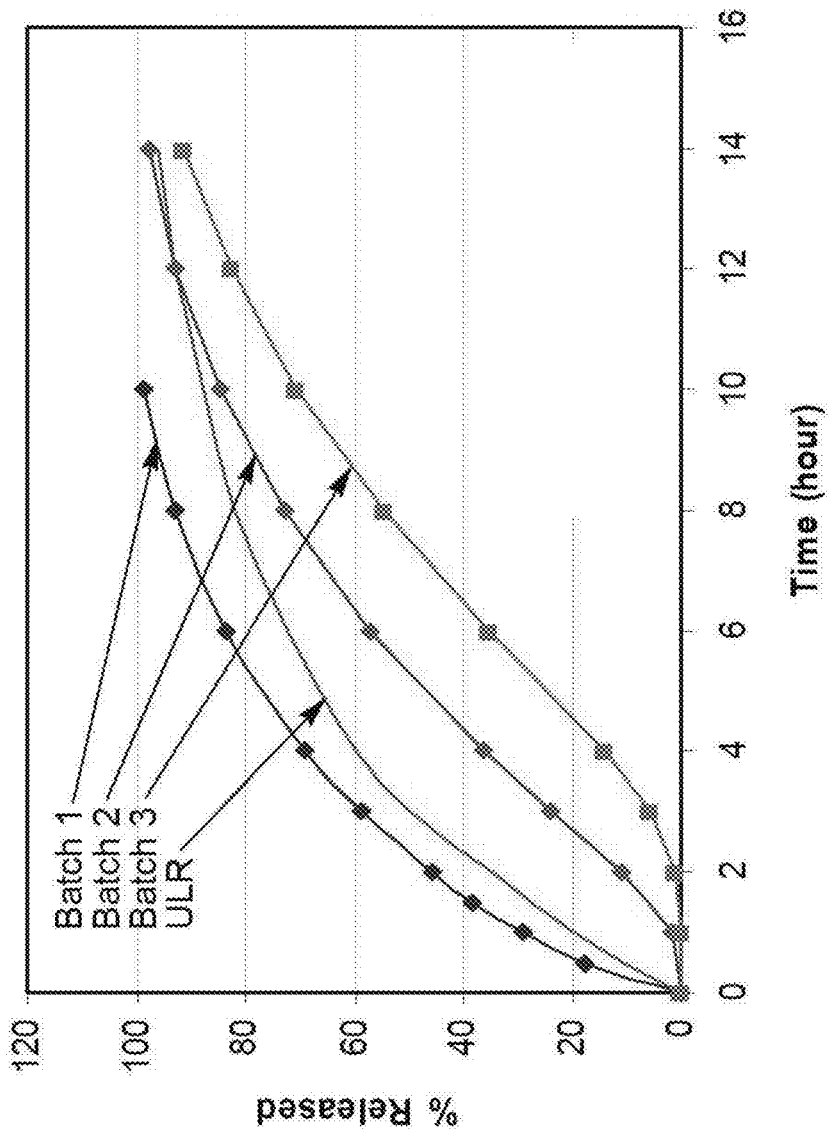
FIG. 44: Dissolution Profile of Compound 1 Hydrochloride Salt Hemihydrate, Form III Tablets Coated with Surelease®/Opadry® (85/15).

Small intestine transit time: 3.3 h
Small intestine radius: 1.2 cm
Small intestine length: 300 cm
Colon volume: 1200 mL Pharmacokinetics Parameters
Body weight: 94 kg
Blood to plasma concentration ratio: 1.3
Clearance: 19.56 L/h
Apparent volume of distribution: 307.36 L Effect of Surelease®/Opadry® Coating A Surelease®/Opadry® ratio of 85/15 was evaluated. FIG. 44 shows the dissolution profiles of Batches 2 and 3 with different coating weight gain. The dissolution profile of Batch 1 coated with Opadry® II Blue was included for comparison.

FIG. 44 shows that application of Surelease®/Opadry® (85/15) coating decreases the release rate of Compound 1 hydrochloride salt hemihydrate, Form III substantially. At a coating weight gain of 2.6% (Batch 2), the percentage of release was reduced by 20% to 30% after a 1-h lag time, compared to the release from Batch 1. Release was further delayed at a higher coating weight gain (4.6%) (Batch 2). T80% of Batch 2 was 9 h and T80% of Batch 3 was 12 h. A lag time of 2 hours was observed for Batch 3. It can be also observed from FIG. 44 that the release kinetics shifted away from first order towards more constant release, especially at a coating weight gain of 4.6%.

Effect of Surelease®/Opadry® Ratio

Figure 45:
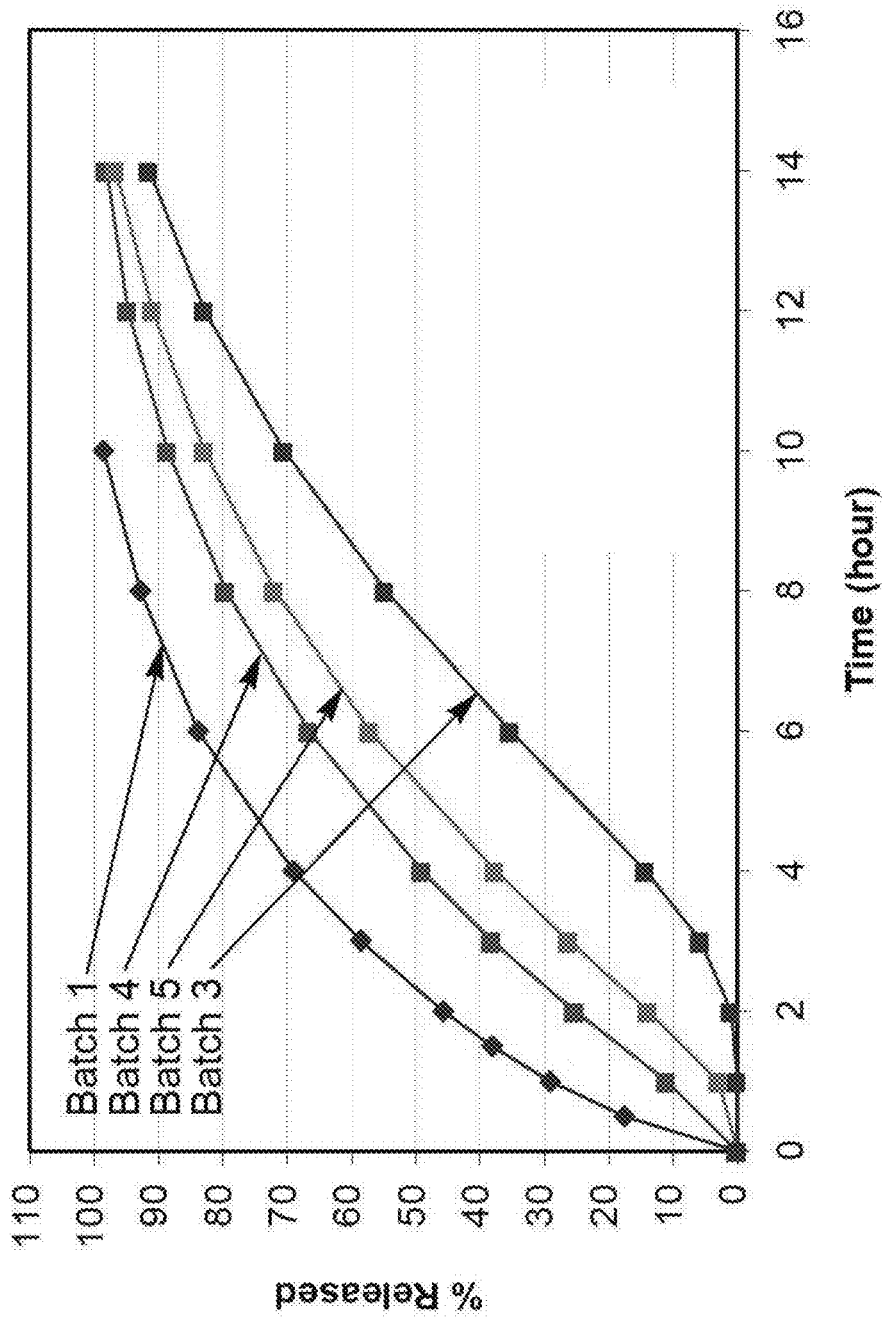
FIG. 45: Effect of the Surelease®/Opadry® Ratio on Compound 1 Hydrochloride Salt Hemihydrate, Form III Release.

FIG. 45 compares the release profiles of tablets coated with different Surelease®/Opadry® ratios at the coating weight gain of approximately 5%. Batch 1 tablets coated with Opadry® II Blue, were included as control. The formulation of core tablets is identical for all batches. As the ratio of Surelease®/Opadry® increases from 75/25 to 85/15, the release rate of Compound 1 is progressively reduced.

Effect of HPMC K4M Level in the Core Tablet

Figure 46:
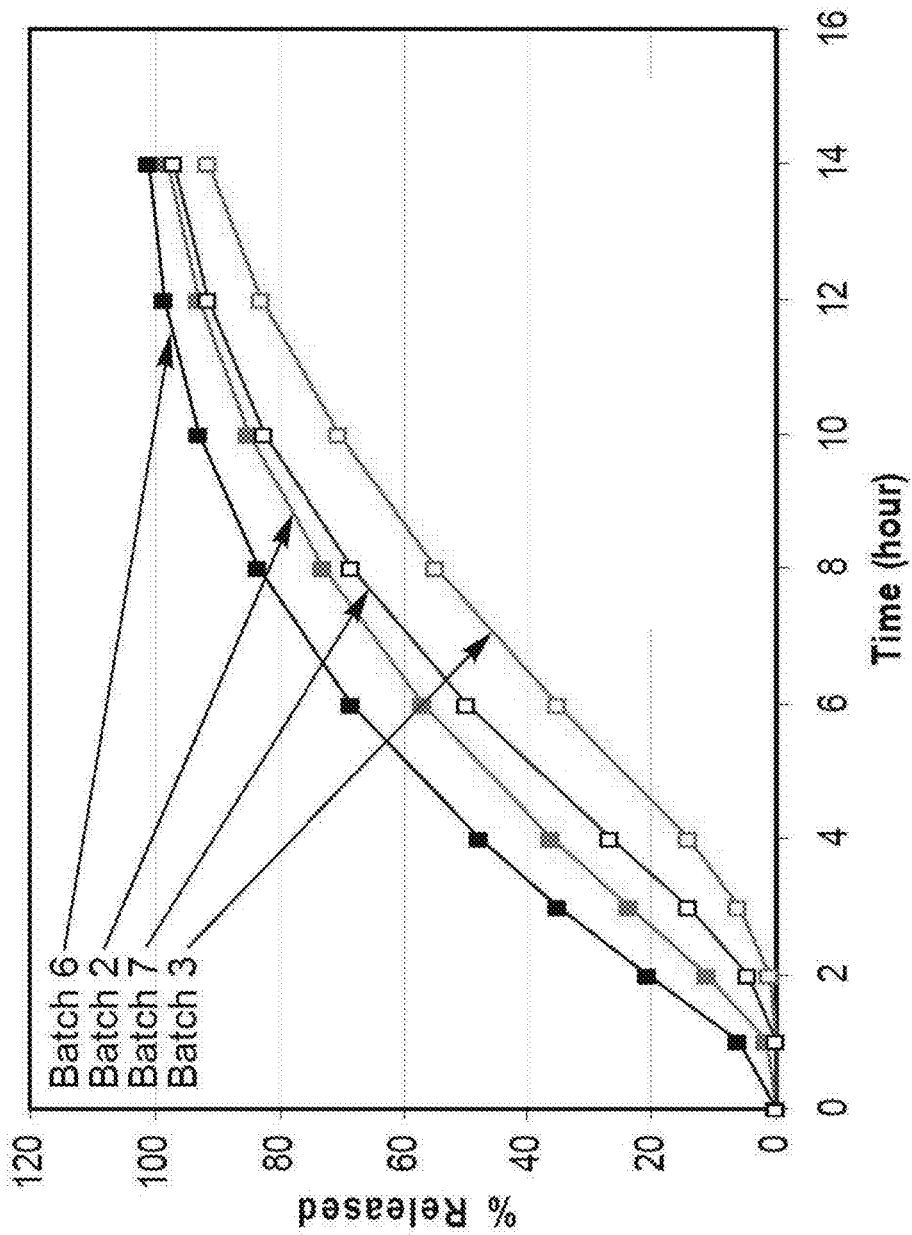
FIG. 46: Effect of HPMC K4M Level on Compound 1 Hydrochloride Salt Hemihydrate, Form III Release.

To evaluate the effect of reducing the level HPMC K4M in the core tablet on the release profile, core tablets were prepared containing 40% HPMC K4M. The amount of mannitol was increased to maintain the 300 mg tablet weight. The tablets were coated with Surelease®/Opadry® (85/15) at a coating weight gain of approximately 3% (Batch 6) and 5% (Batch 7). Dissolution profiles are shown in FIG. 46.

Release of the API was faster by 10% to 15% in Batches 6 and 7 containing 40% HPMC K4M when compared to similarly coated tablets from Batches 2 and 3 containing 50% HPMC K4M.

Effect of the Surelease®/Opadry® Coating Level

Batches 8, 4 and 9 were coated with Surelease®/Opadry® (75/25) at different coating weight gains to assess the effect of coating weight on the release-rate of Compound 1 hydrochloride salt hemihydrate, Form III.

Figure 47:
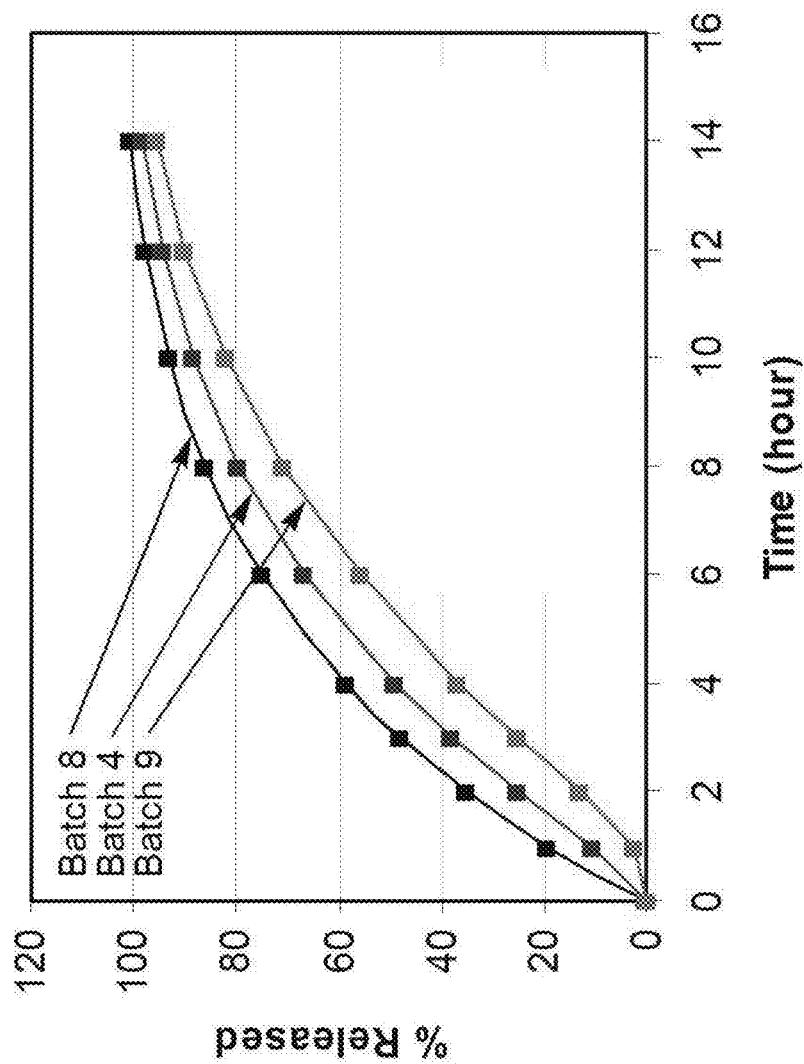
FIG. 47: Effect of Surelease®/Opadry® Coating Level on Compound 1 Hydrochloride Salt Hemihydrate, Form III Release.

FIG. 47 shows a higher coating weight gain reduced the rate of release. T80% is 7 hours, 8 hours, and 10 hours corresponding to a coating weight gain of 2.5%, 5.4%, and 9.9%, respectively.

Effect of API Loading

Batches 10 and 11 were developed to assess the impact of API loading level in the tablet on the release rate. The increase of API was compensated by decreasing the quantity of mannitol by the same amount.

Figure 48:
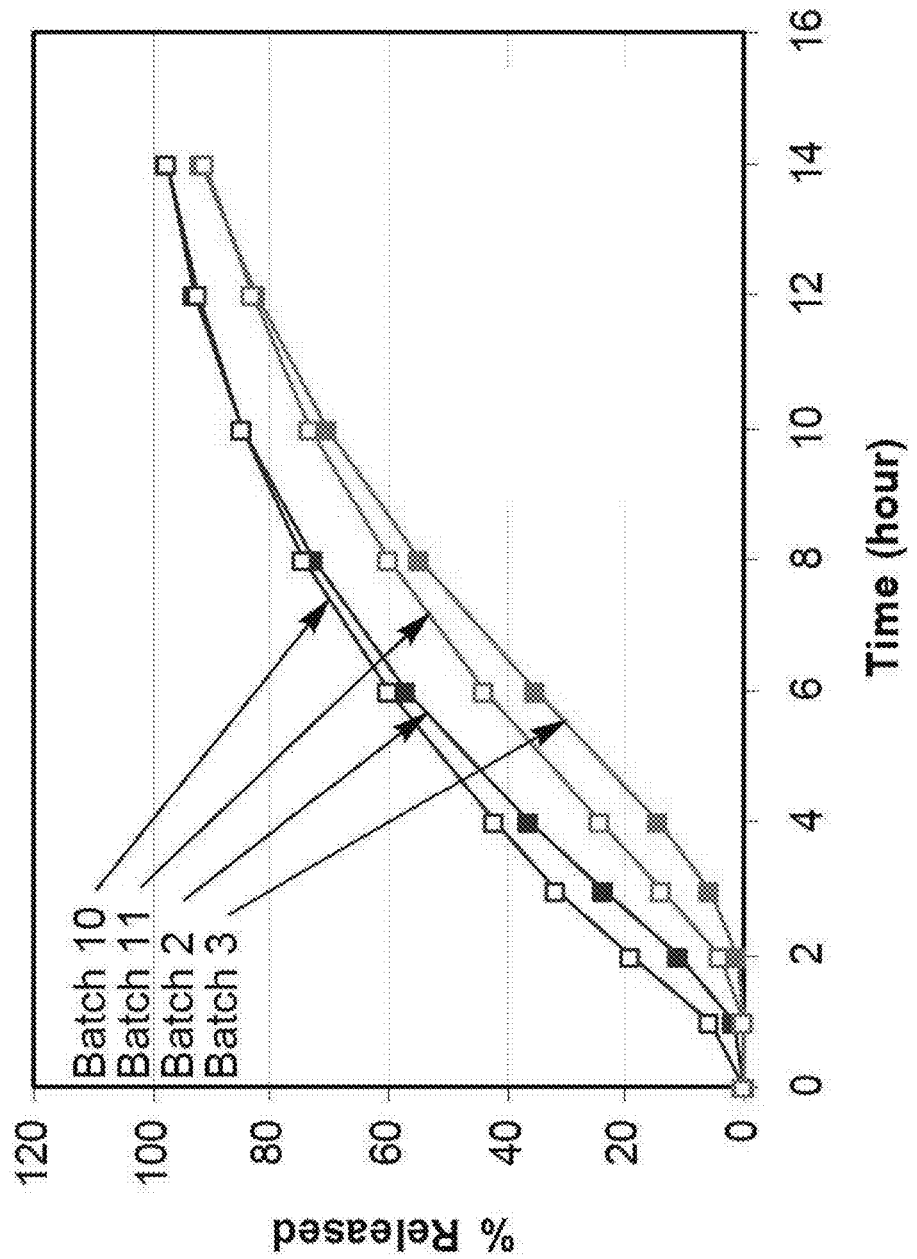
FIG. 48: Effect of Compound 1 Hydrochloride Salt Hemihydrate, Form III Loading.

Increasing the API loading in the core tablets from 6.93% to 10.4% showed a limited impact on the release profile. As shown in FIG. 48, accelerated API release from Batch 10 occurred in the first 6 hours and accelerated API release from Batch 11 occurred in the first 8 hours during dissolution.

After that, the release profiles are essentially converged with the tablets with 6.63% loading (Batches 2 and 3). The impact of higher Compound 1 hydrochloride salt hemihydrate, Form III loading on its release is less pronounced at a coating weight gain of 3% than at a coating weight gain of 5%.

In summary, a flexible and robust modified-release formulation of Compound 1 hydrochloride salt hemihydrate, Form III was developed using two controlling mechanisms: HPMC swelling and ethyl cellulose coating. The Surelease®/Opadry® ratio, coating weight gain, and HPMC level were identified as the critical formulation parameters.

Example 2: In Vivo Pharmacokinetics and Efficacy of Modified-Release Dosage Forms Example 2.1: Dose Calculation Prior to initiating a chronic experiment, preliminary pharmacokinetic experiments were conducted to determine the plasma exposure of Compound 1 at steady-state after once-daily oral administration for six days and constant infusion for four days.

24 h AUC after Repeated Administration of Compound 1 Via Oral Gavage

Male Sprague-Dawley rats were administered a daily dose via oral gavage of Compound 1 hydrochloride salt at 24 mg/kg/day for 6 consecutive days. Compound 1 was dosed as a solution of Compound 1 hydrochloride salt hemihydrate formulated in 0.9% NaCl at 10 mL/kg. The amount of Compound 1 hydrochloride salt hemihydrate to be weighed for formulating was adjusted by using a correction factor of 1.233. Animals were not fasted prior to dosing.

Four cohorts of four rats per group were bled at alternating time points. Blood samples were collected via the jugular sinus under light isoflurane anesthesia at pre-dose (0), 0.083, 0.25, 0.5, 1, 3, 5, 8, and 24 hours post-dose. Blood was treated with potassium EDTA and plasma was separated by centrifugation. Plasma samples were frozen and stored at approximately ~70° C. until assayed. The drug plasma pharmacokinetic parameters for day 6 are summarized in the following table. Pharmacokinetic parameters were determined from composite concentration vs. time profiles, therefore, standard deviations were not calculated.

| Day 6 Pharmacokinetic Parameters | | | |
|---|---|---|---|
| $t_{1/2}$ (h) | $t_{max}$ (h) | $C_{max}$ (ng/mL) | $AUC_{0-inf}$ (h · ng/mL)[a] |
| 4.02 | 0.500 | 700 | 5210 |

[a]$AUC_{0-inf}$ = $AUC_{tau}$ on day 6 extrapolated to infinity 24 h AUC after Repeated Administration of Compound 1 Via Osmotic Minipump Alzet pumps were implanted subcutaneous in four male SD rats. Compound 1 was infused at a rate of 1 mg/kg/h for four days. Infusion volume rate was 5 μL/h. Rat plasma samples were collected at 18, 42, 66, and 90 h post-implantation and assayed. The drug plasma pharmacokinetic parameters are summarized in the following table.

| Parameter | Mean | SD | % CV |
|---|---|---|---|
| Infusion Rate (μg/h/kg)[a] | 1000 | — | — |
| Infusion Volume (μL/h)[b] | 5 | — | — |

-continued

| Parameter | Mean | SD | % CV |
|---|---|---|---|
| $C_{ss}$ from 42 to 90 hours (ng/mL) | 340 | 32 | 9.5 |
| Cl (L/h/kg) | 2.96 | 0.29 | 9.8 |

[a]Infusion rate based on a 24 mg/kg/day dose; delivering 24 mg/kg over a 24 h period
[b]Infusion volume: osmotic pump pre-set Bioanalytical Analysis K$_2$EDTA treated male rat plasma samples were analyzed for Compound 1 and the internal standard (d$_6$-Compound 1). This method was validated from a range of 1.00 up to 3000 ng/mL based on the analysis of 5.00 μL rat plasma. Proteins were removed from plasma with the addition of acetonitrile at a ratio of 4:1 (acetonitrile:plasma), followed by centrifugation. The supernatant from the processed plasma samples was injected into an HPLC system equipped with an API 5000 mass spectrometer. Peak areas for the transitions 196.1→144.2 product ion of Compound 1 were measured against the m/z 202.1→149.1 product ion of the internal standard in positive ion multiple reaction monitoring (MRM) mode. Quantitation was performed with regression analysis generated from calibration standards.

Pharmacokinetic Data Analyses

Noncompartmental pharmacokinetic analysis was performed with a commercial software package (WinNonlin Professional version 5.2., Pharsight, Mountain View, Calif. validation report CSV-0004-SM-R1) with calculation of the following parameters:

| | |
|---|---|
| $t_{max}$ | Time of maximum observed plasma concentration |
| $C_{max}$ | Plasma concentration corresponding to $t_{max}$ |
| $t_{1/2}$ | Terminal phase half-life. |
| $C_{ss}$ | Plasma concentration at steady-state |
| tau | dosing interval |
| AUC$_{tau}$ | Area under the plasma concentration versus time curve from the dosing interval |
| AUC$_{0-inf}$ | Area under the plasma concentration versus time curve from the time of dosing extrapolated to infinity |
| Cl | Total body clearance from plasma |

Infusion Rate Calculation for Chronic Study

An asymptotic rise in plasma concentration occurs between the initiation of an oral dose or a constant infusion to establish the plasma concentration at steady-state. The factor controlling the approach to steady-state is the half-life of the drug. For practical purposes, steady-state is achieved after 3.3 half-lives (90% of theoretical). Compound 1 half-life is 4.0 h. Dosing once daily for 6 days ensures that Compound 1 plasma concentrations will be at steady-state (Rowland and Tozer, *Clinical Pharmacokinetics: Concepts and Applications* 3d ed., Williams and Wilkins. 1995, pp 69 and 85).

The infusion rate for the chronic study was determined as follows:

$C_{ss}$=AUC$_{24hr}$÷Dosing Interval AUC$_{24hr}$(gavage)=
5210 h·μg/mL Dosing Interval=24 h
$C_{ss}$=5210±24=213 ng/mL   Equation 1:

Infusion Rate=$C_{ss}$×Cl Cl$_{systemic}$=2.96±0.29 L/h/kg
(subcutaneous mini-pump) $C_s$, =213 ng/mL
Infusion rate=0.630 mg/h/kg=15.1 mg/day/kg   Equation 2:

In summary, the AUC$_{tau}$ after oral dosing and derived systemic clearance after a constant infusion were used to determine that the subcutaneous osmotic minipump dose required to achieve an AUC$_{tau}$ approximately equivalent to that of a 24 mg/kg/day oral dose was 0.63 mg/kg/hour or 15.1 mg/day/kg.

Example 2.2: Pharmacology 30 male Sprague Dawley rats weighing 275-320 g were singly housed and maintained on a 12 h:12 h light-dark cycle (lights on at 23:00 h). Food and water were available ad libitum at all times except during the first day after pump implantation (see below). All rats were habituated to injection and handling procedures for one week prior to study onset.

For the purposes of dose calculation each rat was assumed to weigh 320 g at the start of the study. Rats receiving Compound 1 hydrochloride salt PO were given a fixed daily dose of 7.68 mg, whereas rats in the pump group received a total fixed daily dose of 4.84 mg (for calculations see Example 2.1).

Osmotic minipumps (Alzet® model 2ML4, Durect Corp, CA) were filled with either vehicle (0.9% saline, n=20), or Compound 1 hydrochloride salt solutions and submerged overnight in a 0.9% saline solution to reach equilibrium. Rats were then assigned to one of three experimental groups (n=10: saline (VEH), Compound 1 hydrochloride salt PO QD (PO), and Compound 1 hydrochloride salt pump (PUMP)), ensuring that average body weights for each group did not substantially differ. All subjects were then implanted with the minipumps. Briefly, under isoflourane anaesthesia the nape of the neck was shaved, a mid-scapular incision was made and a subcutaneous pocket was created for the minipump. A minipump was then inserted into the pocket and the incision was closed using surgical staples. Rats were then returned to homecage for recovery. Rats in VEH and PO groups received pumps primed with vehicle; whereas rats in the PUMP group received Compound 1 hydrochloride salt-filled pumps. Because steady state levels of Compound 1 in vivo in the PUMP group were not predicted to be reached until at least 24 h post-implantation, food was removed from all rats for approximately one day after surgery. At 10:30 h the next day (Day 1) and for all subsequent days, food and body weight was measured for all subjects, and all subjects were administered either saline (for VEH and PUMP groups), or Compound 1 hydrochloride salt (PO group) via oral gavage. Food intake and body weight were measured for a total of 26 days.

Figure 49:
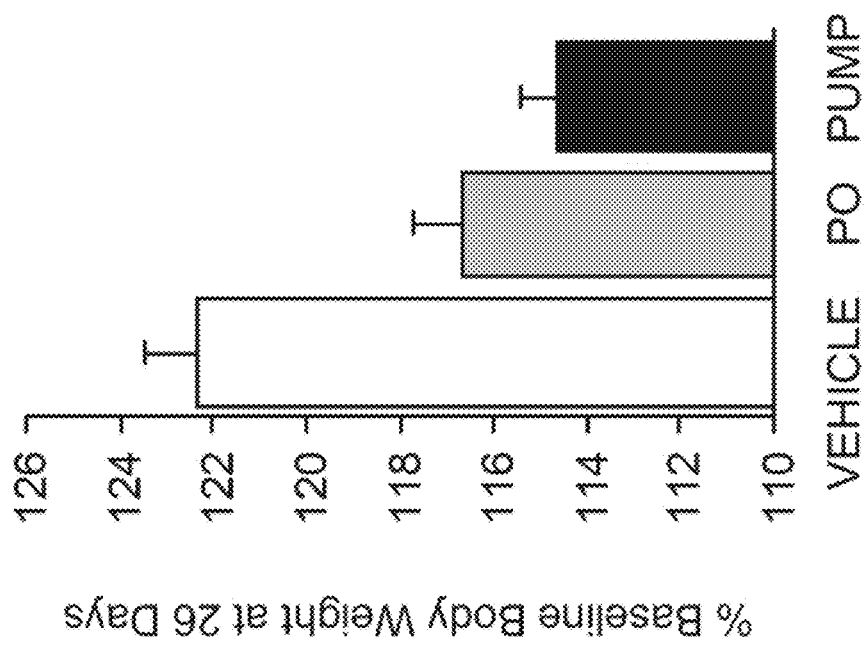
FIG. 49: Day 26 Efficacy of Compound 1 after PO dosed at 24 mg/kg/day or Osmotic Pump Infusion at 15.1 mg/kg/day (Infusion Rate, 0.63 mg/kg/h) in Fed Male SD Rats.
Figure 50:
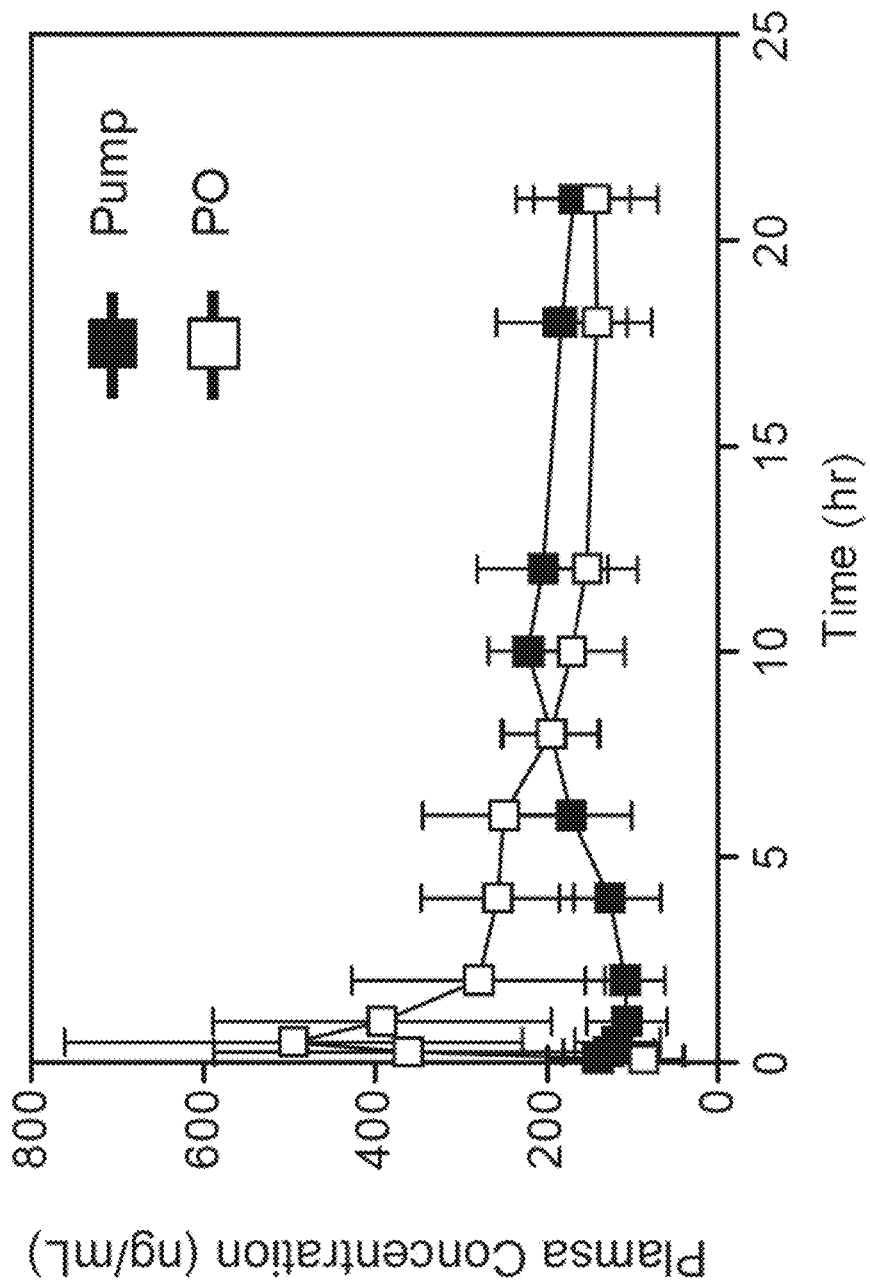
FIG. 50: Mean Plasma Concentration of Compound 1 after PO dosed at 24 mg/kg/day or Osmotic Pump Infusion at 15.1 mg/kg/day (Infusion Rate, 0.63 mg/kg/h) in Fed Male SD Rats.
Figure 54:
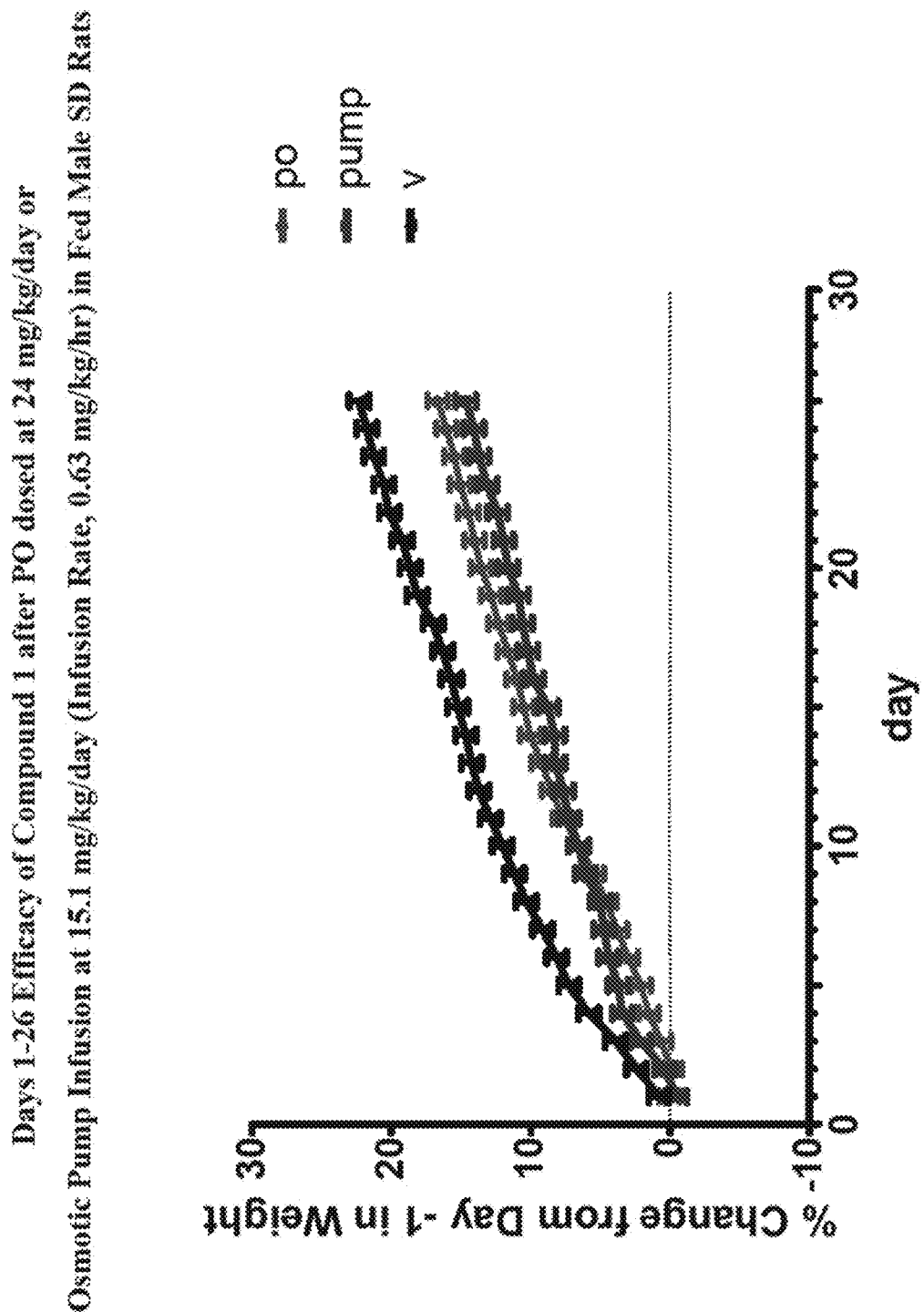
FIG. 54: Days 1-26 Efficacy of Compound 1 after PO dosed at 24 mg/kg/day or Osmotic Pump Infusion at 15.1 mg/kg/day (Infusion Rate, 0.63 mg/kg/h) in Fed Male SD Rats.

Over 26 days of study, the body weight of subjects who received saline increased by approximately 22%. This body weight gain was significantly decreased when Compound 1 hydrochloride salt was administered either by osmotic minipump or by via oral gavage (FIGS. 49 and 54). Overall there was lower weight gain in the PUMP group than in the PO group, an effect which closely approached statistical significance (p=0.0501). Linear models were also fitted to individual body weight data and analyzed for each subject. This revealed differences in slope between PO and PUMP groups (p<0.01), demonstrating body weight gain to differ significantly across the study for the PO and PUMP groups.

Figure 51:
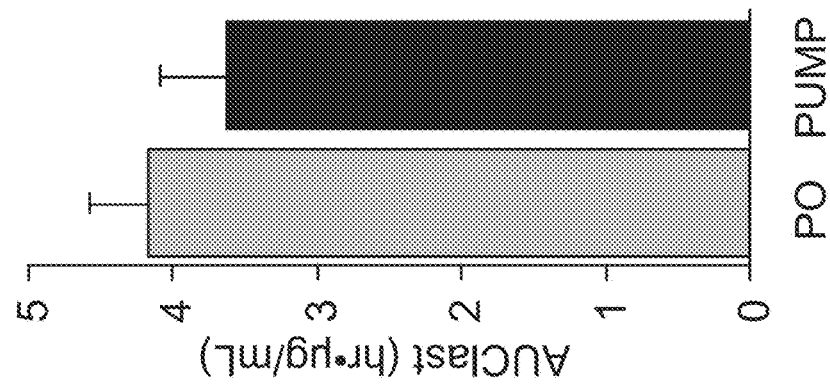
FIG. 51: Mean $AUC_{last}$ of Compound 1 after PO dosed at 24 mg/kg/day or Osmotic Pump Infusion at 15.1 mg/kg/day (Infusion Rate, 0.63 mg/kg/h) in Fed Male SD Rats.
Figure 52:
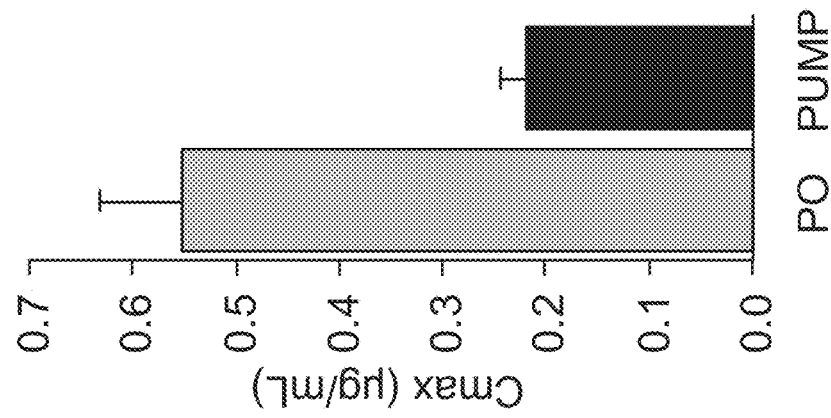
FIG. 52: Mean $C_{max}$ of Compound 1 after PO dosed at 24 mg/kg/day or Osmotic Pump Infusion at 15.1 mg/kg/day (Infusion Rate, 0.63 mg/kg/h) in Fed Male SD Rats.
Figure 53:
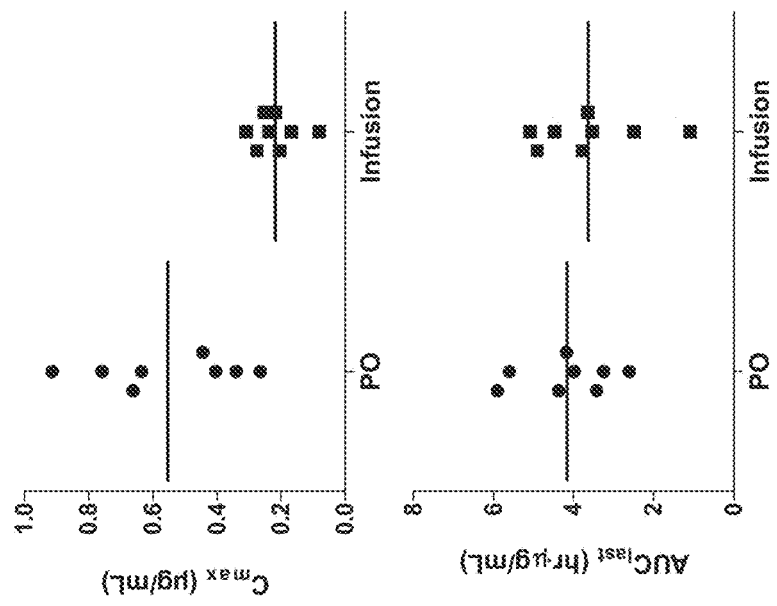
FIG. 53: Individual Compound 1 Exposure Values after PO (24 mg/kg/day) or SC Osmotic Pump Infusion (15.1 mg/kg/day, Infusion Rate, 0.63 mg/kg/h) in Fed Male SD Rats.

The lower weight gain in the PUMP group compared to the PO group occurred despite the fact that based on AUC$_{last}$, total exposure to Compound 1 over the course of the study was the same for both groups (FIG. 51), and the $C_{max}$ values in the PO group were significantly higher than in the pump group (p<0.01) (FIG. 52).

Example 2.3: Pharmacokinetics

Two days prior to blood collections, animals described in Example 2.2 were implanted with carotid artery cannulas. On Day 28, animals were placed in Culex® cages for automated blood collection. Blood samples were collected at 0, 0.083, 0.25, 0.5, 1, 2, 4, 6, 8, 10, 12, 18, and 21 h for PO administration after the 28$^{th}$ dose and beginning at 10:00 am on Day 28 for the SC infusion administration. Analyte plasma concentrations were determined by LC/MS/MS. Noncompartmental PK analysis was performed using WinNonlin® (Pharsight®, Mountain View, Calif.) to determine $t_{1/2}$, $C_{maxss}$, $C_{ss}$ and $AUC_{last}$.

The results are presented in the following Table and in FIGS. 50 to 53.

| Compound 1 Administration | Parameter | Mean | SD | % CV |
|---|---|---|---|---|
| Once-Daily Oral Gavage | PO (mg/kg/day) | 24.0 | — | — |
| | Dose volume (mL/rat) | 0.32 | — | — |
| | $C_{max}$ (µg/mL) | 0.553 | 0.225 | 40.6 |
| | $AUC_{last}$ (h · µg/mL) | 4.17 | 1.14 | 27.2 |
| Continuous Subcutaneous Infusion | Infusion rate (mg/kg/h) | 0.630 | — | — |
| | Infusion volume rate (µL/h) | 5.0 | — | — |
| | $C_{max}$ (µg/mL) | 0.213 | 0.071 | 32.5 |
| | $C_{ss}$ (µg/mL), 0 to 21 h | 0.155 | 0.058 | 37.6 |
| | $AUC_{last}$ (h · µg/mL) | 3.63 | 1.32 | 36.4 |

Example 3: Preparation of Salts of (R)-8-Chloro-1-methyl-2,3,4,5-tetrahydro-1H-3-benzazepine

Example 3.1: Preparation of Form I of (R)-8-Chloro-1-methyl-2,3,4,5-tetrahydro-1H-3-benzazepine Hydroiodide Salt (Compound 1 Hydroiodide Salt, Form I)

The title salt was prepared by the dropwise addition of one equivalent of aqueous HI (~57%) to a solution of (R)-8-chloro-1-methyl-2,3,4,5-tetrahydro-1H-3-benzazepine free base in isopropyl acetate. A precipitate formed after 7 days stirring with evaporation. The solid was slurried in ethyl acetate with ~3% water added for 5 h. The solid was recovered by centrifuge filtration (10,000 rpm for 1 minute, nylon filter).

The title salt was essentially white when removed from the slurry, but did yellow noticeably within hours when exposed to light. The TGA showed the title salt to be anhydrous, which was confirmed by KF analysis. Based on water activity measurement of a saturated aqueous solution with excess solid, the DRH was 99% RH at 25° C.

A known amount of the title salt was dissolved in MeOH and analyzed by UPLC. The amount of Compound 1 in the sample was determined to be 64.6%. This is slightly higher than the calculated amount, 60.5%, for a 1:1 Compound 1 hydroiodide salt. The solubility in water at 27° C. was determined by gravimetry (confirmed by UPLC) and found to be 5.5 mg/mL with a final pH 8.9.

The powder X-ray diffraction pattern of the title salt is shown in FIG. 5. Thermal analysis (TGA and DSC) of the title salt is shown in FIG. 6. DMS analysis of the title salt is shown in FIG. 7.

Example 3.2: Preparation of Form I of (R)-8-Chloro-1-methyl-2,3,4,5-tetrahydro-1H-3-benzazepine Maleate Salt (Compound 1 Maleate Salt, Form I)

The title salt was prepared by dropwise addition of a solution of 1 or 2 equivalents of maleic acid in methanol to a solution of (R)-8-chloro-1-methyl-2,3,4,5-tetrahydro-1H-3-benzazepine free base in isopropyl acetate or acetonitrile with vigorous stirring. The resulting slurry was heated to 60° C. and held at that temperature for ~1 h before it was cooled to room temperature and stirred overnight. The title salt was recovered by filtration, washed with isopropyl acetate or acetonitrile and dried on the filter before characterization.

The same crystalline form was obtained whether 1 or 2 equivalents of maleic acid were used: a 1:1 salt with a melting onset temperature about 166° C. The TGA was consistent with an anhydrous salt. It was not hygroscopic, picking up just 0.15% weight out to and including the 90% RH hold at 25° C. The DRH was determined by water activity measurement of a saturated aqueous solution with excess solid to be 99% RH at 25° C.

A known amount of the title salt was dissolved in water and analyzed by UPLC. The amount of Compound 1 in the sample was 66.5%. This is slightly higher than the theoretical amount for a 1:1 salt, 62.8%, but well below the theoretical for a hemimaleate salt, 77.1%. The solubility of the title salt in water was determined by UPLC and found to be 33 mg/mL with a final pH 3.96.

The powder X-ray diffraction pattern of the title salt is shown in FIG. 8. Thermal analysis (TGA and DSC) of the title salt is shown in FIG. 9. DMS analysis of the title salt is shown in FIG. 10.

Example 3.3: Preparation of Form I of (R)-8-Chloro-1-methyl-2,3,4,5-tetrahydro-1H-3-benzazepine Fumarate Salt (Compound 1 Fumarate Salt, Form I)

Method 1

The title salt was prepared by dropwise addition of an equimolar amount of fumaric acid in 1:1 water:EtOH (~0.6 M) to a solution of (R)-8-chloro-1-methyl-2,3,4,5-tetrahydro-1H-3-benzazepine in isopropyl acetate with vigorous stirring. The resulting suspension was heated to 60° C., held at that temperature for 1 h, and then allowed to cool to ambient temperature while stirring overnight. The mixture was filtered and the solid was washed with isopropyl acetate and dried on the filter.

Method 2

The title salt was prepared by adding either a half molar or an equimolar amount of dry solid fumaric acid to solution of (R)-8-chloro-1-methyl-2,3,4,5-tetrahydro-1H-3-benzazepine in isopropyl acetate. The mixture was slurried at ~60° C. and stirred for ~2 h. The heat source was removed and the mixture was left to stir for 3 days at ~26° C. The solid precipitate was recovered by filtration, and then re-slurried for ~24 h in water or ethanol. The solid was recovered by filtration and slurried for an additional 4 days in n-propanol, acetonitrile, or water.

Both Methods 1 and 2 produced a 1:1 salt.

The DRH of the title compound by water activity meter was 99% RH at 25° C.

A known amount of the title salt was dissolved in water and analyzed by UPLC. The amount of Compound 1 in the sample was 66.8%. This was slightly higher than the theoretical value for an anhydrous 1:1 fumarate salt, 62.8%, but much lower than the theoretical value for an anhydrous 2:1 salt, 77.1%. The solubility of the title salt in water was determined by UPLC and found to be 4.8 mg/mL with a final pH 3.7.

The powder X-ray diffraction pattern of the title salt is shown in FIG. 11. Thermal analysis (TGA and DSC) of the title salt is shown in FIG. 12. DMS analysis of the title salt is shown in FIG. 13.

Example 3.4: Preparation of Form I of (R)-8-Chloro-1-methyl-2,3,4,5-tetrahydro-1H-3-benzazepine Hemifumarate Salt (Compound 1 Hemifumarate Salt, Form I)

The title salt was prepared by dropwise addition of a half-molar amount of fumaric acid in 1:1 water:EtOH (~0.6 M) to a solution of (R)-8-chloro-1-methyl-2,3,4,5-tetrahydro-1H-3-benzazepine in isopropyl acetate with vigorous stirring. A suspension resulted. It was heated to 60° C., held at that temperature for 1 h, and then the heat source was removed and the sample was allowed to cool to ambient temperature while stirring overnight. The suspension was filtered and the solid was washed with isopropyl acetate and dried on the filter.

The title salt had a melting onset of 158° C. by DSC, however, significant weight loss occurred prior to this melting onset based on TGA data. The weight loss is slightly more than the theoretical amount of fumaric acid for an anhydrous hemifumarate salt (27.0% vs. 22.9%).

The title salt formed a hydrate during DMS analysis, which was labile enough to lose the water upon desorption to 5% RH at 25° C. The ~8% weight gain is slightly higher than the theoretical % weight gain (7.1%) for a monohydrate. The DRH was determined by water activity measurement of a saturated aqueous solution with excess solid to be 93% RH at 25° C.

A known amount of the title salt was dissolved in water and analyzed by UPLC. The amount of Compound 1 in the sample was 76.0%. This is in acceptable agreement with the theoretical amount, 77.1%. The solubility of the title salt in water was determined by UPLC to be 99.7 mg/mL with a final pH 5.8.

The powder X-ray diffraction pattern of the title salt is shown in FIG. 14. Thermal analysis (TGA and DSC) of the title salt is shown in FIG. 15. DMS analysis of the title salt is shown in FIG. 16.

Example 3.5: Preparation of Form I of (R)-8-Chloro-1-methyl-2,3,4,5-tetrahydro-1H-3-benzazepine Orotate Salt (Compound 1 Orotate Salt, Form I)

The title salt was prepared by addition of one equivalent of orotic acid to a solution of (R)-8-chloro-1-methyl-2,3,4,5-tetrahydro-1H-3-benzazepine in isopropanol, ethyl acetate, or acetone at 60° C. Orotic acid, at 60° C., was added drop-wise, in the corresponding solvent, with vigorous stirring. Precipitation occurred immediately and the suspension was allowed to cool and stir overnight. The resulting solid was recovered by filtration and air-dried in a fume hood overnight.

Stoichiometry was determined after aqueous slurry of the title salt, which resulted in a hydrate (Example 3.6). It was determined to be a 1:1 salt with respect to Compound 1 and orotate ion. Since the anhydrous and hydrated forms can be interconverted, the ratio of Compound 1 to orotate is the same for the anhydrous and hydrated salt forms.

Solubility of Compound 1 orotate salt was not determined due to conversion of the anhydrous form to the hydrated form in water. The solubility of the hydrated form is given in Example 3.6.

The powder X-ray diffraction pattern of the title salt is shown in FIG. 17. Thermal analysis (TGA and DSC) of the title salt is shown in FIG. 18. DMS analysis of the title salt is shown in FIG. 19.

Example 3.6: Preparation of Form I of (R)-8-Chloro-1-methyl-2,3,4,5-tetrahydro-1H-3-benzazepine Orotate Salt Hydrate (Compound 1 Orotate Salt Hydrate, Form I)

The title salt was prepared by addition of one equivalent of orotic acid to a solution of (R)-8-chloro-1-methyl-2,3,4,5-tetrahydro-1H-3-benzazepine in acetonitrile or isopropanol at 60° C. Orotic acid, at 60° C., was added drop-wise, in the corresponding solvent, with vigorous stirring. Precipitation occurred immediately and the suspension was allowed to cool and stir overnight. Compound 1 orotate salt hydrate prepared in isopropanol consisted of a mixture of the anhydrous and hydrated forms which was converted to the hydrated form by slurring in isopropanol for two days.

The title salt was also prepared by slurrying anhydrous (R)-8-chloro-1-methyl-2,3,4,5-tetrahydro-1H-3-benzazepine orotate salt in water. The resulting solid was recovered by filtration and air-dried in a fume hood overnight.

Compound 1 orotate hydrate was a hydrated crystalline material with dehydration onset temperature ~60° C. by TGA scanned at 10° C./min.

A known amount of Compound 1 orotate hydrate was dissolved in methanol and analyzed by UPLC. The percent of Compound 1 in the salt sample was determined to be 51.2%.

This is slightly lower than the theoretical percent Compound 1 in a 0.75 hydrate of Compound 1 orotate salt (53.6%).

Solubility of Compound 1 orotate hydrate in water was determined by UPLC to be <0.001 mg/mL, with a final pH of 2.88.

The powder X-ray diffraction pattern of the title salt is shown in FIG. 20. Thermal analysis (TGA and DSC) of the title salt is shown in FIG. 21. DMS analysis of the title salt is shown in FIG. 22.

Example 3.7: Preparation of Form I of (R)-8-Chloro-1-methyl-2,3,4,5-tetrahydro-1H-3-benzazepine Di-4-acetamidobenzoate Salt-Cocrystal Methyl Ethyl Ketone Solvate (Compound 1 Di-4-acetamidobenzoate Salt-Cocrystal Methyl Ethyl Ketone Solvate, Form I)

The title salt was prepared by combining one equivalent of 4-acetamidobenzoic acid with (R)-8-chloro-1-methyl-2,3,4,5-tetrahydro-1H-3-benzazepine in n-propanol or methanol at 50° C. then cooling slowly and stirring overnight. The resulting clear solution was evaporated to a mixture of oil and solids. Upon trituration with MEK a white solid formed and was filtered and dried.

The title salt was a crystalline material with a melting onset at 113° C. and was hygroscopic at relative humidities above 80% RH.

A known amount of the title salt, post dynamic moisture-sorption analysis, was dissolved in methanol and analyzed by UPLC. The percent of Compound 1 was determined to be 35-37%. This matches the theoretical percent Compound 1 in a non-solvated Compound 1 di-4-acetamidobenzoate salt (35.3%). Based on the TGA, DMS and stoichiometry data, the crystalline form is composed of one Compound 1 molecule, two 4-acetamidobenzoate molecules and 0.2-0.25 moles of methyl ethyl ketone.

The powder X-ray diffraction pattern of the title salt is shown in FIG. 23. Thermal analysis (TGA and DSC) of the title salt is shown in FIG. 24. DMS analysis of the title salt is shown in FIG. 25.

Example 3.8: Preparation of Form I of (R)-8-Chloro-1-methyl-2,3,4,5-tetrahydro-1H-3-benzazepine trans-Cinnamate Salt (Compound 1 trans-Cinnamate Salt, Form I)

The title salt was prepared by combining one equivalent of trans-cinnamic acid with (R)-8-chloro-1-methyl-2,3,4,5-tetrahydro-1H-3-benzazepine in acetonitrile at 50° C. The sample was cooled slowly and stirred overnight. The resulting white solid was isolated by filtration and dried. Similar samples prepared in isopropanol, acetone or THF produced white solids only after removal of solvent and trituration with MTBE.

Compound 1 trans-cinnamate salt was a crystalline material with a melting onset at 106° C. and was slightly hygroscopic out to and including the 90% RH hold at 25° C.

A known amount of Compound 1 trans-cinnamate salt was dissolved in methanol and analyzed by UPLC. The percentage of Compound 1 in the salt sample was determined to be 62.5%. This is slightly higher than the theoretical percentage of Compound 1 in a 1:1 Compound 1 trans-cinnamate salt (56.9%).

The aqueous solubility of Compound 1 trans-cinnamate was determined to be 11.8 mg/mL at a pH of 7.0.

The powder X-ray diffraction pattern of the title salt is shown in FIG. 26. Thermal analysis (TGA and DSC) of the title salt is shown in FIG. 27. DMS analysis of the title salt is shown in FIG. 28.

Example 3.9: Preparation of Form I of (R)-8-Chloro-1-methyl-2,3,4,5-tetrahydro-1H-3-benzazepine Heminapadisilate Salt (Compound 1 Heminapadisilate Salt, Form I)

The title salt was prepared by addition of a molar equivalent of naphthalene-1,5-disulfonic acid to a solution of (R)-8-chloro-1-methyl-2,3,4,5-tetrahydro-1H-3-benzazepine in isopropanol or acetonitrile at 60° C. Naphthalene-1,5-disulfonic acid, at 60° C., was added drop-wise, in the corresponding solvent, with vigorous stirring. Precipitation occurred immediately in acetonitrile and the suspension was allowed to cool and stir overnight. Addition of water precipitated the salt in isopropanol and the suspension was allowed to cool and stir overnight. The resulting solid was recovered by filtration and air-dried in a fume hood overnight.

Compound 1 heminapadisilate was an anhydrous crystalline material with a melting onset of ~266° C. It was non-hygroscopic by DMS.

A known amount of Compound 1 heminapadisilate was dissolved in methanol and analyzed by UPLC. The percentage of Compound 1 in the salt sample was determined to be 59.7%. This is slightly higher than the theoretical percentage of Compound 1 in an anhydrous Compound 1 heminapadisilate salt (57.6%).

The solubility of Compound 1 heminapadisilate in water was determined by UPLC to be 2.37 mg/mL, with a final pH of 3.23.

The powder X-ray diffraction pattern of the title salt is shown in FIG. 29. Thermal analysis (TGA and DSC) of the title salt is shown in FIG. 30. DMS analysis of the title salt is shown in FIG. 31.

Example 3.10: Preparation of Form I of (R)-8-Chloro-1-methyl-2,3,4,5-tetrahydro-1H-3-benzazepine Heminapadisilate Salt Solvate 1 (Compound 1 Heminapadisilate Salt Solvate 1, Form I)

The title salt was prepared by addition of one equivalent of naphthalene-1,5-disulfonic acid to a solution of (R)-8-chloro-1-methyl-2,3,4,5-tetrahydro-1H-3-benzazepine in ethyl acetate at 60° C. Naphthalene-1,5-disulfonic acid in ethyl acetate, at 60° C., was added dropwise with vigorous stirring. Precipitation occurred immediately and the suspension was allowed to cool and stir overnight. The resulting solid was recovered by filtration and air-dried in a fume hood overnight.

The powder X-ray diffraction pattern of the title salt is shown in FIG. 32. Thermal analysis (TGA and DSC) of the title salt is shown in FIG. 33.

Example 3.11: Preparation of Form I of (R)-8-Chloro-1-methyl-2,3,4,5-tetrahydro-1H-3-benzazepine Heminapadisilate Salt Solvate 2 (Compound 1 Heminapadisilate Salt Solvate 2, Form I)

The title salt was prepared by the addition of one equivalent of naphthalene-1,5-disulfonic acid to a solution of (R)-8-chloro-1-methyl-2,3,4,5-tetrahydro-1H-3-benzazepine in acetone at 60° C. Naphthalene-1,5-disulfonic acid in acetone at 60° C. was added dropwise with vigorous stirring. A yellow oil precipitated and the suspension was allowed to cool and stir overnight. A white precipitate was observed after stirring overnight. The resulting solid was recovered by filtration and air-dried in a fume hood overnight.

Compound 1 heminapadisilate salt solvate 2 was a solvated crystalline material with desolvation onset of ~129° C. by DSC.

The powder X-ray diffraction pattern of the title salt is shown in FIG. 34. Thermal analysis (TGA and DSC) of the title salt is shown in FIG. 35.

Example 3.12: Preparation of Form I of (R)-8-Chloro-1-methyl-2,3,4,5-tetrahydro-1H-3-benzazepine (±)-Mandelate Salt Hydrate (Compound 1 (±)-Mandelate Salt Hydrate, Form I)

The title salt was prepared by the addition of one equivalent of (±)-mandelic acid to a solution of (R)-8-chloro-1-methyl-2,3,4,5-tetrahydro-1H-3-benzazepine in acetonitrile, ethyl acetate, or acetone at 60° C. (±)-Mandelic acid, at 60° C., was added dropwise, in the corresponding solvent, with vigorous stirring. Addition of water to these three samples precipitated the salt and it was allowed to cool and stir overnight. The resulting solids were recovered by filtration and air-dried in a fume hood overnight.

Compound 1 (±)-mandelate salt formed a hydrate with a desolvation onset of ~74° C. by DSC. It was non-hygroscopic by DMS.

A known amount of Compound 1 (±)-mandelate salt hydrate was dissolved in methanol and analyzed by UPLC. The percent of Compound 1 in the salt sample was determined to be 50.0%. This is slightly lower than the theoretical percent Compound 1 in a monohydrate Compound 1 mandelate salt, 53.5%.

Solubility of Compound 1 (±)-mandelate salt hydrate in water was determined by UPLC to be 5.74 mg/mL, with a final pH of 7.47.

The powder X-ray diffraction pattern of the title salt is shown in FIG. 36. Thermal analysis (TGA and DSC) of the title salt is shown in FIG. 37. DMS analysis of the title salt is shown in FIG. 38.

Example 3.13: Preparation of Form I of (R)-8-Chloro-1-methyl-2,3,4,5-tetrahydro-1H-3-benzazepine Hemipamoate Salt Hydrate (Compound 1 Hemipamoate Salt Hydrate, Form I)

The title salt was prepared by the addition of 0.25 molar equivalents of pamoic acid to a solution of (R)-8-chloro-1-methyl-2,3,4,5-tetrahydro-1H-3-benzazepine in isopropanol, acetonitrile, ethyl acetate, or acetone at 60° C. Pamoic acid, at 60° C., was added dropwise, in the corresponding solvent, with vigorous stirring. Precipitation occurred immediately and the suspension was allowed to cool and stir overnight. The resulting solid was recovered by filtration and air-dried in a fume hood overnight.

Compound 1 hemipamoate salt formed a hydrate crystalline material with melting onset well after desolvation of ~244° C.

The title salt was dissolved in methanol and analyzed by UPLC. The percentage of Compound 1 in the salt sample was determined to be 46.52%. This is slightly lower than the theoretical percentage of Compound 1 in a monohydrate Compound 1 hemipamoate salt (47.98%).

Solubility of Compound 1 hemipamoate hydrate in water was determined by UPLC to be 0.024 mg/mL, with a final pH of 9.10.

The powder X-ray diffraction pattern of the title salt is shown in FIG. 39. Thermal analysis (TGA and DSC) of the title salt is shown in FIG. 40. DMS analysis of the title salt is shown in FIG. 41.

Example 4: Preparation of (R)-8-Chloro-1-methyl-2,3,4,5-tetrahydro-1H-3-benzazepine Hydrochloride Salt Hemihydrate, Form III Method 1

Step A: Preparation of 8-Chloro-1-methyl-2,3,4,5-tetrahydro-1H-3-benzazepine

2-Chloro-N-(4-chlorophenethyl)propan-1-amine hydrochloride (about 460 kg, 1.71 kmol, 1.00 eq.), aluminum chloride (about 336 kg, 2.52 kmol, 1.47 eq.), and 1,2-dichloro-benzene (about 1321 kg) are charged to a vessel vented to a caustic scrubber. The mixture is then stirred and heated at about 126° C. under nitrogen for about 16 h. The resulting Friedel-Crafts reaction mixture is then cooled. Silica gel and purified water (about 736 kg) are charged to a second vessel. The cooled Friedel-Crafts reaction mixture is then added to the aqueous silica gel slurry stirred and cooled in the second vessel. The stirred quench mixture is filtered at about 55° C., and the silica gel filter cake is washed with purified water (about 368 kg). Optionally, some or all of this purified water is used to rinse the quench vessel into the filter. The mother and wash liquor filtrates are combined in a vessel and are cooled with stirring to about 22° C. Stirring is then stopped, and upon settling, three phases separate. The brown, lowest phase consists mostly of 1,2-dichlorobenzene and is drained. The lower of the remaining two phases, which is the middle phase of the original three-phase mixture, contains most of the product. The topmost phase is a turbid water phase containing a smaller amount of the product. These upper two phases are partitioned between cyclohexane (about 506 kg) and enough aqueous sodium hydroxide solution, approx. 30 wt %, to achieve an aqueous phase pH of at least 12. The cyclohexane phase is washed with water (at least 300 kg) at about 57° C. and then evaporated at reduced pressure to provide crude 8-chloro-1-methyl-2,3,4,5-tetrahydro-1H-3-benzazepine as an oil.

Step B: Preparation of (R)-8-Chloro-1-methyl-2,3,4,5-tetrahydro-1H-3-benzazepine Hemitartrate Acetone (about 848 kg) is added to the crude 8-chloro-1-methyl-2,3,4,5-tetrahydro-1H-3-benzazepine prepared in Step A. The vessel contents are stirred and heated to about 45° C. To the resulting solution is added a solution of L-(+)-tartaric acid (about 57.0 kg, 380 mol, 0.222 eq.) in purified water (about 98.0 kg) while the stirred vessel contents are maintained at about 45° C. Stirring is continued for about 20 min. (R)-8-chloro-1-methyl-2,3,4,5-tetrahydro-1H-3-benzazepine hemitartrate salt seed crystals are then optionally added to initiate nucleation. Stirring is continued, and more acetone is added. The resulting suspension is then cooled to about 2° C. The resulting precipitate is collected by centrifugation and washed with acetone (about 440 kg), a portion of which is optionally used to rinse the crystallization vessel into the centrifuge. The washed solid is discharged from the centrifuge, mixed with acetone (about 874 kg) and the mixture is stirred and heated to reflux. While reflux is maintained, purified water (at least 329 kg) is added until complete dissolution is achieved at reflux. The resulting mixture is stirred at reflux and then cooled to about 2° C. over about 2.5 hours. The resulting precipitate is collected by centrifugation and washed with acetone (about 184 kg), a portion of which is optionally used to rinse the crystallization vessel into the centrifuge. The washed solid is discharged from the centrifuge and dried at elevated temperature under reduced pressure to provide (R)-8-chloro-1-methyl-2,3,4,5-tetrahydro-1H-3-benzazepine hemitartrate. The yield range is 100 kg to 158 kg.

Step C: Preparation of (R)-8-Chloro-1-methyl-2,3,4,5-tetrahydro-1H-3-benzazepine Hydrochloride Salt Hemihydrate, Form III Purified water (about 740 kg) is added to a stirred mixture of (R)-8-chloro-1-methyl-2,3,4,5-tetrahydro-1H-3-benzazepine hemitartrate from Step B (about 247 kg after correction for assay, 912 mol, 1.00 eq.), potassium carbonate (about 151 kg, 1093 mol, 1.20 eq.), and ethyl acetate (about 663 kg). The mixture is maintained at about 15° C. during the addition, after which it is stirred and then allowed to settle. The lower (aqueous) phase is drained to waste disposal. Purified water (about 740 kg) is added to the upper (organic) phase, and the resulting mixture is stirred at about 22° C. and then allowed to settle. The lower (aqueous) phase is drained to waste disposal.

Solvent is removed from the upper (organic) phase by vacuum distillation at about 40° C. to provide (R)-8-chloro-1-methyl-2,3,4,5-tetrahydro-1H-3-benzazepine as the distillation residue. Ethyl acetate (about 1050 kg) is added, and the mixture is stirred to achieve dissolution. If the water content of the resulting solution is found by Karl Fischer analysis to exceed 1.51 wt %, the procedure of this paragraph is repeated.

Through a polishing filter into a crystallization vessel is added purified water in the approximate amount calculated to provide a water concentration of 1.0 wt % in the (R)-8- chloro-1-methyl-2,3,4,5-tetrahydro-1H-3-benzazepine solution after the final ethyl acetate dilution. The solution is then filtered through the same polishing filter into the crystallization vessel. The vessel in which the (R)-8-chloro-1-methyl-2,3,4,5-tetrahydro-1H-3-benzazepine had been prepared is rinsed with additional fresh ethyl acetate (about 644 kg), and the rinse is filtered through the same polishing filter into the crystallization vessel.

The water content of the solution in the crystallization vessel is determined by Karl Fischer analysis. If the water content is about 0.8 wt % to about 1.2 wt % (0.5 wt % to 1.5 wt % non-critical range), then processing resumes at the beginning of the next paragraph. If the water content is too low, additional purified water is added through the polishing filter. If the water content is too high, then solvent is removed by vacuum distillation, purified water (about 18 kg) is added through the polishing filter, and ethyl acetate (about 1800 kg) is added through the polishing filter. In either case, the resulting solution is tested for water content.

As the contents of the crystallization vessel are stirred, hydrogen chloride gas (about 3.3 kg, 91 mol, 0.10 eq.) is added to the vessel head space. (R)-8-Chloro-1-methyl-2,3,4,5-tetrahydro-1H-3-benzazepine hydrochloride salt hemihydrate seed crystals are then added to initiate nucleation. Additional hydrogen chloride gas is then added to the vessel head space until the pH of the reaction mixture drops to and remains at about 5 or less. The precipitated product is collected by centrifugation and washed with filtered ethyl acetate (about 552 kg). The precipitate is dried under reduced pressure to provide the title salt. The yield range is 184 kg to 217 kg, which is 84% to 99% of theoretical uncorrected for seed charge and 83% to 98% of theoretical corrected for seed charge.

Method 2

Step A: Preparation of 8-Chloro-1-methyl-2,3,4,5-tetrahydro-1H-3-benzazepine 1,2-Dichlorobenzene (about 1522 kg), 2-chloro-N-(4-chlorophenethyl)propan-1-amine hydrochloride (about 530 kg, 1.97 kmol, 1.00 eq.), and aluminum chloride (about 387 kg, 2.90 kmol, 1.47 eq.) are charged to a vessel vented to a caustic scrubber. The mixture is then stirred and heated at about 126° C. under nitrogen for about 16 h. The resulting Friedel-Crafts reaction mixture is then cooled. Purified or potable water (about 1060 kg) and silica gel are charged to a second vessel. The cooled Friedel-Crafts reaction mixture is then added to the aqueous silica gel slurry stirred and cooled in the second vessel. The stirred quench mixture is filtered at about 58° C., and the silica gel filter cake is washed with purified or potable water (about 212 kg). Optionally, some or all of this water may be used to rinse the quench vessel into the filter. The mother and wash liquor filtrates are combined in a vessel and are cooled with stirring to about 22° C. Stirring is then stopped, and upon settling, three phases separate. The brown lowest phase consists mostly of 1,2-dichlorobenzene and is drained to solvent regeneration. The lower of the remaining two phases, which is the middle phase of the original three-phase mixture, contains most of the product. The topmost phase is a turbid water phase containing a smaller amount of the product. These upper two phases are partitioned between cyclohexane (about 583 kg) and enough aqueous sodium hydroxide solution, approx. 30 wt %, to achieve an aqueous phase pH of at least about 13. The cyclohexane phase is washed with purified or potable water (about 1272 kg) at about 57° C. and then distilled at reduced pressure to remove solvent and provide crude title compound, an oil, as the distillation residue.

Step B: Preparation of (R)-8-Chloro-1-methyl-2,3,4,5-tetrahydro-1H-3-benzazepine Hemitartrate Acetone (about 977 kg) is added to the crude 8-chloro-1-methyl-2,3,4,5-tetrahydro-1H-3-benzazepine prepared in Step A. The vessel contents are stirred and heated to about 45° C. To the resulting solution is added a solution of L-(+)-tartaric acid (about 66 kg, 440 mol, 0.223 eq.) in purified or potable water (about 113 kg) while the stirred vessel contents are maintained at about 45° C. About half way through the tartaric acid addition, (R)-8-chloro-1-methyl-2,3,4,5-tetrahydro-1H-3-benzazepine hemitartrate seed crystals are added to the solution to achieve cloudiness and to initiate nucleation. Stirring is continued, and more acetone is added. The resulting suspension is then cooled to about 2° C. The resulting precipitate is collected by centrifugation and washed with acetone (about 508 kg), a portion of which is optionally used to rinse the crystallization vessel into the centrifuge. The washed solid is mixed with acetone (about (1007 kg) and the mixture is stirred and heated to reflux. While reflux is maintained, purified or potable water (at least about 392 kg) is added until complete dissolution is achieved at reflux. The resulting mixture is stirred at reflux and then cooled to about 2° C. over about 2.5 h. The resulting precipitate is collected by centrifugation and washed with acetone (about 212 kg), a portion of which is optionally used to rinse the crystallization vessel into the centrifuge. The washed solid is discharged from the centrifuge and dried at elevated temperature under reduced pressure to provide the title salt.

Step C: Preparation of (R)-8-Chloro-1-methyl-2,3,4,5-tetrahydro-1H-3-benzazepine Hydrochloride Salt Hemihydrate, Form III Purified water (about 779 kg) is combined with (R)-8-chloro-1-methyl-2,3,4,5-tetrahydro-1H-3-benzazepine hemitartrate from Step B (about 260 kg after correction for assay, 960 mol, 1.00 eq.), potassium carbonate (about 159 kg, 1150 mol, 1.20 eq.), and ethyl acetate (about 698 kg) with stirring at about 15° C. The resulting mixture is stirred and then allowed to settle. The lower (aqueous) phase is drained to waste disposal. Purified water (about 779 kg) is added to the upper (organic) phase, and the resulting mixture is stirred at about 22° C. and then allowed to settle. The lower (aqueous) phase is drained to waste disposal.

Solvent is removed from the upper (organic) phase by vacuum distillation with the jacket temperature increasing to about 60° C. (R)-8-chloro-1-methyl-2,3,4,5-tetrahydro-1H-3-benzazepine, an oil, is obtained as the distillation residue. Ethyl acetate (about 1105 kg) is added, and the mixture is stirred to achieve dissolution. If the water content of the resulting solution is found by Karl Fischer analysis to exceed 1.51 wt %, the procedure of this paragraph is repeated.

The solution in is then filtered through a polishing filter into a crystallization vessel. The vessel in which the (R)-8-chloro-1-methyl-2,3,4,5-tetrahydro-1H-3-benzazepine had been prepared is then rinsed with additional ethyl acetate (about 122 kg) through the same polishing filter into the crystallization vessel. To the crystallization vessel is then added purified water in the approximate amount calculated to provide a water concentration of 1.0 wt % in the solution after the final ethyl acetate dilution. Ethyl acetate (about 556 kg) is then added to the crystallization vessel, and the resulting mixture is stirred. The water content of the solution in the crystallization vessel is determined by Karl Fischer analysis. If the water content is about 0.8 wt % to about 1.2 wt % (0.5 wt % to 1.5 wt % qualified range), then processing resumes at the beginning of the next paragraph. If the water content is too low, additional purified water is added. If the water content is too high, then solvent is removed by vacuum distillation, and purified water and ethyl acetate are added. In either case, the resulting solution is retested for water content.

As the contents of the crystallization vessel are stirred, hydrogen chloride gas (about 3.5 kg, 96 mol, 0.10 eq.) is added to the vessel head space. (R)-8-chloro-1-methyl-2,3,4,5-tetrahydro-1H-3-benzazepine hydrochloride salt hemihydrate seed crystals are then added to initiate nucleation. Additional hydrogen chloride gas is then added to the vessel head space until the pH of the reaction mixture drops to and remains at about 3 or less. The precipitated product is collected by centrifugation and washed with ethyl acetate (about 580 kg) to provide the title salt (about 221 kg), which is dried in a tray or tumble dryer (such as a double cone dryer) under reduced pressure at a jacket temperature of about 26° C.

Method 3

Step A: Preparation of 8-Chloro-1-methyl-2,3,4,5-tetrahydro-1H-3-benzazepine

To a reactor equipped with overhead agitation, jacket temperature control, a nitrogen inlet, and a caustic scrubber vent were charged, in the specified order, 2-chloro-N-(4-chlorophenethyl)propan-1-amine hydrochloride (1.00 kg, 3.72 mol), aluminum chloride (0.745 kg, 5.58 mol), and 1,2-dichlorobenzene (2.88 kg). The stirred reactor contents were heated to 125-130° C., and stirring was continued at that temperature for 14-18 h. At 60-70° C., a dark colored solution was obtained. After reaction completion (<1.0% starting material by HPLC peak area) had been verified, the stirred reactor contents were cooled to 30-35° C. To a second reactor vented to a caustic scrubber was charged purified water (1.60 L) and silica gel (0.160 kg). The Friedel-Crafts reaction mixture was transferred from the first reactor to the second reactor sufficiently slowly to maintain the stirred contents of the second reactor at <60° C. After the transfer is completed, the next step may be executed without any hold period. The silica gel was filtered on a medium to coarse filter element at 55-60° C., and the filtered solids were subsequently washed with purified water (800 mL) preheated to 50-60° C. The combined mother and wash liquor filtrates were cooled to 20-25° C. with vigorous agitation. Then the stirring was stopped, and the phases were allowed to separate at 20-25° C. (Process volume peaked at this point at 5.68 L). Three phases separated after 1-2 hours of standing. The lowest layer was drained to waste disposal. This dark layer consisted mostly of 1,2-dichlorobenzene (1.64 kg, 1.33 L) at pH 3-4. About 1% of the product was lost to this layer. The remaining two phases were allowed to stand without agitation for another 2-4 h. The lower layer was drained and saved (Layer A). This light colored phase (2.64 kg, 2.00 L, pH 2-3) contained ~90% 8-chloro-1-methyl-2,3,4,5-tetrahydro-1H-benzazepine. The upper layer (2.24 kg of a turbid water phase at pH 0-1) contains ~1-4% 8-chloro-1-methyl-2,3,4,5-tetrahydro-1H-benzazepine and remained in the reactor for back-extraction. The reactor was charged with cyclohexane (1.10 kg) and then 30% aqueous NaOH (2.44 kg, 18.3 mol). The resulting mixture (5.60 L) was stirred vigorously for 30 min at room temperature. The stirring was stopped, and the phases were allowed to separate for 25-40 min. If the pH of the lower (aqueous) phase was ≥13, it was drained to waste disposal. Otherwise, more 30% aqueous NaOH was added, and this extraction was repeated. At pH 14, the aqueous phase contains <0.1% 8-chloro-1-methyl-2,3,4,5-tetrahydro-1H-benzazepine free base. The remaining upper (organic) phase from the reactor was drained and saved (Layer B). The reactor was rinsed with purified water and followed by a suitable organic solvent to remove residual salts. The lower, light-colored product phase (the middle of the original three phases, Layer A) and the upper phase (organic, Layer B) were returned to the reactor. To the stirred reactor contents was added 30% aqueous NaOH (1.60 kg, 12.0 mol). The reactor contents were stirred vigorously for 0.5 hours. The stirring was discontinued and the phases were allowed to separate over 15-30 minutes. The lower (aqueous) layer was drained to waste disposal. To the upper (organic) phase remaining in the reactor was added purified water (2.40 kg). The reactor contents were stirred vigorously at 60-65° C. for 0.5 h. The stirring was discontinued, and the phases were allowed to separate at 60-65° C. over 1.5-2 h. The lower (aqueous) layer was drained to waste disposal. With a reactor jacket temperature of 55-60° C., solvent from the upper (organic) layer was removed by vacuum distillation at pressures starting at 115-152 torr and falling to 40 torr. The crude product, 8-chloro-1-methyl-2,3,4,5-tetrahydro-1H-benzazepine as the free base, was obtained as a yellow to brown oil distillation residue.

Step B: Preparation of (R)-8-Chloro-1-methyl-2,3,4,5-tetrahydro-1H-3-benzazepine Hemitartrate The distillation residue from Step A (crude 8-chloro-1-methyl-2,3,4,5-tetrahydro-1H-benzazepine as the free base) was dissolved in acetone (0.400 kg). The resulting solution was drained and weighed to assay the 8-chloro-1-methyl-2,3,4,5-tetrahydro-1H-benzazepine content by HPLC. Results of the assay were used to calculate charges of acetone, L-tartaric acid, and water. The quantities indicated below are typical for achievement of the target 8-chloro-1-methyl-2,3,4,5-tetrahydro-1H-benzazepine:acetone:L-tartaric acid:water mole ratio of 1.00:9.6:0.25:3.6 prior to addition of seed crystals. More acetone (1.415 kg) was added to the reactor and the stirred reactor contents were heated to 47-52° C. To the resulting solution was added a solution of L-tartaric acid (0.1223 kg, 0.815 mol) in purified water (0.211 kg) at a steady rate over 5-15 min. A thin suspension formed during the addition but then redissolved when the mixture temperature was reestablished at 50° C. Hemitartrate seed crystals (0.80 g) were added to the 50° C. solution to achieve cloudiness and to initiate nucleation. Nucleation was allowed to continue for 2-3 h with agitation at 47-52° C. Acetone (0.473 kg) was added to the reactor while the stirred reactor contents were maintained at 50° C. The resulting suspension was cooled to 0-5° C. slowly over 3-5 h. Stirring was continued at 0° C. for another 1-3 h. The resulting white precipitate was collected on a medium-to-fine filter element and then washed with a mixture of acetone (0.900 kg) and purified water (0.054 kg). The enantiomeric excess (ee) of the wet cake was determined.

If the ee was <98%, the wet cake was transferred back into the reactor and reslurried in a mixture of acetone (1.90 kg) and purified water (0.400 kg) at 55-60° C. for 0.5-1 h. If dissolution had not been achieved after one h, then water (approximately 0.160 kg) was added until a clear solution was achieved. The resulting mixture was then cooled to 0-5° C. slowly over 2-3 h. Stirring at 0° C. was continued for another 3-5 h. The resulting white precipitate was collected on a medium-to-fine filter element and then washed with acetone (0.400 kg) at 0-4° C.

The washed solid product (296 g wet) was dried at 60-65° C. under full vacuum for 15-20 hours. The yield of (R)-8-chloro-1-methyl-2,3,4,5-tetrahydro-1H-3-benzazepine hemitartrate, with about 99.7% ee and 7.5 wt. % water content, was 295 g (27.1% based on racemic 2-chloro-N-(4-chlorophenethyl)propan-1-amine hydrochloride and corrected for product water content).

Step C: Preparation of (R)-8-Chloro-1-methyl-2,3,4,5-tetrahydro-1H-3-benzazepine Hydrochloride Salt Hemihydrate, Form III To a reactor equipped with overhead agitation and a nitrogen inlet was charged, in the specified order, (R)-8-chloro-1-methyl-2,3,4,5-tetrahydro-1H-3-benzazepine hemitartrate (1.00 kg containing 7.5 wt % water, 1.71 mol), potassium carbonate (0.508 kg, 3.68 moles), ethyl acetate (2.68 kg), and purified water (2.68 kg). The resulting mixture was stirred at 20-25° C. for 30-40 min, and then the phases were allowed to separate over 0.5-1 h. The lower (aqueous) phase was drained to waste disposal. Purified water (2.68 kg) was added to the reactor, and the resulting mixture was vigorously stirred for 10-20 min. The phases were allowed to separate over 1-1.5 h. The lower (aqueous) phase was drained to waste disposal. With the reactor contents at a temperature of 40-45° C., the solvent was removed by vacuum distillation at pressures falling from 153 torr to 46 torr. The residue was cooled to 20-25° C. Ethyl acetate (3.81 kg) was charged to the reactor, and the distillation residue was dissolved with stirring. The water content of the resulting solution was verified by Karl Fischer analysis to be <0.8 wt. %. The solution was filtered through a polishing filter. The reactor was rinsed through the filter with ethyl acetate (2.33 kg) previously verified by Karl Fischer analysis to have <0.05 wt. % water content. Both the solution and rinse filtrates were charged back into the reactor. Purified water (39.9 g) was added to the reactor. The stirred reactor contents were cooled to 0-5° C., and then HCl gas (19.0 g, 0.521 mol) was added while the stirred reactor contents were maintained at 0-5° C. (R)-8-Chloro-1-methyl-2,3,4,5-tetrahydro-1H-3-benzazepine hemihydrate seed crystals (1.33 g) were added to the stirred reactor contents to initiate nucleation at 0-5° C. The remaining HCl gas (107.6 g, 2.95 mol) was charged to the reactor at a steady rate over at least 1.5-2 h while the stirred reactor contents were maintained at 0-5° C. The resulting suspension was stirred at 0-5° C. for 2 h. The resulting white precipitate was collected on a medium-to-fine filter element. The reactor and then the filtered solid product were washed with ethyl acetate (1.33 kg). The wet cake (ca. 867 g) was dried at full vacuum and 33-37° C. for 20 h or until the cake temperature had been stable for 4 hours, whichever occurred first. The resulting (R)-8-chloro-1-methyl-2,3,4,5-tetrahydro-1H-3-benzazepine hydrochloride salt hemihydrate (3.7 wt. % water content, 14.7% chloride content, <0.01% ROI, >99.6% ee, >99% HPLC purity, and <0.1% wrong isomer content) was obtained in a yield of about 741 g (89.9%).

Example 5: Immediate Release Tablets Comprising (R)-8-Chloro-1-methyl-2,3,4,5-tetrahydro-1H-3-benzazepine Hydrochloride Salt Hemihydrate, Form III (10 mg)

Immediate release tablets comprising (R)-8-chloro-1-methyl-2,3,4,5-tetrahydro-1H-3-benzazepine hydrochloride salt hemihydrate, Form III (10 mg) are manufactured by a standard manufacturing process that includes pre-blending, roller compaction, milling, blending, final blending, compression into tablets, and film coating using commonly available equipment in the pharmaceutical industry. The batch formula for a typical 600-kg batch (6,000,000 tablets) is provided in the Table below.

TABLE

| Component | Amount per Batch (kg) |
| --- | --- |
| Core Tablet | 600 |
| Compound 1 Hydrochloride Salt Hemihydrate | 62.4 |
| Silicified microcrystalline cellulose | 465.6 |
| Hydroxypropyl cellulose, NF | 42.0 |
| Croscarmellose sodium, NF | 24.0 |
| Magnesium stearate, NF | 6.0 |
| Coating | 18.6 |
| Opadry® II Blue, 85F90951 | 18.6 |

Approximately 40% of the silicified microcrystalline cellulose (SMCC) and (R)-8-chloro-1-methyl-2,3,4,5-tetrahydro-1H-3-benzazepine hydrochloride salt hemihydrate, Form III (API) is charged into a diffusion mixer through a screening mill (such as a Glatt) using a screen with an approximately 1 mm opening. The mixture is blended for approximately 100 rotations. One-half of the batch quantity of the hydroxypropyl cellulose (HPC), one-half of the batch quantity of the croscarmellose sodium and the remaining (~60%) SMCC is charged into the diffusion mixer through the screening mill This second mixture is blended for approximately 180 rotations. Next, one-half the batch quantity of the magnesium stearate is charged through a screen (20-mesh or finer) into the diffusion mixer. This third mixture is blended for approximately 50 rotations and then compacted using a roller compact. The resulting compacts are milled into granules using a screening mill (such as an Alexanderwerk granulating mill) with an approximately 1 mm opening. The milled granules are charged back into the diffusion mixer, the remaining HPC and croscarmellose sodium are added (through the screening mill) and this fourth mixture is blended for approximately 160 rotations. Next the remaining half of the magnesium stearate is charged through a 20 mesh screen into the diffusion mixer and this fifth mixture is blended for approximately 60 rotations. The resulting final blend is compressed on a rotary tablet press. The tablets are coated with a homogeneously dispersed suspension of Opadry® II Blue 85F90951 and purified water.

Average tablet weight and average tablet hardness are monitored during manufacturing. Friability and disintegration time are also monitored at compression start-up and after completion of compression using composite samples. At the start of compression and at appropriate time intervals during the compression process, average tablet weights are determined.

Example 6: Characterization of the Mechanism of Release of (R)-8-Chloro-1-methyl-2,3,4,5-tetrahydro-1H-3-benzazepine from Modified-release Formulations with Dissolution Profile Modeling Based on Equation 1

Equation 2 was obtained by taking the logarithm of Equation 1 supra.

$$\text{Log}\left(\frac{M_t}{M_\infty}\right) = \text{Log}(k) + n \cdot \text{Log}(t) \quad \text{Equation 2}$$

The values of n and k were calculated by performing linear regression of the dissolution data from the formulations as shown in the following tables.

Modified-Release Formulations with Soluble Coatings

| Ingredient | Formulation 1 | 2 | 3 |
|---|---|---|---|
| | | mg/Tablet | |
| Compound 1 Hydrochloride Salt Hemihydrate | 20.8 | 20.8 | 20.8 |
| Mannitol | 187.7 | 187.7 | 187.7 |
| HPMC K100LV | 90.0 | 30.0 | NA |
| HMPC K4M | NA | 60.0 | 90.0 |
| Magnesium Stearate | 1.5 | 1.5 | 1.5 |
| Core Tablet | 300 | 300 | 300 |
| Film Coating | | | |
| Opadry ® II Blue | 9.00 | 9.00 | 15.0 |

Modified-Release Formulations with Functional Polymer Coating

| Ingredient | Formulation 4 | 5 | 6 | 7 |
|---|---|---|---|---|
| | | mg/Tablet | | |
| Compound 1 Hydrochloride Salt Hemihydrate, Form III | 20.8 | 20.8 | 20.8 | 20.8 |
| Mannitol | 67.7 | 67.7 | 67.7 | 67.7 |
| HMPC K4M | 150 | 150 | 150 | 150 |
| Avicel PH102 | 60 | 60 | 60 | 60 |
| Magnesium Stearate | 1.5 | 1.5 | 1.5 | 1.5 |
| Core Tablet | 300 | 300 | 300 | 300 |
| Film Coating | | | | |
| Opadry ® II Blue | 15 | NA | NA | NA |
| Surelease ®/Opadry ® 75/25 | NA | 15 | NA | NA |
| Surelease ®/Opadry ® 80/20 | NA | NA | 15 | NA |
| Surelease ®/Opadry ® 85/15 | NA | NA | NA | 15 |

Microsoft Excel was used to perform the linear regression. Consistent with the condition of using Equation 1 to characterize the release mechanism the release data up to ~80% were used for the analysis. However, when a lag time of Compound 1 release was present, the data range was adjusted accordingly.

Figure 55:
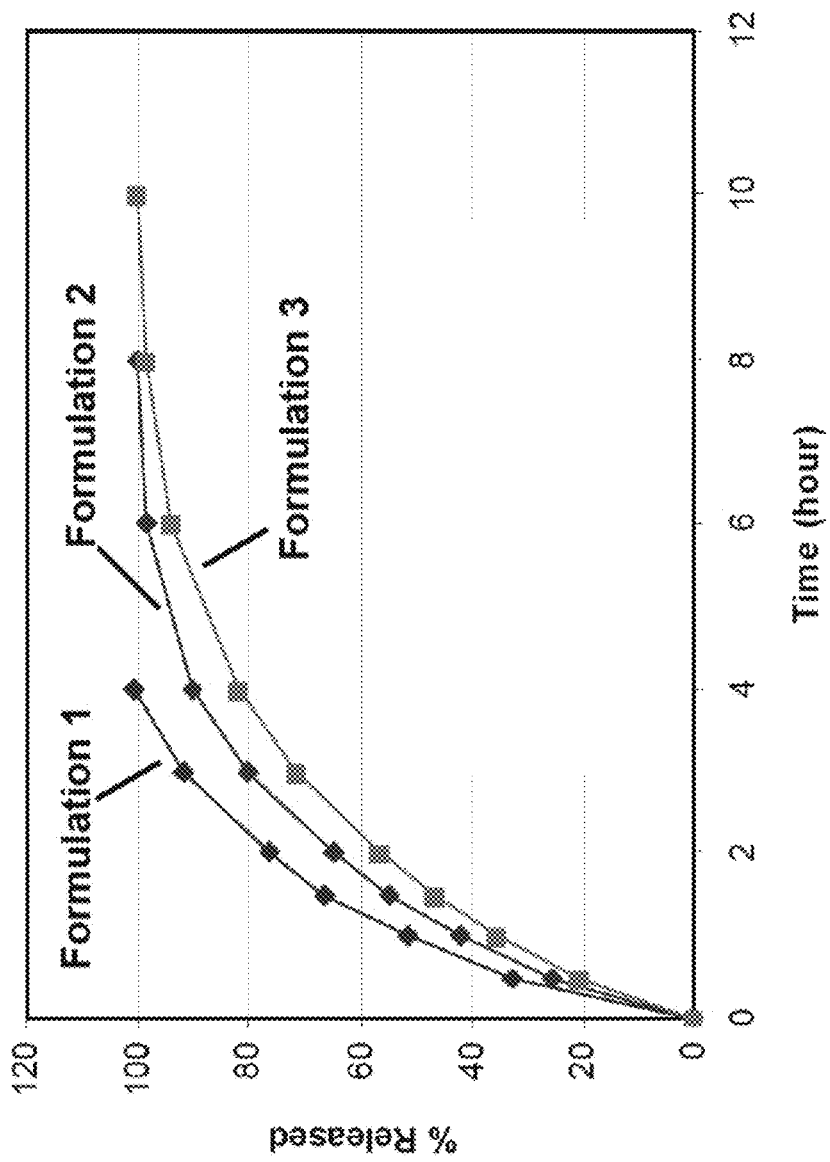
FIG. 55: Dissolution Profiles of Compound 1 Hydrochloride Salt Hemi-hydrate, Form III 20-mg Modified-release Formulations with Soluble Coating.
Figure 56:
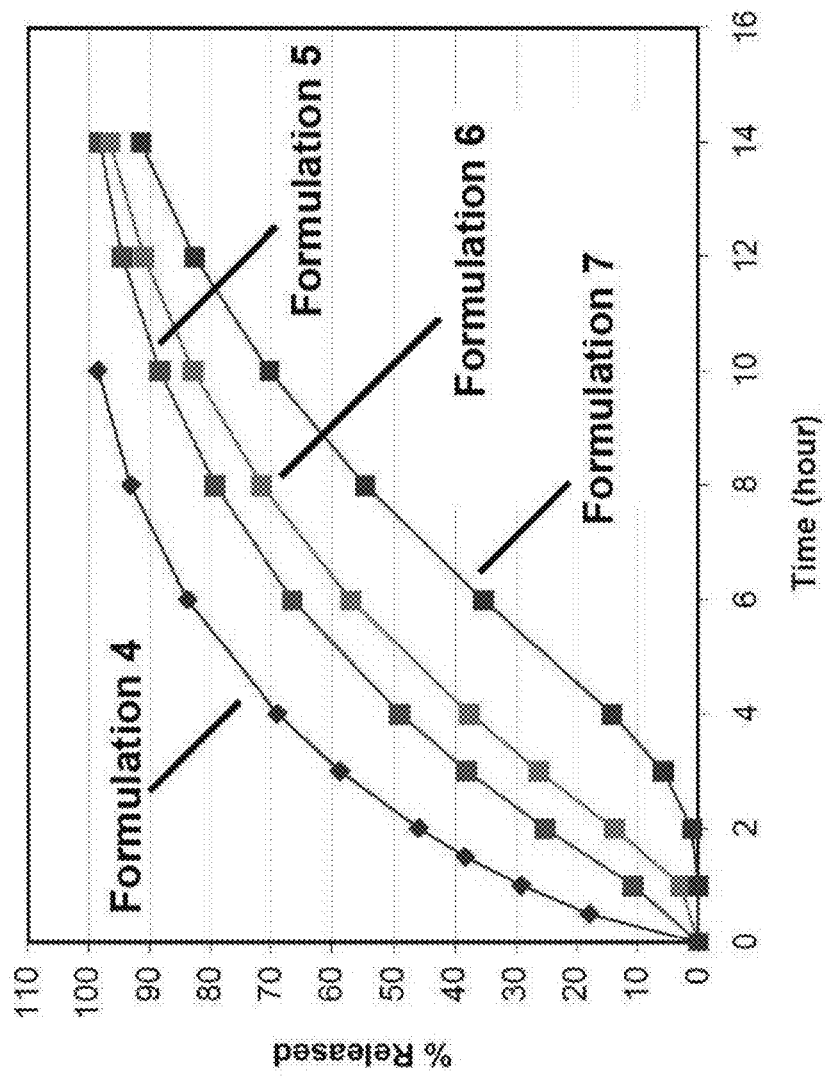
FIG. 56: Dissolution Profiles of Compound 1 Hydrochloride Salt Hemi-hydrate, Form III 20-mg Modified-release Formulations with Functional Polymer Coating.

The dissolution profiles of the formulations in the preceding tables are presented in FIG. 55 and FIG. 56. The calculated n value for each formulation is listed in the following table.

Characterization of the Release Mechanism of (R)-8-Chloro-1-methyl-2,3,4,5-tetrahydro-1H-3-benzazepine 20-mg Modified-Release Formulation According to Equation 1

| Formulation | Coating | k | n | Release Kinetics |
|---|---|---|---|---|
| 1 | Opadry ® II Blue | 50.89 | 0.61 | Non-Fickian |
| 2 | Opadry ® II Blue | 40.98 | 0.64 | Non-Fickian |
| 3 | Opadry ® II Blue | 34.27 | 0.67 | Non-Fickian |
| 4 | Opadry ® II Blue | 28.80 | 0.63 | Non-Fickian |
| 5 | Surelease ®/Opadry ® 75/25 | 12.02 | 0.96 | Zero-order |
| 6 | Surelease ®/Opadry ® 80/20 | 7.99 | 1.03 | Zero-order |
| 7 | Surelease ®/Opadry ® 85/15 | 2.22 | 1.47 | Super-Case II |

The calculated n value was consistently in the range of 0.61-0.67 for the formulations coated with Opadry® II Blue, indicating that the release of Compound 1 was controlled by diffusion and HPMC swelling (i.e., non-Fickian kinetics). HPMC molecular weight and percentage in the core tablet had little impact on the order of Compound 1 release kinetics. However, the value of k was inversely proportional to HPMC molecular weight and percentage in the core tablet. The release of Compound 1 and the value of k decreased progressively as the molecular weight and percentage of HPMC increased (FIG. 55).

When core tablets were coated with Surelease®/Opadry®, the n value was calculated to be >0.89 for all cases, indicating that the mechanism of Compound 1 release shifted from the diffusion and HPMC swelling to primarily HPMC swelling. In the case of Formulation 7, an n value of 1.47 was likely due to the presence of initial slow release of Compound 1. As shown in FIG. 56, release of Compound 1 was accelerated after the 3-h time point. To calculate n for Formulation 7, the release data of 4 h through the last time point (14 h) were selected to minimize the effect of early, slow release on the n value. It was also observed that the value of k was dependent on the Surelease®/Opadry® ratio. The coating film was more porous at a lower Surelease®/Opadry® ratio, resulting in an increase in Compound 1 release, and hence a higher k value. Mechanistically, the Surelease®/Opadry® coating prevented core tablet wetting and initial Compound 1 release during the dissolution process. Following a lag time during which the pores were produced as the result of Opadry® dissolving and leaching out of the coating membrane, the core tablet became gradually wetted and Compound 1 was released. Hence, application of the Surelease®/Opadry® coating altered the hydration rate of the core tablet and the pattern of Compound 1 release, leading to zero-order release kinetics.

The release mechanism of Compound 1 from two modified-release platforms was analyzed according to a widely accepted empirical equation. The results indicated that Compound 1 release from the tablets coated with Opadry® II Blue and Surelease®/Opadry® exhibit non-Fickian and zero-order or Super-Case II kinetics, respectively. The main difference between the two platforms was the solubility of the coating: Opadry® II Blue coating was soluble while Surelease®/Opadry® coating was insoluble but erodible. Therefore, the hydration rate (i.e., swelling) of the core tablet and the pattern of Compound 1 release was modulated in the latter case. This observation is consistent with the finding reported in the literature that drug release modulation can be achieved by physical restrictions of matrix swelling (Colombo P, Conte U, Gazzaniga A, et al. Drug release modulation by physical restrictions of matrix swelling. *Int. J. Pharm.* 1990; 63(1):43-48).

Example 7: Disintegrant-(R)-8-Chloro-1-methyl-2,3,4,5-tetrahydro-1H-3-benzazepine Interaction via Ion-Exchange Binding The following batches containing varying amounts of four different excipients were prepared using a V-blender:

| Batch | Silicified MCC (g) | Hydroxypropyl Cellulose (g) | Croscarmellose Sodium (g) | Magnesium Stearate (g) |
|---|---|---|---|---|
| 1 | 89.35 | 0.00 | 0.00 | 0.25 |
| 2 | 81.60 | 7.00 | 0.00 | 1.00 |
| 3 | 85.35 | 0.00 | 4.00 | 0.25 |
| 4 | 83.60 | 3.50 | 2.00 | 0.50 |
| 5 | 84.60 | 0.00 | 4.00 | 1.00 |
| 6 | 88.60 | 0.00 | 0.00 | 1.00 |
| 7 | 83.60 | 3.50 | 2.00 | 0.50 |
| 8 | 83.60 | 3.50 | 2.00 | 0.50 |
| 9 | 78.35 | 7.00 | 4.00 | 0.25 |
| 10 | 77.60 | 7.00 | 4.00 | 1.00 |
| 11 | 82.35 | 7.00 | 0.00 | 0.25 |

Compound 1 hydrochloride solution in water (5 mL, 0.2 mg/mL) was sonicated for 30 min with each of the above excipient mixtures in 100 mL flasks. The resulting suspensions were then diluted to 100 mL with water and an aliquot of each was centrifuged at 14,000 rpm for 5 min. The supernatants were analyzed by HPLC to determine the recovery of Compound 1.

| Batch | Compound 1 Recovery (%) |
|---|---|
| 1 | 96.9 |
| 2 | 97.9 |
| 3 | 77.9 |
| 4 | 88.0 |
| 5 | 77.0 |
| 6 | 96.7 |
| 7 | 89.5 |
| 8 | 89.4 |
| 9 | 79.0 |
| 10 | 81.2 |
| 11 | 98.6 |

Statistical evaluation of the recovery results indicated that hydroxypropyl cellulose and croscarmellose sodium have an impact on the recovery of Compound 1. Hydroxypropyl cellulose slightly improved the recovery of Compound 1, while croscarmellose sodium significantly reduced recovery. Magnesium stearate displayed no such effect and no two-way interactions were identified.

Example 8: Steady State Pharmacokinetics of Immediate-Release Dosage Form of Compound 1 in Healthy Human Volunteers A study was designed to assess, inter alia, the steady-state pharmacokinetics following repeat oral doses of Compound 1 administered to healthy human male and female subjects with a BMI ≥25 kg/m². There were three treatment groups each comprising six subjects. Treatment A (3 mg), Treatment B (10 mg) and Treatment C (20 mg) were administered as gel caps once a day for 14 days. The immediate-release formulation used in this clinical study was comprised of white, opaque, size 4 hard gelatin capsules containing Compound 1, and microcrystalline cellulose, NF (Emcocel® 50M) as the diluent. Microcrystalline cellulose is an excipient and does not have any pharmacological activity.

Figure 57:
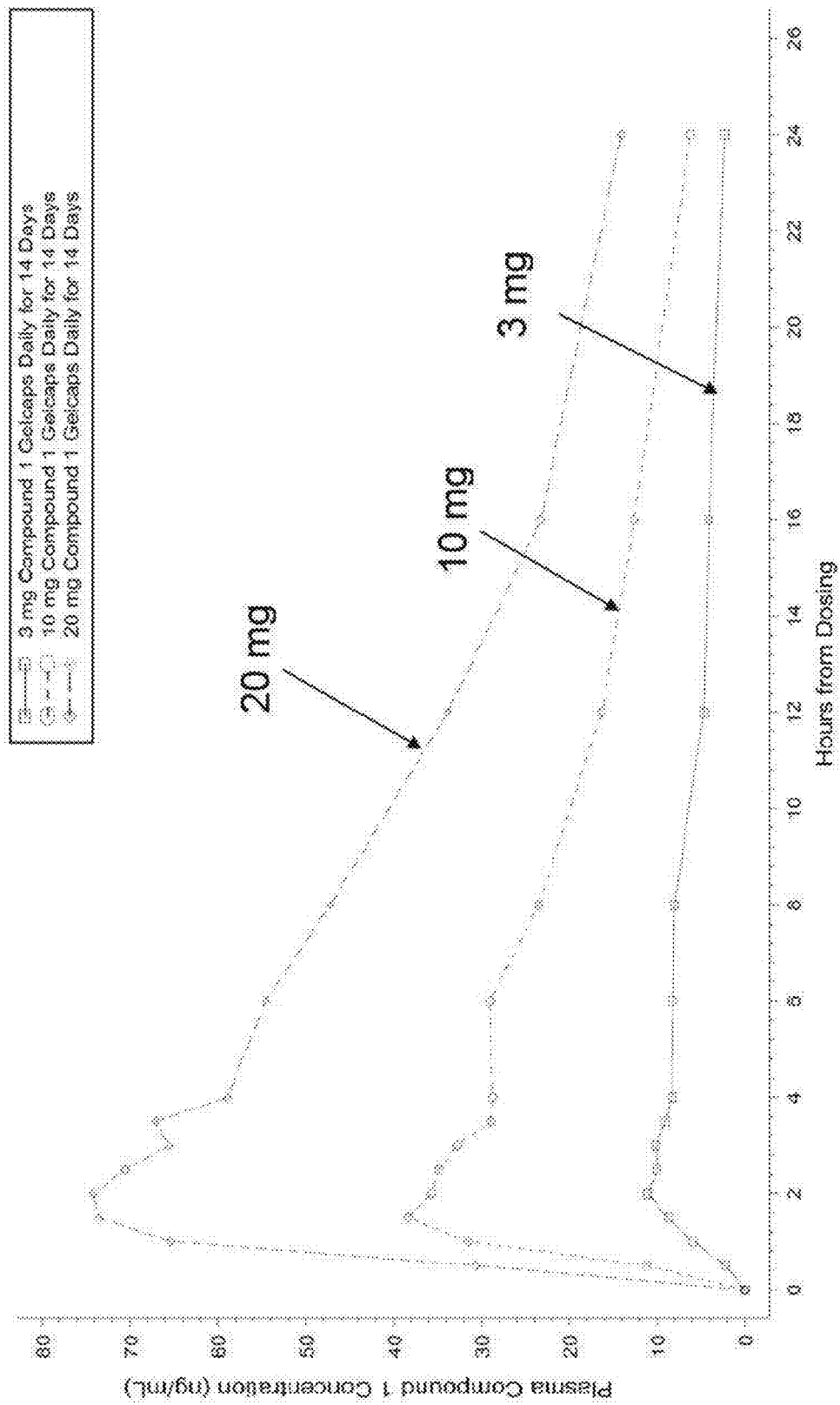
FIG. 57: Immediate-Release Mean Plasma Compound 1 Concentrations Versus Time on Day 1 in Humans.

Blood samples were collected predose and at 0.5, 1, 1.5, 2, 2.5, 3, 3.5, 4, 6, 8, 12, 16, and 24 hours postdose on Day 1 and Day 14. Blood samples were also obtained at predose and 2 hours postdose on Days 3, 5, 7, 9, 11, and 13 as well as at the nominal dosing time (±5 minutes) on Days 17, 19, and 21. At each collection, 7 mL of blood was collected into a vacutainer tube containing sodium heparin (green top) and refrigerated immediately (cryoblock). Within 30 minutes of collection, the plasma fraction was separated by centrifugation at 2,000 rpm for 15 minutes at 4° C. The plasma fraction was separated and transferred into 2 labeled 5 mL polypropylene tubes and frozen at approximately −20° C. The mean plasma concentration of Compound 1 versus time for each treatment group on Day 1 is shown in FIG. 57. The mean plasma concentration of Compound 1 versus time for each treatment group at steady state (Day 14) is shown in FIG. 58.

Those skilled in the art will recognize that various modifications, additions, substitutions, and variations to the illustrative examples set forth herein can be made without departing from the spirit of the invention and are, therefore, considered within the scope of the invention.

What is claimed is:

1. A method of weight management in an individual in need thereof comprising administering once daily to said individual a modified-release dosage form which is a tablet, wherein the dosage form comprises a core tablet and a functional film coating, wherein said core tablet comprises:
   (i) about 7% by weight of (R)-8-chloro-1-methyl-2,3,4,5-tetrahydro-1H-3-benzazepine hydrochloride salt hemihydrate, Form III, and
   (ii) about 50% by weight of (hydroxypropyl)methyl cellulose;
   wherein said functional film coating comprises ethyl cellulose and (hydroxypropyl)methyl cellulose in a weight ratio of about 85:15; and
   wherein said modified-release dosage form provides an in vitro release rate for which the time to achieve 80% release of said (R) 8-chloro-1-methyl-2,3,4,5-tetrahydro-1H-3-benzazepine (T80%) is at least 3 hours as determined by USP Apparatus I Basket Method in 900 mL of 0.1 N HCl solution at 37° C. and 100 rpm.

2. The method of claim 1, wherein the weight to weight ratio of said core tablet to said functional coating is about 20:1.

3. The method of claim 1 or 2, wherein the core tablet further comprises microcrystalline cellulose.

4. The method of claim 3, wherein the core tablet comprises about 20% by weight of microcrystalline cellulose.

5. The method of claim 1 or 2, wherein the dosage form exhibits a release profile comprising super-case II kinetics under in vitro conditions.

6. The method of claim 1 or 2, wherein the core tablet further comprises mannitol.

7. The method of claim 1 or 2, wherein the core tablet further comprises magnesium stearate.

8. The method of claim 1, wherein said weight management comprises one or more of: weight loss, maintenance of weight loss, decreased food consumption, increasing meal-related satiety, reducing pre-meal hunger, and reducing intra-meal food intake.

9. The method of claim 1, as an adjunct to diet and exercise.

10. The method of claim 1, wherein said individual in need of weight management is selected from: an obese patient with an initial body mass index≥30 kg/m²; an overweight patient with an initial body mass index≥27 kg/m² in the presence of at least one weight related comorbid condition; and an overweight patient with an initial body mass index≥27 kg/m² in the presence of at least one weight related comorbid condition; wherein said weight related co-morbid condition is selected from: hypertension, dyslipidemia, cardiovascular disease, glucose intolerance, and sleep apnea.

11. The method of claim 1, further comprising administering a second anti-obesity agent to said individual.

12. The method of claim 1, wherein said second anti-obesity agent is selected from: chlorphentermine, clortermine, phenpentermine, and phentermine, and pharmaceutically acceptable salts, solvates, and hydrates thereof.

13. The method of claim 1, further comprising administering an anti-diabetes agent to said individual.

14. The method of claim 1, wherein said anti-diabetes agent is metformin.

15. The method of claim 1, wherein the amount of (R)-8-chloro-1-methyl-2,3,4,5-tetrahydro-1H-3-benzazepine hydrochloride salt hemihydrate, Form III is 20.8 mg per tablet.

* * * * *

UNITED STATES PATENT AND TRADEMARK OFFICE
CERTIFICATE OF CORRECTION

PATENT NO.         : 10,463,676 B2
APPLICATION NO.    : 16/241337
DATED              : November 5, 2019
INVENTOR(S)        : Zezhi Jesse Shao et al.

Page 1 of 1

It is certified that error appears in the above-identified patent and that said Letters Patent is hereby corrected as shown below:

In the Claims

Claim 1, Column 134, Lines 39-40, delete "(R) 8-chloro-1-methyl-2,3,4,5-tetrahydro-1H-3-benzazepine" and insert -- (R)-8-chloro-1-methyl-2,3,4,5-tetrahydro-1H-3-benzazepine --.

Claim 10, Column 134, Line 66 to Column 135, Line 2, delete "an overweight patient with an initial body mass index≥27 kg/m² in the presence of at least one weight related comorbid condition;".

Claim 12, Column 135, Line 10, delete "claim 1" and insert -- claim 11 --.

Claim 14, Column 135, Line 16, delete "claim 1" and insert -- claim 13 --.

Signed and Sealed this
Thirty-first Day of December, 2019

Andrei Iancu
*Director of the United States Patent and Trademark Office*